(12) United States Patent
Guisot

(10) Patent No.: US 10,399,989 B2
(45) Date of Patent: *Sep. 3, 2019

(54) PYRAZOLOPYRIMIDINE DERIVATIVES AS BTK INHIBITORS FOR THE TREATMENT OF CANCER

(71) Applicant: Loxo Oncology, Inc., Stamford, CT (US)

(72) Inventor: Nicolas Guisot, Cheshire (GB)

(73) Assignee: Loxo Oncology, Inc., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/109,223

(22) Filed: Aug. 22, 2018

(65) Prior Publication Data

US 2018/0362533 A1 Dec. 20, 2018

Related U.S. Application Data

(63) Continuation of application No. 15/762,367, filed as application No. PCT/GB2016/052897 on Sep. 16, 2016.

(51) Int. Cl.
| | | |
|---|---|---|
| C07D 487/04 | (2006.01) | |
| A61K 31/519 | (2006.01) | |
| A61P 35/00 | (2006.01) | |
| A61K 31/538 | (2006.01) | |
| A61K 45/06 | (2006.01) | |

(52) U.S. Cl.
CPC .......... *C07D 487/04* (2013.01); *A61K 31/519* (2013.01); *A61K 31/538* (2013.01); *A61K 45/06* (2013.01); *A61P 35/00* (2018.01)

(58) Field of Classification Search
CPC ............................ C07D 487/04; A61K 31/519
See application file for complete search history.

(56) References Cited

U.S. PATENT DOCUMENTS

| | | |
|---|---|---|
| 6,660,744 B1 | 12/2003 | Hirst et al. |
| 7,718,662 B1 | 5/2010 | Chen et al. |
| 8,673,925 B1 | 3/2014 | Goldstein |
| 9,090,621 B2 | 7/2015 | Goldstein |
| 9,975,897 B2 | 5/2018 | Calder et al. |
| 2002/0156081 A1 | 10/2002 | Hirst et al. |
| 2003/0225098 A1 | 12/2003 | Hirst et al. |
| 2008/0076921 A1 | 3/2008 | Honiberg et al. |
| 2010/0144705 A1 | 6/2010 | Miller |
| 2010/0254905 A1 | 10/2010 | Honigberg et al. |
| 2011/0144068 A1 | 6/2011 | Pulici et al. |
| 2014/0221333 A1 | 8/2014 | De Man et al. |
| 2018/0298008 A1 | 10/2018 | Guisot |
| 2018/0362512 A1 | 12/2018 | Guisot |
| 2018/0362537 A1 | 12/2018 | Guisot |
| 2019/0000806 A1 | 1/2019 | Guisot |

FOREIGN PATENT DOCUMENTS

| | | |
|---|---|---|
| CN | 102159214 | 8/2011 |
| CN | 105085474 | 11/2015 |
| EP | 2548877 | 1/2013 |
| WO | WO 0119829 | 3/2001 |
| WO | WO 02080926 | 10/2002 |
| WO | WO 2008/039218 | 4/2008 |
| WO | WO 2008/054827 | 5/2008 |
| WO | WO 2008/121742 | 10/2008 |
| WO | WO 2009/158571 | 12/2009 |
| WO | WO 2011/046964 | 4/2011 |
| WO | WO 2011/090760 | 7/2011 |
| WO | WO 2011/153514 | 12/2011 |
| WO | WO 2012/158764 | 11/2012 |
| WO | WO 2012/158843 | 11/2012 |
| WO | WO 2013/010136 | 1/2013 |
| WO | WO 2013/102059 | 7/2013 |
| WO | WO 2013/191965 | 12/2013 |
| WO | WO 2014/022569 | 2/2014 |
| WO | WO 2014/068527 | 5/2014 |
| WO | WO 2014/082598 | 6/2014 |
| WO | WO 2014/188173 | 11/2014 |
| WO | WO 2015/048662 | 4/2015 |
| WO | WO 2015/095099 | 6/2015 |
| WO | WO 2015/127310 | 8/2015 |
| WO | WO 2015/140566 | 9/2015 |
| WO | WO 2015/189620 | 12/2015 |
| WO | WO 2017/103611 | 6/2017 |

OTHER PUBLICATIONS

Buggy et al., "Bruton Tyrosine Kinase (BTK) and Its Role in B-cell Malignancy," International Reviews of Immunology, Mar. 21, 2012, 31(2):119-132.
Dubovsky et al., "Ibrutinib is an irreversible molecular inhibitor of ITK driving a Th1-selective pressure in T lymphocytes," Blood, Oct. 10, 2013, 122(15):2539-2549.
Haleblian, "Characterization of habits and crystalline modification of solids and their pharmaceutical applications," J Pharm Sci, Aug. 1975, 64(8):1269-1288.
International Preliminary Report on Patentability in International Application No. PCT/GB2016/052897, dated Mar. 29, 2018, 8 pages.
International Search Report in International Application No. PCT/GB2016/052897, dated Oct. 31, 2016, 10 pages.

(Continued)

*Primary Examiner* — Karen Cheng

(74) *Attorney, Agent, or Firm* — Fish & Richardson P.C.

(57) ABSTRACT

This invention relates to novel compounds. The compounds of the invention are tyrosine kinase inhibitors. Specifically, the compounds of the invention are useful as inhibitors of Bruton's tyrosine kinase (BTK). The invention also contemplates the use of the compounds for treating conditions treatable by the inhibition of Bruton's tyrosine kinase, for example cancer, lymphoma, leukemia and immunological diseases.

24 Claims, No Drawings

(56) References Cited

OTHER PUBLICATIONS

Kohrt et al., "Ibrutinib antagonizes rituximab-dependent NK cell-mediated cytotoxicity," Blood, Mar. 20, 2014, 123(12):1957-1960.
Maddocks et al., "Etiology of Ibrutinib Therapy Discontinuation and Outcomes in Patients With Chronic Lymphocytic Leukemia," JAMA Oncol., Apr. 2015, 1(1):80-87.
Whang et al., "Bruton's tyrosine kinase inhibitors for the treatment of rheumatoid arthritis," Drug Discov Today., Aug. 2014, 19(8):1200-1204.
Woyach et al., "Resistance mechanisms for the Bruton's tyrosine kinase inhibitor ibrutinib," N Engl J Med, Jun. 12, 2014, 370(24):2286-2294.
Zapf et al. "Covalent Inhibitors of Interleukin-2 Inducible T Cell Kinase (Itk) with Nanomolar Potency in a Whole-Blood Assay," J. Med. Chem., Nov. 2012, 55(22):10047-10063.
Zhang et al., "Mechanisms of ibrutinib resistance in chronic lymphocytic leukaemia and non-Hodgkin lymphoma," Br J Haematol, Aug. 2015, 170(4):445-456.

PYRAZOLOPYRIMIDINE DERIVATIVES AS BTK INHIBITORS FOR THE TREATMENT OF CANCER

This application is a continuation of U.S. application Ser. No. 15/762,367, filed on Mar. 22, 2018, which is a National Stage application under 35 U.S.C. § 371 of International Application No. PCT/GB2016/052897, filed Sep. 16, 2016, which claims the benefit of priority to GB 1516445.2, filed Sep. 16, 2015, GB 1522246.6, filed Dec. 16, 2015 and GB 1613947.9, filed Aug. 15, 2016.

This invention relates to compounds. More specifically, the invention relates to compounds useful as kinase inhibitors, along with processes to prepare the compounds and uses of the compounds. Specifically, the invention relates to inhibitors of Bruton's tyrosine kinase (BTK).

BACKGROUND

Kinases are a class of enzyme that control the transfer of phosphate groups from phosphate donor groups, for example ATP, to specific substrates. Protein kinases are a large subset of kinases that play a central role in the regulation of a wide variety of cellular signalling and processes and BTK is one such protein kinase.

BTK is a member of the src-related Tec family of cytoplasmic tyrosine kinases. BTK plays a key role in the B-cell receptor (BCR) signalling pathway of B-cells, which is required for the development, activation and survival of B-cells. BTK inhibitors have therefore been developed with the aim of treating B-cell malignancies that are dependent on BCR signalling, such as chronic lymphocytic leukemia (CLL) and non-Hodgkin's lymphoma (NHL) (Buggy 2012). BTK is also expressed in specific myeloid cells including, monocytes/macrophages, neutrophils and mast cells. In these myeloid cells, BTK has been indicated in the immune complex mediated activation of FcγR and FcεR, which is believed to contribute to the pathogenesis of rheumatoid arthritis (RA) (Whang 2014). In addition, BTK is required for the maturation of osteoclast cells and so inhibiting BTK could prevent the bone erosion that is associated with RA. The critical role of BTK in both B-cells and myeloid cells has led to BTK becoming an attractive target for the treatment of not only B-cell malignancies but also for the treatment of autoimmune diseases.

Ibrutinib is an irreversible BTK inhibitor that has been approved for the treatment of CLL, mantle cell lymphoma (MCL) and Waldenstrom's macroglobulinemia (WM). Since Ibrutinib was first disclosed there have been a number of patent applications concerned with structures closely related to Ibrutinib, for example see WO 2012/158843, WO 2012/158764, WO 2011/153514, WO 2011/046964, US 2010/0254905, US 2010/0144705, U.S. Pat. No. 7,718,662, WO, 2008/054827 and WO 2008/121742.

Further Btk inhibitors are disclosed in WO 2013/010136, U.S. Pat. No. 9,090,621, WO 2015/127310, WO 2015/095099 and US 2014/221333. Kinase inhibitors are also disclosed in U.S. Pat. No. 6,660,744, US 2002/0156081, US 2003/0225098 and WO 01/19829.

Ibrutinib also irreversibly binds to interleukin-2 inducible tyrosine kinase (ITK) (Dubovsky 2013). ITK plays a critical role in FcR-stimulated natural killer (NK) cell function that is required for antibody dependent NK cell mediated cytotoxicity (ADCC). ADCC is the mechanism that anti-CD20 antibodies, such as rituximab are believed to activate and ibrutinib has been shown to antagonise this mechanism in vitro (Kohrt 2014). As rituximab-combination chemotherapy is today's standard of care in B-cell malignancies, it would be desirable to have a BTK inhibitor with high selectivity for BTK over ITK.

In the clinic, adverse events have included atrial fibrillation, diarrhea, rash, arthralgia and bleeding (IMBRUVICA package insert 2014). Known BTK inhibitors, e.g. ibrutinib are also known to have gastrointestinal side effects, which are considered to be as a result of a secondary EGFR inhibitory activity. It is therefore desirable to have a BTK inhibitor with high BTK inhibition and low EGFR inhibition to reduce or avoid the gastrointestinal side effects.

Irreversible and covalent reversible BTK inhibitors specifically target a cysteine residue C481 within BTK. Following treatment with ibrutinib, cases of primary and secondary resistance have emerged. Mutations within BTK such as C481S, C481Y, C481R, C481F have been reported in the literature and clearly interfere with drug binding (Woyach 2014; Maddocks 2015). It has been predicted that the incidence of observed resistance will increase as clinical use outside clinical trials expands over time (Zhang 2015).

Therefore, an aim of the present invention is to provide BTK inhibitors with a different binding mode more specifically reversible inhibitors. In addition the invention aims to provide BTK inhibitors with high selectivity for BTK inhibition over EGFR and ITK inhibition.

Furthermore, it is an aim of certain embodiments of this invention to provide new cancer treatments. In particular, it is an aim of certain embodiments of this invention to provide compounds which have comparable activity to existing cancer treatments but are also effective against mutations. One of the aspects of the invention focus on providing BTK inhibitors effective against the C481 mutations.

It is an aim of certain embodiments of this invention to provide compounds which exhibit reduced cytotoxicity relative to prior art compounds and existing therapies.

Another aim of certain embodiments of this invention is to provide compounds having a convenient pharmacokinetic profile and a suitable duration of action following dosing. A further aim of certain embodiments of this invention is to provide compounds in which the metabolised fragment or fragments of the drug after absorption are GRAS (Generally Regarded As Safe).

Certain embodiments of the present invention satisfy some or all of the above aims.

SUMMARY OF THE DISCLOSURE

In accordance with the present invention there is provided compounds as disclosed below. Furthermore, the invention provides compounds capable of inhibiting Bruton's tyrosine kinase (BTK) and the use of these compounds in inhibiting BTK. In accordance with the invention there is provided a method of treating conditions modulated by BTK. The invention provides compounds for use in treating a condition which is modulated by BTK.

In a first aspect of the invention there is provided a compound according to formula (I) or pharmaceutically acceptable salts thereof:

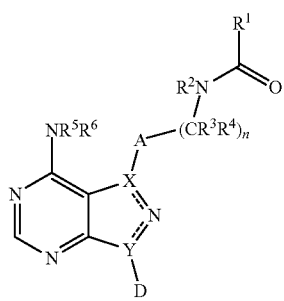

wherein

A represents a ring selected from substituted or unsubstituted: phenyl, pyridyl, pyridazine, pyrimidine, or pyrazine, wherein when substituted A contains from 1 to 4 substitutents independently selected at each occurrence from: H, halo, $C_{1-6}$ alkyl, $C_{1-6}$ alkyl substituted with —$OR^a$, $C_{1-6}$ haloalkyl, —$OR^a$, $C_{2-6}$ alkenyl, $C_{2-6}$ alkynyl, $C_{3-8}$ cycloalkyl, $C_{3-8}$ cycloalkenyl, $NR^aR^b$, —CN, acyl, —C(O)$R^a$, —C(O)O$R^a$, —$SO_2R^a$, and —$SO_3R^a$;

D is selected from substituted or unsubstituted: $C_{1-6}$ alkyl, $C_{3-10}$ cycloalkyl, $C_{3-10}$ cycloalkenyl, $C_{6-10}$ aryl, 3 to 10 membered heterocycloalkyl, 3 to 10 membered heterocycloalkenyl and 5 to 10 membered heteroaryl, wherein, when substituted, D contains from 1 to 9 substituents independently selected at each occurrence from: halo, —$OR^c$, —$NR^cR^d$, =O, —CN, —C(O)O$R^c$, —OC(O)$R^e$, —C(O)$NR^cR^d$, —$NR^cC(O)R^e$, $C_{1-6}$ alkyl, $C_{1-6}$ haloalkyl, $C_{1-6}$ alkyl substituted with —$OR^c$, $C_{3-8}$ cycloalkyl, —$SO_2R^c$, $SO_3R^c$, C(O)$R^c$ and a 3 to 8 membered heterocyclic group;

one of X and Y is N and the other is C, wherein ⫽ represents a single or double bond and a single bond is present between N and X or Y when X or Y is N and a double bond is present between N and X or Y when X or Y is C;

n is selected from 1 or 2;

$R^1$ is a group selected from a substituted or unsubstituted: $C_{3-8}$ cycloalkyl, $C_{3-8}$ heterocycloalkyl, $C_{3-8}$ cycloalkenyl, $C_{3-8}$ heterocycloalkenyl, aryl or heteroaryl moiety, wherein the aryl or heteroaryl moiety either contains 5 or 6 atoms in a single ring or from 7 to 14 atoms in a fused polycyclic ring system, wherein, when substituted, $R^1$ contains from 1 to 9 substituents (optionally 1 to 5) independently selected at each occurrence from the group comprising: halo, —$OR^f$, —$NR^fR^g$, =O, —CN, acyl, $C_{1-6}$ alkyl, $C_{1-6}$ haloalkyl, $C_{1-6}$ alkyl substituted with —$OR^f$, $C_{1-6}$ alkyl substituted with $C_{3-8}$ cycloalkyl, $C_{3-8}$ cycloalkenyl, $C_{3-8}$ heterocycloalkyl, —$SO_2R^f$, $SO_3R^f$, —C(O)$R^f$, —C(O)O$R^f$, —C(O)$NR^fR^g$, aryl optionally substituted by 1 or 2 halo atoms, and 6 membered heteroaryl;

$R^2$ is selected from H, $C_{1-4}$ alkyl, $C_{1-4}$ haloalkyl, $C_{3-7}$ cycloalkyl, and $C_{3-7}$ halocycloalkyl;

$R^3$ and $R^4$ are independently selected at each occurrence from: H, halo, $C_{1-4}$ alkyl, $C_{1-4}$ alkyl substituted with —$OR^h$, $C_{1-4}$ haloalkyl, —$OR^h$, $C_{3-6}$ cycloalkyl and $C_{3-7}$ halocycloalkyl, or $R^3$ and $R^4$ taken together with the atom on which they are substituted, form a 3 to 6 membered cycloalkyl ring;

$R^5$ and $R^6$ are independently selected at each occurrence from: H, $C_{1-4}$ alkyl, $C_{1-4}$ alkyl substituted with —$OR^h$, $C_{1-4}$ haloalkyl, $C_{1-4}$ acyl, $C_{3-7}$ cycloalkyl, and $C_{3-7}$ halocycloalkyl;

$R^a$ and $R^b$ are independently selected at each occurrence from: H, $C_{1-4}$ alkyl, $C_{1-4}$ alkyl substituted with —$OR^i$, $C_{1-4}$ haloalkyl, acyl, $C_{3-7}$ cycloalkyl, and $C_{3-7}$ halocycloalkyl;

$R^c$, $R^d$ and $R^e$ are independently selected at each occurrence from: H, $C_{1-4}$ alkyl, $C_{1-4}$ haloalkyl, $C_{1-4}$ alkyl substituted with —$OR^j$, unsubstituted aryl, aryl substituted with halo or $C_{1-4}$ alkyl or $C_{1-4}$ haloalkyl or a combination thereof, $C_{3-7}$ cycloalkyl, and $C_{3-7}$ halocycloalkyl;

$R^f$ and $R^g$ are independently selected at each occurrence from: H, $C_{1-4}$ alkyl, $C_{1-4}$ alkyl substituted with —$OR^k$, $C_{1-4}$ haloalkyl, acyl, $C_{3-7}$ cycloalkyl, and $C_{3-7}$ halocycloalkyl;

$R^h$, $R^i$, $R^j$, and $R^k$ are independently selected at each occurrence from: H, $C_{1-4}$ alkyl, $C_{1-4}$ alkyl substituted with —$OR^l$ and $C_{1-4}$ haloalkyl; and $R^l$ is independently selected at each occurrence from: H, $C_{1-4}$ alkyl, and $C_{1-4}$ haloalkyl.

In embodiments $R^1$ contains 1 to 9 substituents (optionally 1 to 5). At least one of the substituents and the —C(=O)— (which is bonded to $R^1$) are bonded to adjacent carbon atoms of $R^1$. In other words the substituent and —C(=O) are ortho substituted.

In embodiments $R^1$ is a group selected from a substituted or unsubstituted: $C_{3-8}$ cycloalkyl, $C_{3-8}$ heterocycloalkyl, $C_{3-8}$ cycloalkenyl, $C_{3-8}$ heterocycloalkenyl, aryl or heteroaryl moiety, wherein the aryl or heteroaryl moiety either contains 5 or 6 atoms in a single ring or from 7 to 14 atoms in a fused polycyclic ring system, wherein, when substituted, $R^1$ contains from 1 to 9 substituents independently selected at each occurrence from the group disclosed above. Thus, it is evident that $R^1$ can be a single ring or a fused polycylic (optionally bicyclic ring system) with from 1 to 9 substituents. As discussed in the immediately preceding paragraph (and as evident to the skilled person from the structure of formula (I)) a —C(=O)— group is bonded to $R^1$. Preferably, $R^1$ comprises an acceptor function ortho to the —C(=O)— group. The acceptor function may be a hydrogen bond acceptor. The ortho acceptor function may be a heteroatom within $R^1$ (for example, within a ring which is attached to —C(=O)— or within a ring fused to the ring attached to —C(=O)—) or a substituent on $R^1$.

Where the group $R^1$ is a polycyclic ring system it may be fully or partially aromatic, i.e. one ring is aromatic and the other(s) are not.

In cases where more than one substituent is possible on a carbon atom, two substituents on the same carbon may form a ring system, e.g. a spirocyclic system. An example of this type of spiro substitution is the formation of a ketal from a ketone and a diol. For example, the 3 to 8 membered heterocyclic group that may be a substituent on D may be substituted so as to form a spirocycle. Therefore, D may be:

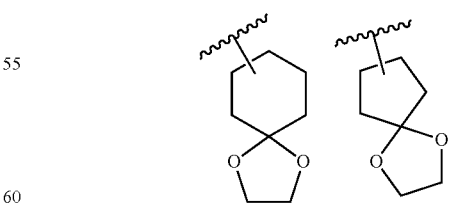

In embodiments $R^2$ is selected from H, $C_{1-4}$ alkyl, $C_{1-4}$ acyl, and $C_{3-7}$ cycloalkyl. Preferably $R^2$ is H or $C_{1-4}$ alkyl (e.g. methyl). Most preferably $R^2$ is H.

Accordingly, in a preferred embodiment the compound of formula (I) may be a compound according to formula (II):

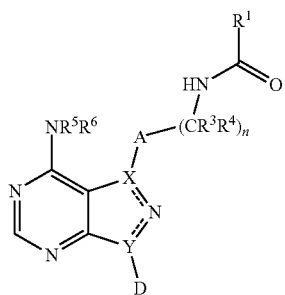

(II)

In an embodiment $R^3$ and $R^4$ are independently selected at each occurrence from: H, halo, $C_{1-4}$ alkyl, $C_{1-4}$ haloalkyl, $C_{1-4}$ alkyl substituted with —$OR^h$, —$OR^h$, or $R^3$ and $R^4$ taken together with the atom on which they are substituted, form a 3 to 6 membered cycloalkyl ring. Preferably, $R^3$ and $R^4$ are independently selected at each occurrence from: H, halo (e.g. fluoro and chloro), $C_{1-4}$ alkyl (e.g. methyl or ethyl), $C_{1-4}$ haloalkyl (e.g. trifluoromethyl or trifluoroethyl), —$OR^h$ (e.g. methoxy, ethoxy and $OCF_3$), $C_{1-4}$ alkyl substituted with —$OR^h$ (e.g. —$CH_2OH$) or $R^3$ and $R^4$ taken together with the atom on which they are substituted form a cyclopropyl ring. Further preferably $R^3$ and $R^4$ are H or methyl. Accordingly, $R^3$ and $R^4$ may be H for compounds of any formulae of the present invention.

In an embodiment $R^3$ is H and $R^4$ is as defined elsewhere herein.

Preferably n is 1.

In an embodiment, $R^5$ and $R^6$ are hydrogen, $C_{1-4}$ alkyl, or $C_{1-4}$ alkyl substituted with —$OR^h$, preferably H, methyl or —$(CH_2)_2OMe$ (optionally H or —$(CH_2)_2OMe$). $R^5$ may be H and $R^6$ may be as defined elsewhere herein. In an embodiment, $R^5$ is H and $R^6$ is hydrogen, $C_{1-4}$ alkyl, or $C_{1-4}$ alkyl substituted with —$OR^h$. Preferably, $R^5$ is H and $R^6$ is H, methyl or —$(CH_2)_2OMe$ (optionally H or —$(CH_2)_2$ OMe). $R^5$ and $R^6$ may both be hydrogen.

In a preferred embodiment, the compound of formula (I) may be a compound according to formulae (IIIa) or (IIIb):

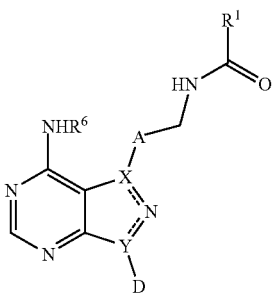

(IIIa)

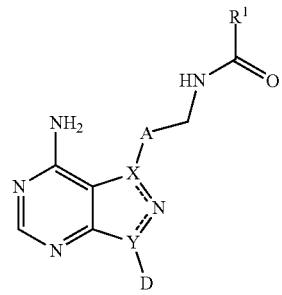

(IIIb)

In embodiments X is N and Y is C thus ⫽ represents a single bond between N and X and a double bond between N and Y. Therefore, the compound of formula (I) may be a compound according to formula (IV):

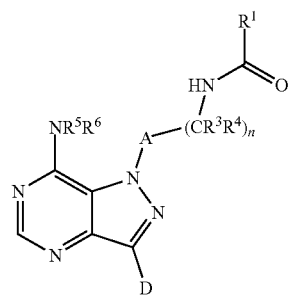

(IV)

In a preferred embodiment, there is provided a compound of formula (IV) wherein $R^3$ and $R^4$ are H, and $R^5$ and $R^6$ are H. In a preferred embodiment, there is provided a compound of formula (IV), wherein A is unsubstituted or substituted phenyl or pyridyl (preferably unsubstituted phenyl or fluorophenyl), $R^3$ and $R^4$ are H, and $R^5$ and $R^6$ are H. In an embodiment, there is provided a compound of formula (IV), wherein A is substituted or unsubstituted fluorophenyl, phenyl or pyridyl (preferably unsubstituted phenyl or fluorophenyl), $R^3$ and $R^4$ are H, $R^5$ and $R^6$ are H, and $R^1$ is substituted or unsubstituted phenyl (preferably substituted phenyl). $R^1$ may be phenyl substituted with 1, 2 or 3 groups selected from: methoxy, fluoro, —$OCF_3$, OEt, $O^iPr$, Cl, Me, $CF_3$, or CN (preferably $R^1$ is methoxyphenyl). $R^1$ may be phenyl substituted at the two position. In other words $R^1$ may be ortho substituted. Preferably, $R^1$ is 2-methoxyphenyl.

In embodiments X is C and Y is N thus ⫽ represents a single bond between N and Y and a double bond between N and X. Therefore, the compound of formula (I) may be a compound according to formula (V):

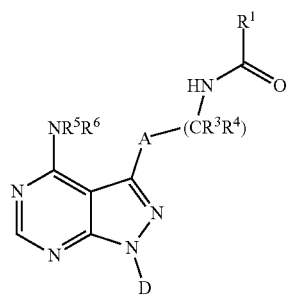
(V)

In a preferred embodiment, there is provided a compound of formula (V) wherein $R^3$ and $R^4$ are H, and $R^5$ and $R^6$ are H. In a preferred embodiment, there is provided a compound of formula (V), wherein A is unsubstituted or substituted phenyl or pyridyl (preferably unsubstituted phenyl or fluorophenyl), $R^3$ and $R^4$ are H, and $R^5$ and $R^6$ are H. In an embodiment, there is provided a compound of formula (V), wherein A is substituted or unsubstituted fluorophenyl, phenyl or pyridyl (preferably unsubstituted phenyl or fluorophenyl), $R^3$ and $R^4$ are H, $R^5$ and $R^6$ are H, and $R^1$ is substituted or unsubstituted phenyl (preferably substituted phenyl). $R^1$ may be phenyl substituted with 1, 2 or 3 groups selected from: methoxy, fluoro, —OCF$_3$, OEt, O$^i$Pr, Cl, Me, CF$_3$, or CN (preferably $R^1$ is methoxyphenyl). $R^1$ may be phenyl substituted at the two position. In other words $R^1$ may be ortho substituted. Preferably, $R^1$ is 2-methoxyphenyl.

In embodiments A is substituted or unsubstituted: phenyl or pyridyl. Preferably, A is substituted or unsubstituted phenyl.

A may be substituted or unsubstituted when substituted A may be substituted by 1, 2 or 3 (preferably 1) substituent selected from: H, halo, $C_{1-6}$ alkyl, $C_{1-6}$ alkyl substituted with —OR$^a$, $C_{1-6}$ haloalkyl, —OR$^a$, NR$^a$R$^b$, or —CN.

When substituted, A may be substituted by: H, halo, e.g. fluoro or chloro, $C_{1-6}$ alkyl, $C_{1-6}$ haloalkyl, or —OR$^a$. In particular A may be substituted with: H, fluoro, chloro, Me, OMe or CF$_3$.

Optionally, A is phenyl, pyridyl, fluorophenyl, difluorophenyl, methylphenyl or methoxyphenyl. A may be pyridyl, difluorophenyl, methylphenyl, methoxyphenyl, fluorophenyl or phenyl. Preferably, A is pyridyl, fluorophenyl or phenyl. Preferably, A is fluorophenyl or phenyl.

$R^a$ and $R^b$ may be selected from $C_{1-4}$ alkyl, $C_{1-4}$ alkyl substituted with —OR$^i$, or $C_{1-4}$ haloalkyl. In particular $R^a$ and $R^b$ may be H, methyl, ethyl, —CH$_2$OR$^i$, —(CH$_2$)$_2$OR$^i$, —CF$_3$, —CHF$_2$, or —CH$_2$CF$_3$. $R^i$ may be H, methyl or ethyl.

As the skilled person will appreciate from the definition of A, A is a 6 membered ring. A may be unsubstituted (except for the 2 groups shown in Formula (I)) or substituted by 1 to 4 further substitutents as defined elsewhere herein. Thus, other than these 1 to 4 further substitutents A is always substituted by

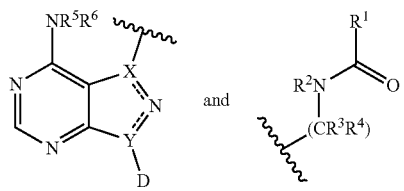

to form the compounds of formula (I), i.e. the compounds of the invention, and these two groups may be substituted at any (chemically possible) positions on the 6 membered ring of A. In other words, the points of attachment of these two groups on ring A may be varied. Thus, the substitution may be ortho, meta or para. Preferably the substitution is meta or para, most preferably para.

In some embodiments A is an optionally further substituted: phenyl, pyridyl, pyrimidinyl, pyrazinyl or pyridazinyl ring with the further substituents being independently selected from fluoro, methyl or methoxy and the two groups

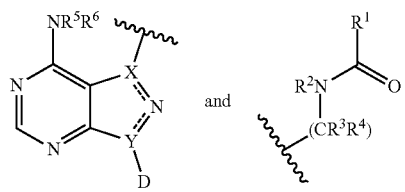

may be substituted meta or para to one another on A.

A may be phenyl, fluorophenyl, methoxyphenyl, methylphenyl, pyridyl, pyrimidinyl, pyrazinyl or pyridazinyl and the two groups

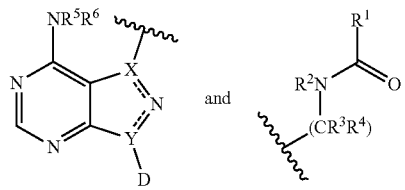

are substituted para to one another on A.

Preferably, A is phenyl or fluorophenyl and the two groups are substituted para to one another. Accordingly the compound of formula (I) may be a compound according to formulae (VIa) or (VIb):

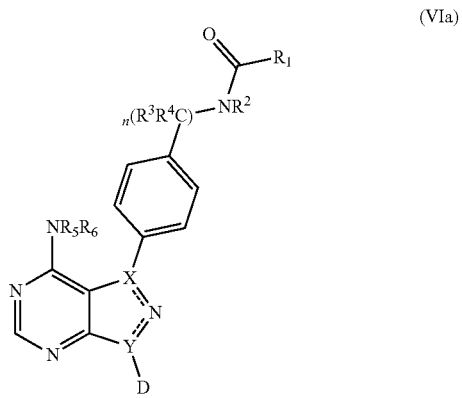

(VIa)

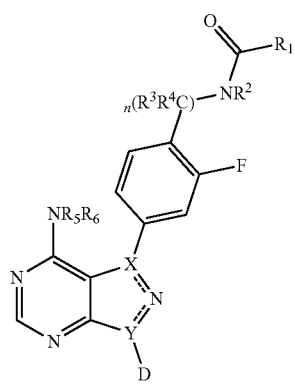

The compound of formula (I) may be a compound according to formulae (VIc) or (VId):

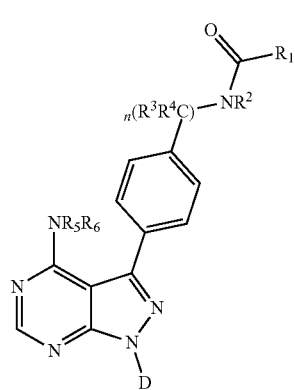

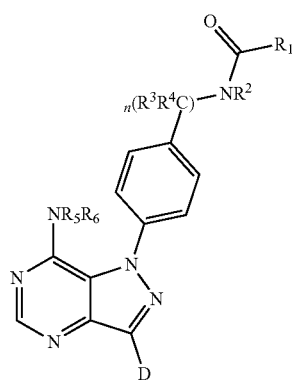

In an embodiment there is provided a compound of formulae (VIa) or (VIb) wherein $R^2$ is H. In a preferred embodiment, there is provided a compound of formulae (VIa) or (VIb) wherein $R^3$ and $R^4$ are H, and $R^5$ and $R^6$ are H. In a particularly preferred embodiment, there is provided a compound of formulae (VIa) or (VIb) wherein $R^2$ is H, $R^3$ and $R^4$ are H, and $R^5$ and $R^6$ are H. In a preferred embodiment, there is provided a compound of formulae (VIa) or (VIb), wherein A is unsubstituted or substituted fluorophenyl, phenyl or pyridyl (preferably unsubstituted phenyl or fluorophenyl), $R^3$ and $R^4$ are H, and $R^5$ and $R^6$ are H. In an embodiment, there is provided a compound of formulae (VIa) or (VIb), wherein A is substituted or unsubstituted phenyl or pyridyl (preferably unsubstituted phenyl or fluorophenyl), $R^3$ and $R^4$ are H, $R^5$ and $R^6$ are H, and $R^1$ is substituted or unsubstituted phenyl (preferably substituted phenyl). $R^1$ may be phenyl substituted with 1, 2 or 3 groups selected from: methoxy, fluoro, —$OCF_3$, OEt, $O^iPr$, Cl, Me, $CF_3$, or CN (preferably $R^1$ is methoxyphenyl). $R^1$ may be phenyl substituted at the two position. In other words $R^1$ may be ortho substituted. Preferably, $R^1$ is 2-methoxyphenyl.

In an embodiment there is provided a compound formulae (VIc) or (VId) wherein $R^2$ is H. In a preferred embodiment, there is provided a compound of formulae (VIc) or (VId) wherein $R^3$ and $R^4$ are H, and $R^5$ and $R^6$ are H. In a particularly preferred embodiment, there is provided a compound of formulae (VIc) or (VId) wherein $R^2$ is H, $R^3$ and $R^4$ are H, and $R^5$ and $R^6$ are H. In a preferred embodiment, there is provided a compound of formulae (VIc) or (VId), wherein $R^3$ and $R^4$ are H, and $R^5$ and $R^6$ are H. In an embodiment, there is provided a compound of formulae (VIc) or (VId), wherein $R^3$ and $R^4$ are H, $R^5$ and $R^6$ are H, and $R^1$ is substituted or unsubstituted phenyl (preferably substituted phenyl). $R^1$ may be phenyl substituted with 1, 2 or 3 groups selected from: methoxy, fluoro, —$OCF_3$, OEt, $O^iPr$, Cl, Me, $CF_3$, or CN (preferably $R^1$ is methoxyphenyl). $R^1$ may be phenyl substituted at the two position. In other words $R^1$ may be ortho substituted. Preferably, $R^1$ is 2-methoxyphenyl.

The group $R^1$ may be a substituted or unsubstituted: $C_{3-8}$ cycloalkyl, $C_{3-8}$ heterocycloalkyl, $C_{3-8}$ cycloalkenyl, or $C_{3-8}$ heterocycloalkenyl. Optionally, $R^1$ is a substituted or unsubstituted: $C_{5-6}$ cycloalkyl, $C_{5-6}$ heterocycloalkyl, $C_{5-6}$ cycloalkenyl, or $C_{5-6}$ heterocycloalkenyl.

The group $R^1$ may be a substituted or unsubstituted: aryl or heteroaryl moiety which either contains 5 or 6 atoms in a single ring. Optionally, $R^1$ is a substituted or unsubstituted: aryl or heteroaryl moiety which contains 6 atoms in a single ring.

The group $R^1$ may be a substituted or unsubstituted: aryl or heteroaryl moiety which contains from 7 to 14 atoms in a fused polycyclic ring system.

For the avoidance of doubt, when $R^1$ is a fused polycyclic system, fusion can occur at any point on the two or more fused rings. Furthermore, the fused polycyclic system can be a 6,6- or 6,5-fused ring system.

In an embodiment $R^1$ is a substituted or unsubstituted: aryl or heteroaryl moiety which contains 6 atoms in a single ring or from 7 to 14 atoms in a fused polycyclic ring system, wherein one of the substituents on the single ring and the —C(=O)— are bonded to adjacent carbon atoms of $R^1$ and the —C(=O)— group is substituted on the fused polycyclic ring system ortho to one of the two points of fusion of the polycyclic system.

The group $R^1$ may be a substituted or unsubstituted: $C_{3-8}$ cycloalkyl (optionally $C_{3-6}$, or $C_{5-6}$ cycloalkyl), $C_{3-8}$ heterocycloalkyl (optionally $C_{3-6}$ or $C_{5-6}$ heterocycloalkyl), $C_{6-14}$ aryl (optionally $C_6$ $C_9$, or $C_{10}$ aryl) or $C_{5-14}$ heteroaryl (optionally $C_5$, $C_6$ or $C_{10}$ heteroaryl). When substituted, $R^1$ may contain 1, 2 or 3 substituents independently selected at each occurrence from the group comprising: halo, —$OR^f$, —$NR^fR^g$, =O, —CN, acyl, $C_{1-6}$ alkyl, $C_{1-6}$ haloalkyl, $C_{1-6}$ alkyl substituted with —$OR^f$, $C_{3-8}$ cycloalkyl, $C_{3-8}$ heterocycloalkyl, —$SO_2R^f$, $SO_3R^f$, —$C(O)R^f$, —$C(O)OR^f$, —$C(O)NR^fR^g$ and aryl optionally substituted by 1 or 2 halo atoms.

In embodiments $R^1$ may be substituted or unsubstituted 6 membered aryl or 6 membered heteroaryl, optionally unsubstituted phenyl, unsubstituted pyridyl, substituted pyridyl or substituted phenyl.

In embodiments R¹ may be substituted or unsubstituted: 9, 10 or 11 membered aryl or heteroaryl in a fused polycyclic system. Thus, R¹ may be substituted or unsubstituted: indene, indane, naphthalene, tetralin, indole, isoindole, indoline, isoindoline, benzofuran, isobenzofuran, benzothiophene, isobenzothiophene, indazole, benzimidazole, benzothiazole, benzopyrazole, benzopyrole, benzoxazole, isobenzothiazole, isobenzoxazole, benzomorpholine, benzothiomorpholine, purine, quinoline, isoquinoline, chromene, chromane, isochromane, cinnoline, quinazoline, quinoxaline, napthyridine, pthalazine, or pteridine.

R¹ may be selected from unsubstituted or substituted: cyclopropyl, cyclobutyl, cyclopentyl, cyclohexyl, cycloheptyl, cyclooctyl, cyclopropenyl, cyclobutenyl, cyclopentenyl, cyclopentadienyl, cyclohexenyl, cyclohexadienyl, cycloheptenyl, cycloheptadiene, cyclooctenyl or cycloatadienyl.

R¹ may be selected from unsubstituted or substituted: oxirane, aziridine, azetidine, oxetane, tetrahydrofuran, pyrrolidine, pyroline, imidazolidine, imidazoline, succinimide, pyrazolidine, pyrazoline, oxazolidine, oxazoline, dioxolane, isoxazolidine, isoxazoline, thiazolidine, thiazoline, isothiazolidine, isothiazoline, piperidine, morpholine, thiomorpholine, piperazine, dioxane, dihydropyran, or tetrahydropyran.

R¹ may be selected from unsubstituted or substituted: cyclopropyl, cyclobutyl, cyclopentyl, cyclohexyl, cycloheptyl, cyclooctyl, cyclopropenyl, cyclobutenyl, cyclopentenyl, cyclopentadienyl, cyclohexenyl, cyclohexadienyl, cycloheptenyl, cycloheptadiene, cyclooctenyl, cycloatadienyl, oxirane, aziridine, azetidine, oxetane, tetrahydrofuran, pyrrolidine, pyroline, imidazolidine, imidazoline, succinimide, pyrazolidine, pyrazoline, oxazolidine, oxazoline, dioxolane, isoxazolidine, isoxazoline, thiazolidine, thiazoline, isothiazolidine, isothiazoline, piperidine, morpholine, thiomorpholine, piperazine, dioxane, dihydropyran, tetrahydropyran, phenyl, pyridyl, pyrimidinyl, pyrazinyl, pyridazinyl, indene, indane, naphthalene, tetralin, indole, isoindole, indoline, isoindoline, benzofuran, isobenzofuran, benzothiophene, isobenzothiophene, indazole, benzimidazole, benzothiazole, benzoxazole, isobenzothiazole, isobenzoxazole, benzopyrazole, benzopyrole, benzomorpholine, benzothiomorpholine, purine, quinoline, isoquinoline, chromene, chromane, isochromane, cinnoline, quinazoline, quinoxaline, napthyridine, pthalazine, or pteridine.

R¹ may be substituted or unsubstituted: phenyl, pyridyl, pyrimidinyl, pyrazinyl, pyridazinyl, indene, indane, naphthalene, tetralin, indole, isoindole, indoline, isoindoline, benzofuran, isobenzofuran, benzothiophene, isobenzothiophene, indazole, benzimidazole, benzothiazole, benzoxazole, purine, quinoline, isoquinoline, chromene, chromane, isochromane, cinnoline, quinazoline, quinoxaline, napthyridine, pthalazine, or pteridine.

The R¹ group is bonded to the rest of the compound by a —C(=O)— group. Optionally, when R¹ is a fused polycyclic ring system the —C(=O)— group is substituted ortho to one of the two points of fusion of the polycyclic system. For example, R¹ may be a naphthalene, quinoline, chromane or benzomorpholine ring and the point of fusion ortho to the position of attachment of the —C(=O)— group is as shown below:

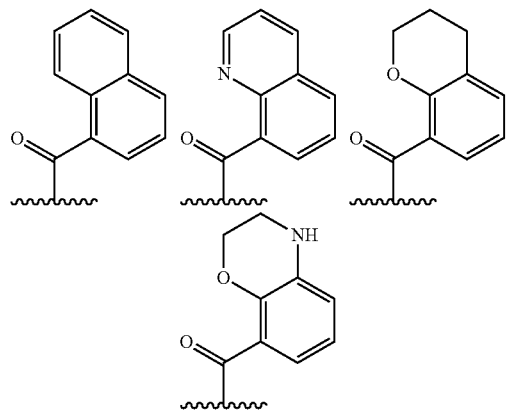

In an embodiment when R¹ is a fused polycyclic ring system, the —C(=O)— group is substituted ortho to one of two points of fusion of the polycyclic system. The point of fusion is a carbon atom with a bond (within one of the fused rings) to an acceptor function, which may be an O, N or S atom. These groups can be represented as follows:

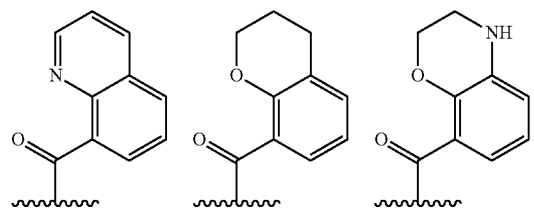

Alternatively, the —C(=O)— group is substituted ortho to a heteroatom within the fused bicyclic system. For example R¹ may be a quinoline, chromane, benzomorpholine, indole, benzofuran, benzothiophene, benzoxazole, or benzothiazole ring where the —C(=O)— group is substituted ortho to one point of fusion and the point of fusion is a carbon atom with a bond to an acceptor function can be represented as follows:

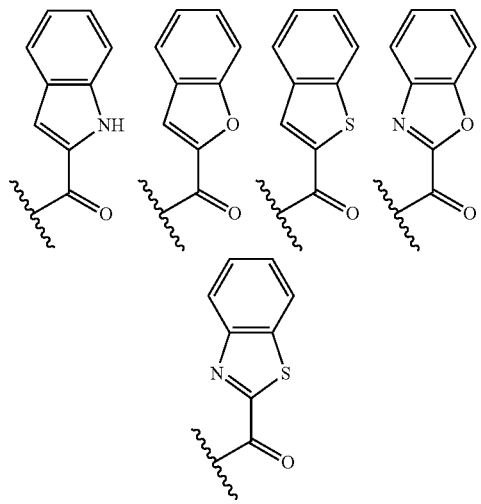

For the avoidance of doubt the fused bicyclic system described in the above two paragraphs may be substituted as described elsewhere herein. For example, the fused systems may be substituted by a substituent ortho to the —C(=O)— group.

Optionally, when $R^1$ is substituted it is substituted by 1, 2 or 3 substituents independently selected at each occurrence from the group comprising: halo, —$OR^f$, —CN, =O, $C_{1-6}$ alkyl, $C_{1-6}$ haloalkyl, $C_{1-6}$ alkyl substituted with —$OR^f$, $C_{1-6}$ alkyl substituted with cycloalkyl, optionally wherein $R^f$ is selected from H, $C_{1-4}$ alkyl and $C_{1-4}$ haloalkyl. Preferably the substituents are independently selected from fluoro, chloro, methoxy, ethoxy, isopropoxy, —CN, methyl, ethyl, trifluoromethyl, trifluoroethyl or —$OCF_3$.

$R^f$ and $R^g$ may be selected from H, $C_{1-4}$ alkyl and $C_{1-4}$ haloalkyl, optionally H, methyl, ethyl, —$CF_3$, or —$CF_2H$.

In embodiments $R^1$ may be unsubstituted phenyl, unsubstituted pyridyl, substituted phenyl or substituted pyridyl and when substituted $R^1$ is substituted with 1, 2 or 3 substituents independently selected at each occurrence from the group comprising: halo, —$OR^h$, —CN, $C_{1-6}$ alkyl, $C_{1-6}$ haloalkyl, wherein $R^h$ is selected from H, $C_{1-4}$ alkyl and $C_{1-4}$ haloalkyl. Preferably the substituents are independently selected from fluoro, chloro, methoxy, ethoxy, isopropoxy, —CN, methyl, ethyl, trifluoromethyl, trifluoroethyl or —$OCF_3$.

In embodiments $R^1$ is selected from: phenyl, fluorophenyl, difluorophenyl, chlorophenyl, methylphenyl (also referred to as tolyl), methoxyphenyl, ethoxyphenyl, isopropoxyphenyl, trifluromethylphenyl, cyanophenyl, trifluoromethoxyphenyl, tert-butylphenyl, methyl-fluorophenyl (also referred to as fluorotolyl), fluoro-methoxyphenyl, fluoro-trifluoromethylphenyl, fluoro-trifluoromethoxyphenyl, chloro-methoxyphenyl, methoxy-methylphenyl (also referred to as methoxytolyl), methoxy-trifluoromethylphenyl, chloro-trifluoromethylphenyl, ethoxy-trifluoromethylphenyl, dimethoxyphenyl, di(trifluoromethyl)phenyl, trifluorophenyl, chloro-methylphenyl (also referred to as chorotolyl), pyridyl, fluoropyridyl, difluoropyridyl, chloropyridyl, methylpyridyl (also referred to as picoline), methoxypyridyl, ethoxypyridyl, isopropoxypyridyl, trifluromethylpyridyl, cyanopyridyl, trifluoromethoxypyridyl, tert-butylpyridyl, methyl-fluoropyridyl (also referred to as fluoropicoline), fluoro-methoxypyridyl, fluoro-trifluoromethylpyridyl, fluoro-trifluoromethoxypyridyl, chloro-methoxypyridyl, methoxy-methylpyridyl (also referred to as methoxypicoline), methoxy-trifluoromethylpyridyl, chloro-trifluoromethylpyridyl, ethoxy-trifluoromethylpyridyl, dimethoxypyridyl, di(trifluoromethyl)pyridyl, trifluoropyridyl and chloro-methylpyridyl (also referred to as choropicoline).

Accordingly, in embodiments the compound of formula (I) may be a compound according to formulae (VIIa) or (VIIb):

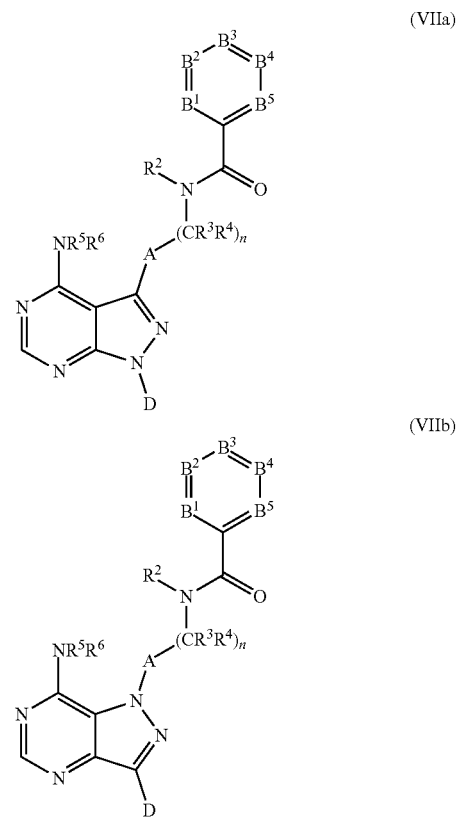

wherein zero, one or two $B^1$, $B^2$, $B^3$, $B^4$ and $B^5$ is N and the remaining are independently selected from CH or $CR^7$. Alternatively, two of $B^1$, $B^2$, $B^3$, $B^4$ and $B^5$ which are adjacent to each other are C and together form a further five or six membered ring which is fused to the ring represented by $B^1$, $B^2$, $B^3$, $B^4$ and $B^5$ to form a bicyclic ring system. This further 5 or 6 membered ring may be selected from a: aryl, heteroaryl, heterocycloalkyl, cycloalkyl, heterocycloalkenyl or cycloalkenyl ring, and zero, one or two $B^1$, $B^2$, $B^3$ and $B^4$ is N and the remaining are independently selected from CH or $CR^7$.

$R^7$ is independently selected at each occurrence from: H, halo, —$OR^f$, —$NR^fR^g$, =O, —CN, acyl, $C_{1-6}$ alkyl, $C_{1-6}$ haloalkyl, $C_{1-6}$ alkyl substituted with —$OR^f$, $C_{3-8}$ cycloalkyl, $C_{3-8}$ heterocycloalkyl, —$SO_2R^f$, $SO_3R^f$, —C(O)$R^f$, —C(O)$OR^f$, —C(O)$NR^fR^g$ and aryl optionally substituted by 1 or 2 halo atoms.

In an embodiment $B^1$ is N or $CR^7$ (optionally $R^7$ is —$OR^f$, preferably —OMe) and either two adjacent $B^2$, $B^3$, $B^4$ and $B^5$ are C and together form a further 5 or 6 membered ring which is fused to the ring represented by $B^2$, $B^3$, $B^4$ and $B^5$ to form a bicyclic ring system, wherein the further 5 or 6 membered ring may be selected from a: aryl, heteroaryl, heterocycloalkyl, cycloalkyl, heterocycloalkenyl or cycloalkenyl ring, and the remainder of $B^2$, $B^3$, $B^4$ and $B^5$ are independently selected from CH or $CR^7$, or $B^2$, $B^3$, $B^4$ and $B^5$ are independently selected from CH or $CR^7$.

In an embodiment $B^1$ is N or $CR^7$ (optionally $R^7$ is —$OR^f$, preferably —OMe), $B^4$ and $B^5$ are C and together form a further 5 or 6 membered ring which is fused to the ring represented by $B^2$, $B^3$, $B^4$ and $B^5$ to form a bicyclic ring system, wherein the further 5 or 6 membered ring may be selected from a: aryl, heteroaryl, heterocycloalkyl, cycloalkyl, heterocycloalkenyl or cycloalkenyl ring, and $B^2$ and $B^3$ are CH.

As discussed above the substituent on $R^1$ and —(C═O)— may be bonded to adjacent carbon atoms of $R^1$. In other words the substituent and —(C═O)— are ortho substituted. The substituent may be $R^7$. Hence, $R^7$ and —(C═O)— may be ortho substituted. Accordingly, in embodiments the compound of formula (I) may be a compound according to formulae (VIIc) or (VIId):

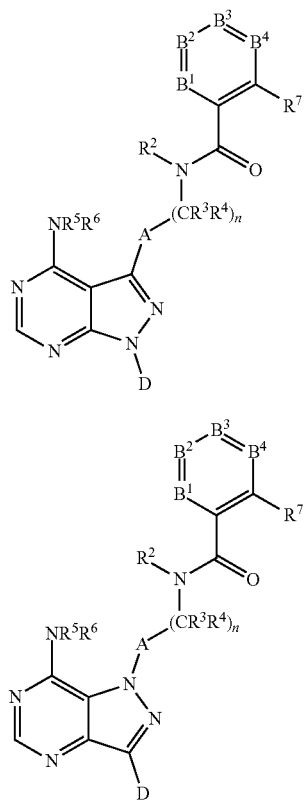

(VIIc)

(VIId)

wherein zero, one or two $B^1$, $B^2$, $B^3$ and $B^4$ is N and the remaining are independently selected from CH or $CR^7$. Alternatively, two of $B^1$, $B^2$, $B^3$ and $B^4$ which are adjacent to each other together form a further five or six membered ring which is fused to the ring represented by $B^1$, $B^2$, $B^3$ and $B^4$ to form a bicyclic ring system. This further 5 or 6 membered ring may be selected from a: aryl, heteroaryl, heterocycloalkyl, cycloalkyl, heterocycloalkenyl or cycloalkenyl ring, and zero, one or two $B^1$, $B^2$, $B^3$ and $B^4$ is N and the remaining are independently selected from CH or $CR^7$.

$R^7$ is independently selected at each occurrence from: H, halo, —$OR^f$, —$NR^fR^g$, ═O, —CN, acyl, $C_{1-6}$ alkyl, $C_{1-6}$ haloalkyl, $C_{1-6}$ alkyl substituted with —$OR^f$, $C_{3-8}$ cycloalkyl, $C_{3-8}$ heterocycloalkyl, —$SO_2R^f$, $SO_3R^f$, —C(O)$R^f$, —C(O)$OR^f$, —C(O)$NR^fR^g$ and aryl optionally substituted by 1 or 2 halo atoms.

Optionally, $B^1$ and $B^2$ form the further five or six membered ring. Further optionally, $B^1$ is N, CH or $CR^7$ and $B^2$, $B^3$ and $B^4$ are independently selected from CH or $CR^7$ or two adjacent $B^2$, $B^3$ and $B^4$ groups together form a five or six membered aryl, heteroaryl, heterocycloalkyl, cycloalkyl, heterocycloalkenyl or cycloalkenyl ring, In embodiments, $R^7$ is —$OR^f$, preferably —OMe, and $B^1$, $B^2$, $B^3$ and $B^4$ is CH or two adjacent atoms form a further 5 or 6 membered ring which is fused to the ring represented by $B^1$, $B^2$, $B^3$ and $B^4$ to form a bicyclic ring system, wherein the further 5 or 6 membered ring may be selected from a: aryl, heteroaryl, heterocycloalkyl, cycloalkyl, heterocycloalkenyl or cycloalkenyl ring. Preferably, the further 5 or 6 membered ring is a phenyl or pyridyl ring. In embodiments, $R^7$ is H, $B^1$ is N and $B^2$, $B^3$ and $B^4$ is CH or two of $B^2$, $B^3$ and $B^4$ which are adjacent are C atoms and together form a further 5 or 6 membered ring which is fused to the ring represented by $B^2$, $B^3$, $B^4$ and $B^5$ to form a bicyclic ring system, wherein the further 5 or 6 membered ring may be selected from a: aryl, heteroaryl, heterocycloalkyl, cycloalkyl, heterocycloalkenyl or cycloalkenyl ring. Preferably the further ring is a phenyl ring. In embodiments, $R^7$ is H or —$OR^f$, preferably H or —OMe, $B^1$ and $B^2$ are C and together form a pyridine ring, preferably wherein the N atom of the pyridine ring is attached to $B^1$.

$R^7$ may be independently selected at each occurrence from the group comprising: H, halo, —$OR^f$, —CN, $C_{1-6}$ alkyl, $C_{1-6}$ haloalkyl, $C_{1-6}$ alkyl substituted with —$OR^f$, optionally wherein $R^f$ is selected from H, $C_{1-4}$ alkyl and $C_{1-4}$ haloalkyl. Preferably, $R^7$ is independently selected from fluoro, chloro, methoxy, ethoxy, isopropoxy, —CN, methyl, ethyl, trifluoromethyl, trifluoroethyl or —$OCF_3$ (optionally methoxy).

As discussed above, when $R^1$ is a fused polycyclic ring system the —C(═O)— group may be substituted ortho to one of the two points of fusion of the polycyclic system. Accordingly, in embodiments the compound of formula (I) may be a compound according to formulae (VIIIa) or (VIIIb):

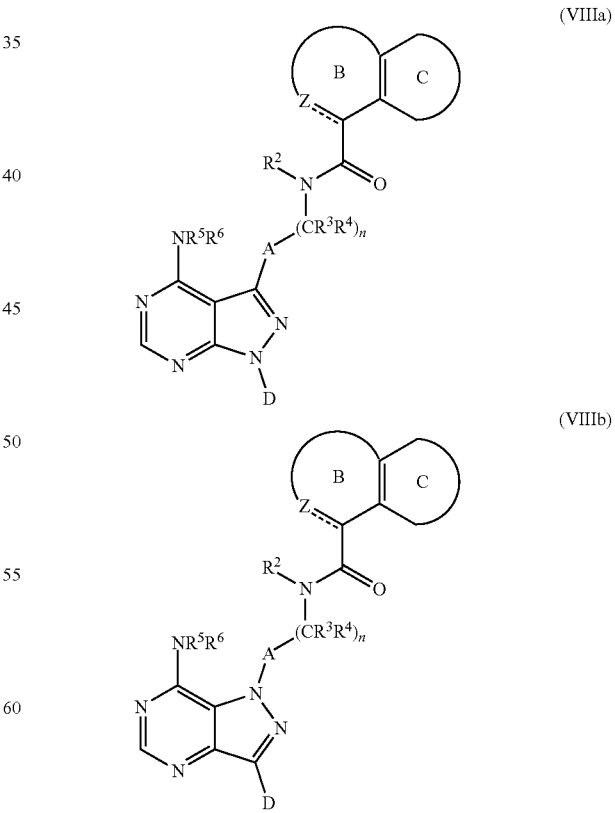

(VIIIa)

(VIIIb)

wherein ring B and ring C represent an independently selected substituted or unsubstituted 5 or 6 membered: aryl, heteroaryl, cycloalkyl, cycloalkylene, heterocycloalkyl or heterocycloalkylene rings wherein at least one of ring B or ring C is an aryl or heteroaryl ring; and Z is $CR^7$, O, N, S or NH.

As discussed above where $R^1$ is a fused polycyclic ring system the —C(=O)— group may be substituted ortho to one of two points of fusion of the polycyclic system and the point of fusion may be a carbon atom with a bond (within one of the fused rings) to an acceptor function, which may be an O, N or S atom. Accordingly, in embodiments the compound of formula (I) may be a compound according to formulae (IXa) or (IXb):

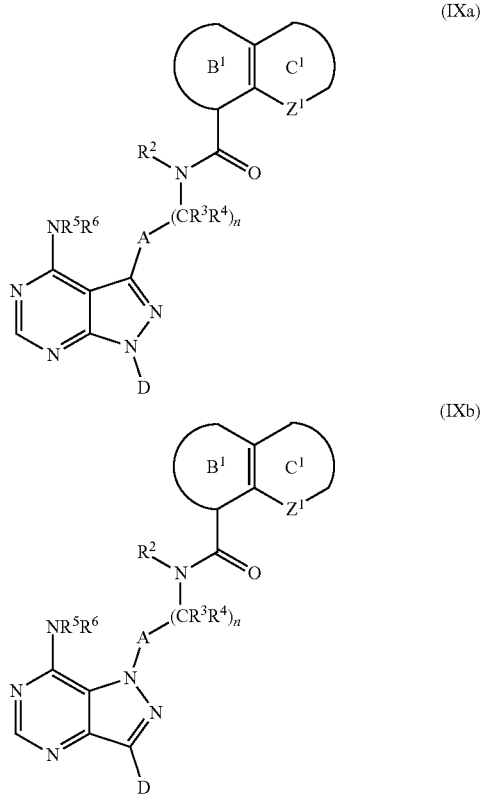

wherein ring $B^1$ represents a substituted or unsubstituted 5 or 6 membered: aryl, heteroaryl, cycloalkyl, cycloalkylene, heterocycloalkyl or heterocycloalkylene ring;

ring $C^1$ represents a heteroaryl, heterocycloalkyl or heterocycloalkylene ring; and $Z^1$ is O, N, S or NH;

wherein at least one of ring $B^1$ or ring $C^1$ is an aryl or heteroaryl ring.

For the avoidance of doubt, rings B and C of formulae (VIIIa) and (VIIIb) and rings $B^1$ and $C^1$ of formulae (IXa) and (IXb) are fused bicyclic ring systems.

Compounds of the invention where $R^1$ comprises an acceptor function ortho to the —C(=O)— group are particularly preferred. The acceptor function being a hydrogen bond acceptor. The ortho acceptor function may be within a ring fused to the ring attached to —C(=O)—, a substituent on $R^1$, or within the ring which is attached to —C(=O)—. Without being bound by theory it is believed that the ortho acceptor function might improve permeability of the compounds of the present invention. Therefore, in certain embodiments of the present invention it is an aim to improve permeability.

In an embodiment there is provided a compound of formulae (VIIIa), (VIIIb), (IXa) and (IXb) wherein $R^2$ is H. In a preferred embodiment, there is provided a compound of formulae (VIIIa), (VIIIb), (IXa) and (IXb) wherein $R^3$ and $R^4$ are H, and $R^5$ and $R^6$ are H. In a particularly preferred embodiment, there is provided a compound of formulae (VIIIa), (VIIIb), (IXa) and (IXb) wherein $R^2$ is H, $R^3$ and $R^4$ are H, and $R^5$ and $R^6$ are H. In a preferred embodiment, there is provided a compound of formulae (VIIIa), (VIIIb), (IXa) and (IXb), wherein A is unsubstituted or substituted phenyl or pyridyl (preferably unsubstituted phenyl or fluorophenyl), $R^3$ and $R^4$ are H, and $R^5$ and $R^6$ are H. In an embodiment, there is provided a compound of formulae (VIIIa), (VIIIb), (IXa) and (IXb), wherein A is substituted or unsubstituted phenyl or pyridyl (preferably unsubstituted phenyl or fluorophenyl), $R^3$ and $R^4$ are H, $R^5$ and $R^6$ are H, and rings B, C, $B^1$ or $C^1$ are independently unsubstituted or substituted with 1, 2 or 3 groups selected from: methoxy, fluoro, —$OCF_3$, OEt, $O^iPr$, Cl, Me, $CF_3$, or CN (preferably methoxy).

In an embodiment, D is selected from substituted or unsubstituted: $C_{1-6}$ alkyl, $C_{5-9}$ cycloalkyl, $C_{5-9}$ cycloalkenyl, $C_{6-10}$ aryl, 5 to 9 membered heterocycloalkyl, 5 to 9 membered heterocycloalkenyl or 5, 6, 9 or 10 membered heteroaryl.

In an embodiment, D is selected from substituted or unsubstituted: $C_{1-6}$ alkyl, $C_{5-9}$ cycloalkyl, $C_{5-9}$ cycloalkenyl, $C_{6-10}$ aryl, 5 to 9 membered heterocycloalkyl, 5 to 9 membered heterocycloalkenyl or 5, 6, 9 or 10 membered heteroaryl.

D may be selected from substituted or unsubstituted: tert-butyl, cyclopentyl, cyclohexyl, bicyclohexyl, cyclopentenyl, cyclohexenyl, indanyl, tetrahydrofuran and tetrahydropyran. Preferably D may be unsubstituted or substituted: cyclopentyl, bicyclohexyl or cyclopentenyl. Alternatively, D may be substituted cyclopentyl, unsubstituted or substituted bicyclohexyl, or unsubstituted or substituted cyclopentenyl.

D may be selected from substituted or unsubstituted: tert-butyl, trifluoroethyl, cyclopentyl, cyclohexyl, bicyclohexyl, cyclopentenyl, cyclohexenyl, indanyl, tetrahydrofuran and tetrahydropyran. Preferably D may be unsubstituted or substituted: cyclopentyl, bicyclohexyl or cyclopentenyl. Alternatively, D may be trifluoroethyl, substituted cyclopentyl, substituted cyclohexyl, unsubstituted or substituted bicyclohexyl, or unsubstituted or substituted cyclopentenyl.

In a preferred embodiment D is tert-butyl or isopropyl.

In a preferred embodiment D is trifluoroethyl, tert-butyl or isopropyl.

D may be selected from substituted or unsubstituted: tert-butyl, isopropyl, 2-hydroxypropyl, cyclopentyl, cyclohexyl, bicyclohexyl, cyclopentenyl, cyclohexenyl, indanyl, tetrahydrofuran and tetrahydropyran. Preferably D may be unsubstituted or substituted: tert-butyl, isopropyl, 2-hydroxypropyl, cyclopentyl, bicyclohexyl or cyclopentenyl. Alternatively, D may be substituted cyclopentyl, unsubstituted or substituted bicyclohexyl, or unsubstituted or substituted tert-butyl, isopropyl, 2-hydroxypropyl, cyclopentenyl.

In a preferred embodiment D is tert-butyl, unsubstituted cyclopentyl, substituted cyclopentenyl, substituted cylopentenol, substituted cyclohexanol, or trifluoroethyl.

D may be substituted or unsubstituted, when substituted D contains 1 to 5 substituents independently selected at each occurrence from the group comprising: halo, —$OR^c$, —$NR^cR^d$, =O, —CN, —$C(O)OR^c$, —$OC(O)R^e$, —$C(O)NR^cR^d$, —$NR^cC(O)R^e$, $C_{1-6}$ alkyl, $C_{1-6}$ haloalkyl, $C_{1-6}$ alkyl substituted with —OR$^c$, and a 3 to 8 membered heterocyclic group. Optionally, the 3 to 8 membered heterocyclic group is a 3 to 6 (e.g. a 5 or 6) membered heterocyclic group. The heterocyclic group may be a heteroaryl group or a hetercycloalkyl group.

D may be substituted or unsubstituted, when substituted D contains 1 to 5 substituents independently selected at each occurrence from the group comprising: chloro, fluoro, —OH, —OMe, —OEt, —O(CH$_2$)$_2$OMe, —NH$_2$, —NHMe, —NMe$_2$, =O, —C(O)OH, —C(O)OMe, —C(O)OEt, —C(O)NH$_2$, —C(O)NHMe, —C(O)NMe$_2$, —OC(O)Me, —OC(O)Et, —OC(O)t-Bu, —OC(O)tolyl, —NHC(O)Me, —NHC(O)Me, —NHC(O)Et, —NHC(O)t-Bu, —NHC(O)tolyl, methyl, ethyl, iso-propyl, tert-butyl, triazole, tetrazole and dioxolane. The dioxolane substituent may be substituted on D so as to form a spirocycle.

R$^c$, R$^d$ and R$^e$ are independently selected at each occurrence from: H, C$_{1-4}$ alkyl, C$_{1-4}$ haloalkyl, C$_{1-4}$ alkyl substituted with —OR$^j$, unsubstituted aryl and aryl substituted with halo or C$_{1-4}$ alkyl or C$_{1-4}$ haloalkyl or a combination thereof.

In an embodiment R$^c$ and R$^d$ are independently selected at each occurrence from: H, C$_{1-4}$ alkyl, C$_{1-4}$ haloalkyl, and C$_{1-4}$ alkyl substituted with —OR$^j$; and R$^e$ is selected from: H, C$_{1-4}$ alkyl, C$_{1-4}$ haloalkyl, C$_{1-4}$ alkyl substituted with —OR$^j$, unsubstituted aryl and aryl substituted with halo or C$_{1-4}$ alkyl or C$_{1-4}$ haloalkyl or a combination thereof.

R$^h$, R$^i$, R$^j$, R$^k$, and R$^l$ may be independently selected at each occurrence from: H, C$_{1-4}$ alkyl and C$_{1-4}$ haloalkyl. R$^h$, R$^i$, R$^j$, R$^k$, and R$^l$ are independently selected at each occurrence from: H, methyl, ethyl, —CF$_3$ or —CF$_2$H, preferably H or methyl.

In embodiments D is not unsubstituted cyclopentyl. In other words, when D is cyclopentyl it is preferably substituted by 1, 2 or 3 substituents as defined above for D. In embodiments where D is unsubstituted cyclopentyl at least one of the substituents on R$^1$ and the —C(=O)— group (which is bonded to R$^1$) are bonded to adjacent carbon atoms of R$^1$. In other words the substituent and —C(=O) are ortho substituted.

In embodiments there are provided compounds where: D is selected from substituted or unsubstituted: C$_{1-6}$ alkyl, C$_{3-10}$ cycloalkenyl, C$_{6-10}$ aryl, 3 to 10 membered heterocycloalkyl, 3 to 10 membered heterocycloalkenyl and 5 to 10 membered heteroaryl, substituted C$_{3-10}$ cycloalkyl, unsubstituted C$_{3-4}$ cycloalkyl or unsubstituted C$_{6-10}$ cycloalkyl, and R$^1$ is a group selected from a substituted or unsubstituted: C$_{3-8}$ cycloalkyl, C$_{3-8}$ heterocycloalkyl, C$_{3-8}$ cycloalkenyl, C$_{3-8}$ heterocycloalkenyl, aryl or heteroaryl moiety, wherein the aryl or heteroaryl moiety either contains 5 or 6 atoms in a single ring or from 7 to 14 atoms in a fused polycyclic ring system; or D is unsubstituted cyclopentyl and R$^1$ is a substituted or unsubstituted: C$_{3-8}$ cycloalkyl, C$_{3-8}$ heterocycloalkyl, C$_{3-8}$ cycloalkenyl, C$_{3-8}$ heterocycloalkenyl, aryl or heteroaryl moiety, wherein the aryl or heteroaryl moiety either contains 5 or 6 atoms in a single ring or from 7 to 14 atoms in a fused polycyclic ring system, wherein the —C(=O)— and one of the substituents on the C$_{3-8}$ cycloalkyl, C$_{3-8}$ heterocycloalkyl, C$_{3-8}$ cycloalkenyl or C$_{3-8}$ heterocycloalkenyl moiety or the aryl or heteroaryl single ring are bonded to adjacent carbon atoms of R$^1$ and the —C(=O)— group is substituted on the aryl or heteroaryl fused polycyclic ring system ortho to one of the two points of fusion of the polycyclic system.

In embodiments there are provided compounds of the invention, wherein:
X is C, Y is N; and
D is selected from substituted or unsubstituted: C$_{1-6}$ alkyl, C$_{3-10}$ cycloalkenyl, C$_{6-10}$ aryl, 3 to 10 membered heterocycloalkyl, 3 to 10 membered heterocycloalkenyl and 5 to 10 membered heteroaryl, substituted C$_{3-10}$ cycloalkyl, unsubstituted C$_{3-4}$ cycloalkyl or unsubstituted C$_{6-10}$ cycloalkyl, and R$^1$ is a group selected from a substituted or unsubstituted: C$_{3-8}$ cycloalkyl, C$_{3-8}$ heterocycloalkyl, C$_{3-8}$ cycloalkenyl, C$_{3-8}$ heterocycloalkenyl, aryl or heteroaryl moiety, wherein the aryl or heteroaryl moiety either contains 5 or 6 atoms in a single ring or from 7 to 14 atoms in a fused polycyclic ring system; or
D is unsubstituted cyclopentyl and R$^1$ is a substituted or unsubstituted: C$_{3-8}$ cycloalkyl, C$_{3-8}$ heterocycloalkyl, C$_{3-8}$ cycloalkenyl, C$_{3-8}$ heterocycloalkenyl, aryl or heteroaryl moiety, wherein the aryl or heteroaryl moiety either contains 5 or 6 atoms in a single ring or from 7 to 14 atoms in a fused polycyclic ring system, wherein the —C(=O)— and one of the substituents on the C$_{3-8}$ cycloalkyl, C$_{3-8}$ heterocycloalkyl, C$_{3-8}$ cycloalkenyl or C$_{3-8}$ heterocycloalkenyl moiety or the aryl or heteroaryl single ring are bonded to adjacent carbon atoms of R$^1$ and the —C(=O)— group is substituted on the aryl or heteroaryl fused polycyclic ring system ortho to one of the two points of fusion of the polycyclic system;
or
X is N, Y is C;
D is selected from substituted or unsubstituted: C$_{1-6}$ alkyl, C$_{3-10}$ cycloalkyl, C$_{3-10}$ cycloalkenyl, C$_{6-10}$ aryl, 3 to 10 membered heterocycloalkyl, 3 to 10 membered heterocycloalkenyl and 5 to 10 membered heteroaryl; and
R$^1$ is a group selected from a substituted or unsubstituted: C$_{3-8}$ cycloalkyl, C$_{3-8}$ heterocycloalkyl, C$_{3-8}$ cycloalkenyl, C$_{3-8}$ heterocycloalkenyl, aryl or heteroaryl moiety, wherein the aryl or heteroaryl moiety either contains 5 or 6 atoms in a single ring or from 7 to 14 atoms in a fused polycyclic ring system.

In an embodiment of the invention there is provided a compound according to formula (X):

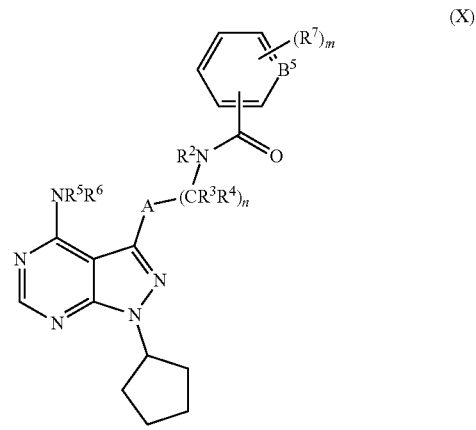

wherein B$^5$ is CH or N and m is 1, 2, 3 or 4 (preferably m is 1 or 2); and at least one R$^7$ is substituted orto to the —C(=O)— group.

In an embodiment there is provided a compound of formula (X) wherein R$^2$ is H. In a preferred embodiment, there is provided a compound of formula (X) wherein R$^3$ and R$^4$ are H, and R$^5$ and R$^6$ are H. In a particularly preferred embodiment, there is provided a compound of formula (X) wherein R$^2$ is H, R$^3$ and R$^4$ are H, and R$^5$ and R$^6$ are H. In a preferred embodiment, there is provided a compound of formula (X), wherein A is unsubstituted or substituted phenyl or pyridyl (preferably unsubstituted phenyl or fluorophenyl), $R^3$ and $R^4$ are H, and $R^5$ and $R^6$ are H. In an embodiment, there is provided a compound of formula (X), wherein A is substituted or unsubstituted phenyl or pyridyl (preferably unsubstituted phenyl or fluorophenyl), $R^3$ and $R^4$ are H, $R^5$ and $R^6$ are H, $R^2$ is H, and $B^5$ is CH. $R^7$ may be selected from: methoxy, fluoro, —$OCF_3$, OEt, $O^iPr$, Cl, Me, $CF_3$, or CN (preferably $R^7$ is methoxy). One $R^7$ group may be substituted at the two position. In other words the ring containing $B^5$ may be ortho substituted by one $R^7$. Additional $R^7$ groups may be present. Preferably, $R^7$ is 2-methoxy.

In an embodiment the compounds of formula (X) A is phenyl or fluorophenyl.

In embodiments the compound of formula (I) may be a compound according to formulae (XI):

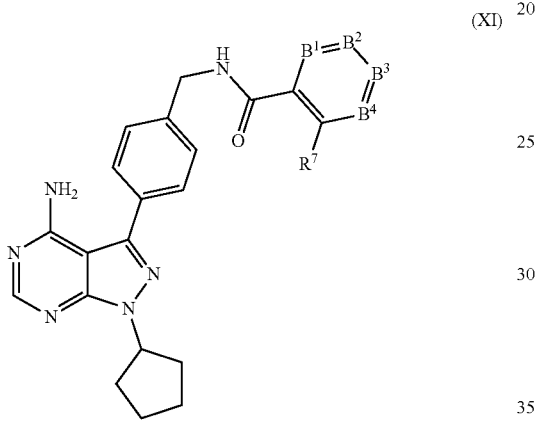

(XI)

wherein zero, one or two $B^1$, $B^2$, $B^3$ and $B^4$ is N and the remaining are independently selected from CH or $CR^7$, and $R^7$ is independently selected at each occurrence from: halo, —$OR^f$, —$NR^fR^g$, =O, —CN, acyl, $C_{1-6}$ alkyl, $C_{1-6}$ haloalkyl, $C_{1-6}$ alkyl substituted with —$OR^f$, $C_{3-8}$ cycloalkyl, $C_{3-8}$ heterocycloalkyl, —$SO_2R^f$, $SO_3R^f$, —C(O)$R^f$, —C(O)$OR^f$, —C(O)$NR^fR^g$ and aryl optionally substituted by 1 or 2 halo atoms.

Preferred compounds of the invention include:

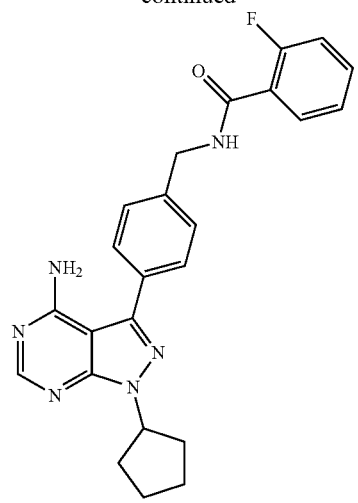

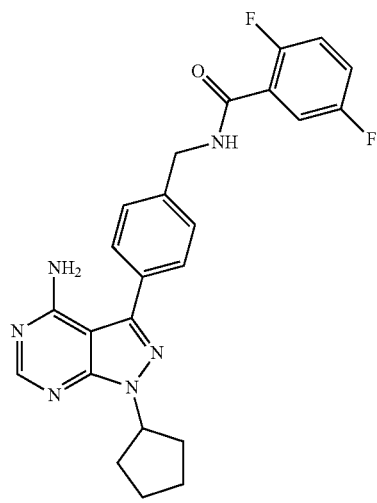

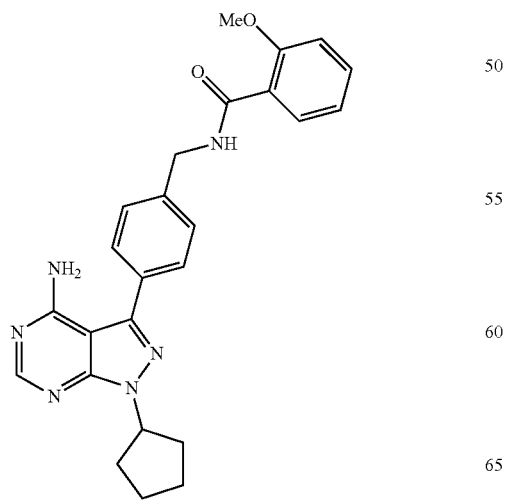

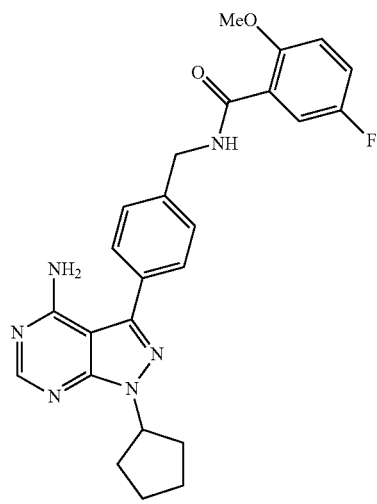

23
-continued
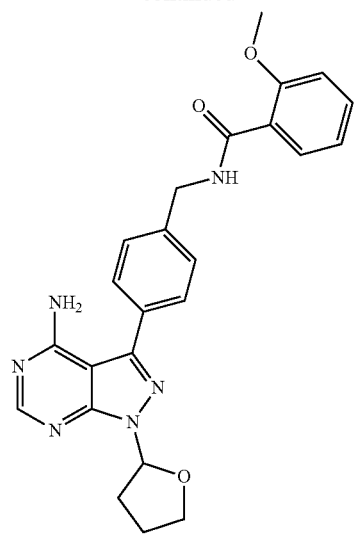
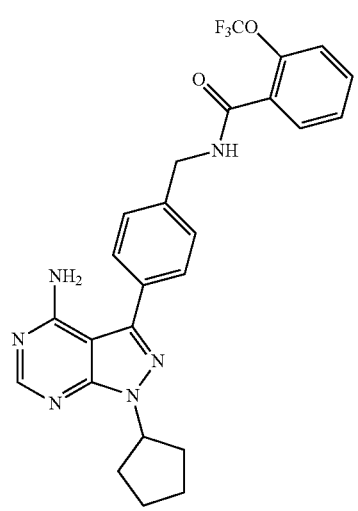
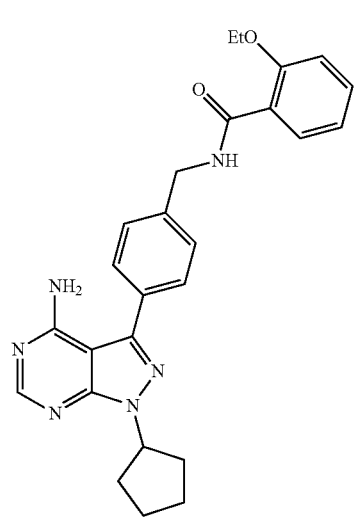
24
-continued
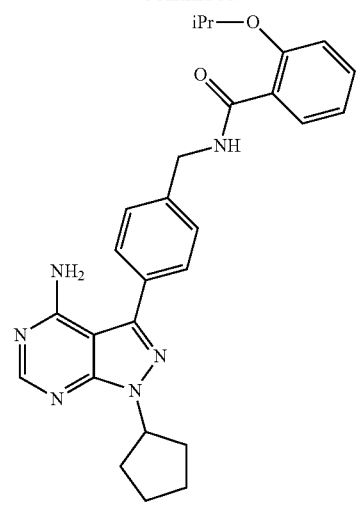
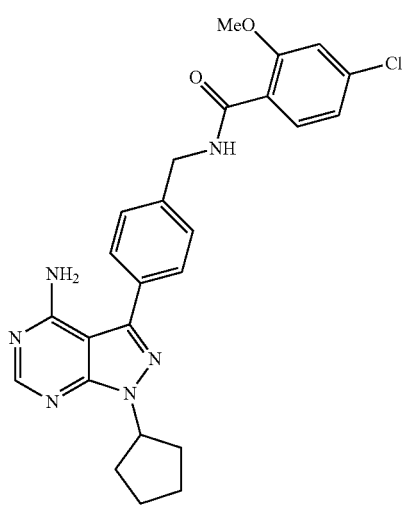
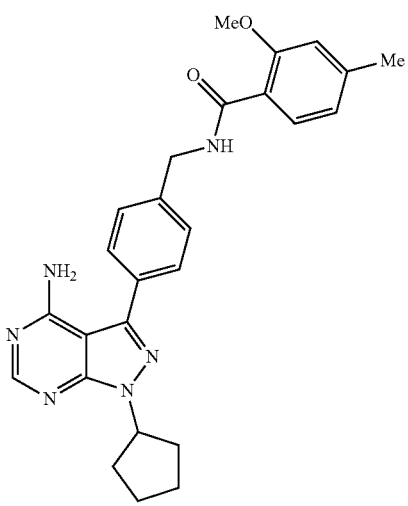

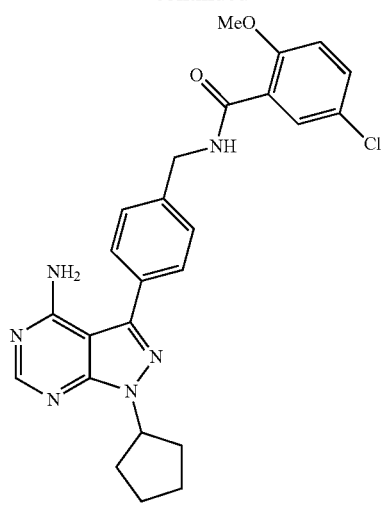
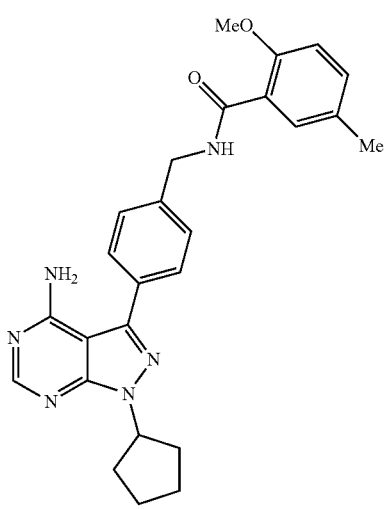
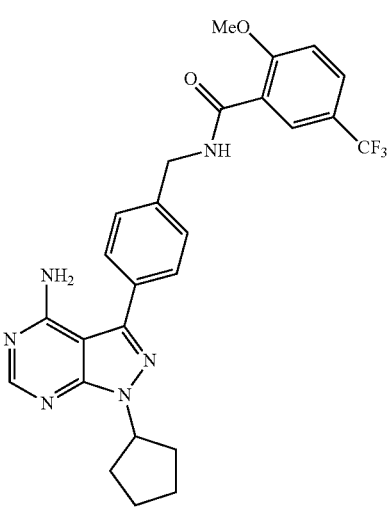
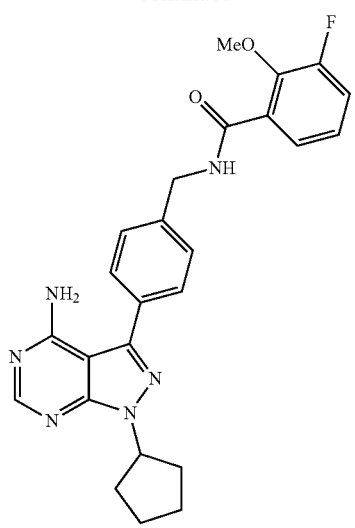

-continued
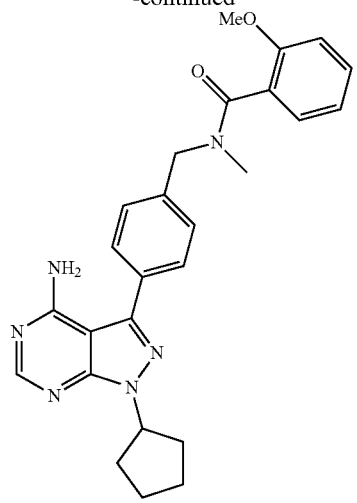
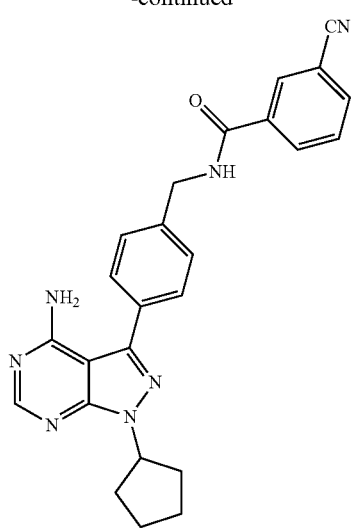
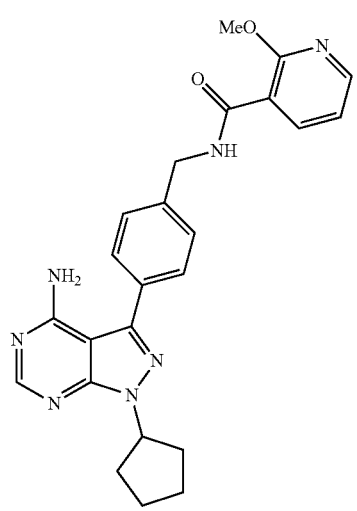
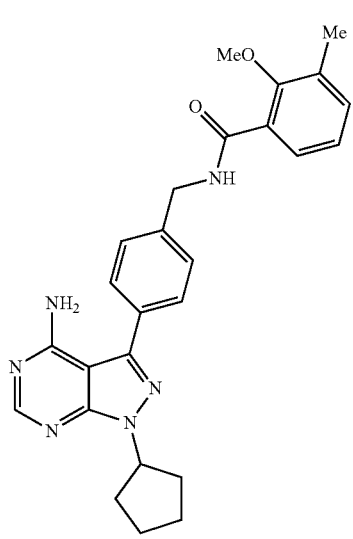
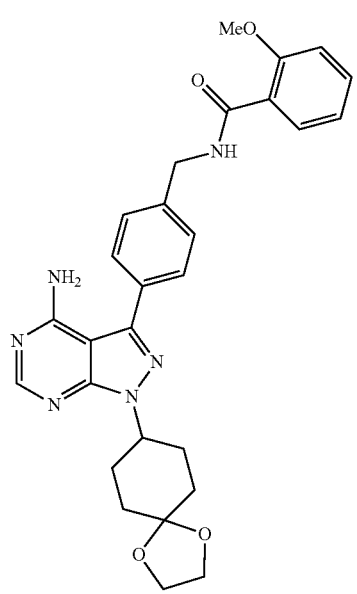
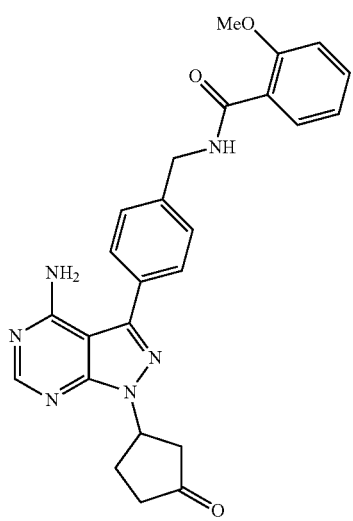

29
-continued
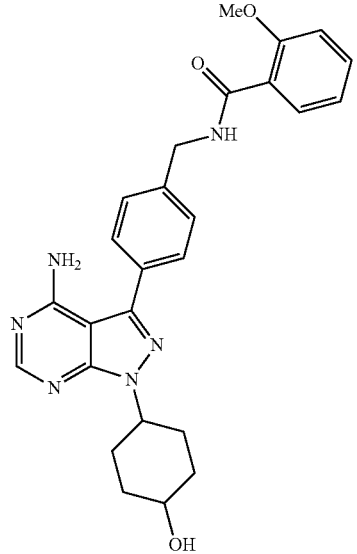
30
-continued
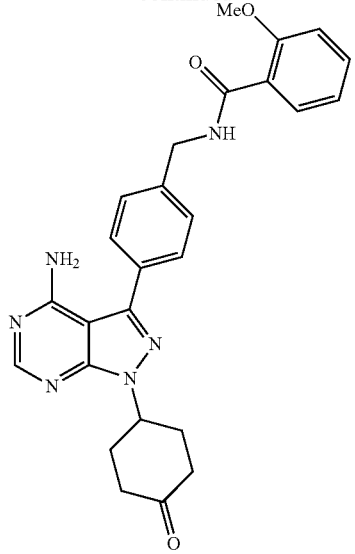
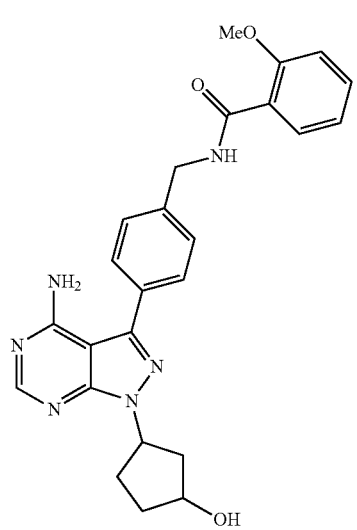
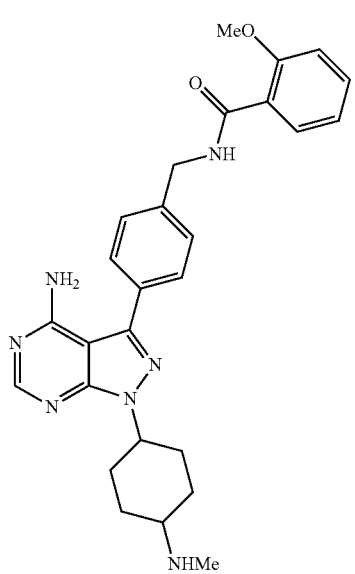
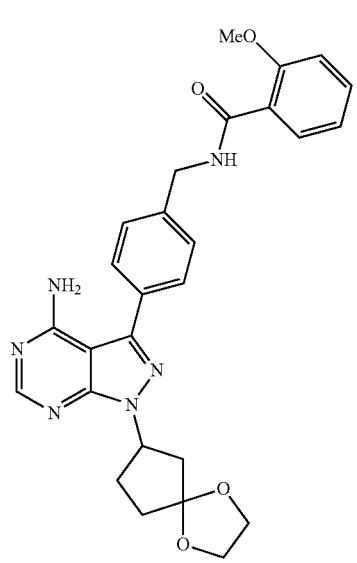

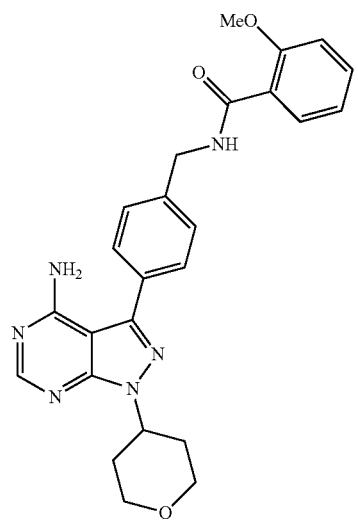
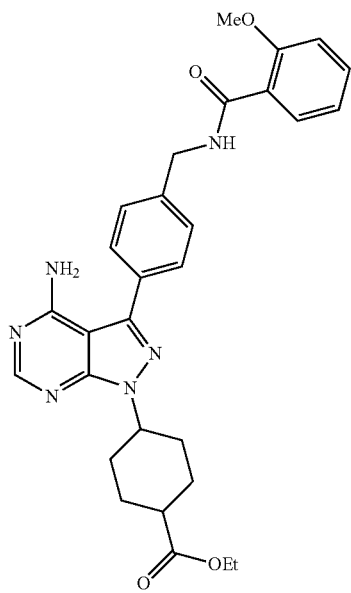
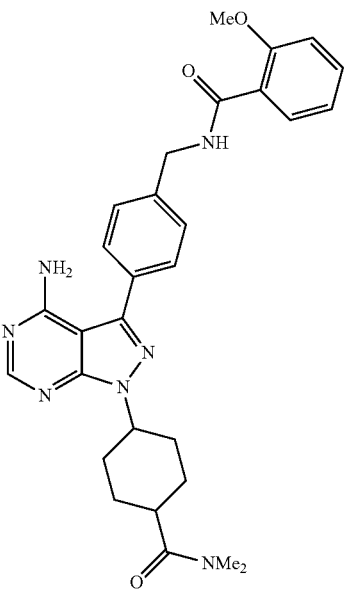
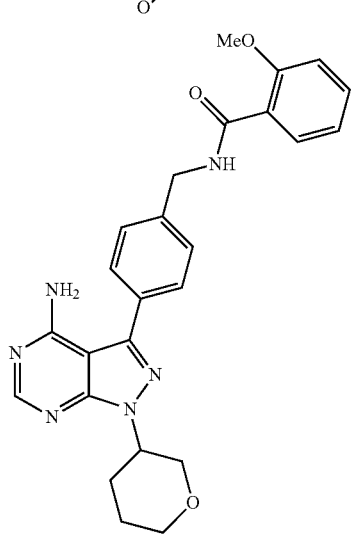

33
-continued
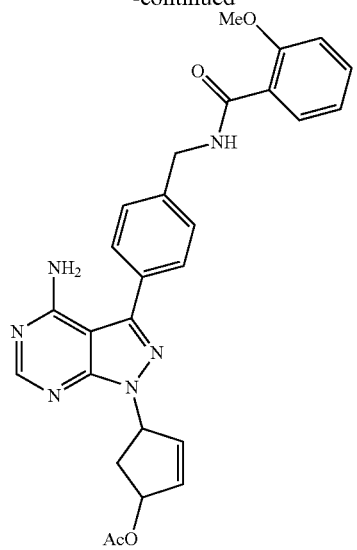
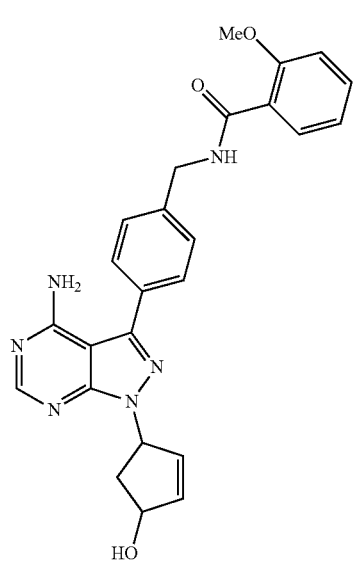
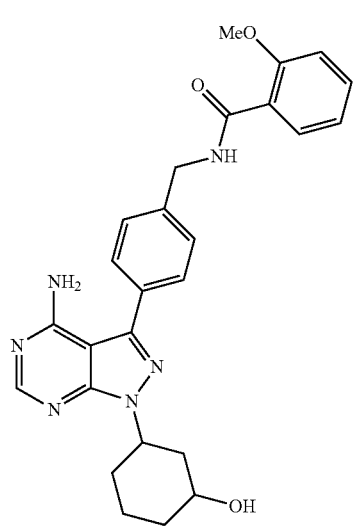
34
-continued
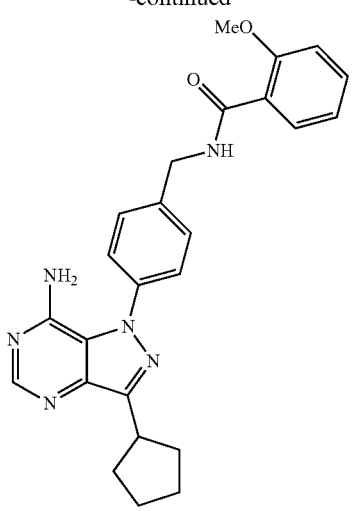
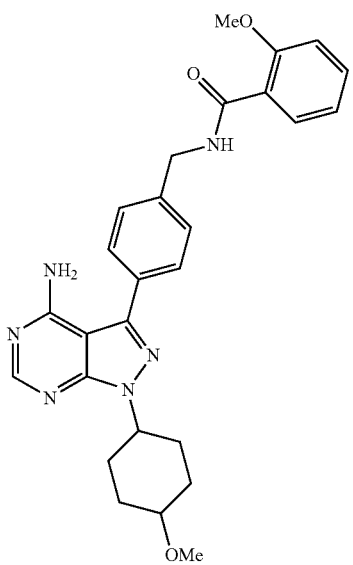
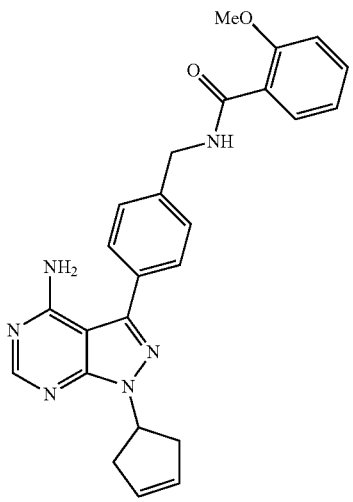

35
-continued
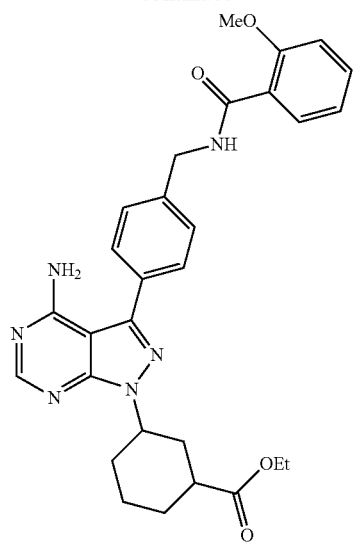
36
-continued
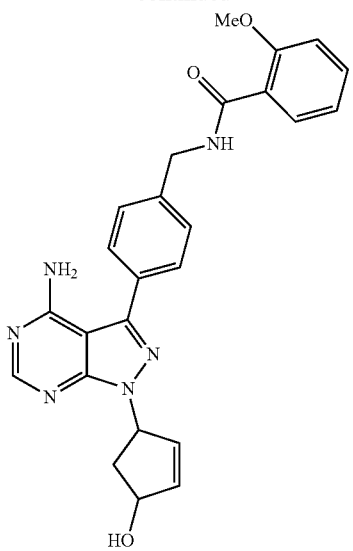

37
-continued
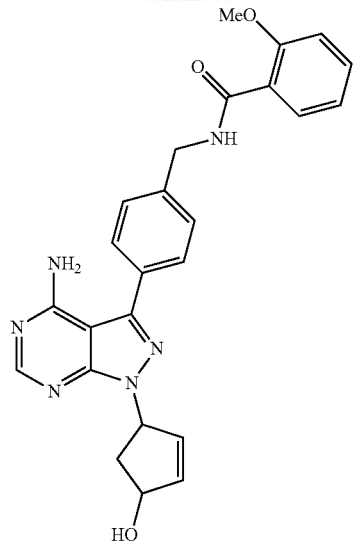
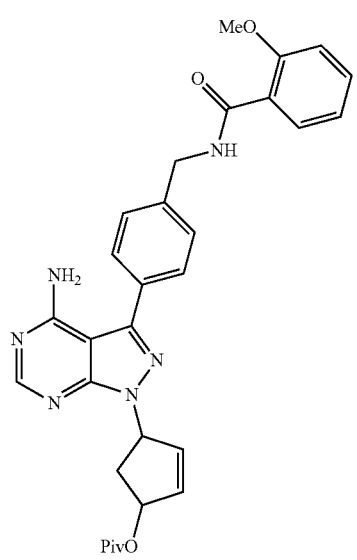
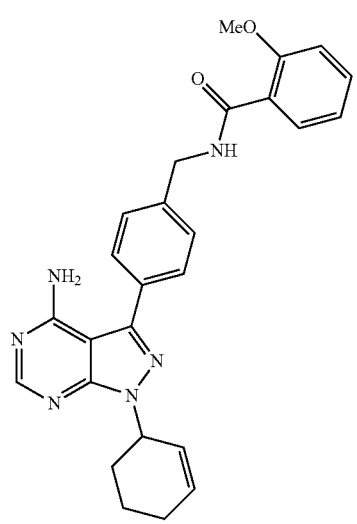
38
-continued
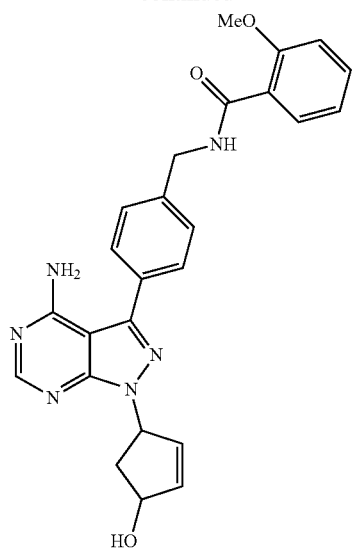
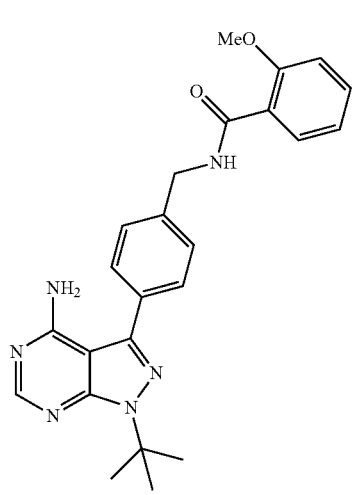
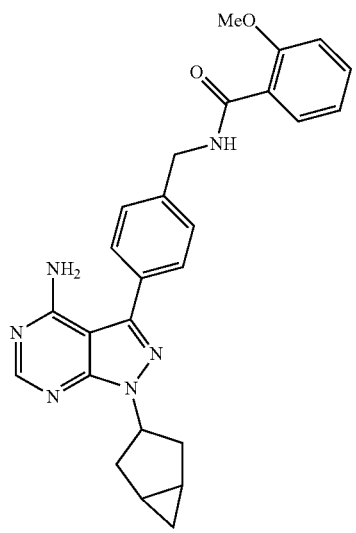

39
-continued
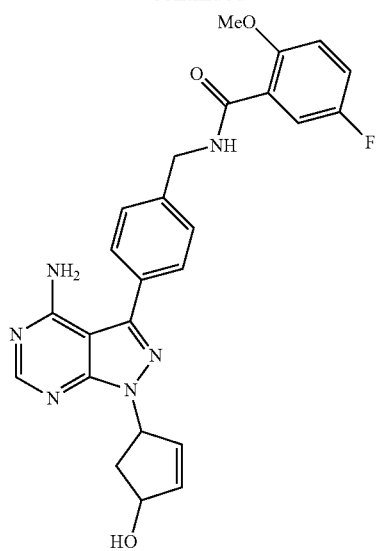
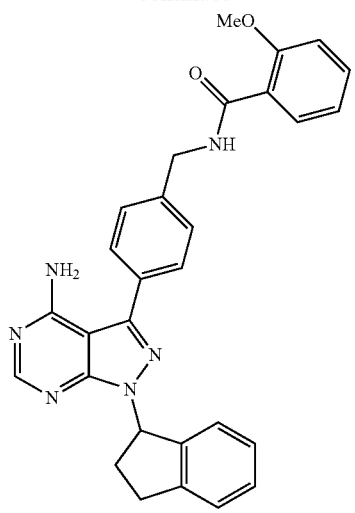
40
-continued
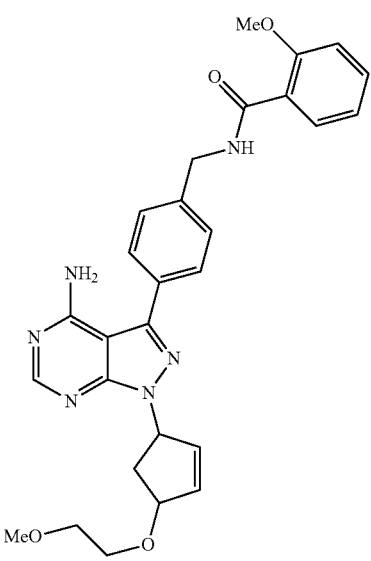
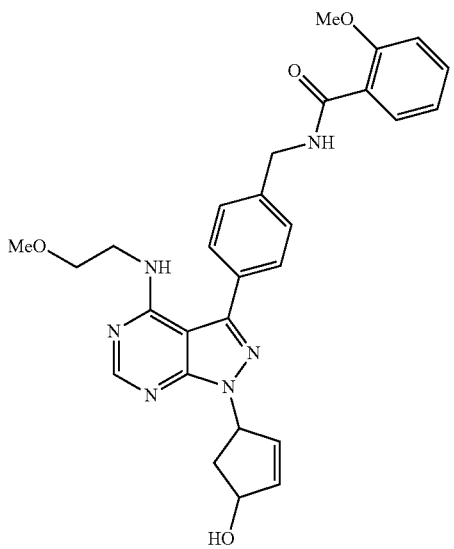

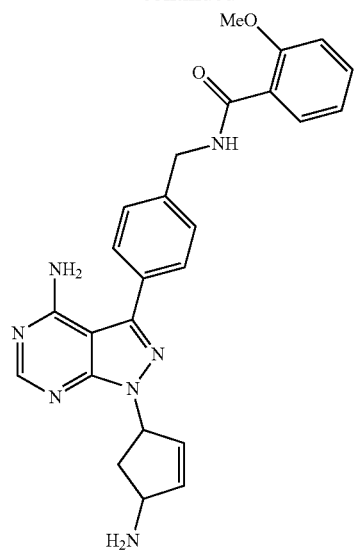
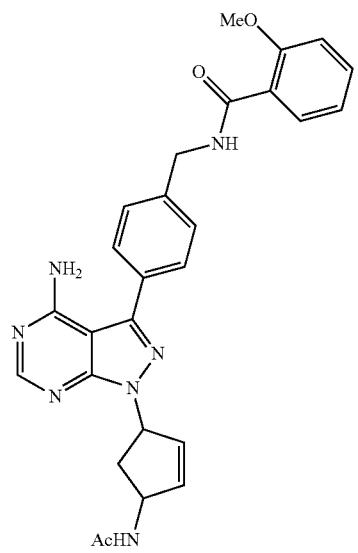
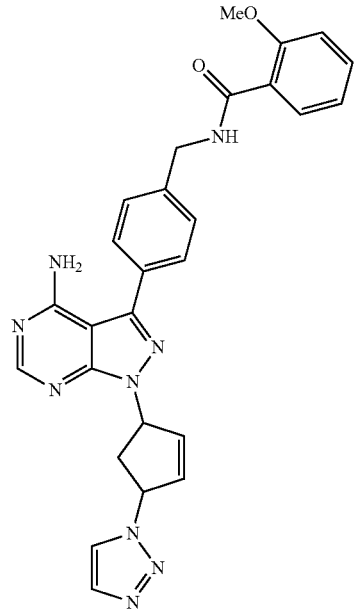
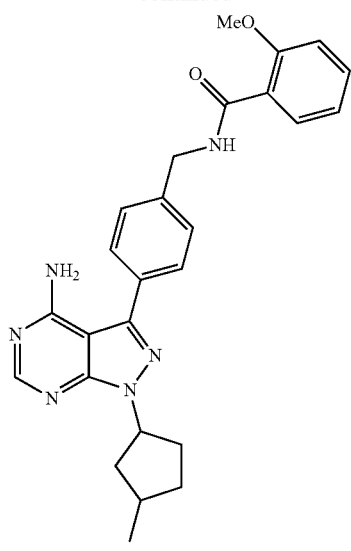
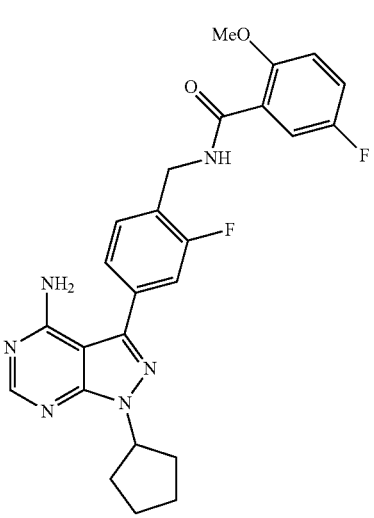
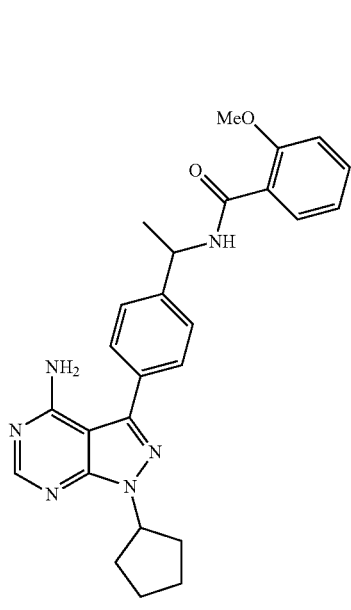

-continued
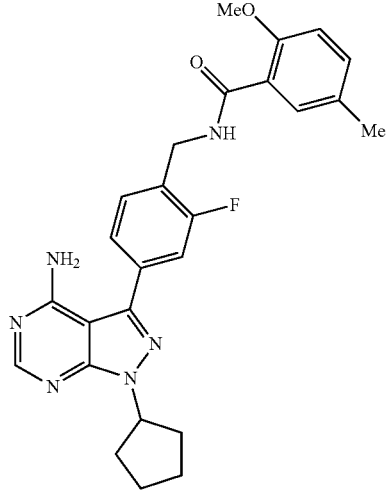
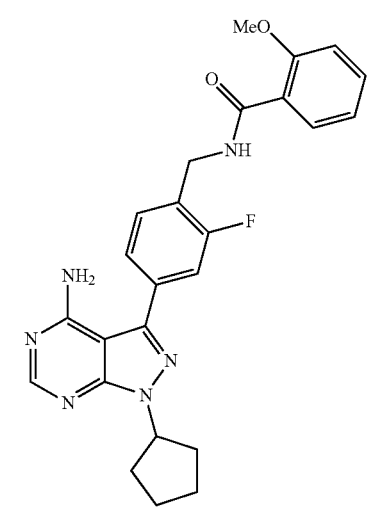
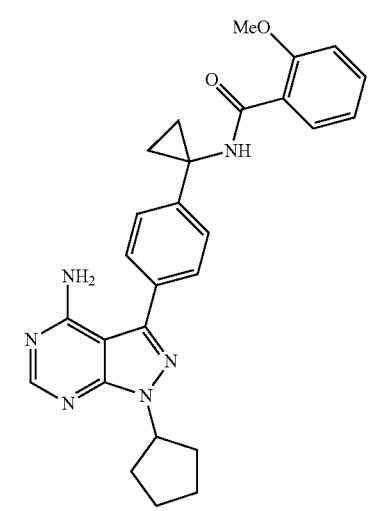 [SMILES: COc1ccccc1C(=O)NC1(c2ccc(-c3nn(C4CCCC4)c4ncnc(N)c34)cc2)CC1]
Further preferred compounds of the invention include:
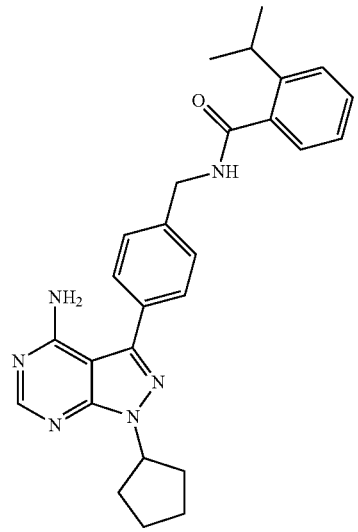
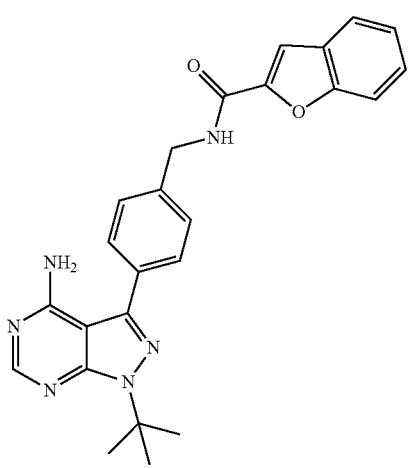
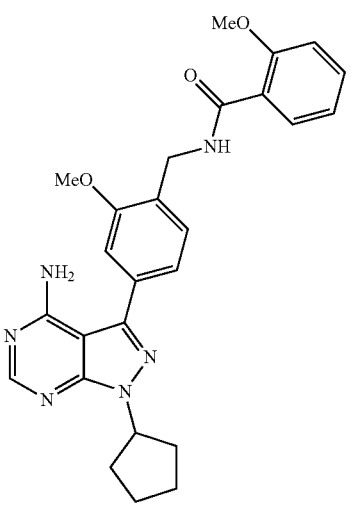

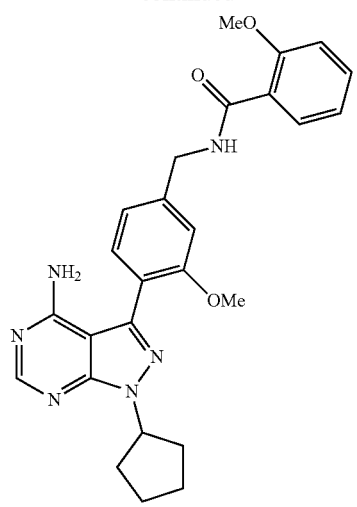
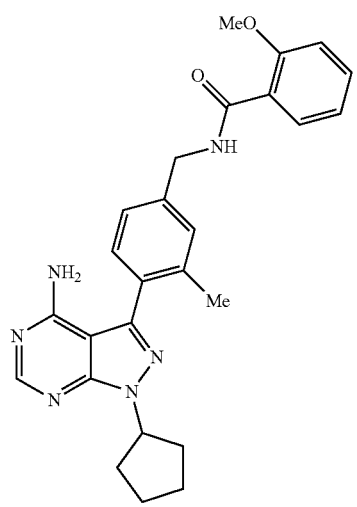
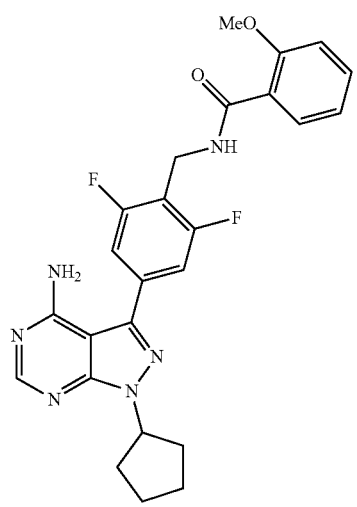
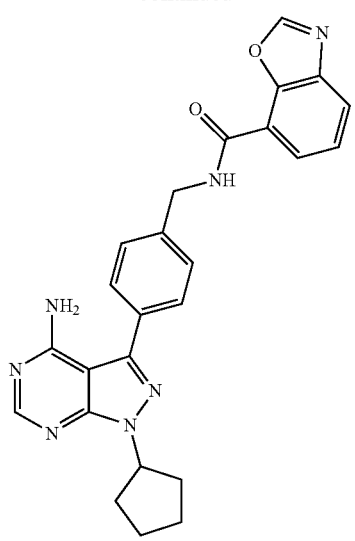
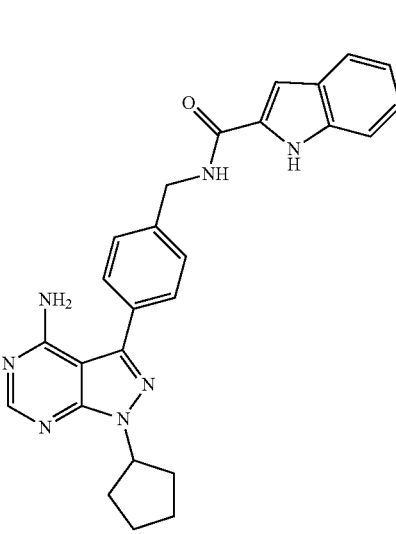
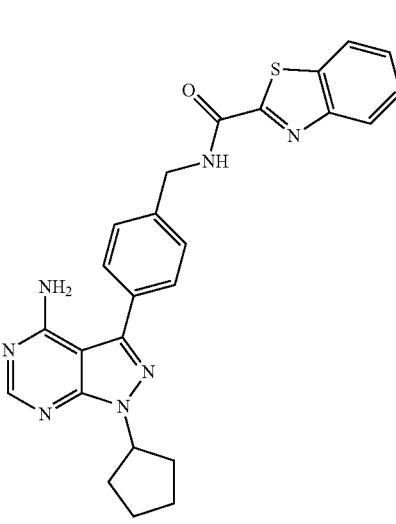

47
-continued
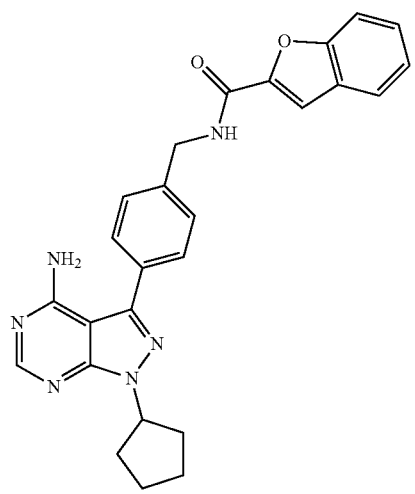
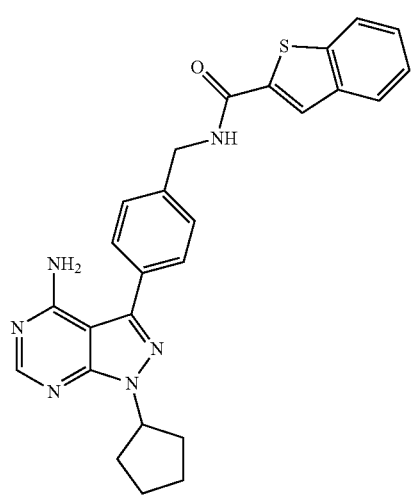
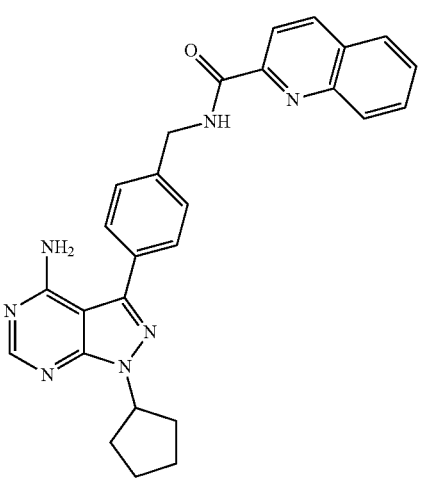
48
-continued
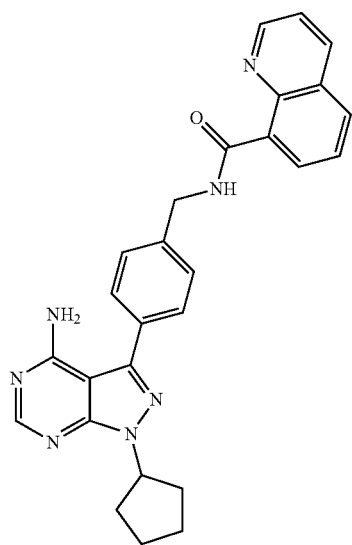
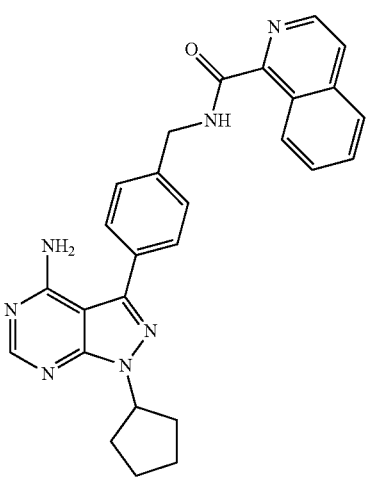
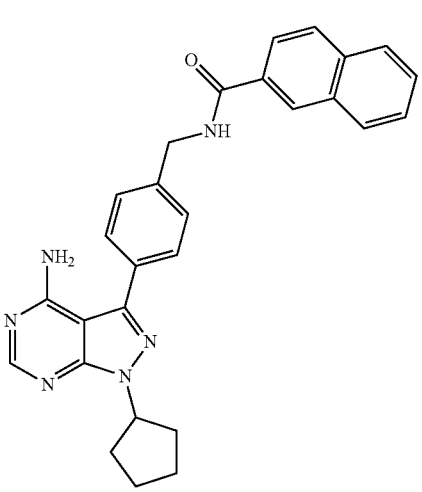

-continued
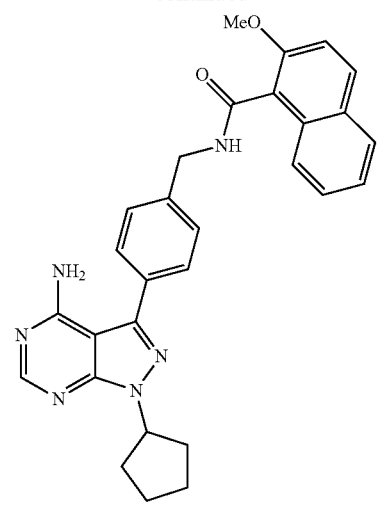
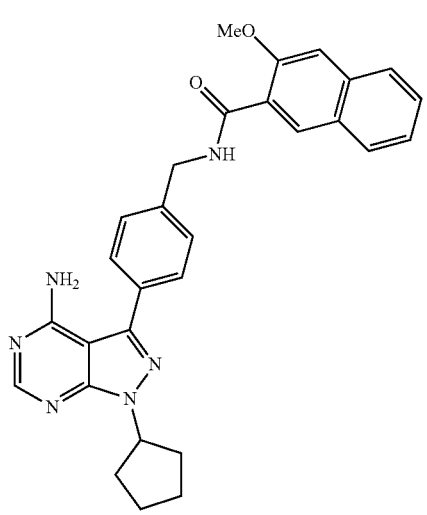
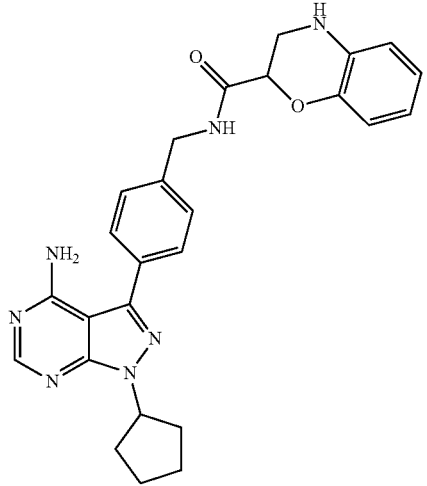
-continued
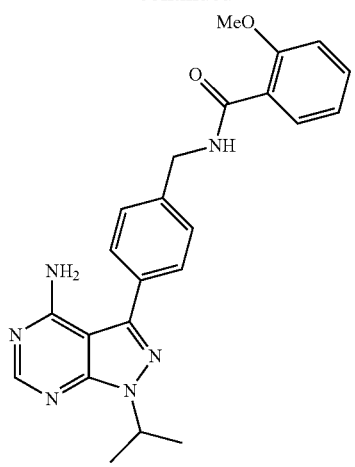
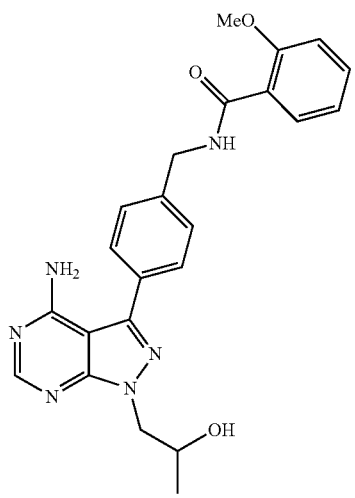
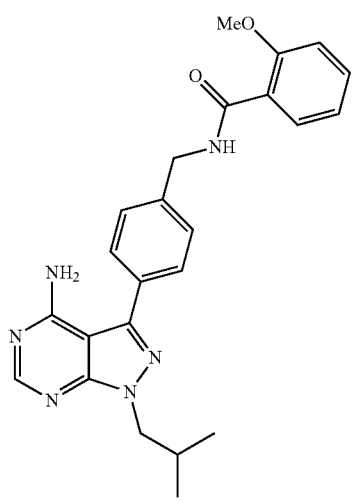

51
-continued
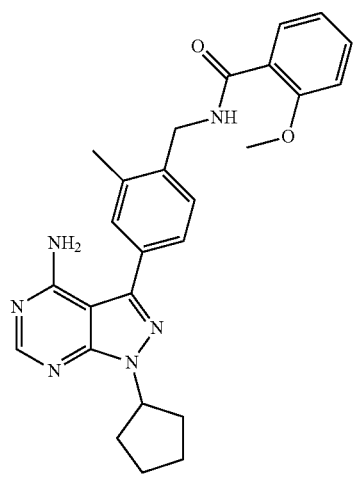
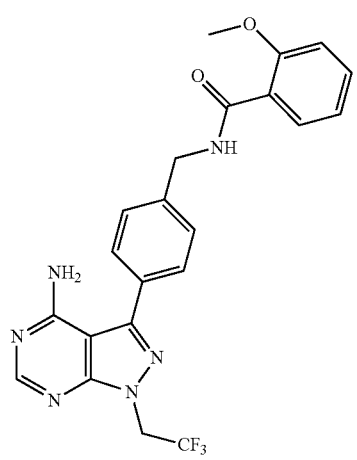
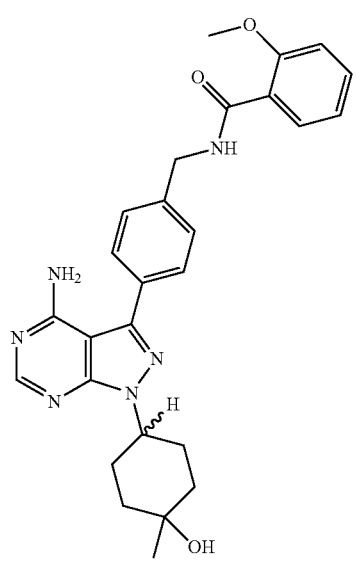
52
-continued
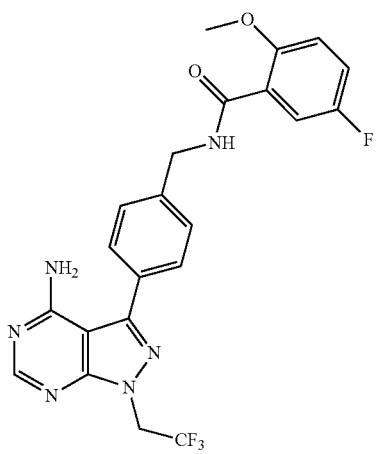
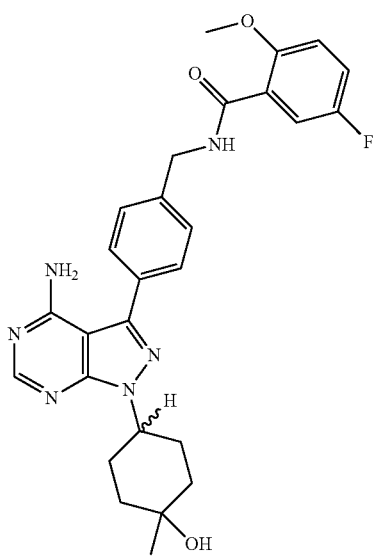
Compounds which may form part of the invention include:
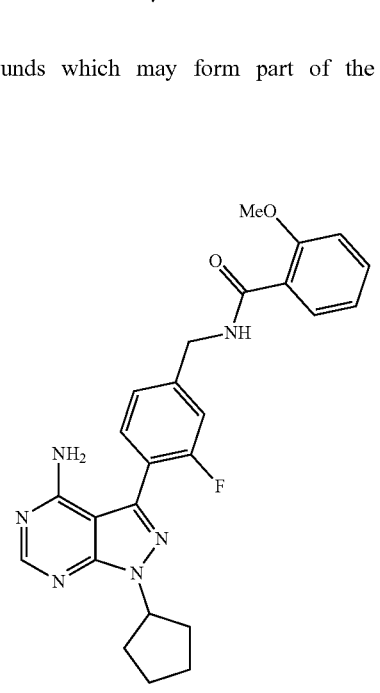

53
-continued
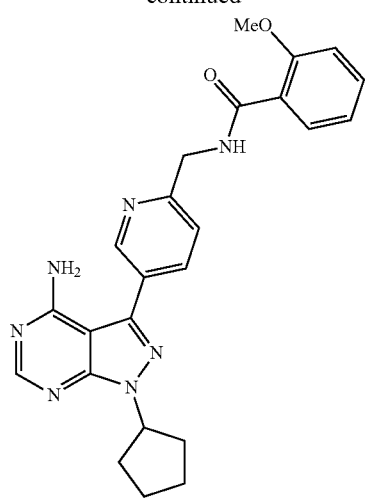
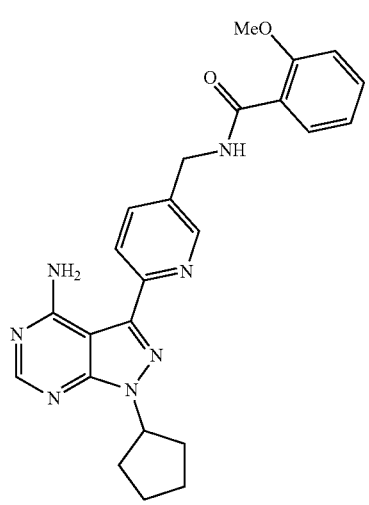
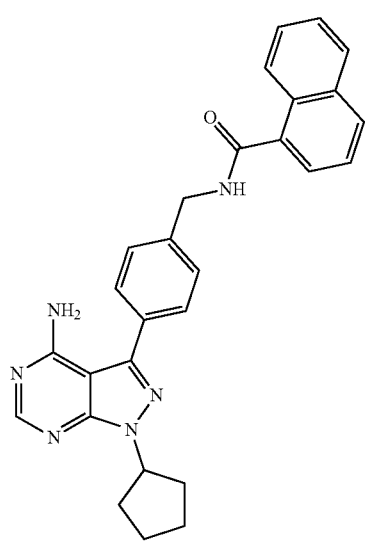
54
-continued
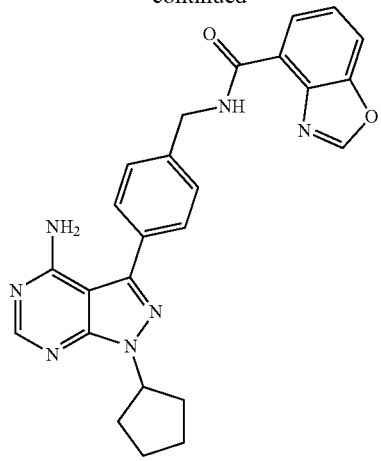
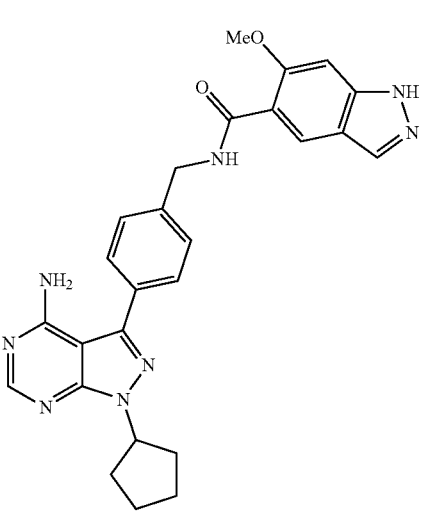
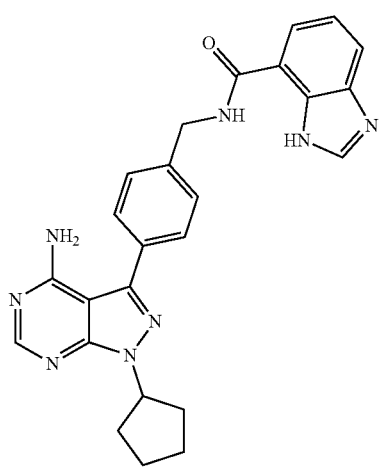 [SMILES: Nc1ncnc2c1c(-c1ccc(CNC(=O)c3cccc4nc[nH]c34)cc1)nn2C1CCCC1]

Further compounds which may form part of the invention include:
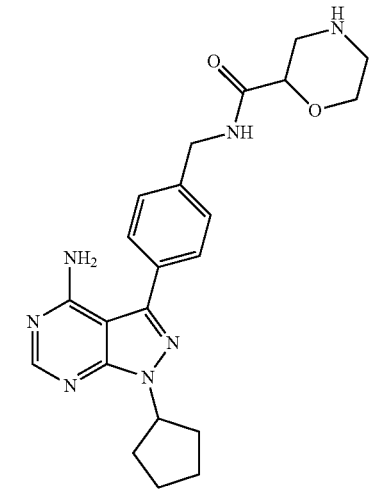
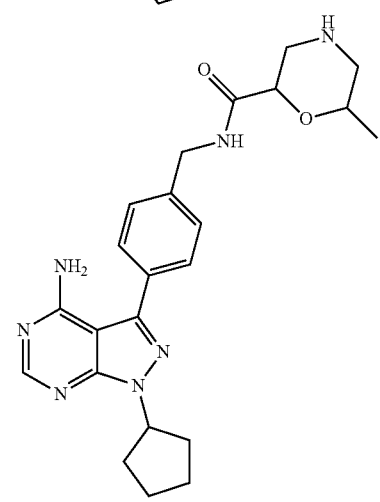
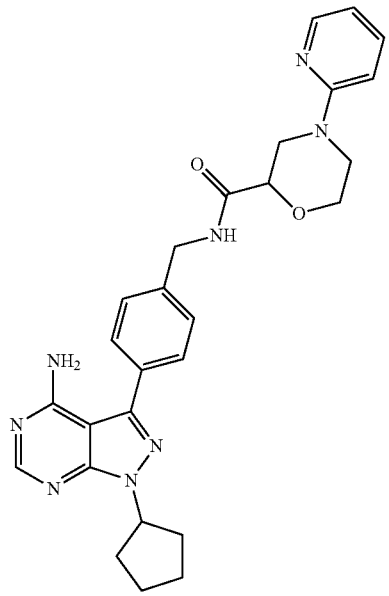
-continued
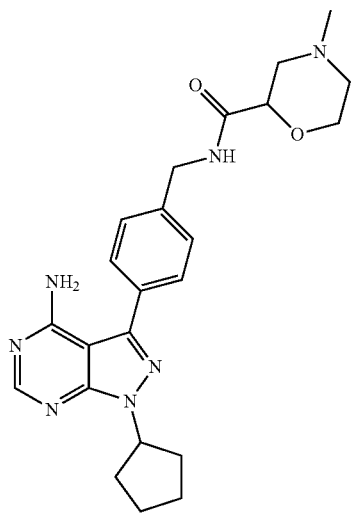
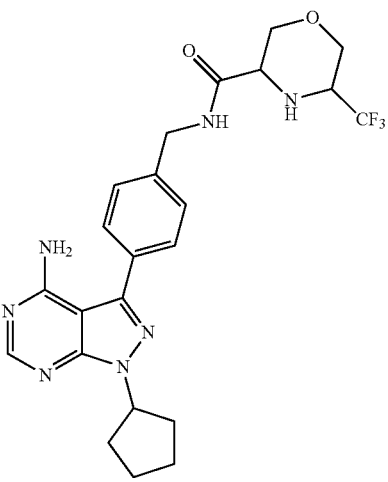
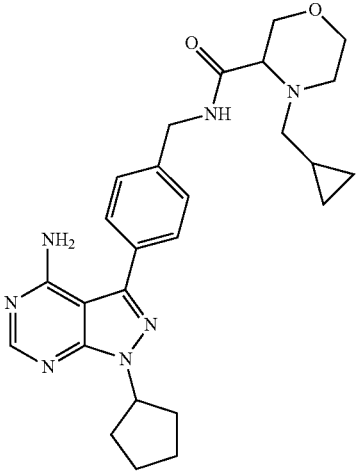

57
-continued
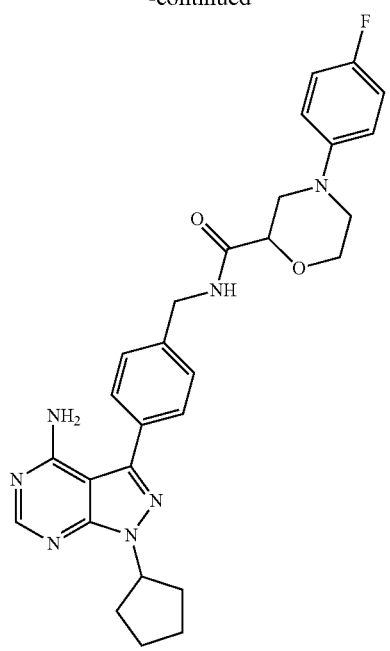
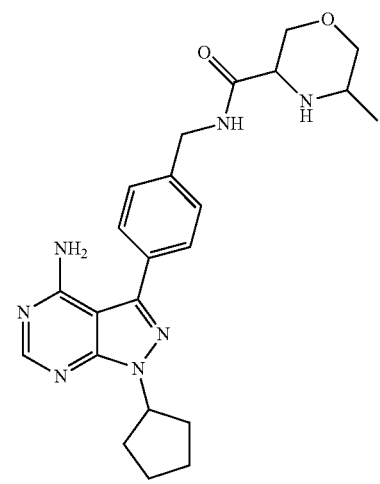
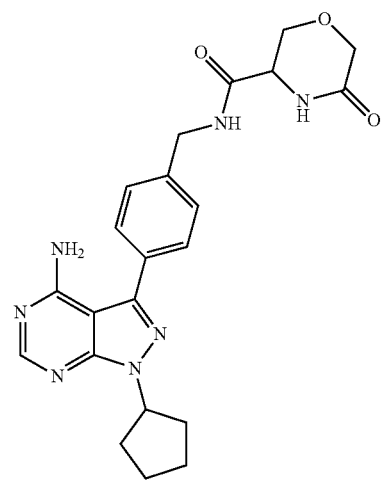
58
-continued
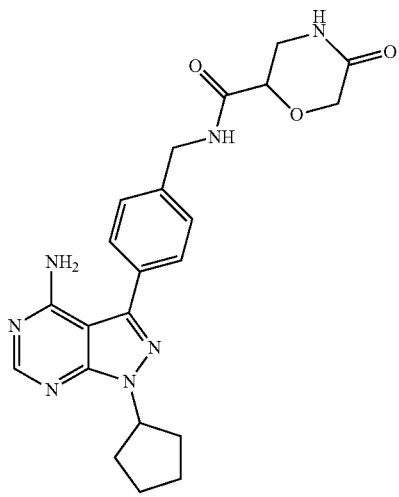
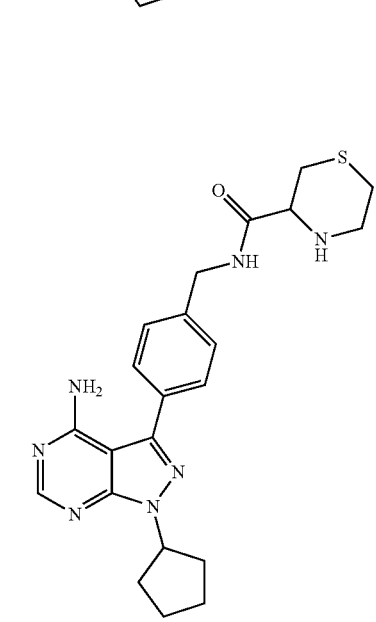
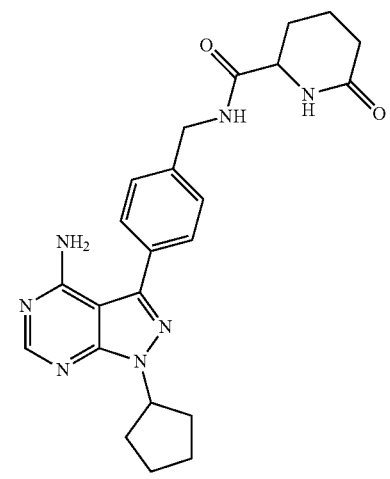

59
-continued
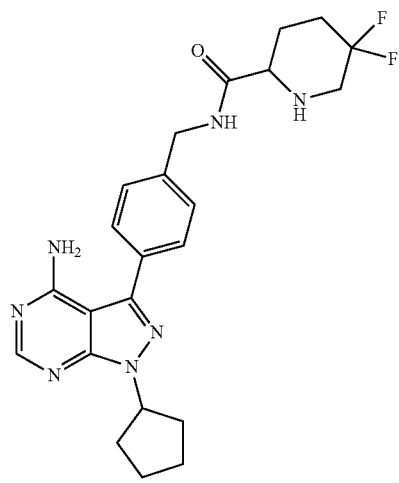
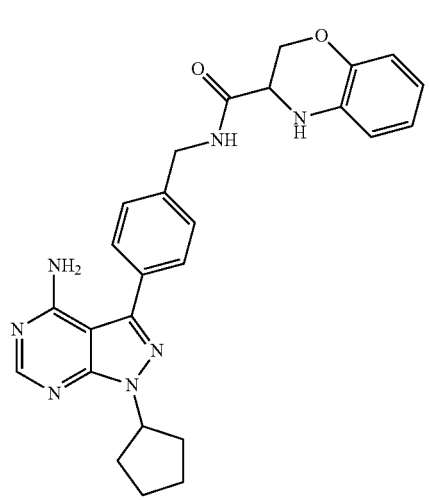
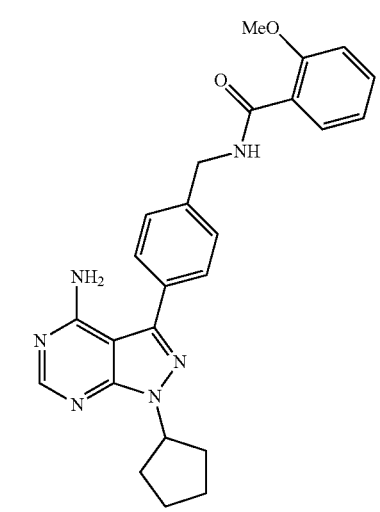
60
-continued
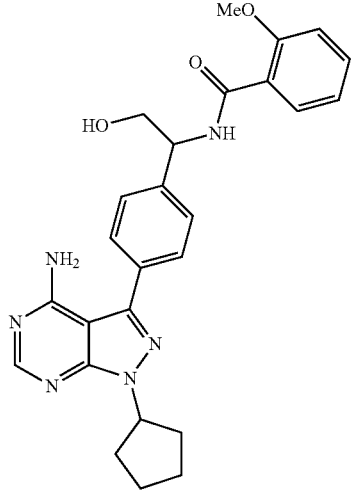
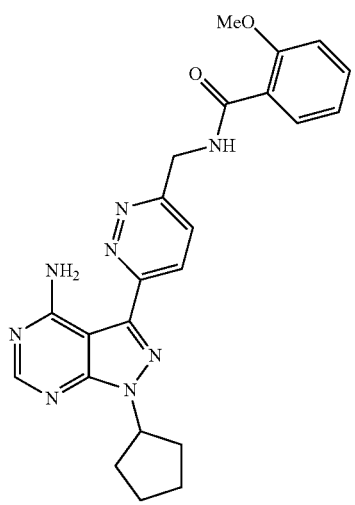
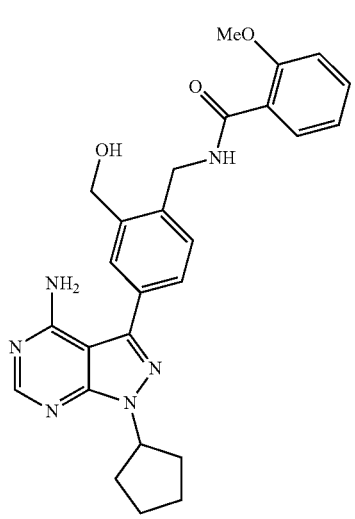

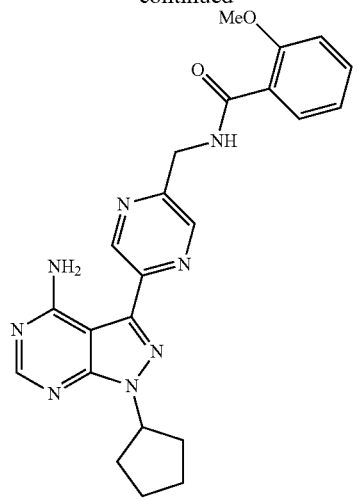
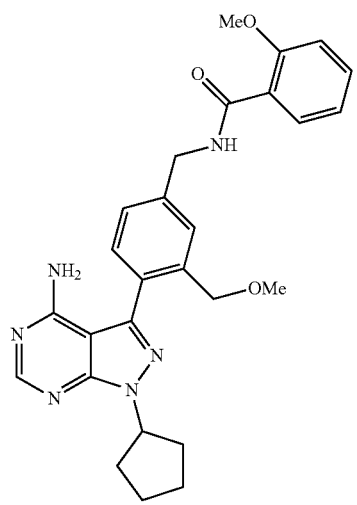
Compounds of the invention may also be:
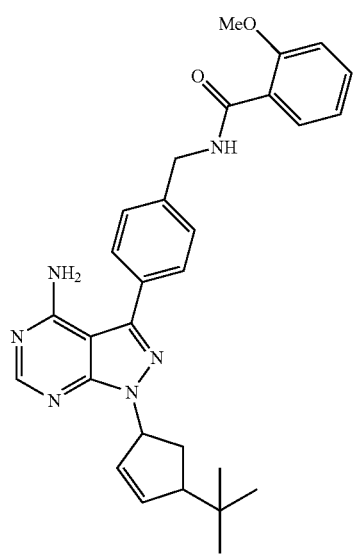
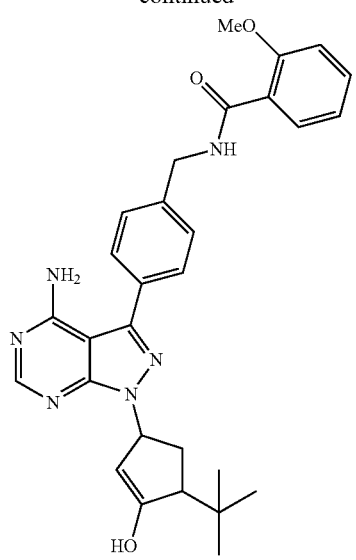
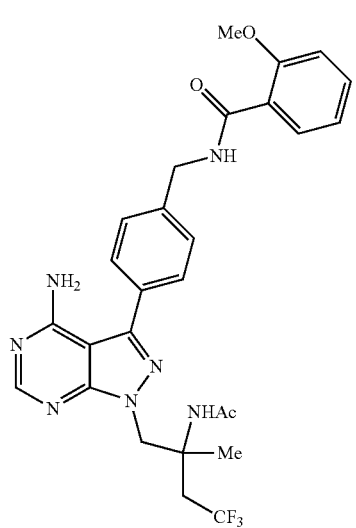
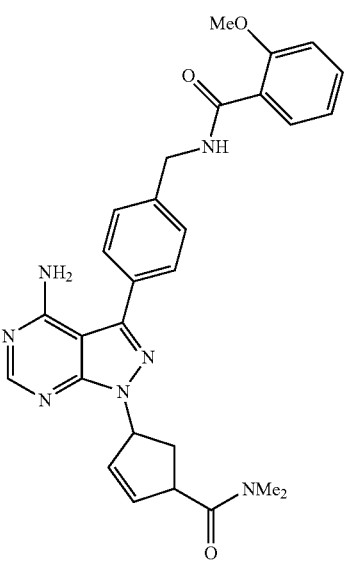

63
-continued
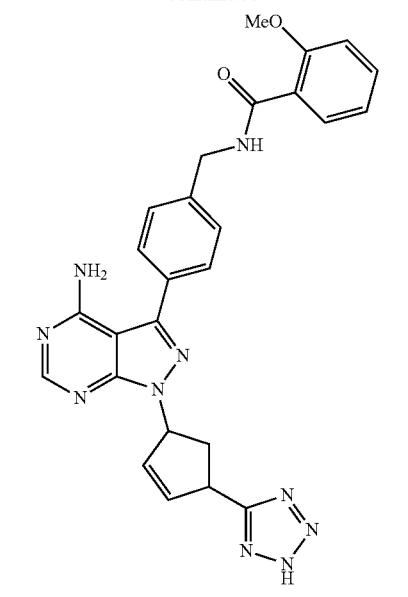
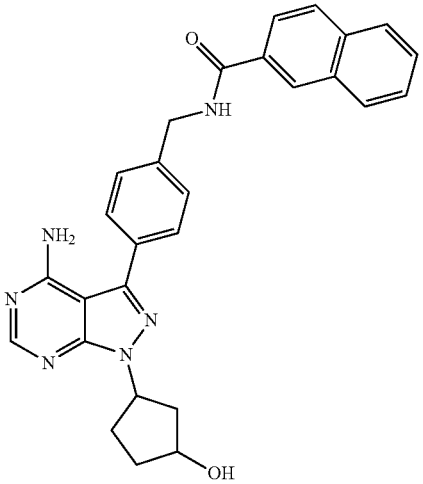
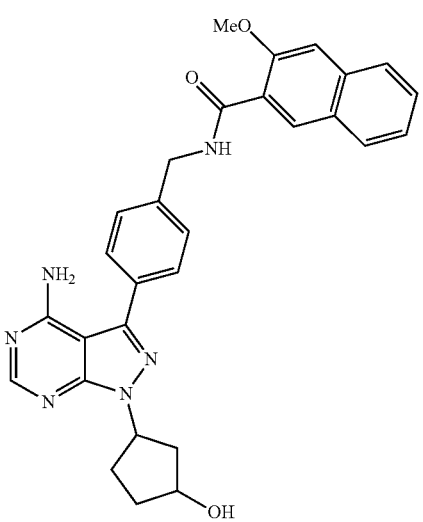
64
-continued
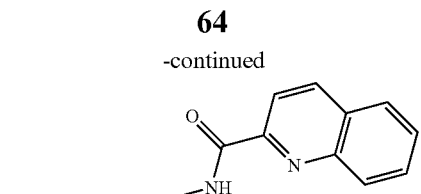
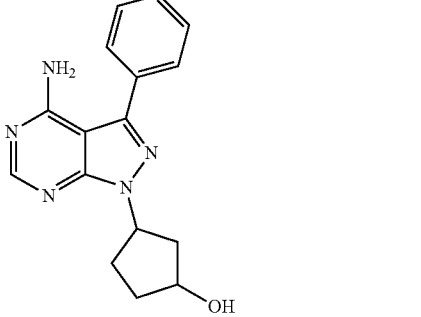
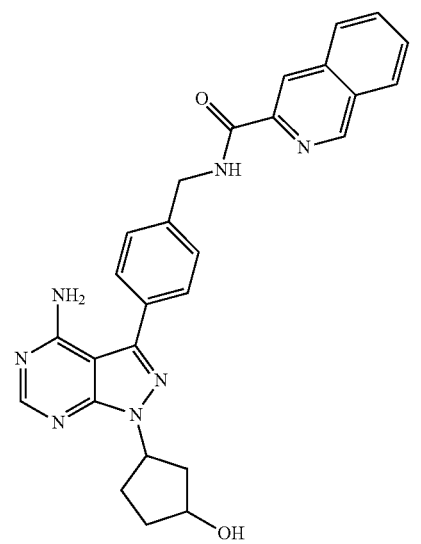
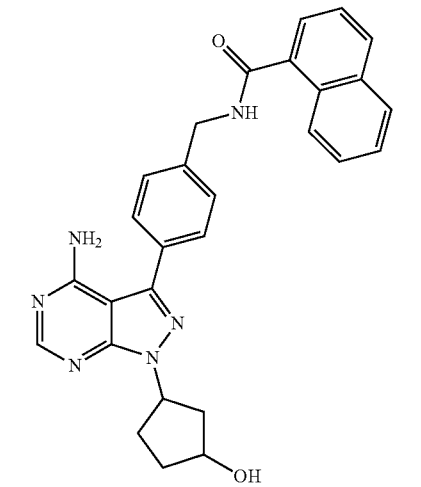

65
-continued
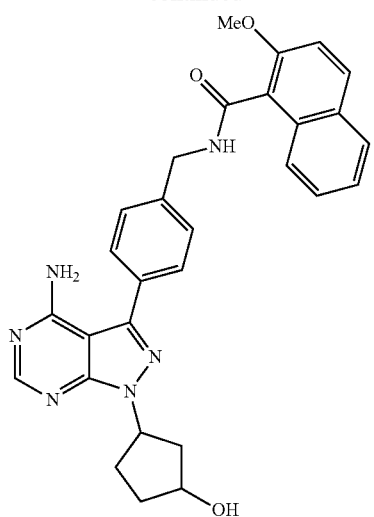
66
-continued
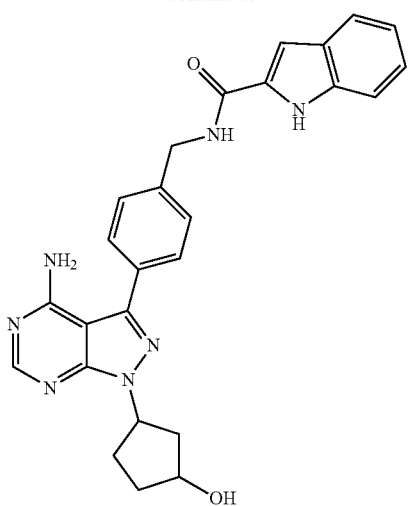
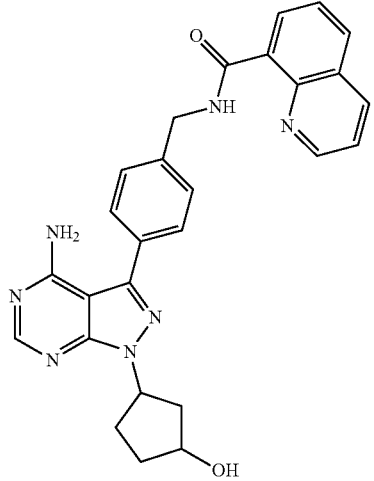
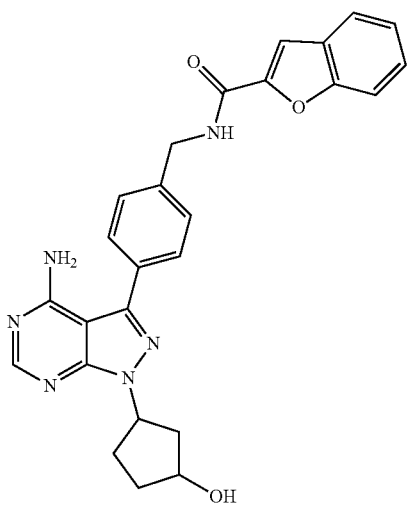
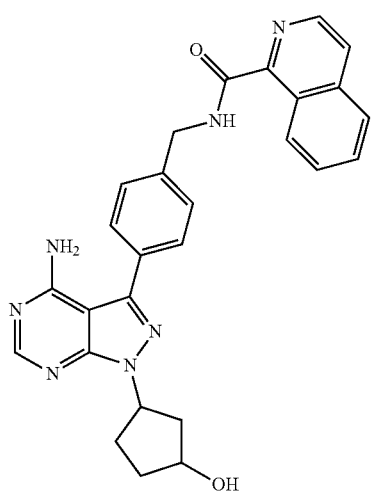
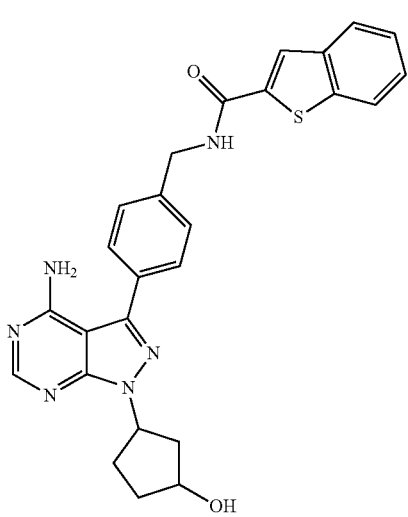

67
-continued
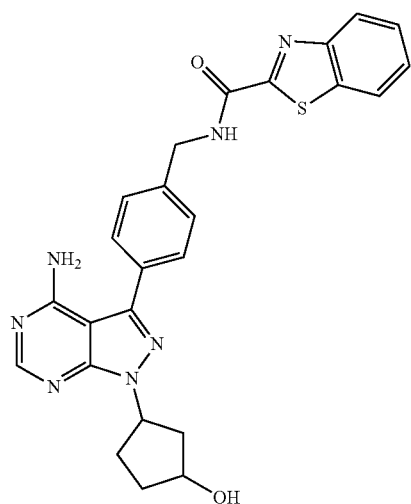
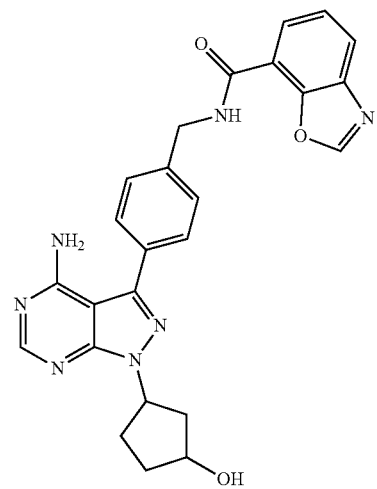
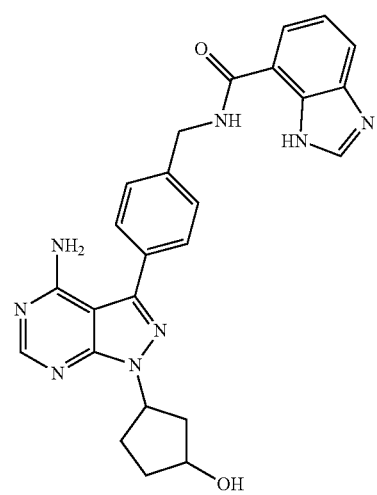
68
-continued
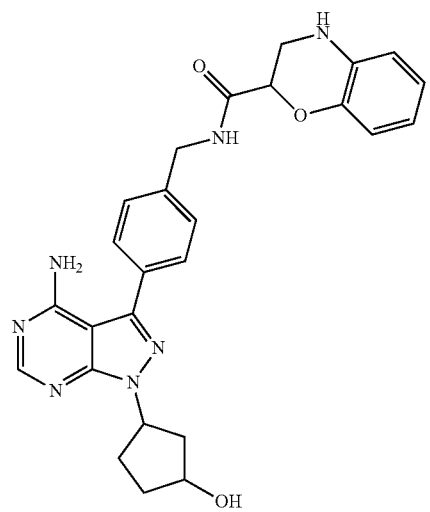
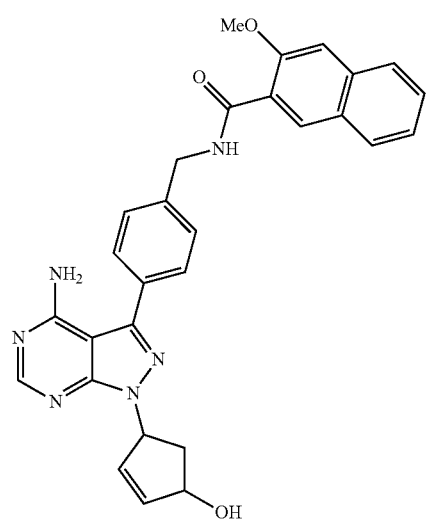

69
-continued
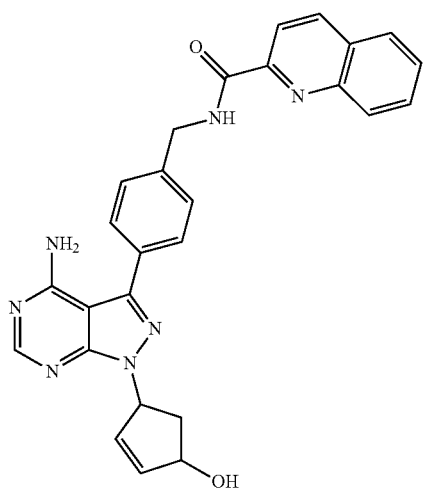
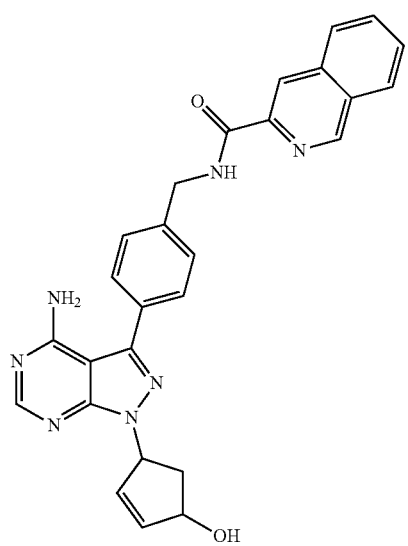
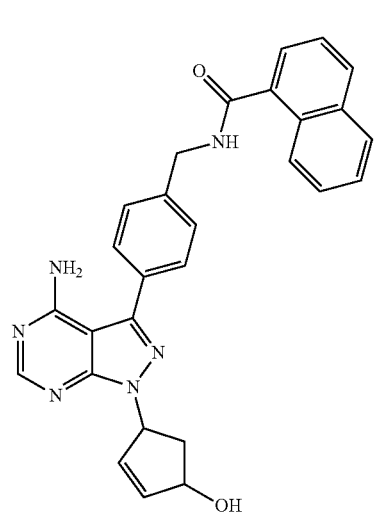
70
-continued
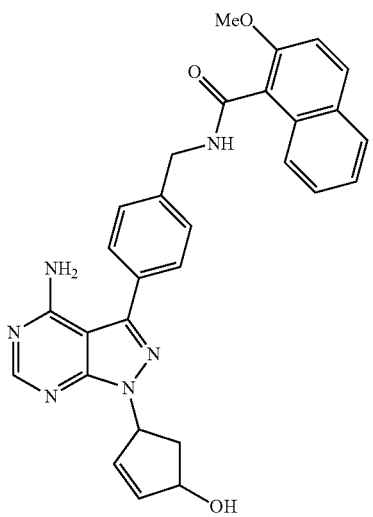
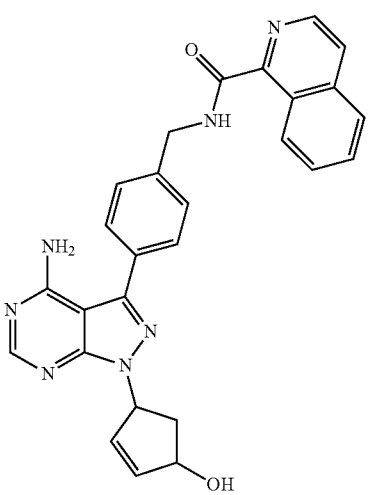

71
-continued
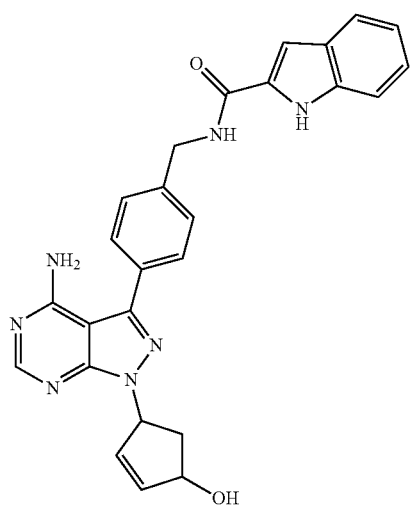
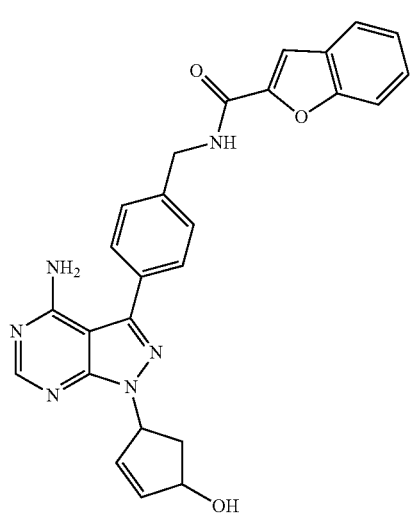
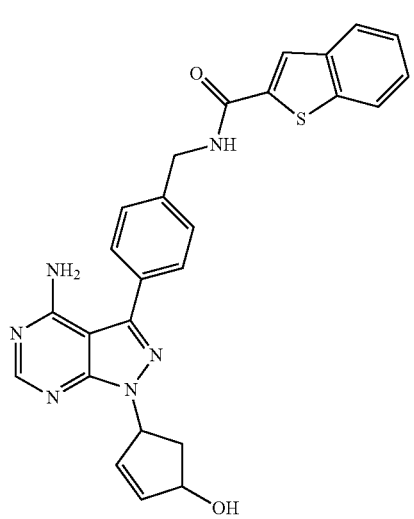
72
-continued
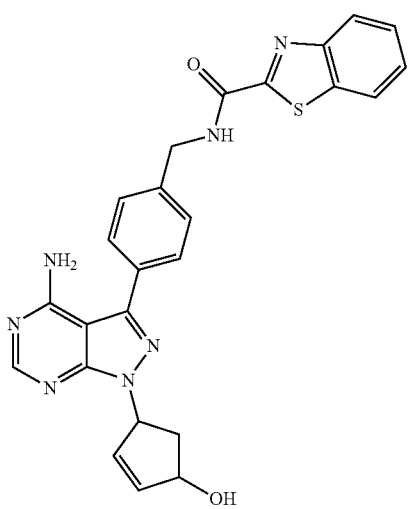
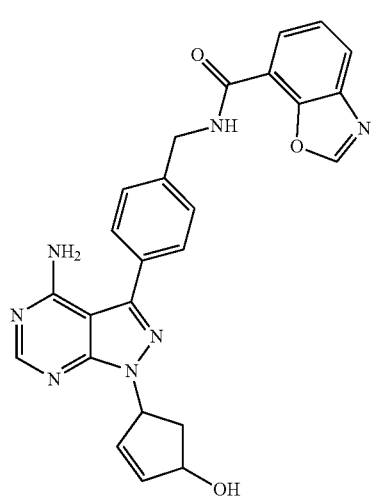
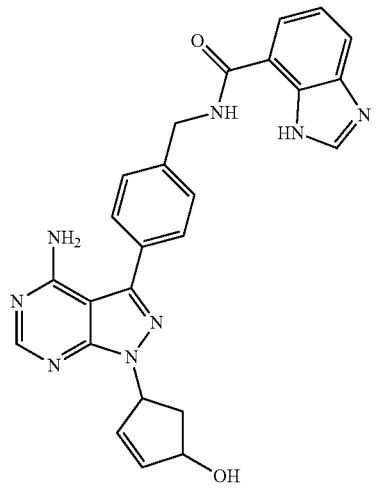

73
-continued
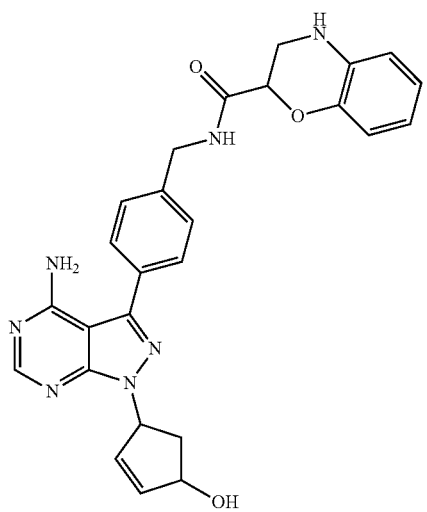
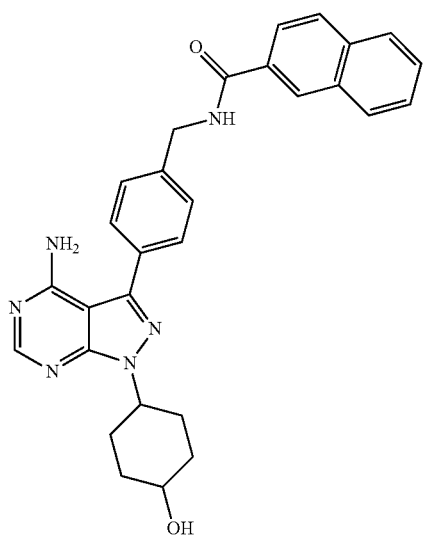
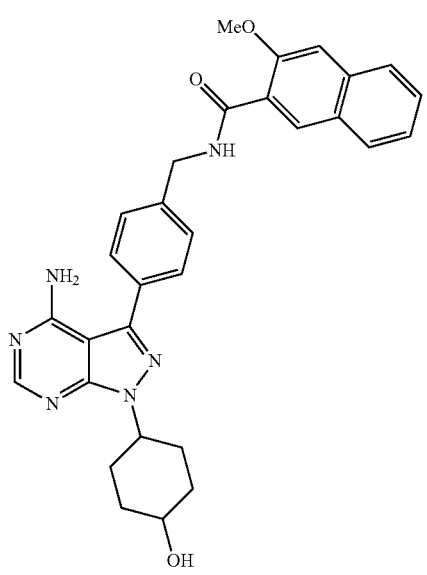
74
-continued
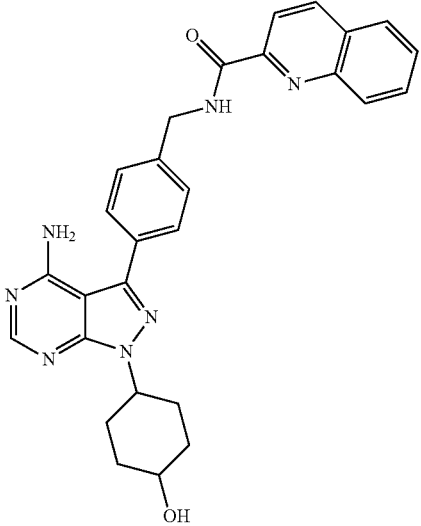
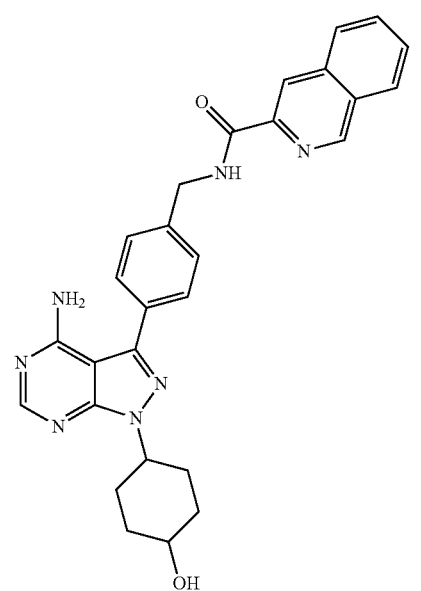
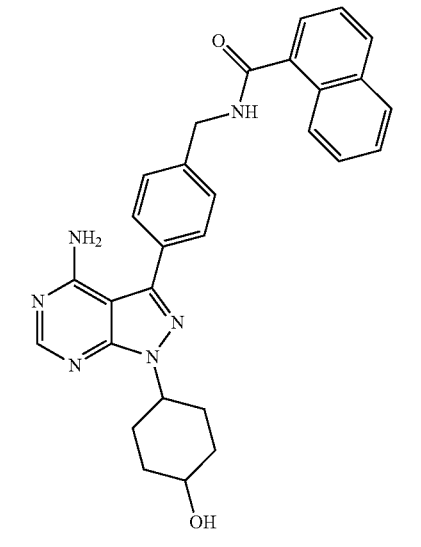

75
-continued
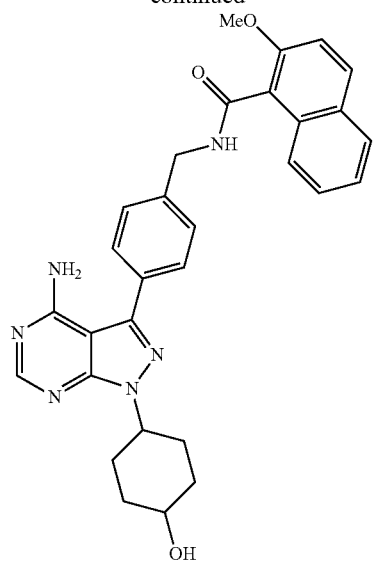
76
-continued
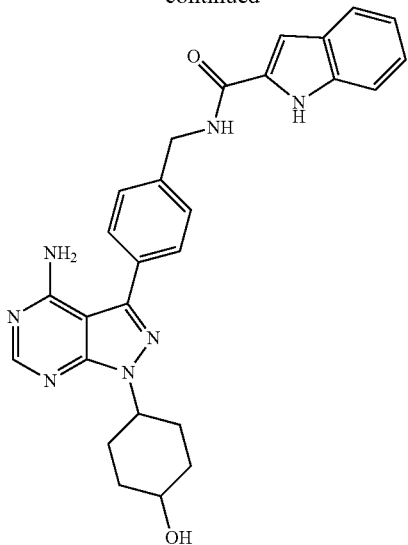
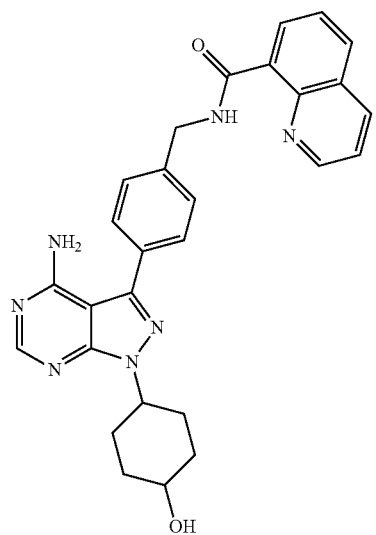
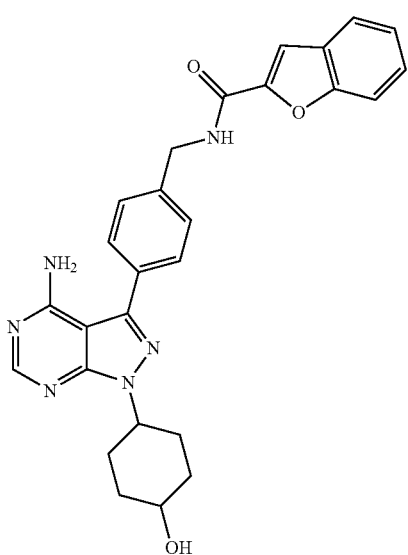
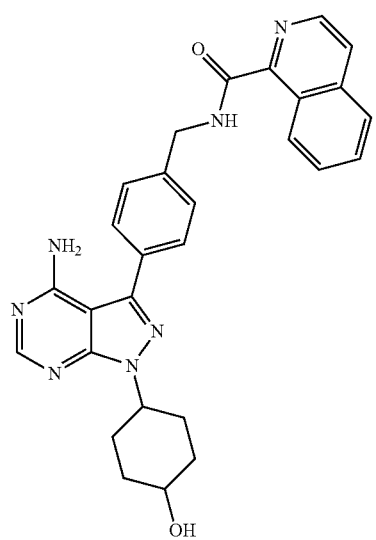
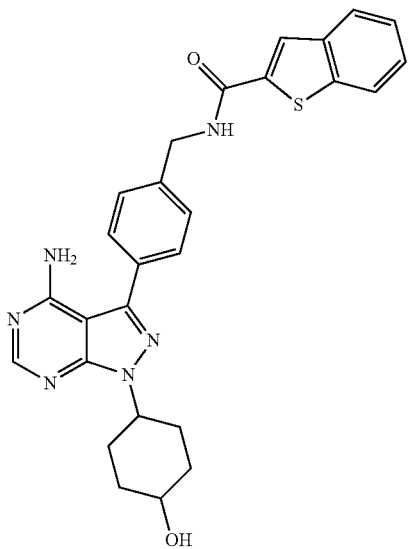

77
-continued

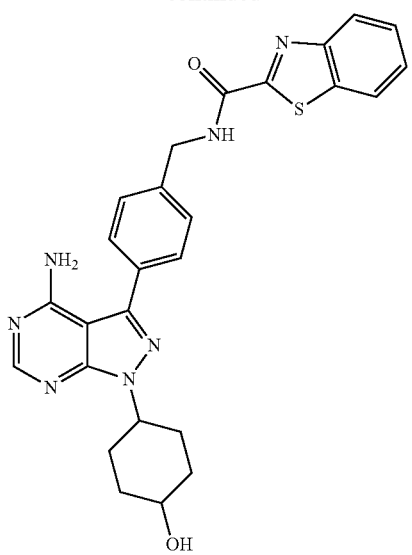

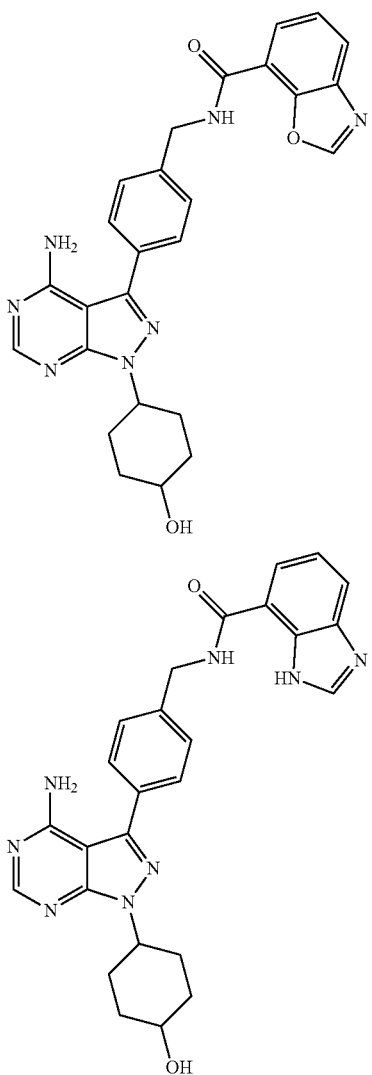

78
-continued

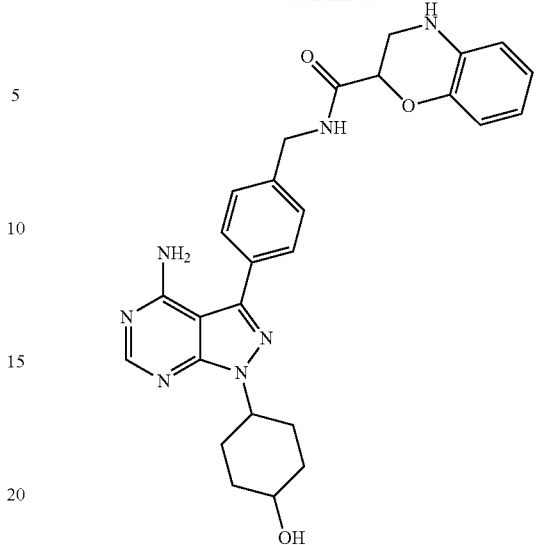

In another aspect of the invention there is provided a compound of formula (I) for use as a medicament.

In another aspect a compound of formula (I) is for use in the treatment of a condition which is modulated by Bruton's tyrosine kinase (BTK). Usually conditions that are modulated by BTK are conditions that would be treated by the inhibition of BTK using a compound of the present invention. A compound of formula (I) may be for use in the treatment of a condition treatable by the inhibition of Bruton's tyrosine kinase (BTK).

BTK inhibition is a novel approach for treating many different human diseases associated with the inappropriate activation of B-cells, including B-cell proliferative disorders, B-cell malignancies, immunological disease for example, autoimmune, heteroimmune conditions, and inflammatory disorders, or fibrosis. In particular, BTK inhibition is a novel approach for treating many different human diseases associated with the inappropriate activation of B-cells, including B-cell malignancies, immunological disease for example, autoimmune and inflammatory disorders.

In embodiments the condition treatable by the inhibition of BTK may be selected from: cancer, lymphoma, leukemia, autoimmune diseases, inflammatory disorders, heteroimune conditions, or fibrosis. Specific conditions treatable by the inhibition of BTK may be selected from: B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia, multiple myeloma, bone cancer, bone metastasis, follicular lymphoma, chronic lymphocytic lymphoma, B-cell prolymphocyte leukemia, lymphoplasmacytic lymphoma/, splenic marginal zone lymphoma, plasma cell myeloma, plasmacytoma, extranodal marginal zone B-cell lymphoma, nodal marginal zone B-cell lymphoma, mediastinal (thymic) large B-cell lymphoma, intravascular large B-cell lymphoma, primary effusion lymphoma, burkitt lymphoma/leukemia, lymphomatoid granulomatosis, inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease Sjogren's syndrome, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, vulvodynia, graft versus host disease, transplantation, transfusion, anaphylaxis, allergy, type I hypersensitivity, allergic conjunctivitis, allergic rhinitis, atopic dermatitis, asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, vulvitis, pulmonary fibrosis, idiopathic pulmonary fibrosis (IPF), usual interstitial pneumonitis (UIP), interstitial lung disease, cryptogenic fibrosing alveolitis (CFA), bronchiolitis obliterans, bronchiectasis, fatty liver disease, steatosis (e.g., nonalcoholic steatohepatitis (NASH), cholestatic liver disease (e.g., primary biliary cirrhosis (PBC), cirrhosis, alcohol-induced liver fibrosis, biliary duct injury, biliary fibrosis, cholestasis or cholangiopathies. In some embodiments, hepatic or liver fibrosis includes, but is not limited to, hepatic fibrosis associated with alcoholism, viral infection, e.g., hepatitis (e.g., hepatitis C, B or D), autoimmune hepatitis, nonalcoholic fatty liver disease (NAFLD), progressive massive fibrosis, exposure to toxins or irritants (e.g., alcohol, pharmaceutical drugs and environmental toxins), renal fibrosis (e.g., chronic kidney fibrosis), nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, or a chemotherapeutic agent, fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease, age-related macular degeneration, diabetic retinopathy, retinopathy of prematurity and neovascular glaucoma In embodiments the condition treatable by the inhibition of BTK may be selected from: cancer, lymphoma, leukemia, autoimmune diseases and inflammatory disorders. Specific conditions treatable by the inhibition of BTK may be selected from: B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia, multiple myeloma, bone cancer, bone metastasis, arthritis, multiple sclerosis osteoporosis, irritable bowel syndrome, inflammatory bowel disease, Crohn's disease, lupus and Sjögren's syndrome.

B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia, multiple myeloma, bone cancer, bone metastasis, chronic lymphocytic lymphoma, B-cell prolymphocyte leukemia, lymphoplasmacytic lymphoma/, splenic marginal zone lymphoma, plasma cell myeloma, plasmacytoma, extranodal marginal zone B-cell lymphoma, nodal marginal zone B-cell lymphoma, mediastinal (thymic) large B-cell lymphoma, intravascular large B-cell lymphoma, primary effusion lymphoma, burkitt lymphoma/leukemia, and lymphomatoid granulomatosis are examples of cancer, lymphoma and leukemia treatable by BTK inhibition.

B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia, multiple myeloma, bone cancer and bone metastasis are examples of cancer, lymphoma and leukemia treatable by BTK inhibition.

Arthritis, multiple sclerosis, osteoporosis, irritable bowel syndrome, inflammatory bowel disease, Crohn's disease, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, and vulvodynia, asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, vulvitis graft versus host disease, transplantation, transfusion, anaphylaxis, allergy, type I hypersensitivity, allergic conjunctivitis, allergic rhinitis, and atopic dermatitis are examples of immunological diseases treatable by BTK inhibition.

Arthritis, asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis are examples of an inflammatory disorder treatable by BTK inhibition.

Lupus and Sjögren's syndrome, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, and vulvodynia are examples of an autoimmune disease treatable by BTK inhibition.

Graft versus host disease, transplantation, transfusion, anaphylaxis, allergy, type I hypersensitivity, allergic conjunctivitis, allergic rhinitis, and atopic dermatitis are examples of a heteroimmune condition treatable by BTK inhibition.

Pulmonary fibrosis, idiopathic pulmonary fibrosis (IPF), usual interstitial pneumonitis (UIP), interstitial lung disease, cryptogenic fibrosing alveolitis (CFA), bronchiolitis obliterans, bronchiectasis, fatty liver disease, steatosis (e.g., nonalcoholic steatohepatitis (NASH), cholestatic liver disease (e.g., primary biliary cirrhosis (PBC), cirrhosis, alcohol-induced liver fibrosis, biliary duct injury, biliary fibrosis, cholestasis or cholangiopathies. In some embodiments, hepatic or liver fibrosis includes, but is not limited to, hepatic fibrosis associated with alcoholism, viral infection, e.g., hepatitis (e.g., hepatitis C, B or D), autoimmune hepatitis, nonalcoholic fatty liver disease (NAFLD), progressive massive fibrosis, exposure to toxins or irritants (e.g. alcohol, pharmaceutical drugs and environmental toxins), renal fibrosis (e.g. chronic kidney fibrosis), nephropathies associated with injury/fibrosis (e.g., chronic nephropathies associated with diabetes (e.g. diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, a chemotherapeutic agent, fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease, age-related macular degeneration, diabetic retinopathy, retinopathy of prematurity and neovascular glaucoma are examples of fibrosis treatable by BTK inhibition.

Arthritis, multiple sclerosis, osteoporosis, irritable bowel syndrome, inflammatory bowel disease, Crohn's disease and lupus are examples of immunological diseases treatable by BTK inhibition. Arthritis is an example of an inflammatory disorder treatable by BTK inhibition. Lupus and Sjögren's syndrome is an example of an autoimmune disease treatable by BTK inhibition.

Any of the conditions disclosed above as being treatable by BTK inhibition may be treated by a compound of the invention, or may be treated in a method comprising administering a compound of the invention, or may be treated by a medicament manufactured through the use of a compound of the present invention.

In embodiments, a compound of the invention may be for use in the treatment of: cancer, lymphoma, leukemia, immunological diseases, autoimmune diseases and inflammatory disorders. The compound of the invention may be for use in the treatment of specific conditions selected from: B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia, multiple myeloma, bone cancer, bone metastasis, arthritis, multiple sclerosis osteoporosis, irritable bowel syndrome, inflammatory bowel disease, Crohn's disease, Sjögren's syndrome and lupus. The compounds may also be used for the treatment of disorders associated with renal transplant.

In an embodiment the compound of the invention may be for use in the treatment of specific conditions selected from: B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia, multiple myeloma, lupus and arthritis.

In an aspect of the invention there is provided a method of treatment of a condition which is modulated by Bruton's tyrosine kinase, wherein the method comprises administering a therapeutic amount of a compound of the invention, to a patient in need thereof.

The method of treatment may be a method of treating a condition treatable by the inhibition of Bruton's tyrosine kinase.

The invention also provides a method of treating a condition selected from: cancer, lymphoma, leukemia, immunological diseases autoimmune diseases and inflammatory disorders, wherein the method comprises administering a therapeutic amount of a compound of the invention, to a patient in need thereof. The invention also provides a method of treating a specific condition selected from: B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia, multiple myeloma, bone cancer, bone metastasis, arthritis, multiple sclerosis osteoporosis, irritable bowel syndrome, inflammatory bowel disease, Crohn's disease, Sjögren's syndrome and lupus, wherein the method comprises administering a therapeutic amount of a compound of formula (I), to a patient in need thereof. The method may also treat disorders associated with renal transplant.

In an embodiment the method may be for treating a specific condition selected from: B-cell malignancy, B-cell lymphoma, diffuse large B cell lymphoma, chronic lymphocyte leukemia, non-Hodgkin lymphoma for example ABC- DLBCL, mantle cell lymphoma, follicular lymphoma, hairy cell leukemia B-cell non-Hodgkin lymphoma, Waldenstrom's macroglobulinemia, multiple myeloma, arthritis and lupus.

In another aspect of the invention there is provided a pharmaceutical composition, wherein the composition comprises a compound of the invention and pharmaceutically acceptable excipients.

In an embodiment the pharmaceutical composition may be a combination product comprising an additional pharmaceutically active agent. The additional pharmaceutically active agent may be an anti-tumor agent described below.

In certain embodiments the present invention does not include compounds of formulae (X) and/or (XI).

D may be selected from substituted or unsubstituted: $C_{3-10}$ cycloalkyl, $C_{3-10}$ cycloalkenyl, $C_{6-10}$ aryl, 3 to 10 membered heterocycloalkyl, 3 to 10 membered heterocycloalkenyl and 5 to 10 membered heteroaryl, wherein, when substituted, D contains from 1 to 9 substituents independently selected at each occurrence from: halo, —$OR^c$, —$NR^cR^d$, =O, —$C(O)OR^c$, —$OC(O)R^e$, —$C(O)NR^cR^d$, —$NR^cC(O)R^e$, $C_{1-6}$ alkyl, $C_{1-6}$ haloalkyl, $C_{1-6}$ alkyl substituted with —$OR^c$, $C_{3-8}$ cycloalkyl, —$SO_2R^c$, $SO_3R^e$, and a 5 to 8 membered heterocyclic group.

In an embodiment, D is selected from substituted or unsubstituted: $C_{1-6}$ alkyl, $C_{5-9}$ cycloalkyl, $C_{5-9}$ cycloalkenyl, $C_{6-10}$ aryl, 5 to 9 membered heterocycloalkyl, or 5, 6, 9 or 10 membered heteroaryl In an embodiment D is not $C_{1-6}$ alkyl.

D may be substituted or unsubstituted, when substituted D contains 1 to 5 substituents independently selected at each occurrence from the group comprising: halo, —$OR^c$, —$NR^cR^d$, =O, —$C(O)OR^c$, —$OC(O)R^e$, —$C(O)NR^cR^d$, —$NR^cC(O)R^e$, $C_{1-6}$ alkyl, $C_{1-6}$ haloalkyl, $C_{1-6}$ alkyl substituted with —$OR^c$, and a 5 to 8 membered heterocyclic group. The heterocyclic group may optionally be a heteroaryl group or a hetercycloalkyl group.

Optionally, D is not substituted pyrolidine, substituted piperidine, substituted azepane, amine substituted cyclopentyl, amine substituted cyclohexyl, amine substituted cycloheptanyl or amine substituted phenyl.

The present invention provides compounds optionally with the proviso that when X is C and Y is N then D is not substituted with a group selected from: $C_{1-4}$ alkyl, or:

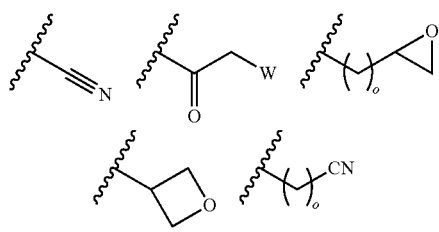

wherein W is selected from H, methyl or CN and o is selected from 0, 1, 2, 3 and 4.

The present invention provides compounds optionally with the proviso that when X is C and Y is N and D is substituted pyrolidine, substituted piperidine, substituted azepane, amine substituted cyclopentyl, amine substituted cyclohexyl, amine substituted cycloheptanyl or amine substituted phenyl then D is not substituted with a group selected from: $C_{1-4}$ alkyl, or:

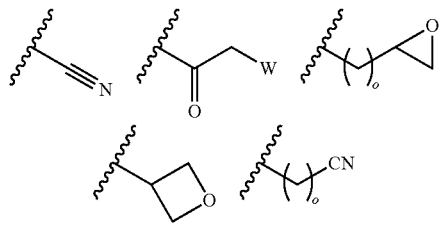

wherein W is selected from H, methyl or CN and o is selected from 0, 1, 2, 3 and 4.

The present invention provides compounds optionally with the proviso that when X is C and Y is N then D is not substituted with a group selected from: $C_{1-4}$ alkyl, or:

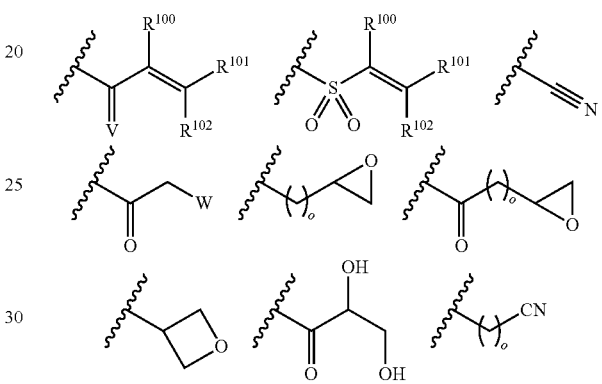

wherein V is either O or $NR^y$; W is selected from H, methyl or CN; o is selected from 0, 1, 2, 3 and 4; and $R^{100}$, $R^{101}$, and $R^{102}$ are independently selected from H, halo, —$OR^y$, —CN, —$NR^yR^z$, —$CH_2NR^yR^z$, —$CO_2R^y$, —$C(O)R^b$, —$C(O)NR^yR^z$, $C_{1-6}$ alkoxy, $C_{1-6}$ alkyl, $C_{1-6}$ alkyl substituted with $C_{3-8}$ cycloalkyl, $C_{1-6}$ alkyl substituted with $C_{3-8}$ heterocycloalkyl, $C_{2-6}$ alkenyl, $C_{2-6}$ alkynyl, $C_{1-6}$ haloalkyl, $C_{3-8}$ cycloalkyl, $C_{3-8}$ heterocycloalkyl, $C_{3-8}$ cycloalkenyl, $C_{3-8}$ heterocycloalkenyl, aryl, heteroaryl, alkaryl and alkheteroaryl;

or $R^{100}$ and $R^{101}$ taken together with the carbon atoms to which they are attached form a $C_{3-8}$ cycloalkene and $R^{102}$ is independently selected as above;

or $R^{101}$ and $R^{102}$ taken together with the carbon atom to which they are attached form a $C_{3-8}$ cycloalkyl and $R^{100}$ is independently selected as above;

or $R^{100}$ and $R^{102}$ taken together with the carbon atoms to which they are attached form a C—C triple bond and $R^{101}$ is independently selected as above, wherein $R^y$ and $R^z$ are independently selected at each occurrence from: H, $C_{1-4}$ alkyl, $C_{1-4}$ haloalkyl, $C_{1-4}$ acyl, $C_{3-7}$ cycloalkyl, and $C_{3-7}$ halocycloalkyl.

The present invention provides compounds optionally with the proviso that D is not:

either a substituted or unsubstituted $C_{1-6}$ alkylene chain which is saturated or unsaturated and which may also contain, where chemically possible, 1, 2 or 3 N, O, or S atoms in the chain which are independently chosen at each occurrence;

or wherein D does not represent a substituted or unsubstituted carbocyclic or heterocyclic moiety which is saturated or unsaturated and which contains from 3 to 8 atoms in the carbocyclic or heterocyclic ring, wherein the ring is optionally substituted with —NR$^{b-}$, wherein —NR$^b$— is bonded to the ring; when
X is C and Y is N and
D is substituted by a group selected from: C$_{1-4}$ alkyl, or:

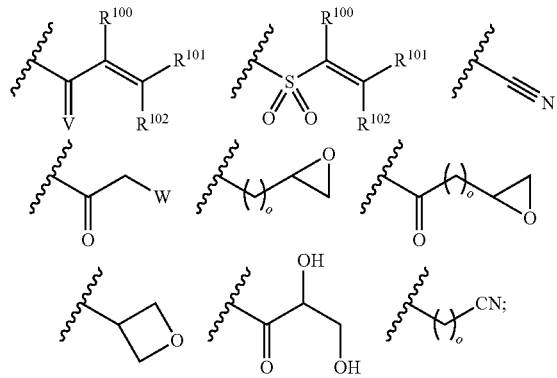

wherein V is either O or NR$^y$; W is selected from H, methyl or CN; o is selected from 0, 1, 2, 3 and 4; and R$^{100}$, R$^{101}$, and R$^{102}$ are independently selected from H, halo, —OR$^y$, —CN, —NR$^y$R$^z$, —CH$_2$NR$^y$R$^z$, —CO$_2$R$^y$, —C(O)R$^b$, —C(O)NR$^y$R$^z$, C$_{1-6}$ alkoxy, C$_{1-6}$ alkyl, C$_{1-6}$ alkyl substituted with C$_{3-8}$ cycloalkyl, C$_{1-6}$ alkyl substituted with C$_{3-8}$ heterocycloalkyl, C$_{2-6}$ alkenyl, C$_{2-6}$ alkynyl, C$_{1-6}$ haloalkyl, C$_{3-8}$ cycloalkyl, C$_{3-8}$ heterocycloalkyl, C$_{3-8}$ cycloalkenyl, C$_{3-8}$ heterocycloalkenyl, aryl, heteroaryl, alkaryl and alkheteroaryl;
or R$^{100}$ and R$^{101}$ taken together with the carbon atoms to which they are attached form a C$_{3-8}$ cycloalkene and R$^{102}$ is independently selected as above;
or R$^{101}$ and R$^{102}$ taken together with the carbon atom to which they are attached form a C$_{3-8}$ cycloalkyl and R$^{100}$ is independently selected as above;
or R$^{100}$ and R$^{102}$ taken together with the carbon atoms to which they are attached form a C—C triple bond and R$^{101}$ is independently selected as above,
wherein R$^w$ and R$^z$ are independently selected at each occurrence from: H, C$_{1-4}$ alkyl, C$_{1-4}$ haloalkyl, C$_{1-4}$ acyl, C$_{3-7}$ cycloalkyl, and C$_{3-7}$ halocycloalkyl.
The provisos in the above four paragraphs occur when X is C and Y is N. In an embodiment the provisos may also independently occur when one of X and Y is C and the other is N.
In certain embodiments when D is cyclopentyl then D is not substituted with 1 to 5 substituents independently selected at each occurrence from the group comprising: halo, —OR$^w$, —SR$^w$, —NR$^w$R$^x$, NO, =O, —CN, acyl, C$_{1-6}$ alkyl, C$_{1-6}$ haloalkyl, C$_{3-8}$ cycloalkyl, —SO$_2$R$^w$, and SO$_3$R$^w$, —C(O)R$^w$ and C(O)OR$^w$; wherein R$^w$ and R$^x$ are independently selected at each occurrence from: H, C$_{1-4}$ alkyl, C$_{1-4}$ haloalkyl, C$_{1-4}$ acyl, C$_{3-7}$ cycloalkyl, and C$_{3-7}$ halocycloalkyl.

DETAILED DESCRIPTION

Given below are definitions of terms used in this application. Any term not defined herein takes the normal meaning as the skilled person would understand the term.
The term "halo" refers to one of the halogens, group 17 of the periodic table. In particular the term refers to fluorine, chlorine, bromine and iodine. Preferably, the term refers to fluorine or chlorine.

The term "C$_{1-6}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. Alkylene groups may likewise be linear or branched and may have two places of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, C$_{1-6}$ alkoxy.
The term "C$_{1-6}$ alkoxy" refers to an alkyl group which is attached to a molecule via oxygen. This includes moieties where the alkyl part may be linear or branched and may contain 1, 2, 3, 4, 5 or 6 carbon atoms, for example methyl, ethyl, n-propyl, iso-propyl, n-butyl, sec-butyl, tert-butyl, n-pentyl and n-hexyl. Therefore, the alkoxy group may be methoxy, ethoxy, n-propoxy, iso-propoxy, n-butoxy, sec-butoxy, tert-butoxy, n-pentoxy and n-hexoxy. The alkyl part of the alkoxy group may be unsubstituted or substituted by one or more substituents. Possible substituents are described below. Substituents for the alkyl group may be halogen, e.g. fluorine, chlorine, bromine and iodine, OH, C$_{1-6}$ alkoxy.
The term "C$_{1-6}$ haloalkyl" refers to a hydrocarbon chain substituted with at least one halogen atom independently chosen at each occurrence, for example fluorine, chlorine, bromine and iodine. The halogen atom may be present at any position on the hydrocarbon chain. For example, C$_{1-6}$ haloalkyl may refer to chloromethyl, flouromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.
The term "C$_{2-6}$ alkenyl" refers to a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "C$_{2-6}$ alkenyl" may be ethenyl, propenyl, butenyl, butadienyl, pentenyl, pentadienyl, hexenyl and hexadienyl.
The term "C$_{2-6}$ alkynyl" refers to a branded or linear hydrocarbon chain containing at least one triple bond and having 2, 3, 4, 5 or 6 carbon atoms. The triple bond may be at any possible position of the hydrocarbon chain. For example, the "C$_{2-6}$ alkynyl" may be ethynyl, propynyl, butynyl, pentynyl and hexynyl.
The term "C$_{1-6}$ heteroalkyl" refers to a branded or linear hydrocarbon chain containing 1, 2, 3, 4, 5, or 6 carbon atoms and at least one heteroatom selected from N, O and S positioned between any carbon in the chain or at an end of the chain. For example, the hydrocarbon chain may contain one or two heteroatoms. The C$_{1-6}$ heteroalkyl may be bonded to the rest of the molecule through a carbon or a heteroatom. For example, the "C$_{1-6}$ heteroalkyl" may be C$_{1-6}$ N-alkyl, C$_{1-6}$ N,N-alkyl, or C$_{1-6}$ O-alkyl.
The term "carbocyclic" refers to a saturated or unsaturated carbon containing ring system. A "carbocyclic" system may be monocyclic or a fused polycyclic ring system, for example, bicyclic or tricyclic. A "carbocyclic" moiety may contain from 3 to 14 carbon atoms, for example, 3 to 8 carbon atoms in a monocyclic system and 7 to 14 carbon atoms in a polycyclic system. "Carbocyclic" encompasses cycloalkyl moieties, cycloalkenyl moieties, aryl ring systems and fused ring systems including an aromatic portion.

The term "heterocyclic" refers to a saturated or unsaturated ring system containing at least one heteroatom selected from N, O or S. A "heterocyclic" system may contain 1, 2, 3 or 4 heteroatoms, for example 1 or 2. A "heterocyclic" system may be monocyclic or a fused polycyclic ring system, for example, bicyclic or tricyclic. A "heterocyclic" moiety may contain from 3 to 14 carbon atoms, for example, 3 to 8 carbon atoms in a monocyclic system and 7 to 14 carbon atoms in a polycyclic system. "Heterocyclic" encompasses heterocycloalkyl moieties, heterocycloalkenyl moieties and heteroaromatic moieties. For example, the heterocyclic group may be: oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "cycloalkyl" refers to a saturated hydrocarbon ring system. The "cycloalkyl" group may be denoted as a "$C_{3-10}$ cycloalkyl" containing 3, 4, 5, 6, 7, 8, 9 or 10 carbon atoms. The ring system may be a single ring or a bi-cyclic or tri-cyclic ring system. For example, the "cycloalkyl" may be cyclopropyl, cyclobutyl, cyclopentyl, cyclohexyl, bicyclohexyl, cycloheptyl and cyclooctyl.

The term "cycloalkenyl" refers to an unsaturated hydrocarbon ring system that is not aromatic. The "cycloalkenyl" group may be denoted as a "$C_{3-10}$ cycloalkenyl". A "$C_{3-10}$ cycloalkenyl" is a ring system containing 3, 4, 5, 6, 7, 8, 9 or 10 carbon atoms. The ring may contain more than one double bond provided that the ring system is not aromatic. The ring system may be a single ring or a bi-cyclic or tri-cyclic ring system. For example, the "cycloalkenyl" may be cyclopropenyl, cyclobutenyl, cyclopentenyl, cyclopentadienyl, cyclohexenyl, cyclohexadienly, cycloheptenyl, cycloheptadiene, cyclooctenyl and cycloatadienyl.

The term "heterocycloalkyl" refers to a saturated hydrocarbon ring system with at least one heteroatom within the ring selected from N, O and S. The "heterocycloalkyl" group may be denoted as a "$C_{3-10}$ heterocycloalkyl". A "$C_{3-10}$ heterocycloalkyl" is a ring system containing 3, 4, 5, 6, 7, 8, 9 or 10 atoms at least one being a heteroatom. For example there may be 1, 2 or 3 heteroatoms, optionally 1 or 2. The "heterocycloalkyl" group may also be denoted as a "3 to 10 membered heterocycloalkyl" which is also a ring system containing 3, 4, 5, 6, 7, 8, 9 or 10 atoms at least one being a heteroatom. The ring system may be a single ring or a bi-cyclic or tri-cyclic ring system. Where the ring system is bicyclic one of the rings may be an aromatic ring, for example as in indane. The "heterocycloalkyl" may be bonded to the rest of the molecule through any carbon atom or heteroatom. The "heterocycloalkyl" may have one or more, e.g. one or two, bonds to the rest of the molecule: these bonds may be through any of the atoms in the ring. For example, the "heterocycloalkyl" may be oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, tetrahydropyran, and indane.

The term "heterocycloalkenyl" refers to an unsaturated hydrocarbon ring system, that is not aromatic, having at least one heteroatom within the ring selected from N, O and S. The "heterocycloalkenyl" group may be denoted as a "$C_{3-10}$ heterocycloalkenyl". A "$C_{3-10}$ heterocycloalkenyl" is a ring system containing 3, 4, 5, 6, 7, 8, 9 or 10 atoms at least one being a heteroatom. For example there may be 1, 2 or 3 heteroatoms, optionally 1 or 2. The "heterocycloalkenyl" group may also be denoted as a "3 to 10 membered heterocycloalkenyl" which is also a ring system containing 3, 4, 5, 6, 7, 8, 9 or 10 atoms at least one being a heteroatom. The ring system may be a single ring or a bi-cyclic or tri-cyclic ring system. Where the ring system is bicyclic one of the rings may be an aromatic ring, for example as in indoline and dihydrobenzofuran. The "heterocycloalkenyl" may be bonded to the rest of the molecule through any carbon atom or heteroatom. The "heterocycloalkenyl" may have one or more, e.g. one or two, bonds to the rest of the molecule: these bonds may be through any of the atoms in the ring. For example, the "$C_{3-8}$ heterocycloalkenyl" may be tetrahydropyridine, dihydropyran, dihydrofuran, pyrroline, dihydrobenzofuran, dihydrobenzothiophene and indoline.

The term "aromatic" when applied to a substituent as a whole means a single ring or polycyclic ring system with 4n+2 electrons in a conjugated π system within the ring or ring system where all atoms contributing to the conjugated π system are in the same plane.

The term "aryl" refers to an aromatic hydrocarbon ring system. The ring system has 4n+2 electrons in a conjugated π system within a ring where all atoms contributing to the conjugated π system are in the same plane. The ring system may be a single ring or a bi-cyclic or tri-cyclic ring system. For example, the "aryl" may be phenyl and naphthyl. The aryl system itself may be substituted with other groups.

The term "heteroaryl" refers to an aromatic hydrocarbon ring system with at least one heteroatom within a single ring or within a fused ring system, selected from O, N and S. The ring or ring system has 4n+2 electrons in a conjugated π system where all atoms contributing to the conjugated π system are in the same plane. The ring system may be a single ring or a bi-cyclic or tri-cyclic ring system. For example, the "heteroaryl" may be imidazole, thiene, furane, thianthrene, pyrrol, benzimidazole, pyrazole, pyrazine, pyridine, pyrimidine and indole.

The term "alkaryl" refers to an aryl group, as defined above, bonded to a $C_{1-4}$ alkyl, where the $C_{1-4}$ alkyl group provides attachment to the remainder of the molecule.

The term "alkheteroaryl" refers to a heteroaryl group, as defined above, bonded to a $C_{1-4}$ alkyl, where the alkyl group provides attachment to the remainder of the molecule.

The term "halogen" herein includes reference to F, Cl, Br and I. Halogen may be Cl. Halogen may be F.

When —$NR^b$— is bonded to the carbocyclic or heterocyclic ring of D, the group E is bonded directly to —$NR^b$—.

A bond terminating in a "⌢" represents that the bond is connected to another atom that is not shown in the structure. A bond terminating inside a cyclic structure and not terminating at an atom of the ring structure represents that the bond may be connected to any of the atoms in the ring structure where allowed by valency.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different. The substituent(s) may be selected from: OH, $NHR^g$, amidino, guanidino, hydroxyguanidino, formamidino, isothioureido, ureido, mercapto, C(O)H, acyl, acyloxy, carboxy, sulfo, sulfamoyl, carbamoyl, cyano, azo, nitro, halo, $C_{1-6}$ alkyl, $C_{1-6}$ alkoxy, $C_{1-6}$ haloalkyl, $C_{3-8}$ cycloalkyl, $C_{2-6}$ alkenyl, $C_{2-6}$ alkynyl, aryl, heteroaryl or alkaryl. Where the group to be substituted is an alkyl group the substituent may be =O. Where the moiety is substituted with two or more substituents and two of the substituents are adjacent the adjacent substituents may form a $C_{4-8}$ ring along with the atoms of the moiety on which the substituents are substituted, wherein the $C_{4-8}$ ring is a saturated or unsaturated hydrocarbon ring with 4, 5, 6, 7, or 8 carbon atoms or a saturated or unsaturated hydrocarbon ring with 4, 5, 6, 7, or 8 carbon atoms and 1, 2 or 3 heteroatoms.

If chemically possible to do so, a cyclic substituent may be substituted on a group so as to form a spiro-cycle.

Substituents are only present at positions where they are chemically possible, the person skilled in the art being able to decide (either experimentally or theoretically) without inappropriate effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in " ".

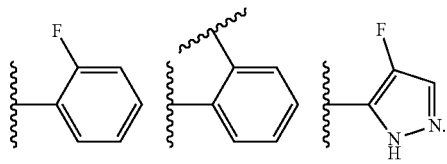

"Meta" substitution is a substitution pattern where two substituents are on carbons one carbon removed from each other, i.e with a single carbon atom between the substituted carbons. In other words there is a substituent on the second atom away from the atom with another substituent. For example the groups below are meta substituted.

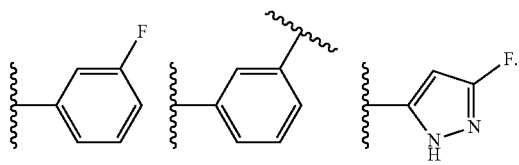

"Para" substitution is a substitution pattern where two substituents are on carbons two carbons removed from each other, i.e with two carbon atoms between the substituted carbons. In other words there is a substituent on the third atom away from the atom with another substituent. For example the groups below are para substituted.

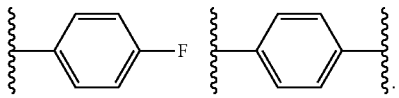

By "acyl" is meant an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, eg R is H or $C_{1-3}$ alkyl. In one embodiment acyl is alkyl-carbonyl. Examples of acyl groups include, but are not limited to, formyl, acetyl, propionyl and butyryl. A particular acyl group is acetyl.

In embodiments where there is a single enantiomer of the compounds of the invention, the compounds of the invention may have an enantiomeric purity of at least about 90% enantiomeric excess (ee), at least about 95% enantiomeric excess (ee), at least about 98% enantiomeric excess (ee), at least about 99% enantiomeric excess (ee), or 100% enantiomeric excess (ee). In embodiments where there is a mixture of enantiomers of the compounds of the invention, the compounds of the invention may be a racemic mixture or any other mixture of enantiomers, for example the compounds of the invention may have an enantiomeric purity of at least about 50% enantiomeric excess (ee), at least about 60% enantiomeric excess (ee), at least about 70% enantiomeric excess (ee), at least about 80% enantiomeric excess (ee), at least about 90% enantiomeric excess (ee), or at least about 95% enantiomeric excess (ee).

Throughout the description the disclosure of a compound also encompasses pharmaceutically acceptable salts, solvates and stereoisomers thereof. Where a compound has a stereocentre, both (R) and (S) stereoisomers are contemplated by the invention, equally mixtures of stereoisomers or a racemic mixture are completed by the present application. Where a compound of the invention has two or more stereocentres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diastereoemeric mixtures. Where the mixture is a mixture of enantiomers the enantiomeric excess may be any of those disclosed above. Where the compound is a single stereoisomer the compounds may still contain other diasteroisomers or enantiomers as impurities. Hence a single stereoisomer does not necessarily have an enantiomeric excess (e.e.) or diastereomeric excess (d.e.) of 100% but could have an e.e. or d.e. of about at least 85%

The invention contemplates pharmaceutically acceptable salts of the compounds of formula (I). These may include the acid addition and base salts of the compounds. These may be acid addition and base salts of the compounds. In addition the invention contemplates solvates of the compounds. These may be hydrates or other solvated forms of the compound.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of any formula include references to salts, solvates and complexes thereof and to solvates and complexes of salts thereof.

The compounds of the invention include compounds of a number of formula as herein defined, including all polymorphs and crystal habits thereof, prodrugs and isomers thereof (including optical, geometric and tautomeric isomers) as hereinafter defined and isotopically-labeled compounds of the invention.

Before purification, the compounds of the present invention may exist as a mixture of enantiomers depending on the synthetic procedure used. The enantiomers can be separated by conventional techniques known in the art. Thus the invention covers individual enantiomers as well as mixtures thereof.

For some of the steps of the process of preparation of the compounds of formula (I), it may be necessary to protect potential reactive functions that are not wished to react, and to cleave said protecting groups in consequence. In such a case, any compatible protecting radical can be used. In particular methods of protection and deprotection such as those described by T. W. GREENE (Protective Groups in Organic Synthesis, A. Wiley-Interscience Publication, 1981) or by P. J. Kocienski (Protecting groups, Georg Thieme Verlag, 1994), can be used. All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of the present invention as well as intermediates for the preparation thereof can be purified according to various well-known methods, such as for example crystallization or chromatography.

The method of treatment or the compound for use in the treatment of cancer, lymphoma, leukemia or immunological diseases as defined hereinbefore may be applied as a sole therapy or be a combination therapy with an additional active agent.

The method of treatment or the compound for use in the treatment of cancer, lymphoma or leukemia may involve, in addition to the compound of the invention, conventional surgery or radiotherapy or chemotherapy. Such chemotherapy may include one or more of the following categories of anti-tumor agents:
(i) antiproliferative/antineoplastic drugs and combinations thereof, such as alkylating agents (for example cis-platin, oxaliplatin, carboplatin, cyclophosphamide, nitrogen mustard, bendamustin, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, pemetrexed, cytosine arabinoside, and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin);
(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;
(iii) anti-invasion agents, for example dasatinib and bosutinib (SKI-606), and metalloproteinase inhibitors, inhibitors of urokinase plasminogen activator receptor function or antibodies to Heparanase;
(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); and toll-like receptor modulators for example TLR-7 or TLR-9 agonists; and (viii) cytotoxic agents for example fludaribine (fludara), cladribine, pentostatin (Nipent™);

(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd inhibitors, for example idelalisib and perifosine.

The method of treatment or the compound for use in the treatment of immunological diseases may involve, in addition to the compound of the invention, additional active agents. The additional active agents may be one or more active agents used to treat the condition being treated by the compound of formula (I) and additional active agent. The additional active agents may include one or more of the following active agents:—

(i) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(ii) TNF inhibitors for example etanercept; monoclonal antibodies (e.g. infliximab (Remicade), adalimumab (Humira), certolizumab pegol (Cimzia), golimumab (Simponi)); fusion proteins (e.g. etanercept (Enbrel)); and 5-HT$_{2A}$ agonists (e.g. 2,5-dimethoxy-4-iodoamphetamine, TCB-2, lysergic acid diethylamide (LSD), lysergic acid dimethylazetidide);

(iii) anti-inflammatory drugs, for example non-steroidal anti-inflammatory drugs;

(iv) dihydrofolate reductase inhibitors/antifolates, for example methotrexate, trimethoprim, brodimoprim, tetroxoprim, iclaprim, pemetrexed, ralitrexed and pralatrexate; and (v) immunosuppressants for example cyclosporins, tacrolimus, sirolimus pimecrolimus, angiotensin II inhibitors (e.g. Valsartan, Telmisartan, Losartan, Irbesatan, Azilsartan, Olmesartan, Candesartan, Eprosartan) and ACE inhibitors e.g. sulfhydryl-containing agents (e.g. Captopril, Zofenopril), dicarboxylate-containing agents (e.g. Enalapril, Ramipril, Quinapril, Perindopril, Lisinopril, Benazepril, Imidapril, Zofenopril, Trandolapril), phosphate-containing agents (e.g. Fosinopril), casokinins, lactokinins and lactotripeptides.

Such combination treatment may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

According to a further aspect of the invention there is provided a pharmaceutical product comprising a compound of formula (I), or a pharmaceutically acceptable salt thereof as defined hereinbefore and an additional active agent. The additional active agent may be an anti-tumour agent as defined hereinbefore for the combination treatment of a condition modulated by BTK.

According to a further aspect of the invention there is provided a method of treatment a condition modulated by BTK comprising administering a therapeutically effective amount of a compound of formula (I), or a pharmaceutically acceptable salt thereof simultaneously, sequentially or separately with an additional anti-tumor agent, as defined hereinbefore, to a patient in need thereof.

According to a further aspect of the invention there is provided a compound of formula (I), or a pharmaceutically acceptable salt thereof for use simultaneously, sequentially or separately with an additional anti-tumour agent as defined hereinbefore, in the treatment of a condition modulated by BTK.

According to another aspect of the invention there is provided a use of the compound of formula (I) in combination with an anti-tumor agent as hereinbefore described. The compound of formula (I) may be used simultaneously, sequentially or separately with the additional anti-tumor agent The use may be in a single combination product comprising the compound of formula (I) and the anti-tumor agent.

According to a further aspect there is provided a method of providing a combination product, wherein the method comprises providing a compound of formula (I) simultaneously, sequentially or separately with an anti-tumor agent, as defined hereinbefore. The method may comprise combining the compound of formula (I) and the anti-tumor agent in a single dosage form. Alternatively the method may comprise providing the anti-tumor agent as separate dosage forms.

According to a further aspect there is provided a method of providing a combination product, wherein the method comprises providing a compound of formula (I) simultaneously, sequentially or separately with an anti-tumor agent, as defined hereinbefore. The method may comprise combining the compound of formula (I) and the anti-tumor agent in a single dosage form. Alternatively the method may comprise providing the anti-tumor agent as separate dosage forms.

The condition modulated by BTK described above may be cancer, leukemia or cancer. More specifically the condition modulated by BTK may be selected from: B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia and multiple myeloma.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered orally, then the daily dosage of the compound of the invention may be in the range from 0.01 micrograms per kilogram body weight (μg/kg) to 100 milligrams per kilogram body weight (mg/kg).

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); by rectal administration in the form of suppositories; or by inhalation in the form of an aerosol.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For intravenous (parenteral) administration the compounds of the invention may be administered as a sterile aqueous or oily solution.

The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and co-morbid medical conditions of the patient. The standard duration of treatment with compounds of the invention is expected to vary between one and seven days for most clinical indications. It may be necessary to extend the duration of treatment beyond seven days in instances of recurrent infections or infections associated with tissues or implanted materials to which there is poor blood supply including bones/joints, respiratory tract, endocardium, and dental tissues.

EXAMPLES AND SYNTHESIS

As used herein the following terms have the meanings given: "Boc" refers to tert-butoxycarbonyl; "DCM" refers to dichloromethane; "DIPEA" refers to N,N-Diisopropylethylamine; "LCMS" refers to liquid chromatography/mass spectrometry; "MIM" refers to monoisotopic mass; "min" refers to minutes; "NMP" refers to N-methylpyrrolidinone; "TLC" refers to thin layer chromatography; "Rf" refers to Retention factor; "RT" refers to retention time; "SCX" refers to strong cation exchange; "TFA" refers to trifluoroacetic acid; "THF" refers to tetrahydrofuran; and "TBME" refers to tert-Butyl methyl ether.

Solvents, reagents and starting materials were purchased from commercial vendors and used as received unless otherwise described. All reactions were performed at room temperature unless otherwise stated.

Compound identity and purity confirmations were performed by LCMS UV using a Waters Acquity SQ Detector 2 (ACQ-SQD2#LCA081). The diode array detector wavelength was 254 nM and the MS was in positive and negative electrospray mode (m z: 150-800). A 2 µL aliquot was injected onto a guard column (0.2 µm×2 mm filters) and UPLC column (C18, 50×2.1 mm, <2 µm) in sequence maintained at 40° C. The samples were eluted at a flow rate of 0.6 mL/min with a mobile phase system composed of A (0.1% (v/v) Formic Acid in Water) and B (0.1% (v/v) Formic Acid in Acetonitrile) according to the gradients outlined in Table 1 below. Retention times RT are reported in minutes.

TABLE 1

| Time (min) | % A | % B |
|---|---|---|
| Long Acidic | | |
| 0 | 95 | 5 |
| 1.1 | 95 | 5 |
| 6.1 | 5 | 95 |
| 7 | 5 | 95 |
| 7.5 | 95 | 5 |
| 8 | 95 | 5 |
| Short acidic | | |
| 0 | 95 | 5 |
| 0.3 | 95 | 5 |
| 2 | 5 | 95 |
| 2.6 | 95 | 5 |
| 3 | 95 | 5 |

Compound identity confirmations were also performed by LCMS UV using a Waters Alliance 2695 micromass ZQ (K98SM4 512M-LAA434). The diode array detector wavelength was 254 nM and the MS was in positive and negative electrospray mode (m/z: 150-650). A 10 µL aliquot was injected onto an HPLC column (C18, 75×4.6 mm, 2.5 µm) at room temperature which was controlled at 19° C. The samples were eluted at a flow rate of 0.9 mL/min with a mobile phase system composed of A (0.1% (v/v) Formic Acid in 95:5 (v/v) Water: Acetonitrile) and B (0.1% (v/v) Formic Acid in 95:5 (v/v) Acetonitrile: Water) according to the gradients outlined in Table 2 below. Retention times RT are reported in minutes.

TABLE 2

| Time (min) | % A | % B |
|---|---|---|
| Method 1 | | |
| 0 | 100 | 0 |
| 5.5 | 0 | 100 |
| 6.0 | 5 | 100 |
| 6.5 | 100 | 0 |
| 7 | 100 | 0 |

Compound identity and purity confirmations were performed by LCMS UV using a Waters Alliance 2790 Micromass ZQ (C00SM0 019M LAB 1923). The diode array detector wavelength was 254 nM and the MS was in positive and negative electrospray mode (m/z: 100-850). A 10 µL aliquot was injected onto an HPLC column (C18, 50×2.0 mm, 5 µm) at room temperature (20° C.). The samples were eluted at a flow rate of 0.8 mL/min with a mobile phase system composed of A (HPLC-grade Water); B (0.1% (HPLC-grade Acetonitrile); C (1.0% (v/v) Formic Acid in 50:50 (v/v) Water:Acetonitrile) and D (1.0% (v/v) Ammonia in 50:50 (v/v) Water:Acetonitrile) according to the gradients outlined in Table 3 below. Retention times RT are reported in minutes.

TABLE 3

| Time (min) | % A | % B | % C | % D |
|---|---|---|---|---|
| Method 2 (5 minute acidic) | | | | |
| 0 | 90 | 5 | 5 | 0 |
| 4.0 | 0 | 95 | 5 | 0 |
| 4.49 | 0 | 95 | 5 | 0 |
| 4.5 | 95 | 5 | 0 | 0 |
| Method 3 (7 minute acidic) | | | | |
| 0 | 90 | 5 | 5 | 0 |
| 0.5 | 90 | 5 | 5 | 0 |
| 5.0 | 0 | 95 | 5 | 0 |
| 5.49 | 0 | 95 | 5 | 0 |
| 6.0 | 90 | 10 | 0 | 0 |
| 7.0 | 90 | 10 | 0 | 0 |
| Method 4 (15 minute acidic) | | | | |
| 0 | 95 | 0 | 5 | 0 |
| 2.0 | 95 | 0 | 5 | 0 |
| 12.0 | 0 | 95 | 5 | 0 |
| 14.0 | 0 | 95 | 5 | 0 |
| 14.1 | 95 | 0 | 5 | 0 |

NMR was also used to characterise final compounds. NMR spectra were obtained on a Bruker AVIII 400 Nanobay with 5 mm BBFO probe. Optionally, compound Rf values on silica thin layer chromatography (TLC) plates were measured.

Compound purification was performed by flash column chromatography on silica or by preparative LCMS. LCMS purification was performed using a Waters 3100 Mass detector in positive and negative electrospray mode (m/z: 150-800) with a Waters 2489 UV/Vis detector. Samples were eluted at a flow rate of 20 mL/min on a XBridge™ prep C18 5 µM OBD 19×100 mm column with a mobile phase system composed of A (0.1% (v/v) Formic Acid in Water) and B (0.1% (v/v) Formic Acid in Acetonitrile) according to the gradient outlined in Table 4 below.

TABLE 4

| Time (min) | % A | % B |
|---|---|---|
| 0 | 90 | 10 |
| 1.5 | 90 | 10 |
| 11.7 | 5 | 95 |

TABLE 4-continued

| Time (min) | % A | % B |
|---|---|---|
| 13.7 | 5 | 95 |
| 14 | 90 | 90 |
| 15 | 90 | 90 |

Chemical names in this document were generated using mol2nam-Structure to Name Conversion by OpenEye Scientific Software. Starting materials were purchased from commercial sources or synthesised according to literature procedures.

General Procedures

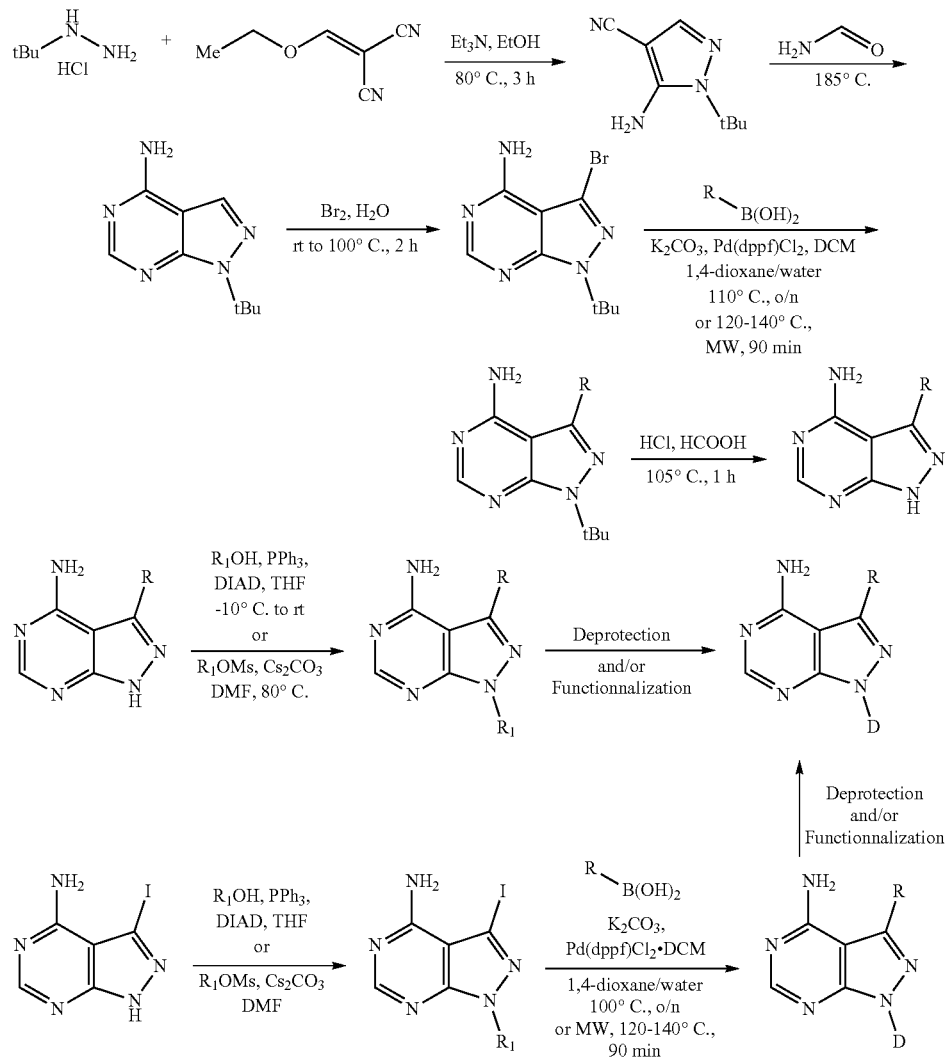

General Procedure A

To a suspension of 4-(aminomethyl)phenyl]boronic acid hydrochloride (1.1 eq.) and the corresponding benzoic acid (1.0 eq.) in anhydrous THE (0.49 M), under a nitrogen atmosphere, was added successively, N,N-diisopropylethylamine (5.0 eq.) and propylphosphonic anhydride (50% wt in EtOAc) (1.5 eq.). The reaction mixture was heated under reflux at 70° C. overnight with stirring. The mixture was diluted with water and DCM, then partitioned. The aqueous layer was extracted with DCM (×2). The combined organic extracts were filtered over a phase separator and concentrated under reduced pressure to afford the desired boronic acid. No further purification was attempted and the product was used directly in the next step.

General Procedure B

To a suspension of 4-(aminomethyl)phenyl]boronic acid hydrochloride (1.0 eq.) and DIPEA (3.0 eq.) in anhydrous THE (0.2 M) under a nitrogen atmosphere was added a solution of the corresponding benzoyl chloride derivative (1.1 eq.) in anhydrous THE (0.2 M). The reaction mixture was stirred overnight at room temperature, quenched with a saturated aqueous solution of ammonium chloride and then extracted into ethyl acetate (×3). The combined organics were washed with brine, dried over $Na_2SO_4$ and filtered then concentrated under reduced pressure to afford the desired boronic acid derivative. No further purification was attempted and the product was used directly in the next step.

General Procedure C

A mixture of halide (1.0 eq.), boronic acid or pinacol ester (1.5 eq.) and potassium carbonate (2.0 eq.) in 1,4-dioxane and water (3:1, 0.1 M) was degassed by bubbling nitrogen through it for 25 min. 1,1′-bis(diphenylphosphino)ferrocene-palladium(II) dichloride dichloromethane complex (0.05 eq.) was added and the mixture was degassed again by bubbling nitrogen through it for 30 min. The mixture was then heated at 120° C. for 14 h. The reaction mixture was filtered over Celite®. The cake was rinsed with DCM. Water was added to the filtrate and the layers were partitioned. The aqueous layer was extracted with DCM (×2). The combined organic extracts were filtered over phase separator and then concentrated under reduced pressure to give a dark solid. Further purification by flash column chromatography (DCM/MeOH 100:0 to 90:10) gave the desired compound.

General Procedure D

A mixture of halide (1.0 eq.), boronic acid or pinacol ester (1.5 eq.) and potassium carbonate (2.0 eq.) in 1,4-dioxane and water (3:1, 0.1 M) was degassed by bubbling nitrogen through it for 15 min. 1,1'-bis(diphenylphosphino)ferrocene-palladium(II) dichloride dichloromethane complex (0.05 eq.) was added and the mixture was degassed again by bubbling nitrogen through it for 15 min. The mixture was then heated under microwave irradiation at 120-140 OC for 60-90 min. The reaction mixture was either purified by SCX SPE cartridge and used as such or purified using the following procedure, unless stated used crude. The mixture filtered over Celite®. The cake was rinsed with DCM. Water was added to the filtrate and the layers were partitioned. The aqueous layer was extracted with DCM (×2). The combined organic extracts were filtered over phase separator and then concentrated under reduced pressure to give a dark solid. Further purification by flash column chromatography gave the desired compound.

General Procedure E

A mixture of tert-butyl derivative (1.0 eq), formic acid (285.0 eq) and concentrated hydrochloric acid (44 eq) was heated to reflux and stirred for 90 min. Upon completion, the reaction mixture was cooled to room temperature and concentrated to dryness. The resulting residue was purified by SCX SPE cartridge to give the desired compound.

General Procedure F

To a suspension of amine (1.0 eq.) and acid (1.0 eq.) in anhydrous THF (0.3 M) were added successively N,N-diisopropylethylamine (3.0 eq.) and propylphosphonic anhydride (1.5 eq.). The reaction mixture was stirred overnight at room temperature, diluted with water and DCM. The layers were partitioned. The aqueous layer was extracted with DCM (×2). The combined organic extracts were filtered over phase separator and concentrated to give a foam. Further purification by flash column chromatography on silica gel gave the title compound.

General Procedure G

To a suspension of nucleophile (1.0 eq), corresponding alcohol (1.7 eq) and triphenylphosphine (1.7 eq) in anhydrous THF (0.18 M), cooled to −10° C., was added diisopropyl azodicarboxylate (1.7 eq) dropwise while keeping the internal temperature below −8° C. The reaction mixture was allowed to return to room temperature over 30 min, stirred overnight and then concentrated under reduced pressure. Further purification by flash column chromatography (EtOAc/MeOH 100:0 to 80:20) afforded the desired product.

General Procedure H

To a solution of acetyl derivative (1.0 eq) in anhydrous MeOH (0.05 M), at room temperature under a $N_2$ atmosphere, was added a 30% sodium methoxide solution in MeOH (2.0 eq). The reaction mixture was stirred for 30 min, partitioned between EtOAc and water. The aqueous layer was extracted with EtOAc. The combined organic extracts were dried over $Na_2SO_4$ and concentrated under vacuum to give the desired product.

General Procedure I

A solution of pivalate derivative (1.0 eq) in DCM (0.03 M) under nitrogen was treated with 1 M diisobutylaluminium hydride in heptane (2.0 eq) at −78° C. The reaction was stirred for 1 h before being quenched with MeOH (5 mL) and evaporated in vacuo. The crude material was purified by flash column chromatography (EtOAc/MeOH 100:0 to 60:40) to give the desired product.

General Procedure J

To a solution of potassium hydroxide (6.0 eq) in a DMSO/water mixture (1 M, 4:1) was added a solution of pivalate derivative (1.0 eq) in a DMSO/water mixture (0.03 M, 4:1). The reaction mixture was heated to 80° C. and stirred for 15 min, cooled to room temperature and then partitioned between DCM and water. The aqueous layer was extracted with DCM. The combined organic extracts were dried over $Na_2SO_4$ and concentrated under vacuum. The crude material was purified by flash column chromatography on silica gel to give the desired product.

General Procedure K

A mixture of halide derivative (1.0 eq.), Molander salt (1.0 eq.), cesium carbonate (3.0 eq.) and XPhos (0.1 eq) in THF and water (10:1, 0.14 M) was degassed by bubbling nitrogen through it for 15 min. Palladium acetate (0.05 eq.) was then added and the mixture was degassed again by bubbling nitrogen through it for 5 min. The mixture was then heated to 85° C. for 16 h, filtered over Celite®. The cake was rinsed with DCM. Water was added to the filtrate and the layers were partitioned. The aqueous layer was extracted with DCM (×2). The combined organic extracts were filtered over phase separator and then concentrated under reduced pressure. Further purification by flash column chromatography on silica gel gave the desired compound.

General Procedure L

To a stirred solution of alcohol (1.0 eq) in DCM (0.9 M), cooled at 0° C. under a nitrogen atmosphere, was added triethylamine (1.1 eq). The resulting solution was left to stir for 10 minutes before adding dropwise methanesulfonyl chloride (1.1 eq). The reaction mixture was stirred at 0° C. for 1 h, quenched with water, and extracted with DCM (×2). The combined organic extracts were filtered over a phase separator and concentrated under reduced pressure to afford the desired mesylated product.

General Procedure M

A mixture of 3-iodo-1H-pyrazolo[3,4-d]pyrimidin-4-amine (1.0 eq), mesylated alcohol (1.2 eq), and cesium carbonate (2.5 eq) in DMF (0.2 M) was heated to 80° C. and stirred for 16 h. Once cooled, the reaction mixture was concentrated under reduced pressure to leave a brown residue. EtOAc was added and the mixture was then sonicated then filtered. The filtrate was washed with water (×2) then brine (×2), dried over $Na_2SO_4$ and concentrated under vacuum. Further purification by flash column chromatography on silica gel afforded the desired compound.

General Procedure N

To a nitrogen degassed solution of potassium acetate (3.0 eq), bis(pinacolato)diboron (1.5 eq) and halide derivative (1.0 eq) in 1,4-dioxane (0.12 M) was added 1,1'-bis(diphenylphosphino)ferrocene-palladium(II) dichloride dichloromethane complex (0.05 eq). The reaction mixture was then degassed with nitrogen for a further 5 min and then the reaction mixture was allowed to stir at 90° C. until completion of the reaction. Once cooled, the mixture was filtered through Celite®. Water was added to the filtrate and the mixture was partitioned. The aqueous layer was extracted with ethyl acetate (×3). The combined organic layers were washed with brine, dried over sodium sulfate, filtered and all volatiles were removed under reduced pressure. The resulting residue was either used crude or further purified by flash column chromatography on silica gel (EtOAc/MeOH 100:0 to 90:10) to afford the desired pinacol ester.

General Procedure O

A solution of acid (1.1 eq.), 1-hydroxybenzotriazole hydrate (1.1 eq.) and N-(3-dimethylaminopropyl)-N'-ethylcarbodiimide hydrochloride (1.1 eq.) in DMF (0.5 M) was stirred at room temperature for 30 min and then treated with the corresponding amine (1.0 eq.), followed by triethylamine (5.0 eq.). The reaction mixture was then stirred at room temperature for 18 h, poured into brine and extracted with ethyl acetate. The organic layer was washed with 0.2 M aq HCl and brine. The organic layer was then dried, filtered and the solvent evaporated under reduced pressure to yield the desired crude amide.

General Procedure P

1 M borane THF complex (5.0 eq.) was added dropwise under nitrogen to a stirred solution of nitrile derivative (1.0 eq.) in anhydrous THF (0.10 M). The reaction mixture was then heated at reflux for 4 h before being cooled to room temperature. Methanol was added carefully dropwise until evolution of gas ceased. The solvent was removed under reduced pressure and the residue was dissolved in methanol and treated with conc. aq. HCl. The resultant mixture was heated at reflux for 10 min and then cooled to room temperature. The solvent was removed under reduced pressure and the residue was treated cautiously with excess aq. sodium bicarbonate solution. The resultant suspension was extracted with ethyl acetate and the organic layer was dried, filtered and evaporated under reduced pressure to yield the corresponding amine.

General Procedure Q

To a solution of cobalt (II) chloride (1 eq.) and nitrile derivative (1 eq.) in anhydrous MeOH (0.05 M), cooled to 0° C. under a nitrogen atmosphere, was added sodium borohydride (10 eq) portion wise over 10 min. The reaction mixture was then stirred for 20 min at 0° C. and then stirred for a further 60 min at room temperature, quenched with an aqueous solution of ammonium chloride, and allowed to stand overnight. Most of methanol was removed under reduced pressure and the remaining aqueous mixture was diluted with water and washed with Et$_2$O (×2). The aqueous layer was basified to pH=12 with 1 M NaOH and extracted with CHCl$_3$ (×3). The combined organics were dried (phase separator) and concentrated to give the desired amine.

General Procedure R

A mixture of halide (1 eq.), bis(pinacolato)diboron (1.25 eq.) and potassium acetate (46 mg, 0.47 mmol) in anhydrous DMSO (0.05 M) was degassed with nitrogen for 10 min and then treated with [1,1'-bis(diphenylphosphino)ferrocene]palladium(II) chloride dichloromethane complex (0.13 eq). The reaction mixture was heated under nitrogen at 120° C. for 30 min and then cooled to room temperature. The mixture was partitioned between ethyl acetate and brine. The organic layer was washed with brine (×2), dried over sodium sulfate, filtered and concentrated under reduced pressure to yield to the corresponding product.

General Procedure S

To a stirred solution of pyrazole-4-carbonitrile (1.0 eq.) and formamidine acetate (10.0 eq.) in ethanol (0.4 M), N,N-diisopropylethylamine (10.0 eq.) was added. The reaction mixture was heated to 110° C. for 16 h. The mixture was cooled to room temperature and the volatiles removed under reduced pressure. The residue was suspended in EtOAc and washed with water, a saturated aqueous solution of ammonium chloride and brine. The organic layer was dried over sodium sulfate, filtered and concentrated under reduced pressure. Further purification by flash column chromatography on silica gel gave the desired compound.

5-Amino-1-tert-butyl-pyrazole-4-carbonitrile

To a suspension of tert-butylhydrazine hydrochloride (15.0 g, 120.4 mmol) in ethanol (600 mL) was added triethylamine (16.8 mL, 120.4 mmol). The mixture was stirred for 60 min until the hydrazine had dissolved. Ethoxymethylenemalononitrile (14.7 g, 120.4 mmol) was added in portions and the reaction mixture was heated to 80° C. and stirred at this temperature overnight. The reaction mixture was concentrated to dryness and the obtained residue was taken up in EtOAc. The organic layer was washed with water, dried over Na$_2$SO$_4$, filtered and concentrated under reduced pressure. The solid was then recrystallized in DCM to afford 5-amino-1-tert-butyl-pyrazole-4-carbonitrile (18.6 g, 113.4 mmol, 94% yield) as a light yellow solid.

LC-MS (ES$^+$, method 1): 1.36 min, m/z 165.1 [M+H]$^+$ 1-tert-Butylpyrazolo[3,4-d]pyrimidin-4-amine A solution of 5-amino-1-tert-butyl-pyrazole-4-carbonitrile (18.0 g, 0.11 mol) in formamide (131 mL, 3.29 mol) was stirred at 185° C. overnight. Subsequently, the reaction mixture was cooled to room temperature, water was added and the aqueous phase was extracted with EtOAc. The combined organics were washed with sat. NaHCO$_3$ solution, dried over Na$_2$SO$_4$, filtered and concentrated in vacuo. The obtained crude product was recrystallized in DCM to afford 1-tert-butylpyrazolo[3,4-d]pyrimidin-4-amine (12.3 g, 64.3 mmol, 59% yield) as a white solid.

UPLC-MS (ES$^+$, Short acidic): 1.04 min, m/z 192.0 [M+H]$^+$

3-Bromo-1-tert-butyl-pyrazolo[3,4-d]pyrimidin-4-amine

To a suspension of 1-tert-butylpyrazolo[3,4-d]pyrimidin-4-amine (7.65 g, 40.0 mmol) in water (200 mL) was added bromine (4.10 mL, 80.0 mmol) dropwise and the reaction mixture was stirred for 1 h at 100° C. The reaction mixture was cooled to room temperature and filtered. The obtained solid was suspended in saturated aqueous Na$_2$S$_2$O$_3$ solution and stirred for 1.5 h. A saturated NaHCO$_3$ solution was added and the precipitate was collected by filtration and subsequently washed with EtOAc. The filtrate was washed with water and brine, dried over Na$_2$SO$_4$, filtrated and concentrated under reduced pressure. The obtained solid was recrystallized in DCM to afford 3-bromo-1-tert-butyl-pyrazolo[3,4-d]pyrimidin-4-amine (7.74 g, 28.7 mmol, 72% yield) as a pale yellow solid.

UPLC-MS (ES$^+$, Short acidic): 1.46 min, m/z 272.0 [M+2]$^+$

1-Cyclopentyl-3-iodo-pyrazolo[3,4-d]pyrimidin-4-amine

Potassium carbonate (4.66 g, 33.71 mmol) and bromocyclopentane (3.6 mL, 33.71 mmol) were added to a solution of 3-iodo-1H-pyrazolo[3,4-d]pyrimidin-4-amine (8.00 g, 30.65 mmol) in DMF (300 mL) at room temperature. The resulting mixture was left to stir at 80° C. overnight, diluted with water (500 mL), extracted with DCM (3×300 mL), and washed with saturated brine (200 mL) solution. The combined organic extracts was dried over Na$_2$SO$_4$, filtered and concentrated under reduced pressure. Further purification by flash column chromatography (DCM/MeOH 100:0 to 95:5) followed trituration with methanol afforded 1-cyclopentyl-3-iodo-pyrazolo[3,4-d]pyrimidin-4-amine (2.20 g, 5.90 mmol, 19% yield) as a white solid.

UPLC-MS (ES+, Short acidic): 1.45 min, m/z 330.0 [M+H]+

Example 1: N-[[4-(4-amino-1-cyclopentyl-pyrazolo[3,4-d]pyrimidin-3-yl)phenyl]methyl]-2-methoxy-benzamide

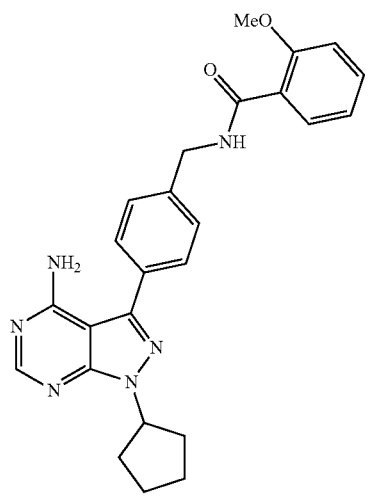

[4-[[(2-Methoxybenzoyl)amino]methyl]phenyl]boronic acid

Following general procedure A, 2-methoxybenzoic acid (0.25 mL, 1.76 mmol) and [4-(aminomethyl)phenyl]boronic acid hydrochloride (300 mg, 1.60 mmol) afforded the title compound (370 mg, 1.3 mmol, 81% yield).

UPLC-MS (ES+, Short acidic): 1.31 min, m/z 285.9 [M+H]+

N-[[4-(4-Amino-1-cyclopentyl-pyrazolo[3,4-d]pyrimidin-3-yl)phenyl]methyl]-2-methoxy-benzamide Following general procedure D, 1-cyclopentyl-3-iodo-pyrazolo[3,4-d]pyrimidin-4-amine (80 mg, 0.24 mmol) and [4-[[(2-methoxybenzoyl)amino]methyl]phenyl]boronic acid (104 mg, 0.36 mmol) afforded, after purification by mass-directed semi-preparative HPLC, N-[[4-(4-amino-1-cyclopentyl-pyrazolo[3,4-d]pyrimidin-3-yl)phenyl]methyl]-2-methoxy-benzamide (70 mg, 0.15 mmol, 63% yield) as a white solid.

UPLC-MS (ES+, Short acidic): 1.55 min, m/z 443.5 [M+H]+

UPLC-MS (ES+, Long acidic): 3.50 min, m/z 443.4 [M+H]+

$^1$H NMR (400 MHz, DMSO-$d_6$, δ): 8.77 (t, J=6.1 Hz, 1H), 8.24 (s, 1H), 7.77 (dd, J=7.6, 1.9 Hz, 1H), 7.64 (d, J=8.3 Hz, 2H), 7.52-7.47 (m, 3H), 7.17 (d, J=7.6 Hz, 1H), 7.05 (t, J=6.8 Hz, 1H), 5.29-5-19 (m, 1H), 4.59 (d, J=6.1 Hz, 2H), 3.92 (s, 3H), 2.15-2.00 (m, 4H), 1.94-1.85 (m, 2H), 1.75-1.67 (m, 2H).

Example 2: N-[[4-(4-amino-1-cyclopentyl-pyrazolo[3,4-d]pyrimidin-3-yl)phenyl]methyl]-2-fluoro-benzamide

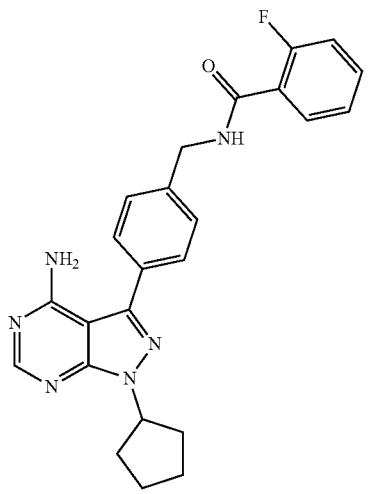 [SMILES: Nc1ncnc2c1c(-c1ccc(CNC(=O)c3ccccc3F)cc1)nn2C1CCCC1]

[4-[[(2-Fluorobenzoyl)amino]methyl]phenyl]boronic acid

Following general procedure A, 2-fluorobenzoic acid (183 mg, 1.30 mmol) and [4-(aminomethyl)phenyl]boronic acid hydrochloride (269 mg, 1.43 mmol) afforded crude [4-[[(2-fluorobenzoyl)amino]methyl]phenyl]boronic acid (237 mg, 0.87 mmol, 67% yield).

UPLC-MS (ES+, Short acidic): 1.25 min, m/z 274.1 [M+H]+

N-[[4-(4-Amino-1-cyclopentyl-pyrazolo[3,4-d]pyrimidin-3-yl)phenyl]methyl]-2-fluoro-benzamide Following general procedure D, 1-cyclopentyl-3-iodo-pyrazolo[3,4-d]pyrimidin-4-amine (80 mg, 0.24 mmol) and [4-[[(2-fluorobenzoyl)amino]methyl]phenyl]boronic acid (100 mg, 0.36 mmol) afforded, after purification by mass-directed semi-preparative HPLC, N-[[4-(4-amino-1-cyclopentyl-pyrazolo[3,4-d]pyrimidin-3-yl)phenyl]methyl]-2-fluoro-benzamide (29 mg, 0.07 mmol, 28% yield) as a white solid.

UPLC-MS (ES+, Short acidic): 1.53 min, m/z 431.4 [M+H]+

UPLC-MS (ES+, Long acidic): 3.48 min, m/z 431.3 [M+H]+

$^1$H NMR (400 MHz, DMSO-$d_6$, δ): 8.95 (t, J=6.1 Hz, 1H), 8.24 (s, 1H), 7.71-7.64 (m, 3H), 7.59-7.50 (m, 3H), 7.35-7.29 (m, 2H), 5.29-5-19 (m, 1H), 4.56 (d, J=6.1 Hz, 2H), 2.15-2.00 (m, 4H), 1.95-1.85 (m, 2H), 1.74-1.64 (m, 2H).

Example 3: N-[[4-(4-Amino-1-cyclopentyl-pyrazolo[3,4-d]pyrimidin-3-yl)phenyl]methyl]-2,5-difluoro-benzamide

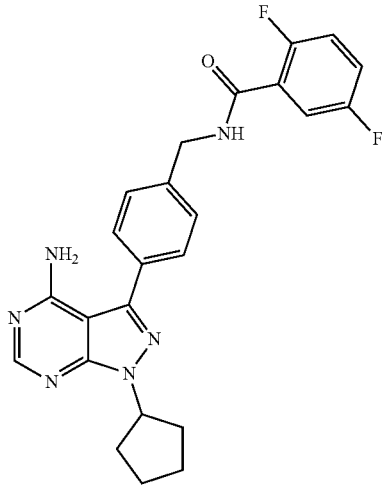 [SMILES: Nc1ncnc2c1c(-c1ccc(CNC(=O)c3cc(F)ccc3F)cc1)nn2C1CCCC1]

[4-[[(2,5-Difluorobenzoyl)amino]methyl]phenyl]boronic acid

Following general procedure B, a mixture of 2,5-difluorobenzoyl chloride (0.75 mL, 6.03 mmol) and [4-(aminomethyl)phenyl]boronic acid hydrochloride (1.03 g, 5.48 mmol) afforded [4-[[(2,5-difluorobenzoyl)amino]methyl]phenyl]boronic acid (1.46 g, 5.03 mmol, 92% yield) as an off-white solid.

UPLC-MS (ES+, Short acidic): 1.34 min, m/z 292.1 [M+H]+

N-[[4-(4-Amino-1-cyclopentyl-pyrazolo[3,4-d]pyrimidin-3-yl)phenyl]methyl]-2,5-difluoro-benzamide Following general procedure D, 1-cyclopentyl-3-iodo-pyrazolo[3,4-d]pyrimidin-4-amine (80 mg, 0.24 mmol) and [4-[[(2,5-difluorobenzoyl)amino]methyl]phenyl]boronic acid (106 mg, 0.36 mmol) afforded, after purification by mass-directed semi-preparative HPLC, N-[[4-(4-amino-1-cyclopentyl-pyrazolo[3,4-d]pyrimidin-3-yl)phenyl]methyl]-2,5-difluoro-benzamide (37 mg, 0.08 mmol, 33% yield) as a cream solid.

UPLC-MS (ES+, Short acidic): 1.58 min, m/z 449.3 [M+H]+

UPLC-MS (ES+, Long acidic): 3.59 min, m/z 449.3 [M+H]+

$^1$H NMR (400 MHz, DMSO-$d_6$, δ): 9.05 (t, J=6.0 Hz, 1H), 8.24 (s, 1H), 7.65 (d, J 8.3 Hz, 2H), 7.52-7.47 (m, 3H), 7.46-7.37 (m, 2H), 5.28-5.19 (m, 1H), 4.56 (d, J=6.0 Hz, 2H), 2.15-2.00 (m, 4H), 1.95-1.85 (m, 2H), 1.75-1.64 (m, 2H).

Example 4: N-[[4-(4-Amino-1-cyclopentyl-pyrazolo[3,4-d]pyrimidin-3-yl)phenyl]methyl]-5-fluoro-2-methoxy-benzamide

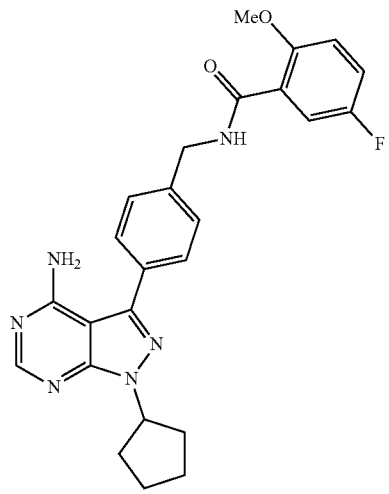 [SMILES: COc1ccc(F)cc1C(=O)NCc1ccc(-c2nn(C3CCCC3)c3ncnc(N)c23)cc1]

[4-[[(5-Fluoro-2-methoxy-benzoyl)amino]methyl]phenyl]boronic acid

Following general procedure A, a solution of 5-fluoro-2-methoxybenzoic acid (250 mg, 1.47 mmol) and [4-(aminomethyl)phenyl]boronic acid hydrochloride (303 mg, 1.62 mmol) afforded [4-[[(5-fluoro-2-methoxy-benzoyl)amino]methyl]phenyl]boronic acid (106 mg, 0.36 mmol, 24% yield) as a pale yellow solid.

UPLC-MS (ES+, Short acidic): 1.35 min, m/z 303.8 [M+H]+

N-[[4-(4-Amino-1-cyclopentyl-pyrazolo[3,4-d]pyrimidin-3-yl)phenyl]methyl]-5-fluoro-2-methoxy-benzamide Following general procedure D, 1-cyclopentyl-3-iodo-pyrazolo[3,4-d]pyrimidin-4-amine (80 mg, 0.24 mmol) and [4-[[(5-fluoro-2-methoxy-benzoyl)amino]methyl]phenyl]boronic acid (106 mg, 0.36 mmol) afforded, after additional purification by mass-directed semi-preparative HPLC, N-[[4-(4-amino-1-cyclopentyl-pyrazolo[3,4-d]pyrimidin-3-yl)phenyl]methyl]-5-fluoro-2-methoxy-benzamide (19 mg, 0.04 mmol, 17% yield) as a white solid.

UPLC-MS (ES+, Short acidic): 1.66 min, m/z 461.4 [M+H]+

UPLC-MS (ES+, Long acidic): 3.68 min, m/z 461.4 [M+H]+

$^1$H NMR (400 MHz, DMSO-$d_6$, δ): 8.87 (t, J=6.7 Hz, 1H), 8.24 (s, 1H), 7.64 (d, J 8.6 Hz, 2H), 7.55-7.52 (m, 1H), 7.51 (d, J 8.6 Hz, 2H), 7.38-7.32 (m, 1H), 7.20 (dd, J=9.2, 4.3 Hz, 1H), 5.28-5.19 (m, 1H), 4.59 (d, J=6.7 Hz, 2H), 3.91 (s, 3H), 2.15-2.00 (m, 4H), 1.95-1.85 (m, 2H), 1.74-1.64 (m, 2H).

Example 5: N-[[4-(4-amino-1-tetrahydrofuran-2-yl-pyrazolo[3,4-d]pyrimidin-3-yl)phenyl]methyl]-2-methoxy-benzamide

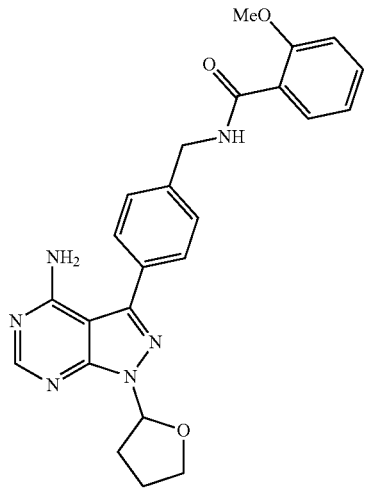 [SMILES: COc1ccccc1C(=O)NCc1ccc(-c2nn(C3CCCO3)c3ncnc(N)c23)cc1]

N-[[4-(4-Amino-1H-pyrazolo[3,4-d]pyrimidin-3-yl)phenyl]methyl]-2-methoxy-benzamide Following general procedure D, 3-iodo-1H-pyrazolo[3,4-d]pyrimidin-4-amine (2.61 g, 10.0 mmol) and [4-[[(2-methoxybenzoyl)amino]methyl]phenyl]boronic acid (4.28 g, 15.0 mmol) afforded the title compound (286 mg, 0.76 mmol, 8% yield) as a light brown solid.

LC-MS (ES$^+$, method 1): 1.14 min, m/z 375.1 [M+H]$^+$

N-[[4-(4-Amino-1-tetrahydrofuran-2-yl-pyrazolo[3,4-d]pyrimidin-3-yl)phenyl]methyl]-2-methoxy-benzamide To a solution of N-[[4-(4-amino-1H-pyrazolo[3,4-d]pyrimidin-3-yl)phenyl]methyl]-2-methoxy-benzamide (50 mg, 0.13 mmol) in dihydrofuran (0.5 mL, 6.68 mmol) was added p-toluenesulfonic acid (12 mg, 0.07 mmol). The reaction mixture was stirred for 5 minutes and subsequently quenched with water. The suspension was extracted into ethyl acetate and washed with water and brine. The organic phase was dried over Na$_2$SO$_4$, filtered and concentrated in vacuo. Further purification by flash column chromatography (EtOAc 100%) afforded N-[[4-(4-amino-1-tetrahydrofuran-2-yl-pyrazolo[3,4-d]pyrimidin-3-yl)phenyl]methyl]-2-methoxy-benzamide (8 mg, 0.02 mmol, 13% yield) as a colourless solid.

UPLC-MS (ES$^+$, Short acidic): 1.45 min, m/z 445.3 [M+H]$^+$

UPLC-MS (ES$^+$, Long acidic): 3.19 min, m/z 445.5 [M+H]$^+$ $^1$H NMR (400 MHz, DMSO-d$_6$, δ): 8.77 (t, J=6.1 Hz, 1H), 8.26 (s, 1H), 7.77 (dd, J=7.7, 1.7 Hz, 1H), 7.67-7.61 (m, 2H), 7.51 (d, J=8.5 Hz, 2H), 7.50-7.45 (m, 1H), 7.15 (dd, J=8.5, 1.0 Hz, 1H), 7.04 (dt, J=7.7, 1.0 Hz, 1H), 6.55 (dd, J=7.0, 3.3 Hz, 1H), 4.58 (d, J=6.1 Hz, 2H), 4.04-3.97 (m, 1H), 3.91 (s, 3H), 3.89-3.84 (m, 1H), 2.55 (m, 1H), 2.45-2.30 (m, 2H), 2.05-1.99 (m, 1H).

Example 6: N-[[4-(4-Amino-1-cyclopentyl-pyrazolo[3,4-d]pyrimidin-3-yl)phenyl]methyl]-2-(trifluoromethoxy)benzamide

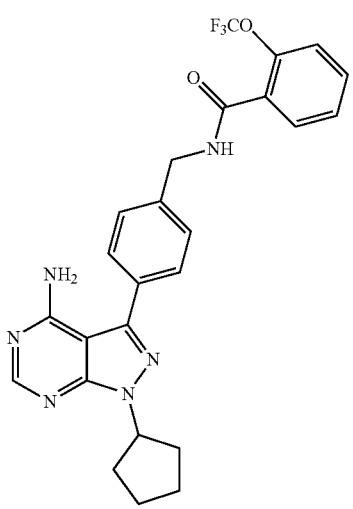

[4-[[[2-(Trifluoromethoxy)benzoyl]amino]methyl]phenyl]boronic acid

Following general procedure A, [4-(aminomethyl)phenyl]boronic acid hydrochloride (300 mg, 1.60 mmol) and 2-(trifluoromethoxy)benzoyl chloride (395 mg, 1.76 mmol) gave [4-[[[2-(trifluoromethoxy)benzoyl]amino]methyl]phenyl]boronic acid (421 mg, 0.93 mmol, 58% yield) as an off-white solid.

UPLC-MS (ES$^+$, Short acidic): 1.39 min, m/z 339.8 [M]

N-[[4-(4-Amino-1-cyclopentyl-pyrazolo[3,4-d]pyrimidin-3-yl)phenyl]methyl]-2-(trifluoromethoxy)benzamide Following general procedure D, [4-[[[2-(trifluoromethoxy)benzoyl]amino]methyl]phenyl]boronic acid (232 mg, 0.68 mmol) and 1-cyclopentyl-3-iodo-pyrazolo[3,4-d]pyrimidin-4-amine (150 mg, 0.46 mmol) afforded N-[[4-(4-amino-1-cyclopentyl-pyrazolo[3,4-d]pyrimidin-3-yl)phenyl]methyl]-2-(trifluoromethoxy)benzamide (5 mg, 0.01 mmol, 2% yield) as a thin film.

UPLC-MS (ES$^+$, Short acidic): 1.71 min, m/z 497.1 [M+H]$^+$

UPLC-MS (ES$^+$, Long acidic): 3.78 min, m/z 497.1 [M+H]$^+$ $^1$H NMR (400 MHz, DMSO-d$_6$, δ): 9.06 (t, J=6.2 Hz, 1H), 8.25 (s, 1H), 7.65-7.58 (m, 2H), 7.63 (d, J=7.8 Hz, 2H), 7.50 (d, J=7.8 Hz, 2H), 7.51-7.44 (m, 2H), 5.27-5.20 (m, 1H), 4.53 (d, J=6.2 Hz, 2H), 2.12-1.95 (m, 4H), 1.93-1.83 (m, 2H), 1.73-1.62 (m, 2H)

Example 7: N-[[4-(4-amino-1-cyclopentyl-pyrazolo[3,4-d]pyrimidin-3-yl)phenyl]methyl]-2-ethoxy-benzamide

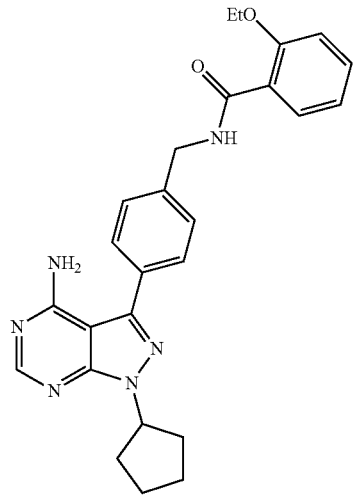

[4-[[(2-Ethoxybenzoyl)amino]methyl]phenyl]boronic acid

Following general procedure B, 2-ethoxybenzoyl chloride (0.27 mL, 1.76 mmol) and [4-(aminomethyl)phenyl]boronic acid hydrochloride (300 mg, 1.60 mmol) afforded crude [4-[[(2-ethoxybenzoyl)amino]methyl]phenyl]boronic acid (472 mg, 1.26 mmol, 79% yield) as a pale yellow solid.

UPLC-MS (ES$^+$, Short acidic): 1.40 min, m/z 299.9 [M+H]$^+$

N-[[4-(4-Amino-1-cyclopentyl-pyrazolo[3,4-d]pyrimidin-3-yl)phenyl]methyl]-2-ethoxy-benzamide Following general procedure D, 1-cyclopentyl-3-iodo-pyrazolo[3,4-d]pyrimidin-4-amine (150 mg, 0.46 mmol) and [4-[[(2-ethoxybenzoyl)amino]methyl]phenyl]boronic acid (205 mg, 0.68 mmol) afforded, after further purification by flash column chromatography (DCM/MeOH 100:0 to 95:5), N-[[4-(4-amino-1-cyclopentyl-pyrazolo[3,4-d]pyrimidin-3-yl)phenyl]methyl]-2-ethoxy-benzamide (137 mg, 0.27 mmol, 59% yield) as a white solid.

UPLC-MS (ES$^+$, Short acidic): 1.65 min, m/z 457.5 [M+H]$^+$

UPLC-MS (ES$^+$, Long acidic): 3.83 min, m/z 457.5 [M+H]$^+$ $^1$H NMR (400 MHz, DMSO-d$_6$, δ): 8.66 (t, J=6.0 Hz, 1H), 8.24 (s, 1H), 7.75 (dd, J=7.7, 1.8 Hz, 1H), 7.66 (d, J=8.3 Hz, 2H), 7.55 (d, J=8.3 Hz, 2H), 7.48-7.44 (m, 1H), 7.15 (d, J=7.7 Hz, 1H), 7.04 (td, J=7.5, 1.0 Hz, 1H), 5.23 (m, 1H), 4.60 (d, J=6.0 Hz, 2H), 4.17 (q, J=7.0 Hz, 2H), 2.14-2.00 (m, 4H), 1.95-1.85 (m, 2H), 1.74-1.64 (m, 2H), 1.37 (t, J=6.9 Hz, 3H).

Example 8: N-[[4-(4-amino-1-cyclopentyl-pyrazolo[3,4-d]pyrimidin-3-yl)phenyl]methyl]-2-isopropoxy-benzamide

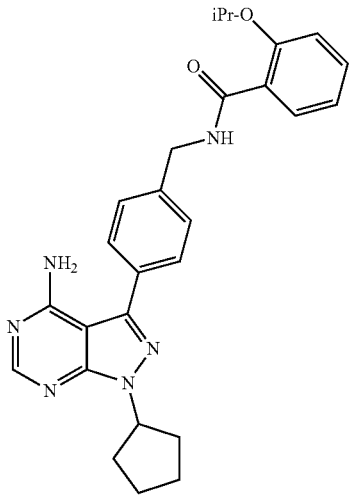

[4-[[(2-Isopropoxbenzol)amino]methyl]phenyl]boronic acid

Following general procedure A, 2-isopropoxybenzoic acid (350 mg, 1.94 mmol) and [4-(aminomethyl)phenyl]boronic acid hydrochloride (400 mg, 2.14 mmol) afforded crude [4-[[(2-isopropoxybenzoyl)amino]methyl]phenyl]boronic acid (378 mg, 1.03 mmol, 53% yield) as a yellow solid.

UPLC-MS (ES$^+$, Short acidic): 1.47 min, m/z 313.9 [M+H]$^+$

N-[[4-(4-Amino-1-cyclopentyl-pyrazolo[3,4-d]pyrimidin-3-yl)phenyl]methyl]-2-isopropoxy-benzamide Following general procedure D, 1-cyclopentyl-3-iodo-pyrazolo[3,4-d]pyrimidin-4-amine (150 mg, 0.46 mmol) and [4-[[(2-isopropoxybenzoyl)amino]methyl]phenyl]boronic acid (214 mg, 0.68 mmol) afforded, after further purification by flash column chromatography (DCM/MeOH 100:0 to 95:5), N-[[4-(4-amino-1-cyclopentyl-pyrazolo[3,4-d]pyrimidin-3-yl)phenyl]methyl]-2-isopropoxy-benzamide (69 mg, 0.13 mmol, 29% yield) as a white solid.

UPLC-MS (ES$^+$, Short acidic): 1.72 min, m/z 471.5 [M+H]$^+$

UPLC-MS (ES$^+$, Long acidic): 3.99 min, m/z 471.5 [M+H]$^+$ $^1$H NMR (400 MHz, DMSO-d$_6$, δ): 8.60 (t, J=6.0 Hz, 1H), 8.24 (s, 1H), 7.76 (dd, J=7.6, 1.8 Hz, 1H), 7.65 (d, J=8.2 Hz, 2H), 7.54 (d, J=8.2 Hz, 2H), 7.48-7.43 (m, 1H), 7.17 (d, J=8.2 Hz, 1H), 7.03 (td, J=7.6, 1.0 Hz, 1H), 5.29-5.18 (m, 1H), 4.81-4.72 (m, 1H), 4.60 (d, J=6.0 Hz, 2H), 2.15-2.00 (m, 4H), 1.95-1.85 (m, 2H), 1.74-1.64 (m, 2H), 1.30 (d, J=6.0 Hz, 6H).

Example 9: N-[[4-(4-amino-1-cyclopentyl-pyrazolo[3,4-d]pyrimidin-3-yl)phenyl]methyl]-4-chloro-2-methoxy-benzamide

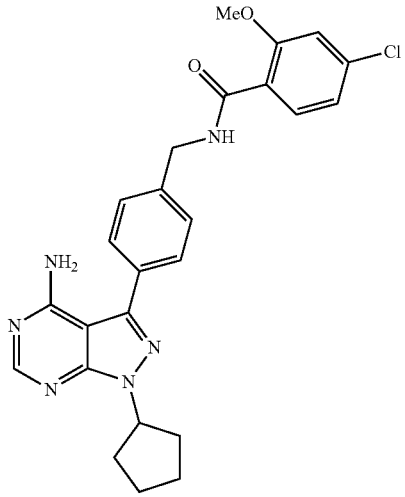 [SMILES: COc1cc(Cl)ccc1C(=O)NCc1ccc(-c2nn(C3CCCC3)c3ncnc(N)c23)cc1]

[4-[[(4-Chloro-2-methoxy-benzoyl)amino]methyl]phenyl]boronic acid

Following general procedure A, 5-fluoro-2-methoxy-benzoic acid (350 mg, 1.88 mmol) and [4-(aminomethyl)phenyl]boronic acid hydrochloride (387 mg, 2.06 mmol) afforded crude [4-[[(4-chloro-2-methoxy-benzoyl)amino]methyl]phenyl]boronic acid (488 mg, 0.99 mmol, 53% yield) as a yellow solid.

UPLC-MS (ES$^+$, Short acidic): 1.45 min, m/z 319.8 [M+H]$^+$

N-[[4-(4-Amino-1-cyclopentyl-pyrazolo[3,4-d]pyrimidin-3-yl)phenyl]methyl]-4-chloro-2-methoxy-benzamide Following general procedure D, 1-cyclopentyl-3-iodo-pyrazolo[3,4-d]pyrimidin-4-amine (150 mg, 0.46 mmol) and [4-[[(4-chloro-2-methoxy-benzoyl)amino]methyl]phenyl]boronic acid (218 mg, 0.68 mmol) afforded, after further purification by flash column chromatography (DCM/MeOH 100:0 to 95:5), N-[[4-(4-amino-1-cyclopentyl-pyrazolo[3,4-d]pyrimidin-3-yl)phenyl]methyl]-4-chloro-2-methoxy-benzamide (150 mg, 0.28 mmol, 62% yield) as a white solid.

UPLC-MS (ES$^+$, Short acidic): 1.67 min, m/z 477.2 [M+H]$^+$

UPLC-MS (ES$^+$, Long acidic): 3.91 min, m/z 477.2 [M+H]$^+$ $^1$H NMR (400 MHz, DMSO-d$_6$, δ): 8.77 (t, J=6.0 Hz, 1H), 8.24 (s, 1H), 7.76 (d, J=8.3, 1H), 7.64 (d, J=8.2 Hz, 2H), 7.50 (d, J=8.2 Hz, 2H), 7.26 (d, J=1.9, 1H), 7.11 (dd, J=8.3, 1.9 Hz, 1H), 5.23 (m, 1H), 4.57 (d, J=6.0 Hz, 2H), 3.94 (s, 3H), 2.14-2.00 (m, 4H), 1.94-1.84 (m, 2H), 1.74-1.64 (m, 2H).

Example 10: N-[[4-(4-amino-1-cyclopentyl-pyrazolo[3,4-d]pyrimidin-3-yl)phenyl]methyl]-2-methoxy-4-methyl-benzamide

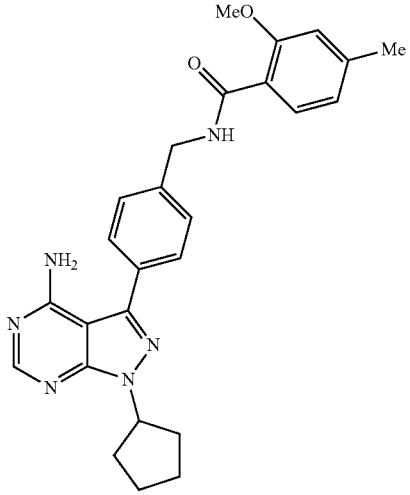 [SMILES: COc1cc(C)ccc1C(=O)NCc1ccc(-c2nn(C3CCCC3)c3ncnc(N)c23)cc1]

[4-[[(2-Methoxy-4-methyl-benzoyl)amino]methyl]phenyl]boronic acid

Following general procedure A, 2-methoxy-4-methylbenzoic acid (300 mg, 1.81 mmol) and [4-(aminomethyl)phenyl]boronic acid hydrochloride (372 mg, 1.99 mmol) afforded crude [4-[[(2-methoxy-4-methyl-benzoyl)amino]methyl]phenyl]boronic acid (379 mg, 1.01 mmol, 56% yield) as a yellow solid.

UPLC-MS (ES$^+$, Short acidic): 1.41 min, m/z 300.0 [M+H]$^+$

N-[[4-(4-Amino-1-cyclopentyl-pyrazolo[3,4-d]pyrimidin-3-yl)phenyl]methyl]-2-methoxy-4-methyl-benzamide Following general procedure D, 1-cyclopentyl-3-iodopyrazolo[3,4-d]pyrimidin-4-amine (150 mg, 0.46 mmol) and [4-[[(2-methoxy-4-methyl-benzoyl)amino]methyl]phenyl]boronic acid (205 mg, 0.68 mmol) afforded, after further purification by flash column chromatography (DCM/MeOH 100:0 to 95:5) and SCX, N-[[4-(4-amino-1-cyclopentyl-pyrazolo[3,4-d]pyrimidin-3-yl)phenyl]methyl]-2-methoxy-4-methyl-benzamide (111 mg, 0.22 mmol, 48% yield) as a white solid.

UPLC-MS (ES$^+$, Short acidic): 1.63 min, m/z 457.4 [M+H]$^+$

UPLC-MS (ES$^+$, Long acidic): 3.79 min, m/z 457.4 [M+H]$^+$ $^1$H NMR (400 MHz, DMSO-d$_6$, δ): 8.69 (t, J=6.1 Hz, 1H), 8.24 (s, 1H), 7.73 (d, J=7.8, 1H), 7.64 (d, J=8.3 Hz, 2H), 7.50 (d, J=8.3 Hz, 2H), 6.99 (s, 1H), 6.86 (d, J=7.8, 1.9 Hz, 1H), 5.29-5.19 (m, 1H), 4.58 (d, J=6.1 Hz, 2H), 3.91 (s, 3H), 2.36 (s, 3H), 2.14-2.00 (m, 4H), 1.94-1.84 (m, 2H), 1.74-1.64 (m, 2H).

Example 11: N-[[4-(4-amino-1-cyclopentyl-pyrazolo[3,4-d]pyrimidin-3-yl)phenyl]methyl]-5-chloro-2-methoxy-benzamide

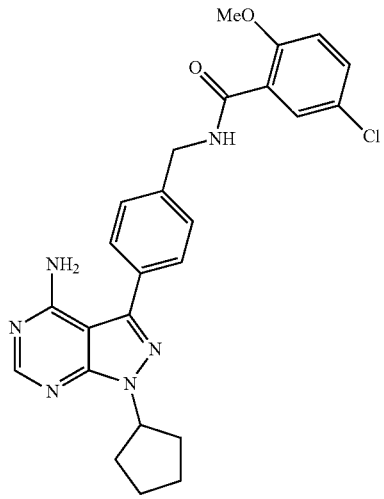 [SMILES: COc1ccc(Cl)cc1C(=O)NCc1ccc(-c2nn(C3CCCC3)c3ncnc(N)c23)cc1]

4-[[(5-Chloro-2-methoxy-benzoyl)amino]methyl]phenyl]boronic acid

Following general procedure A, [4-(aminomethyl)phenyl]boronic acid hydrochloride (387 mg, 2.06 mmol) and 5-chloro-2-methoxybenzoic acid (350 mg, 1.88 mmol) gave [4-[[(5-chloro-2-methoxy-benzoyl)amino]methyl]phenyl]boronic acid (259 mg, 0.53 mmol, 28% yield as a yellow oil.

UPLC-MS (ES$^+$, Short acidic): 1.45 min, m/z 319.8 [M+H]$^+$

N-[[4-(4-Amino-1-cyclopentyl-pyrazolo[3,4-d]pyrimidin-3-yl)phenyl]methyl]-5-chloro-2-methoxy-benzamide Following general procedure D, 1-cyclopentyl-3-iodo-pyrazolo[3,4-d]pyrimidin-4-amine (80 mg, 0.24 mmol) and [4-[[(5-chloro-2-methoxy-benzoyl)amino]methyl]phenyl]boronic acid (117 mg, 0.36 mmol) gave, after further purification by flash column chromatography, eluting with 0-10% MeOH in EtOAc, N-[[4-(4-amino-1-cyclopentyl-pyrazolo[3,4-d]pyrimidin-3-yl)phenyl]methyl]-5-chloro-2-methoxy-benzamide (50 mg, 0.10 mmol, 41% yield) as a cream solid.

UPLC-MS (ES$^+$, Short acidic): 1.66 min, m/z 477.2 [M+H]$^+$

UPLC-MS (ES$^+$, Long acidic): 3.83 min, m/z 477.3 [M+H]$^+$ $^1$H NMR (400 MHz, DMSO-d$_6$, δ): 8.85 (t, J=6.1 Hz, 1H), 8.24 (s, 1H), 7.70 (d, J=2.8 Hz, 1H), 7.66-7.61 (m, 2H), 7.53 (dd, J=8.8, 2.8 Hz, 1H), 7.52-7.47 (m, 2H), 7.20 (d, J=8.8 Hz, 1H), 5.27-5.18 (m, 1H), 4.57 (d, J=6.1 Hz, 2H), 3.91 (s, 3H), 2.15-1.97 (m, 4H), 1.94-1.83 (m, 2H), 1.75-1.62 (m, 2H).

Example 12: N-[[4-(4-amino-1-cyclopentyl-pyrazolo[3,4-d]pyrimidin-3-yl)phenyl]methyl]-2-methoxy-5-methyl-benzamide

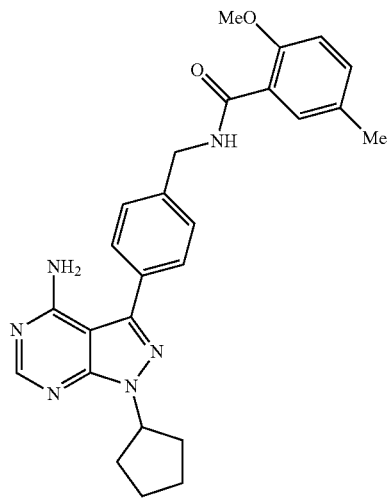 [SMILES: COc1ccc(C)cc1C(=O)NCc1ccc(-c2nn(C3CCCC3)c3ncnc(N)c23)cc1]

[4-[[(2-Methoxy-5-methyl-benzoyl)amino]methyl]phenyl]boronic acid

Following general procedure A, [4-(aminomethyl)phenyl]boronic acid hydrochloride (434 mg, 2.32 mmol) and 5-fluoro-2-methoxy-benzoic acid (350 mg, 2.06 mmol) gave [4-[[(2-methoxy-5-methyl-benzoyl)amino]methyl]phenyl]boronic acid (215 mg, 0.36 mmol, 17% yield) as an off-white solid.

UPLC-MS (ES$^+$, Short acidic): 1.40 min, m/z 299.9 [M+H]$^+$

N-[[4-(4-Amino-1-cyclopentyl-pyrazolo[3,4-d]pyrimidin-3-yl)phenyl]methyl]-2-methoxy-5-methyl-benzamide Following general procedure D, [4-[[(2-methoxy-5-methyl-benzoyl)amino]methyl]phenyl]boronic acid (136 mg, 0.46 mmol) and 1-cyclopentyl-3-iodo-pyrazolo[3,4-d]pyrimidin-4-amine (100 mg, 0.30 mmol) afforded N-[[4-(4-amino-1-cyclopentyl-pyrazolo[3,4-d]pyrimidin-3-yl)phenyl]methyl]-2-methoxy-5-methyl-benzamide (22 mg, 0.05 mmol, 15% yield) as a crystalline off-white solid.

UPLC-MS (ES$^+$, Short acidic): 1.66 min, m/z 477.2 [M+Na]$^+$

UPLC-MS (ES$^+$, Long acidic): 3.74 min, m/z 457.4 [M+H]$^+$ $^1$H NMR (400 MHz, DMSO-d$_6$, δ): 8.74 (t, J=6.1 Hz, 1H), 8.23 (s, 1H), 7.66-7.61 (m, 2H), 7.60-7.57 (m, 1H), 7.52-7.47 (m, 2H), 7.31-7.26 (m, 1H), 7.05 (d, J=8.4 Hz, 1H), 5.27-5.18 (m, 1H), 4.57 (d, J=6.1 Hz, 2H), 3.88 (s, 3H), 2.28 (s, 3H), 2.15-1.97 (m, 4H), 1.94-1.82 (m, 2H), 1.74-1.62 (m, 2H).

Example 13: N-[[4-(4-amino-1-cyclopentyl-pyrazolo[3,4-d]pyrimidin-3-yl)phenyl]methyl]-2-methoxy-5-(trifluoromethyl)benzamide

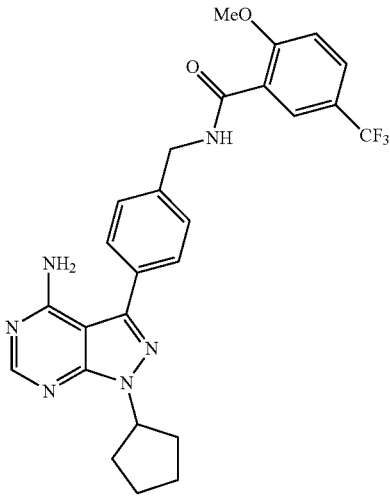 [SMILES: COc1ccc(C(F)(F)F)cc1C(=O)NCc1ccc(-c2nn(C3CCCC3)c3ncnc(N)c23)cc1]

[4-[[[2-Methoxy-5-(trifluoromethyl)benzoyl]amino]methyl]phenyl]boronic acid

Following general procedure B, [4-(aminomethyl)phenyl]boronic acid hydrochloride (300 mg, 1.60 mmol) and 2-methoxy-5-(trifluoromethyl)benzoyl chloride (420 mg, 1.76 mmol) gave [4-[[[2-methoxy-5-(trifluoromethyl)benzoyl]amino]methyl]phenyl]boronic acid (559 mg, 1.34 mmol, 84% yield) as a pale yellow solid.

UPLC-MS (ES$^+$, Short acidic): 1.51 min, m/z 353.9 [M+H]$^+$

N-[[4-(4-Amino-1-cyclopentyl-pyrazolo[3,4-d]pyrimidin-3-yl)phenyl]methyl]-2-methoxy-5-(trifluoromethyl)benzamide Following general procedure D, [4-[[[2-methoxy-5-(trifluoromethyl)benzoyl]amino]methyl]phenyl]boronic acid (161 mg, 0.46 mmol) and 1-cyclopentyl-3-iodo-pyrazolo[3,4-d]pyrimidin-4-amine (100 mg, 0.30 mmol) gave N-[[4-(4-amino-1-cyclopentyl-pyrazolo[3,4-d]pyrimidin-3-yl)phenyl]methyl]-2-methoxy-5-(trifluoromethyl)benzamide (78 mg, 0.14 mmol, 45% yield) as a cream solid.

UPLC-MS (ES$^+$, Short acidic): 1.71 min, m/z 511.4 [M+H]$^+$

UPLC-MS (ES$^+$, Long acidic): 3.95 min, m/z 511.4 [M+H]$^+$ $^1$H NMR (400 MHz, CDCl$_3$, δ): 8.56 (d, J=2.3 Hz, 1H), 8.37 (s, 1H), 8.21-8.14 (m, 1H), 7.76-7.71 (m, 1H), 7.71-7.66 (m, 2H), 7.55-7.49 (m, 2H), 7.12-7.07 (m, 1H), 5.45-5.38 (m, 2H), 5.36-5.27 (m, 1H), 4.77 (d, J=5.9 Hz, 2H), 4.03 (s, 3H), 2.23-2.13 (m, 4H), 2.02-1.92 (m, 2H), 1.79-1.67 (m, 2H).

Example 14: N-[[4-(4-amino-1-cyclopentyl-pyrazolo[3,4-d]pyrimidin-3-yl)phenyl]methyl]-3-fluoro-2-methoxy-benzamide

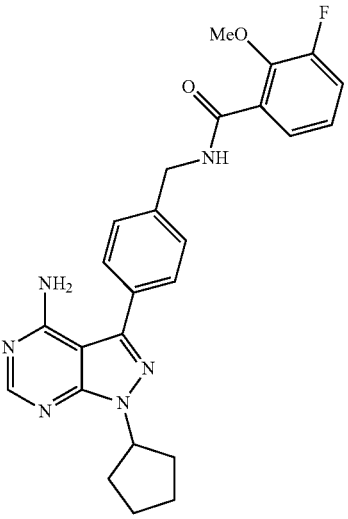

[4-[[(3-Fluoro-2-methoxy-benzoyl)amino]methyl]phenyl]boronic acid

Following general procedure A, 3-fluoro-2-methoxybenzoic acid (300 mg, 1.76 mmol) and [4-(aminomethyl)phenyl]boronic acid hydrochloride (364 mg, 1.94 mmol) afforded crude [4-[[(3-fluoro-2-methoxy-benzoyl)amino]methyl]phenyl]boronic acid (382 mg, 0.88 mmol, 50% yield) as a brown solid UPLC-MS: UPLC-MS (ES$^+$, Short acidic): 1.37 min, m/z 304.0 [M+H]$^+$

N-[[4-(4-Amino-1-cyclopentyl-pyrazolo[3,4-d]pyrimidin-3-yl)phenyl]methyl]-3-fluoro-2-methoxy-benzamide Following general procedure D, 1-cyclopentyl-3-iodo-pyrazolo[3,4-d]pyrimidin-4-amine (100 mg, 0.30 mmol) and [4-[[(3-fluoro-2-methoxy-benzoyl)amino]methyl]phenyl]boronic acid (138 mg, 0.46 mmol) afforded, after further purification by flash column chromatography (DCM/MeOH 100:0 to 95:5) and SCX, N-[[4-(4-amino-1-cyclopentyl-pyrazolo[3,4-d]pyrimidin-3-yl)phenyl]methyl]-3-fluoro-2-methoxy-benzamide (83 mg, 0.16 mmol, 53% yield) as a yellow solid.

UPLC-MS (ES$^+$, Short acidic): 1.59 min, m/z 461.4 [M+H]$^+$

UPLC-MS (ES$^+$, Long acidic): 3.65 min, m/z 461.4 [M+H]$^+$ $^1$H NMR (400 MHz, DMSO-d$_6$, δ): 8.89 (t, J=6.1 Hz, 1H), 8.24 (s, 1H), 7.65 (d, J=8.2 Hz, 2H), 7.52 (d, J=8.2 Hz, 2H), 7.43-7.38 (m, 2H), 7.22-7.17 (m, 1H), 5.23 (m, 1H), 4.57 (d, J=6.1 Hz, 2H), 3.91 (d, J=1.6 Hz, 3H), 2.14-2.00 (m, 4H), 1.94-1.84 (m, 2H), 1.74-1.64 (m, 2H).

Example 15: N-[[4-(4-amino-1-cyclopentyl-pyrazolo[3,4-d]pyrimidin-3-yl)phenyl]methyl]-4-fluoro-2-methoxy-benzamide

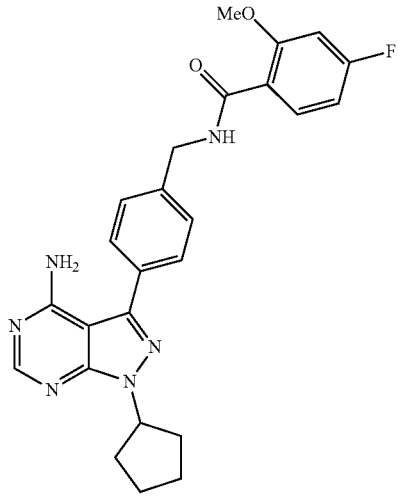 [SMILES: COc1cc(F)ccc1C(=O)NCc1ccc(-c2nn(C3CCCC3)c3ncnc(N)c23)cc1]

Example 16: N-[[4-(4-amino-1-cyclopentyl-pyrazolo[3,4-d]pyrimidin-3-yl)phenyl]methyl]-2-fluoro-6-methoxy-benzamide

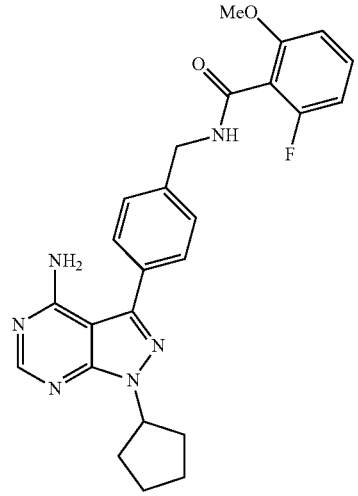

[4-[[(4-fluoro-2-methoxy-benzoyl)amino]methyl]phenyl]boronic acid

Following general procedure A, 4-fluoro-2-methoxybenzoic acid (300 mg, 1.76 mmol) and [4-(aminomethyl)phenyl]boronic acid hydrochloride (364 mg, 1.94 mmol) afforded crude [4-[[(4-fluoro-2-methoxy-benzoyl)amino]methyl]phenyl]boronic acid (399 mg, 1.18 mmol, 67% yield) as a yellow solid.

UPLC-MS (ES$^+$, Short acidic): 1.36 min, m/z 303.9 [M+H]$^+$

N-[[4-(4-Amino-1-cyclopentyl-pyrazolo[3,4-d]pyrimidin-3-yl)phenyl]methyl]-4-fluoro-2-methoxy-benzamide Following general procedure D, 1-cyclopentyl-3-iodo-pyrazolo[3,4-d]pyrimidin-4-amine (100 mg, 0.30 mmol) and [4-[[(4-fluoro-2-methoxy-benzoyl)amino]methyl]phenyl]boronic acid (138 mg, 0.46 mmol) afforded, after further purification by flash column chromatography (DCM/MeOH 100:0 to 95:5) and SCX, N-[[4-(4-amino-1-cyclopentyl-pyrazolo[3,4-d]pyrimidin-3-yl)phenyl]methyl]-4-fluoro-2-methoxy-benzamide (83 mg, 0.16 mmol, 53% yield) as a white solid.

UPLC-MS (ES$^+$, Short acidic): 1.59 min, m/z 461.3 [M+H]$^+$

UPLC-MS (ES$^+$, Long acidic): 3.63 min, m/z 461.4 [M+H]$^+$ $^1$H NMR (400 MHz, DMSO-d$_6$, δ): 8.73 (t, J=6.1 Hz, 1H), 8.24 (s, 1H), 7.86-7.82 (m, 1H), 7.63 (d, J=8.2 Hz, 2H), 7.49 (d, J=8.3 Hz, 2H), 7.09 (dd, J=11.4, 2.4 Hz, 1H), 6.88 (td, J=8.4, 2.4 Hz, 1H), 5.23 (m, 1H), 4.58 (d, J=6.1 Hz, 2H), 3.94 (s, 3H), 2.14-2.00 (m, 4H), 1.94-1.84 (m, 2H), 1.74-1.64 (m, 2H).

[4-[[(2-Fluoro-6-methoxy-benzoyl)amino]methyl]phenyl]boronic acid

Following procedure B, 2-fluoro-6-methoxybenzoyl chloride (0.21 mL, 1.47 mmol) and 4-aminomethylphenylboronic acid hydrochloride (250 mg, 1.33 mmol) gave crude [4-[[(2-fluoro-6-methoxy-benzoyl)amino]methyl]phenyl]boronic acid (447 mg, 0.74 mmol, 55% yield) as a yellow solid.

LC-MS (ES$^+$, Short acidic): 2.85 min, m/z 304 [M+H]$^+$

N-[[4-(4-Amino-1-cyclopentyl-pyrazolo[3,4-d]pyrimidin-3-yl)phenyl]methyl]-2-fluoro-6-methoxy-benzamide Following general procedure D, 1-cyclopentyl-3-iodo-pyrazolo[3,4-d]pyrimidin-4-amine (73 mg, 0.22 mmol) and [4-[[(2-fluoro-6-methoxy-benzoyl)amino]methyl]phenyl]boronic acid (201 mg, 0.33 mmol) gave N-[[4-(4-amino-1-cyclopentyl-pyrazolo[3,4-d]pyrimidin-3-yl)phenyl]methyl]-2-fluoro-6-methoxy-benzamide (71 mg, 0.15 mmol, 70% yield).

UPLC-MS: (ES$^+$, Short acidic): 1.47 min, m/z 461.3 [M+H]$^+$

UPLC-MS (ES$^+$, Long acidic): 3.36 min, m/z 461.1 [M+H]$^+$ $^1$H NMR (400 MHz, DMSO-d$_6$, δ): 8.99 (t, J=6.4 Hz, 1H), 8.24 (s, 1H), 7.65 (d, J=8.2 Hz, 2H), 7.52 (d, J=8.2 Hz, 2H), 7.42-7.40 (m, 1H), 6.95 (d, J=8.2 Hz, 1H), 6.87 (t, J=8.6 Hz, 1H), 5.28-5.20 (m, 1H), 4.53 (d, J=6.4 Hz, 2H), 3.84 (s, 3H), 2.11-2.04 (m, 4H), 1.93-1.89 (m, 2H), 1.72-1.68 (m, 2H).

Example 17: N-[[4-(4-Amino-1-cyclopentyl-pyrazolo[3,4-d]pyrimidin-3-yl)phenyl]methyl]-2-methoxy-N-methyl-benzamide

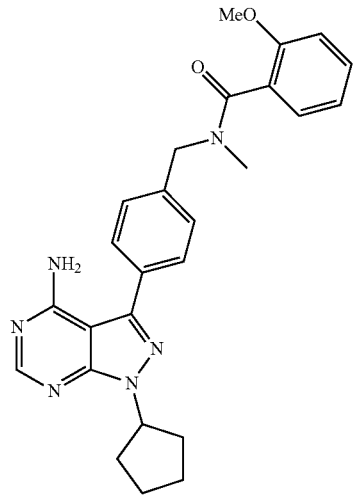

[4-[[(2-Methoxybenzoyl)-methyl-amino]methyl]phenyl]boronic acid

[4-[[(2-Methoxybenzoyl)amino]methyl]phenyl]boronic acid (30 mg, 0.11 mmol) was dissolved in DMF (1 mL). Sodium hydride (42 mg, 1.05 mmol) was added and the reaction mixture stirred for 30 minutes before iodomethane (0.33 mL, 0.53 mmol) was added. The reaction mixture was stirred at room temperature overnight. The reaction mixture was quenched with ammonium chloride and extracted with EtOAc. The combined organic phase was dried over sodium sulfate and reduced under reduced pressure to give [4-[[(2-methoxybenzoyl)-methyl-amino]methyl]phenyl]boronic acid (49 mg, 0.11 mmol, assumed quantitative).

LC-MS (ES+, method 1): 3.08 min, m/z 300.1 [M+H]+

N-[[4-(4-Amino-1-cyclopentyl-pyrazolo[3,4-d]pyrimidin-3-yl)phenyl]methyl]-2-methoxy-N-methyl-benzamide Following the general procedure D, 1-cyclopentyl-3-iodo-pyrazolo[3,4-d]pyrimidin-4-amine (15 mg, 0.05 mmol) and [4-[[(2-methoxybenzoyl)-methyl-amino]methyl]phenyl]boronic acid (41 mg, 0.07 mmol) gave N-[[4-(4-amino-1-cyclopentyl-pyrazolo[3,4-d]pyrimidin-3-yl)phenyl]methyl]-2-methoxy-N-methyl-benzamide (17 mg, 0.03 mmol, 71% yield) as a white solid.

LC-MS (ES+, method 1): 3.29 min, m/z 457.2 [M+H]+

UPLC-MS (ES+, Long acidic): 3.67 min, m/z 457.3 [M+H]+

$^1$H NMR (400 MHz, DMSO-$d_6$, δ) (mixture of rotamers): 8.24 (s, 0.6H), 8.23 9 (s, 0.4H), 7.71-7.59 (m, 1H), 7.53-7.20 (m, 5H), 7.15-6.95 (3H), 5.29-5.18 (m, 1H), 4.99-4.51 (m, 1.2H), 4.38 (s, 0.8H), (3.85 (s, 1.8H), 3.81 (s, 1.2H), 2.92 (s, 1.2H), 2.72 (s, 1.8H), 2.15-1.97 (m, 4H), 1.95-1.83 (m, 2H), 1.75-1.61 (m, 2H).

Example 18: N-[[4-(4-amino-1-cyclopentyl-pyrazolo[3,4-d]pyrimidin-3-yl)phenyl]methyl]-2-methoxy-pyridine-3-carboxamide

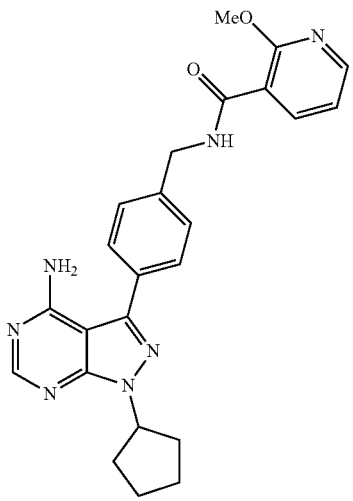

4-[[(2-Methoxypyridine-3-carbonyl)amino]methyl]phenyl]boronic acid

Following general procedure A, [4-(aminomethyl)phenyl]boronic acid hydrochloride (404 mg, 2.15 mmol) and 2-methoxy-nicotinic acid (300 mg, 1.96 mmol) afforded crude [4-[[(2-methoxypyridine-3-carbonyl)amino]methyl]phenyl]boronic acid (287 mg, 0.80 mmol, 41% yield) as a yellow solid.

UPLC-MS (ES+, Short acidic): 1.20 min, m/z 287.0 [M+H]+

N-[[4-(4-Amino-1-cyclopentyl-pyrazolo[3,4-d]pyrimidin-3-yl)phenyl]methyl]-2-methoxy-pyridine-3-carboxamide Following general procedure D, 1-cyclopentyl-3-iodo-pyrazolo[3,4-d]pyrimidin-4-amine (100 mg, 0.30 mmol) and [4-[[(2-methoxypyridine-3-carbonyl)amino]methyl]phenyl]boronic acid (130 mg, 0.46 mmol) afforded, after further purification by flash column chromatography on silica gel (DCM/MeOH 100:0 to 95:5), N-[[4-(4-amino-1-cyclopentyl-pyrazolo[3,4-d]pyrimidin-3-yl)phenyl]methyl]-2-methoxy-pyridine-3-carboxamide (87 mg, 0.18 mmol, 58% yield) as a white solid.

UPLC-MS (ES+, Short acidic): 1.49 min, m/z 444.3 [M+H]+

UPLC-MS (ES+, Long acidic): 3.46 min, m/z 444.3 [M+H]+

$^1$H NMR (400 MHz, DMSO-$d_6$, δ): 8.87 (t, J=6.1 Hz, 1H), 8.32 (dd, J=4.9, 2.0 Hz, 1H), 8.24 (s, 1H), 8.17 (dd, J=7.4, 2.0 Hz, 1H), 7.64 (d, J=8.2 Hz, 2H), 7.51 (d, J=8.3 Hz, 2H), 7.14 (dd, J=7.4, 4.9 Hz, 1H), 5.23 (m, 1H), 4.59 (d, J=6.1 Hz, 2H), 4.00 (s, 3H), 2.14-2.00 (m, 4H), 1.94-1.84 (m, 2H), 1.74-1.64 (m, 2H).

Example 19: N-[[4-[4-amino-1-(1,4-dioxaspiro[4.5]decan-8-yl)pyrazolo[3,4-d]pyrimidin-3-yl]phenyl]methyl]-2-methoxy-benzamide

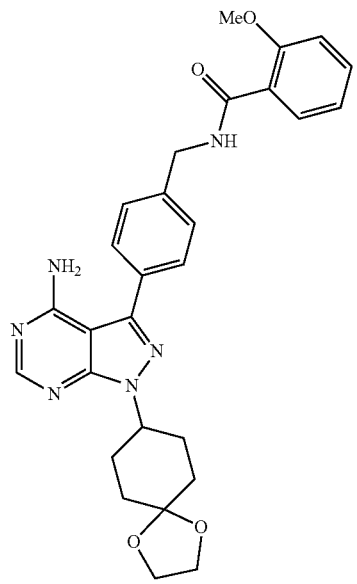 [SMILES: COc1ccccc1C(=O)NCc1ccc(-c2nn(C3CCC4(CC3)OCCO4)c3ncnc(N)c23)cc1]

1,4-Dioxaspiro[4.5]decan-8-ol

To a solution of 1,4-cyclohexanedione monoethylene acetal (2.0 g, 12.81 mmol) in methanol (25 mL), cooled to 0° C., was added sodium borohydride (0.5 g, 14.09 mmol). After 30 min of stirring at room temperature, a saturated solution of aqueous NH$_4$Cl (20 mL) was added carefully. The aqueous layer was extracted with DCM (3×20 mL) and the combined organic extracts were filtered over a phase separator, concentrated under reduced pressure to give the crude 1,4-dioxaspiro[4.5]decan-8-ol (2.0 g, 12.81 mmol, 100% yield) as a colourless oil.

$^1$H NMR (400 MHz, CDCl$_3$, δ): 3.96-3.88 (m, 4H), 3.83-3.73 (m, 1H), 1.92-1.75 (m, 4H), 1.70-1.51 (m, 4H), 1.31 (d, J=3.1 Hz, 1H).

1,4-Dioxaspiro[4.5]decan-8-yl methanesulfonate

Following general procedure L, 1,4-dioxaspiro[4.5]decan-8-ol (400 mg, 2.53 mmol) gave 1,4-dioxaspiro[4.5]decan-8-yl methanesulfonate (598 mg, 2.53 mmol, assumed quantitative) as a colourless solid $^1$H NMR (400 MHz, CDCl$_3$, δ): 4.82-4.74 (m, 1H), 3.93-3.83 (m, 4H), 2.95 (s, 3H), 2.00-1.86 (m, 4H), 1.86-1.73 (m, 2H), 1.63-1.52 (m, 2H)

1-(1,4-Dioxaspiro[4.5]decan-8-yl)-3-iodo-pyrazolo[3,4-d]pyrimidin-4-amine

Following general procedure M, 1,4-dioxaspiro[4.5]decan-8-yl methanesulfonate (592 mg, 2.51 mmol) and 3-iodo-1H-pyrazolo[3,4-d]pyrimidin-4-amine (330 mg, 1.26 mmol) gave 1-(1,4-dioxaspiro[4.5]decan-8-yl)-3-iodo-pyrazolo[3,4-d]pyrimidin-4-amine (100 mg, 0.24 mmol, 19% yield) as a yellow-white solid.

LC-MS (ES$^+$, Method 1): 2.80 min, m/z 402.0 [M+H]$^+$

N-[[4-[4-Amino-1-(1,4-dioxaspiro[4.5]decan-8-yl)pyrazolo[3,4-d]pyrimidin-3-yl]phenyl]methyl]-2-methoxy-benzamide Following general procedure C, 1-(1,4-dioxaspiro[4.5]decan-8-yl)-3-iodo-pyrazolo[3,4-d]pyrimidin-4-amine (280 mg, 0.70 mmol) and [4-[[(2-methoxybenzoyl)amino]methyl]phenyl]boronic acid (279 mg, 0.98 mmol) gave N-[[4-[4-amino-1-(1,4-dioxaspiro[4.5]decan-8-yl)pyrazolo[3,4-d]pyrimidin-3-yl]phenyl]methyl]-2-methoxy-benzamide (182 mg, 0.34 mmol, 48% yield) as an off-white powder.

UPLC-MS (ES$^+$, Long acidic): 3.27 min, m/z 515.3 [M+H]$^+$ $^1$H NMR (400 MHz, DMSO-d$_6$, δ): 8.77 (t, J=6.2 Hz, 1H), 8.24 (s, 1H), 7.77 (dd, J=7.6, 1.8 Hz, 1H), 7.65 (d, J=8.2 Hz, 2H), 7.54-7.45 (m, 3H), 7.17 (d, J=7.2 Hz, 1H), 7.05 (dt, J=7.6, 0.8 Hz, 1H), 4.85-4.73 (m, 1H), 4.59 (d, J=6.2 Hz, 2H), 3.96-3.86 (m, 7H), 2.31-2.18 (m, 2H), 1.95-1.70 (m, 6H)

Example 20: N-[[4-(4-amino-1-cyclopentyl-pyrazolo[3,4-d]pyrimidin-3-yl)phenyl]methyl]-3-cyano-benzamide

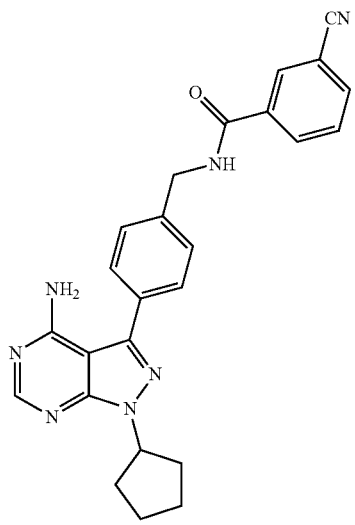 [SMILES: N#Cc1cccc(C(=O)NCc2ccc(-c3nn(C4CCCC4)c4ncnc(N)c34)cc2)c1]

[4-[[(3-Cyanobenzoyl)amino]methyl]phenyl]boronic acid

Following general procedure A, 4-(aminomethyl)phenyl boronic acid hydrochloride (350 mg, 1.87 mmol) and 3-cyanobenzoic acid (250 mg, 1.70 mmol) afforded crude [4-[[(3-cyanobenzoyl)amino]methyl]phenyl]boronic acid (284 mg, 0.86 mmol, 51% yield) as a brown solid.

LC-MS (ES$^+$, Method 1): 3.06 min, m/z 281.0 [M+H]$^+$

N-[[4-(4-Amino-1-cyclopentyl-pyrazolo[3,4-d]pyrimidin-3-yl)phenyl]methyl]-3-cyano-benzamide Following general procedure C, 1-cyclopentyl-3-iodo-pyrazolo[3,4-d]pyrimidin-4-amine (100 mg, 0.30 mmol) and [4-[[(3-cyanobenzoyl)amino]methyl]phenyl]boronic acid (128 mg, 0.46 mmol) gave N-[[4-(4-amino-1-cyclopentyl-pyrazolo[3,4-d]pyrimidin-3-yl)phenyl]methyl]-3-cyano-benzamide (81 mg, 0.17 mmol, 58% yield) as an off-white solid.

UPLC-MS (ES+, Long acidic): 3.39 min, m/z 438.3 [M+H]+

¹H NMR (400 MHz, DMSO-d₆, δ): 9.32 (t, J=5.9 Hz, 1H), 8.37-8.32 (m, 1H), 8.25-8.20 (m, 2H), 8.06-8.01 (m, 1H), 7.73 (t, J=8.2 Hz, 1H), 7.64 (d, J=8.2 Hz, 2H), 7.51 (d, J=8.2 Hz, 2H), 5.23 (quint, J=7.4 Hz, 1H), 4.58 (d, J=5.9 Hz, 2H), 2.15-1.97 (m, 4H), 1.96-1.82 (m, 2H), 1.75-1.62 (m, 2H)

Example 21: N-[[4-[4-amino-1-(3-oxocyclopentyl)pyrazolo[3,4-d]pyrimidin-3-yl]phenyl]methyl]-2-methoxy-benzamide

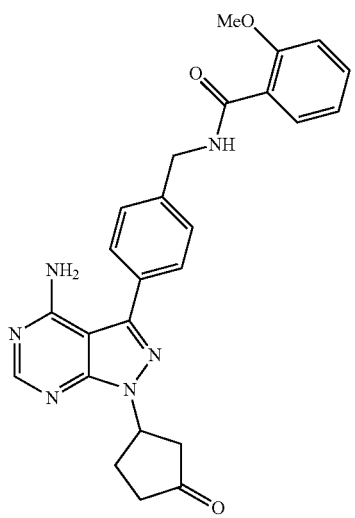 [SMILES: COc1ccccc1C(=O)NCc1ccc(-c2nn(C3CCC(=O)C3)c3ncnc(N)c23)cc1]

3-(4-Amino-3-iodo-pyrazolo[3,4-d]pyrimidin-1-yl)cyclopentanone

At room temperature, 1,8-diazabicyclo[5.4.0]undec-7-ene (0.23 mL, 1.53 mmol) was added slowly dropwise to a suspension of 3-iodo-1H-pyrazolo[3,4-d]pyrimidin-4-amine (800 mg, 3.06 mmol) and 2-cyclopentenone (0.31 mL, 3.68 mmol) in MeCN (6 mL). After allowing the reaction mixture to stir at room temperature overnight, silica was added and all volatiles were removed under reduced pressure. Further purification by flash column chromatography on silica gel (DCM/MeOH 100:0 to 92:8) afforded 3-(4-amino-3-iodo-pyrazolo[3,4-d]pyrimidin-1-yl)cyclopentanone (361 mg, 1.05 mmol, 34% yield) as an off-white solid.

UPLC-MS (ES+, Short acidic): 2.69 min, m/z 344.0 [M+H]+

N-[[4-[4-Amino-1-(3-oxocyclopentyl)pyrazolo[3,4-d]pyrimidin-3-yl]phenyl]methyl]-2-methoxy-benzamide Following general procedure C, 3-(4-amino-3-iodo-pyrazolo[3,4-d]pyrimidin-1-yl)cyclopentanone (80.0 mg, 0.23 mmol) and [4-[[(2-methoxybenzoyl)amino]methyl]phenyl]boronic acid (100 mg, 0.35 mmol) gave N-[[4-[4-amino-1-(3-oxocyclopentyl)pyrazolo[3,4-d]pyrimidin-3-yl]phenyl]methyl]-2-methoxy-benzamide (31.7 mg, 0.06 mmol, 28% yield) as a brown solid.

LC-MS (ES+, Method 1): 2.82 min, m/z 457.1 [M+H]+
UPLC-MS (ES+, Long acidic): 2.98 min, m/z 457.2 [M+H]+

¹H NMR (400 MHz, DMSO-d₆, δ): 8.77 (t, J=6.0 Hz, 1H), 8.27 (s, 1H), 7.77 (dd, J=7.6, 1.8 Hz, 1H), 7.63 (d, J=8.2 Hz, 2H), 7.51 (d, J=8.2 Hz, 2H), 7.51-7.45 (m, 1H), 7.17 (d, J=8.2 Hz, 1H), 7.05 (t, J=7.6 Hz, 1H), 5.64-5.55 (m, 1H), 4.59 (d, J=6.0 Hz, 2H), 3.91 (s, 3H), 2.86-2.65 (m, 2H), 2.50-2.26 (m, 4H)

Example 22: N-[[4-(4-amino-1-cyclopentyl-pyrazolo[3,4-d]pyrimidin-3-yl)phenyl]methyl]-2-methoxy-3-methyl-benzamide

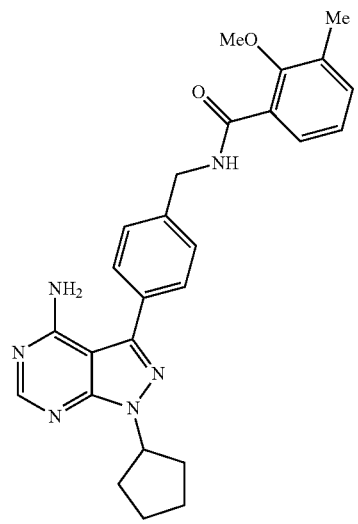 [SMILES: COc1c(C)cccc1C(=O)NCc1ccc(-c2nn(C3CCCC3)c3ncnc(N)c23)cc1]

[4-[[(2-Methoxy-3-methyl-benzoyl)amino]methyl]phenyl]boronic acid

Following general procedure A, 4-(aminomethyl)phenyl]boronic acid hydrochloride (248 mg, 1.32 mmol) and 2-methoxy-3-methylbenzoic acid (200 mg, 1.20 mmol) afforded crude [4-[[(2-methoxy-3-methyl-benzoyl)amino]methyl]phenyl]boronic acid (213 mg, 0.61 mmol, 50% yield) as a white solid.

UPLC-MS (ES+, Short acidic): 1.37 min, m/z 299.8 [M+H]+

N-[[4-(4-Amino-1-cyclopentyl-pyrazolo[3,4-d]pyrimidin-3-yl)phenyl]methyl]-2-methoxy-3-methyl-benzamide Following general procedure C, 1-cyclopentyl-3-iodo-pyrazolo[3,4-d]pyrimidin-4-amine (100 mg, 0.30 mmol) and [4-[[(2-methoxy-3-methyl-benzoyl)amino]methyl]phenyl]boronic acid (136 mg, 0.46 mmol) gave N-[[4-(4-amino-1-cyclopentyl-pyrazolo[3,4-d]pyrimidin-3-yl)phenyl]methyl]-2-methoxy-3-methyl-benzamide (116 mg, 0.24 mmol, 80% yield) as a pink solid.

UPLC-MS (ES+, Short acidic): 1.61 min, m/z 457.4 [M+H]+
UPLC-MS (ES+, Long acidic): 3.77 min, m/z 457.3 [M+H]+

¹H NMR (400 MHz, DMSO-d₆, δ): 8.82 (t, J=6.0 Hz, 1H), 8.24 (s, 1H), 7.65 (d, J=8.1 Hz, 2H), 7.53 (d, J=8.0 Hz,

2H), 7.45-7.38 (m, 1H), 7.37-7.30 (m, 1H), 7.10 (t, J=7.6 Hz, 1H), 5.23 (quint, J=7.4 Hz, 1H), 4.55 (d, J=6.1 Hz, 2H), 3.71 (s, 3H), 2.28 (s, 3H), 2.17-1.96 (m, 4H), 1.96-1.81 (m, 2H), 1.76-1.61 (m, 2H)

Example 23: N-[[4-[4-amino-1-(4-hydroxycyclohexyl)pyrazolo[3,4-d]pyrimidin-3-yl]phenyl]methyl]-2-methoxy-benzamide

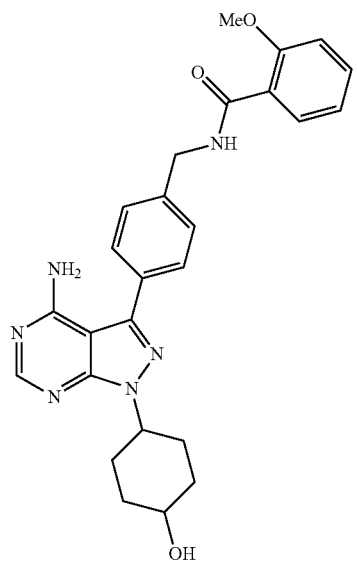 [SMILES: COc1ccccc1C(=O)NCc1ccc(-c2nn(C3CCC(O)CC3)c3ncnc(N)c23)cc1]

N-[[4-[4-Amino-1-(4-hydroxycyclohexyl)pyrazolo[3,4-d]pyrimidin-3-yl]phenyl]methyl]-2-methoxy-benzamide To a solution of N-[[4-[4-amino-1-(4-oxocyclohexyl)pyrazolo[3,4-d]pyrimidin-3-yl]phenyl]methyl]-2-methoxy-benzamide (120 mg, 0.26 mmol) in methanol (1 mL), cooled to 0° C., was added sodium borohydride (11 mg, 0.28 mmol). The reaction mixture was stirred at 70° C. overnight, cooled and then carefully quenched with a saturated solution of aqueous $NH_4Cl$ (20 mL). The aqueous layer was extracted with DCM (3×10 mL) and the combined organic extracts were filtered over a phase separator, concentrated under reduced pressure to give the crude alcohol. Further purification by flash column chromatography on silica gel (DCM/MeOH 100:0 to 95:5) afforded isomer 1 (43 mg, 0.09 mmol, 34% yield, isomer 1) as a white solid and isomer 2 (34 mg, 0.07 mmol, 26% yield, isomer 2) as a white solid.

UPLC-MS (ES$^+$, Short acidic, isomer 1): 1.24 min, m/z 473.2 [M+H]$^+$

UPLC-MS (ES$^+$, Long acidic, isomer 1): 2.82 min, m/z 473.1 [M+H]$^+$ $^1$H NMR (400 MHz, DMSO-d$_6$, δ, isomer 1): 8.77 (t, J=6.1 Hz, 1H), 8.23 (s, 1H), 7.78 (dd, J=7.6, 1.8 Hz, 1H), 7.65 (d, J=8.1 Hz, 2H), 7.53-7.46 (m, 3H), 7.17 (d, J=8.3 Hz, 1H), 7.05 (t, J=7.4 Hz, 1H), 4.75-4.64 (m, 1H), 4.59 (d, J=6.1 Hz, 2H), 4.48 (d, J=2.6 Hz, 1H), 3.92 (s, 3H), 3.90 (s, 1H), 2.44-2.29 (m, 2H), 1.88-1.76 (m, 2H), 1.72-1.56 (m, 4H)

UPLC-MS (ES$^+$, Long acidic, isomer 2): 2.79 min, m/z 473.3 [M+H]$^+$ $^1$H NMR (400 MHz, DMSO-d$_6$, δ, isomer 2): 8.77 (t, J=6.0 Hz, 1H), 8.24 (s, 1H), 7.77 (dd, J=7.6, 1.8 Hz, 1H), 7.63 (d, J=8.2 Hz, 2H), 7.54-7.45 (m, 3H), 7.17 (d, J=8.2 Hz, 1H), 7.08-7.02 (m, 1H), 4.69 (d, J=4.4 Hz, 1H), 4.68-4.59 (m, 1H), 4.59 (d, J=6.1 Hz, 2H), 3.92 (s, 3H), 3.61-3.48 (m, 1H), 2.11-1.84 (m, 6H), 1.50-1.34 (m, 2H)

Example 24: N-[[4-[4-amino-1-[(1R*,3S*)-3-hydroxycyclopentyl]pyrazolo[3,4-d]pyrimidin-3-yl]phenyl]methyl]-2-methoxy-benzamide

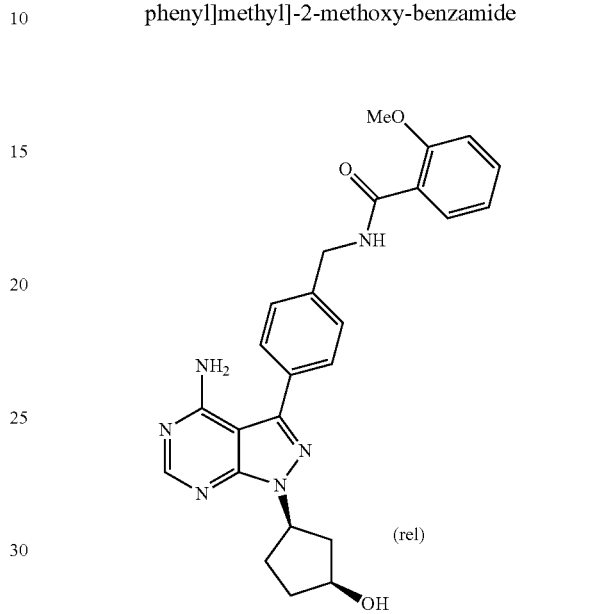

N-[[4-[4-Amino-1-[(1R*,3S*)-3-hydroxycyclopentyl]pyrazolo[3,4-d]pyrimidin-3-yl]phenyl]methyl]-2-methoxy-benzamide To a solution of N-[[4-[4-amino-1-(3-oxocyclopentyl)pyrazolo[3,4-d]pyrimidin-3-yl]phenyl]methyl]-2-methoxy-benzamide (60 mg, 0.13 mmol) in methanol (0.80 mL), cooled and then carefully quenched with a saturated solution of aqueous $NH_4Cl$ (20 mL). The aqueous layer was extracted with DCM (3×10 mL) and the combined organic extracts were filtered over a phase separator, concentrated under reduced pressure to give the crude alcohol. Further purification by flash column chromatography on silica gel (DCM/MeOH 100:0 to 95:5) afforded N-[[4-[4-amino-1-[(1R*,3S*)-3-hydroxycyclopentyl]pyrazolo[3,4-d]pyrimidin-3-yl]phenyl]methyl]-2-methoxy-benzamide (20 mg, 0.04 mmol, 34% yield) as an off-white solid UPLC-MS (ES$^+$, Long acidic): 2.86 min, m/z 459.2 [M+H]$^+$ $^1$H NMR (400 MHz, DMSO-d$_6$, δ): 8.77 (t, J=6.2 Hz, 1H), 8.24 (s, 1H), 7.77 (dd, J=7.6, 2.0 Hz, 1H), 7.65 (d, J=8.2 Hz, 2H), 7.55-7.46 (m, 3H), 7.17 (d, J=7.7 Hz, 1H), 7.05 (dt, J=7.5, 0.9 Hz, 1H), 5.18 (quint, J=8.2 Hz, 1H), 4.95 (d, J=5.0 Hz, 1H), 4.59 (d, J=6.2 Hz, 2H), 4.29-4.15 (m, 1H), 3.92 (s, 3H), 2.46-2.31 (m, 1H), 2.25-2.12 (m, 1H), 2.12-1.70 (m, 4H)

Example 25: N-[[4-[4-amino-1-(1,4-dioxaspiro[4.4]nonan-8-yl)pyrazolo[3,4-d]pyrimidin-3-yl]phenyl]methyl]-2-methoxy-benzamide

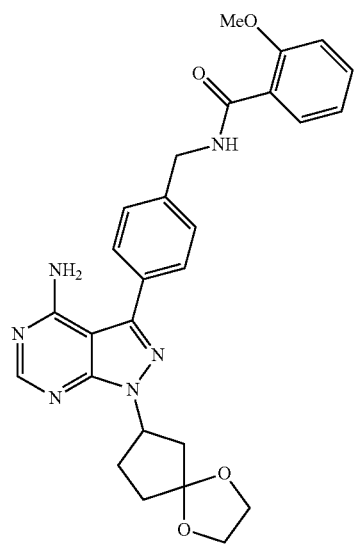 [SMILES: COc1ccccc1C(=O)NCc1ccc(-c2nn(C3CCC4(C3)OCCO4)c3ncnc(N)c23)cc1]

1-(1,4-Dioxaspiro[4.4]nonan-8-yl)-3-iodo-pyrazolo[3,4-d]pyrimidin-4-amine

At room temperature and under an atmosphere of nitrogen, a mixture of 3-(4-amino-3-iodo-pyrazolo[3,4-d]pyrimidin-1-yl)cyclopentanone (270 mg, 0.79 mmol), ethylene glycol (0.18 mL, 3.15 mmol), p-toluenesulfonic acid monohydrate (15 mg, 0.08 mmol) and anhydrous trimethyl orthoformate (0.17 mL, 1.57 mmol) in DCM (2 mL) was heated to 80° C. and stirred overnight. The mixture was cooled and additional ethylene glycol (0.18 mL, 3.15 mmol) and anhydrous trimethyl orthoformate (0.17 mL, 1.57 mmol) were added. The mixture was heated to 90° C. and stirred overnight. The mixture was cooled and additional ethylene glycol (0.36 mL, 6.30 mmol) and anhydrous trimethyl orthoformate (0.34 mL, 3.14 mmol) were added. After 72 h at 90° C., the reaction was carefully quenched with a saturated solution of ammonium chloride. Water (15 mL) and DCM (15 mL) were then added. The aqueous layer was extracted with DCM (2×20 mL) and the combined organic extracts were filtered over a phase separator and concentrated under reduced pressure. Further purification by flash column chromatography on silica gel (DCM/MeOH 100:0 to 96:4) afforded 1-(1,4-dioxaspiro[4.4]nonan-8-yl)-3-iodo-pyrazolo[3,4-d]pyrimidin-4-amine (221 mg, 0.57 mmol, 73% yield) as an off-white solid UPLC-MS (ES$^+$, Short acidic): 1.22 min, m/z 388.0 [M+H]$^+$

N-[[4-[4-Amino-1-(1,4-dioxaspiro[4.4]nonan-8-yl)pyrazolo[3,4-d]pyrimidin-3-yl]phenyl]methyl]-2-methoxy-benzamide Following general procedure C, 1-(1,4-dioxaspiro[4.4]nonan-8-yl)-3-iodo-pyrazolo[3,4-d]pyrimidin-4-amine (176 mg, 0.45 mmol) and [4-[[(2-methoxybenzoyl)amino]methyl]phenyl]boronic acid (168 mg, 0.59 mmol) gave N-[[4-[4-amino-1-(1,4-dioxaspiro[4.4]nonan-8-yl)pyrazolo[3,4-d]pyrimidin-3-yl]phenyl]methyl]-2-methoxy-benzamide (220 mg, 0.42 mmol, 92% yield) as an orange solid.

UPLC-MS (ES$^+$, Long acidic): 3.20 min, m/z 501.2 [M+H]$^+$ $^1$H NMR (400 MHz, DMSO-d$_6$, δ): 8.77 (t, J=6.1 Hz, 1H), 8.25 (s, 1H), 7.78 (dd, J=7.6, 1.6 Hz, 1H), 7.65 (d, J=8.0 Hz, 2H), 7.55-7.45 (m, 3H), 7.17 (d, J=8.3 Hz, 1H), 7.05 (t, J=7.5 Hz, 1H), 5.25 (quint, J=8.2 Hz, 1H), 4.59 (d, J=6.1 Hz, 2H), 3.97-3.81 (m, 7H), 2.44-2.26 (m, 2H), 2.24-2.07 (m, 3H), 2.05-1.79 (m, 1H)

Example 26: N-[[4-[4-amino-1-(4-oxocyclohexyl)pyrazolo[3,4-d]pyrimidin-3-yl]phenyl]methyl]-2-methoxy-benzamide

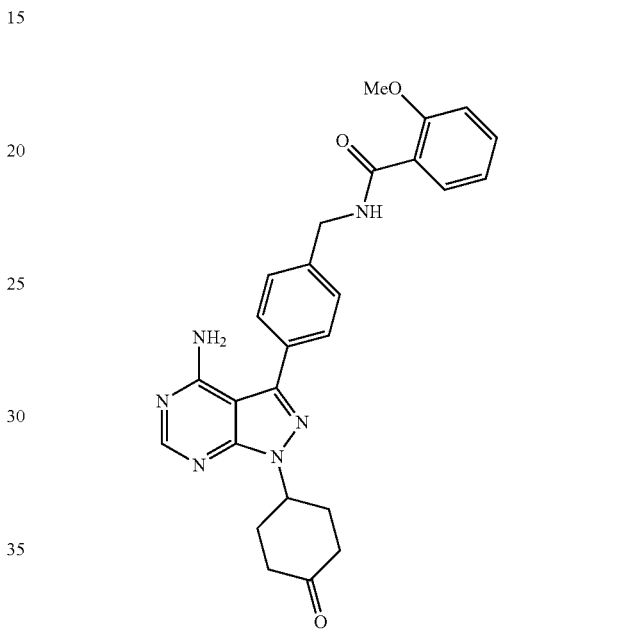

N-[[4-[4-Amino-1-(4-oxocyclohexyl)pyrazolo[3,4-d]pyrimidin-3-yl]phenyl]methyl]-2-methoxy-benzamide Under an atmosphere of nitrogen and at 0° C., trifluoromethanesulfonic acid (0.28 mL, 3.11 mmol) was added to a suspension of N-[[4-[4-amino-1-(1,4-dioxaspiro[4.5]decan-8-yl)pyrazolo[3,4-d]pyrimidin-3-yl]phenyl]methyl]-2-methoxy-benzamide (80 mg, 0.16 mmol) in DCM (0.75 mL) and water (0.08 mL). The reaction mixture was allowed to return to room temperature and stirred overnight, then carefully quenched with a saturated solution of NaHCO$_3$. The aqueous layer was extracted with DCM (3×10 mL). The combined organic extracts were filtered over a phase separator and concentrated under reduced pressure. Further purification by flash column chromatography on silica gel (DCM/MeOH 100:0 to 96:4) afforded N-[[4-[4-amino-1-(4-oxocyclohexyl)pyrazolo[3,4-d]pyrimidin-3-yl]phenyl]methyl]-2-methoxy-benzamide (70 mg, 0.15 mmol, 96% yield) as a white solid.

UPLC-MS (ES$^+$, Short acidic): 1.45 min, m/z 471.2 [M+H]$^+$

UPLC-MS (ES$^+$, Long acidic): 2.98 min, m/z 471.2 [M+H]$^+$ $^1$H NMR (400 MHz, DMSO-d$_6$, δ): 8.77 (t, J=6.1 Hz, 1H), 8.28 (s, 1H), 7.77 (dd, J=7.6, 1.6 Hz, 1H), 7.65 (d, J=8.0 Hz, 2H), 7.56-7.45 (m, 3H), 7.17 (d, J=8.4 Hz, 1H), 7.05 (t, J=7.7 Hz, 1H), 5.31-5.20 (m, 1H), 4.59 (d, J=6.1 Hz, 2H), 3.92 (s, 3H), 2.80-2.63 (m, 2H), 2.46-2.31 (m, 4H), 2.31-2.17 (m, 2H)

Example 27: N-[[4-(4-amino-1-cyclopentyl-pyrazolo[3,4-d]pyrimidin-3-yl)phenyl]methyl]-4-methoxy-pyridine-3-carboxamide

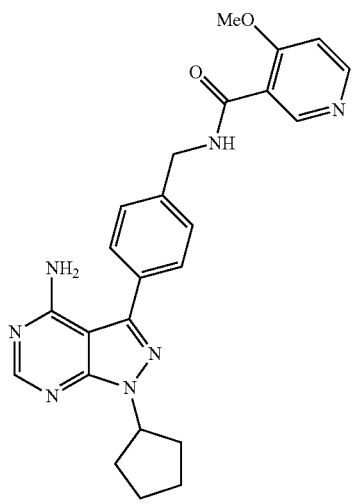 [SMILES: COc1ccncc1C(=O)NCc1ccc(-c2nn(C3CCCC3)c3ncnc(N)c23)cc1]

N-[(4-Bromophenyl)methyl]-4-methoxy-pyridine-3-carboxamide

Following general procedure F, a mixture of 4-methoxynicotinic acid (150 mg, 0.98 mmol) and 4-bromobenzylamine hydrochloride (240 mg, 1.08 mmol) afforded crude N-[(4-bromophenyl)methyl]-4-methoxy-pyridine-3-carboxamide (200 mg, 0.53 mmol, 54% yield) as a clear oil which was used directly in the next step.

LC-MS (ES$^+$, Method 1): 2.49 min, m/z 321.0 [M]$^+$

4-Methoxy-N-[[4-(4,4,5,5-tetramethyl-1,3,2-dioxaborolan-2-yl)phenyl]methyl]pyridine-3-carboxamide Following general procedure N, N-[(4-bromophenyl)methyl]-4-methoxy-pyridine-3-carboxamide (200 mg, 0.62 mmol) afforded, after further purified by flash column chromatography on silica gel (EtOAc/MeOH 100:0 to 90:10), 4-methoxy-N-[[4-(4,4,5,5-tetramethyl-1,3,2-dioxaborolan-2-yl)phenyl]methyl]pyridine-3-carboxamide (125 mg, 0.34 mmol, 54% yield) as a brown solid.

UPLC-MS (ES$^+$, Short acidic): 1.35 min, m/z 368.9 [M+H]$^+$

N-[[4-(4-Amino-1-cyclopentyl-pyrazolo[3,4-d]pyrimidin-3-yl)phenyl]methyl]-4-methoxy-pyridine-3-carboxamide Following general procedure C, 1-cyclopentyl-3-iodo-pyrazolo[3,4-d]pyrimidin-4-amine (90 mg, 0.27 mmol) and 4-methoxy-N-[[4-(4,4,5,5-tetramethyl-1,3,2-dioxaborolan-2-yl)phenyl]methyl]pyridine-3-carboxamide (126 mg, 0.34 mmol) gave N-[[4-(4-amino-1-cyclopentyl-pyrazolo[3,4-d]pyrimidin-3-yl)phenyl]methyl]-4-methoxy-pyridine-3-carboxamide (83 mg, 0.18 mmol, 65% yield) as an off-white solid.

UPLC-MS (ES$^+$, Long acidic): 2.60 min, m/z 444.1 [M+H]$^+$ $^1$H NMR (400 MHz, DMSO-d$_6$, δ): 8.82 (t, J=6.1 Hz, 1H), 8.71 (s, 1H), 8.55 (d, J=5.8 Hz, 1H), 8.24 (s, 1H), 7.65 (d, J=8.2 Hz, 2H), 7.51 (d, J=8.2 Hz, 2H), 7.21 (d, J=5.9 Hz, 1H), 5.24 (quint, J=7.4 Hz, 1H), 4.58 (d, J=6.1 Hz, 2H), 3.97 (s, 3H), 2.18-1.96 (m, 4H), 1.96-1.81 (m, 2H), 1.76-1.61 (m, 2H)

Example 28: N-[[4-[4-amino-1-[4-(methylamino)cyclohexyl]pyrazolo[3,4-d]pyrimidin-3-yl]phenyl]methyl]-2-methoxy-benzamide

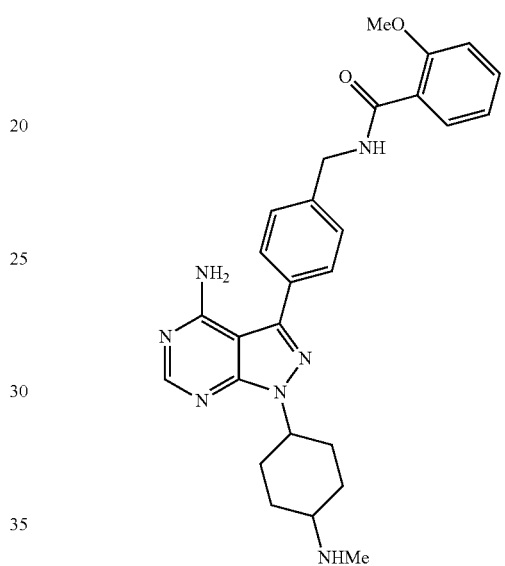

N-[[4-[4-Amino-1-[4-(methylamino)cyclohexyl]pyrazolo[3,4-d]pyrimidin-3-yl]phenyl]methyl]-2-methoxy-benzamide To a solution of 2 M methylamine in THF (0.05 mL, 0.11 mmol) and N-[[4-[4-amino-1-(4-oxocyclohexyl)pyrazolo[3,4-d]pyrimidin-3-yl]phenyl]methyl]-2-methoxy-benzamide (50 mg, 0.11 mmol) in DCM (0.30 mL) was added acetic acid (0.05 mL). The reaction mixture was stirred for 30 min, then sodium triacetoxyborohydride (32 mg, 0.15 mmol) was added. The reaction mixture was then stirred for 1 h, quenched with a 1 M aqueous solution of NaOH (5 mL). The aqueous layer was extracted with DCM (3×10 mL). The combined organic extracts were filtered over a phase separator and concentrated under reduced pressure. Further purification by flash column chromatography on silica gel (DCM/MeOH 94:6 to 0:100) afforded N-[[4-[4-amino-1-[4-(methylamino)cyclohexyl]pyrazolo[3,4-d]pyrimidin-3-yl]phenyl]methyl]-2-methoxy-benzamide (28 mg, 0.06 mmol, 54% yield) as a white solid.

LC-MS (ES$^+$, Method 1): 2.46 min, m/z 486.2 [M+H]$^+$

UPLC-MS (ES$^+$, Long acidic): 2.43 min, m/z 486.1 [M+H]$^+$ $^1$H NMR (400 MHz, DMSO-d$_6$, δ) (2:1 mixture of conformers): 8.77 (t, J=6.1 Hz, 1H), 8.25-8.22 (m, 1H), 7.78 (dd, J=7.6, 1.6 Hz, 1H), 7.68-7.61 (m, 2H), 7.54-7.46 (m, 3H), 7.17 (d, J=8.3 Hz, 1H), 7.05 (t, J=7.5 Hz, 1H), 4.78-4.61 (m, 1H), 4.59 (d, J=4.6 Hz, 2H), 3.92 (s, 3H), 2.70-2.63 (m, 1H), 2.50-2.31 (m, 1H), 2.31 (s, 1H), 2.28 (s, 2H), 2.11-1.90 (m, 2.7H), 1.90-1.78 (m, 1.3H), 1.70-1.55 (m, 3H).

Example 29: N-[[4-(4-amino-1-tetrahydropyran-4-yl-pyrazolo[3,4-d]pyrimidin-3-yl)phenyl]methyl]-2-methoxy-benzamide

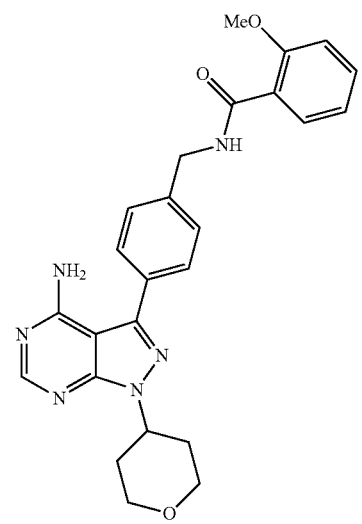 [SMILES: COc1ccccc1C(=O)NCc1ccc(-c2nn(C3CCOCC3)c3ncnc(N)c23)cc1]

Tetrahydropyran-4-yl methanesulfonate

Following general procedure L, tetrahydro-2H-pyran-4-ol (0.97 mL, 8.81 mmol) afforded tetrahydropyran-4-yl methanesulfonate (1.60 g, 7.77 mmol, 88% yield) as a colourless oil.
$^1$H NMR (400 MHz, CDCl$_3$, δ): 4.91 (m, 1H), 3.98-3.92 (m, 2H), 3.58-3.52 (m, 2H), 3.05 (s, 3H), 2.09-2.02 (m, 2H), 1.93-1.84 (m, 2H).

3-Iodo-1-tetrahydropyran-4-yl-pyrazolo[3,4-d]pyrimidin-4-amine

Following general procedure M, 3-iodo-1H-pyrazolo[3,4-d]pyrimidin-4-amine (1.00 g, 3.83 mmol) and tetrahydropyran-4-yl methanesulfonate (1.38 g, 7.67 mmol) afforded, after further purification by flash column chromatography on silica gel (DCM/MeOH 100:0 to 90:10), 3-iodo-1-tetrahydropyran-4-yl-pyrazolo[3,4-d]pyrimidin-4-amine (0.49 g, 1.26 mmol, 33% yield) as a yellow solid.
UPLC-MS (ES$^+$, Short acidic): 1.09 min, m/z 345.9 [M+H]$^+$ N-[[4-(4-Amino-1-tetrahydropyran-4-yl-pyrazolo[3,4-d]pyrimidin-3-yl)phenyl]methyl]-2-methoxy-benzamide Following general procedure D, 3-iodo-1-tetrahydropyran-4-yl-pyrazolo[3,4-d]pyrimidin-4-amine (150 mg, 0.43 mmol) and [4-[[(2-methoxybenzoyl)amino]methyl]phenyl] boronic acid (186 mg, 0.65 mmol) afforded, after further purification by flash column chromatography on silica gel (DCM/MeOH 100:0 to 95:5), N-[[4-(4-amino-1-tetrahydropyran-4-yl-pyrazolo[3,4-d]pyrimidin-3-yl)phenyl]methyl]-2-methoxy-benzamide (109 mg, 0.21 mmol, 49% yield) as a red-orange solid.

UPLC-MS (ES$^+$, Short acidic): 1.31 min, m/z 459.3 [M+H]$^+$
UPLC-MS (ES$^+$, Long acidic): 2.97 min, m/z 459.3 [M+H]$^+$
$^1$H NMR (400 MHz, DMSO-d$_6$, δ): 8.77 (t, J=6.1 Hz, 1H), 8.25 (s, 1H), 7.77 (dd, J=7.6, 1.8 Hz, 1H), 7.65 (d, J=8.2 Hz, 2H), 7.52-7.47 (m, 3H), 7.17 (d, J=8.2 Hz, 1H), 7.05 (td, J=14.0, 1.0 Hz, 1H), 5.00-4.94 (m, 1H), 4.59 (d, J=6.1 Hz, 2H), 4.01 (dd, J=10.2, 3.4 Hz, 2H), 3.92 (s, 3H), 3.55 (t, J=11.1 Hz, 2H), 2.26-2.16 (m, 2H), 1.89 (d, J=10.2 Hz, 2H).

Example 30: 4-[4-amino-3-[4-[[(2-methoxybenzoyl)amino]methyl]phenyl]pyrazolo[3,4-d]pyrimidin-1-yl]cyclohexanecarboxylic acid

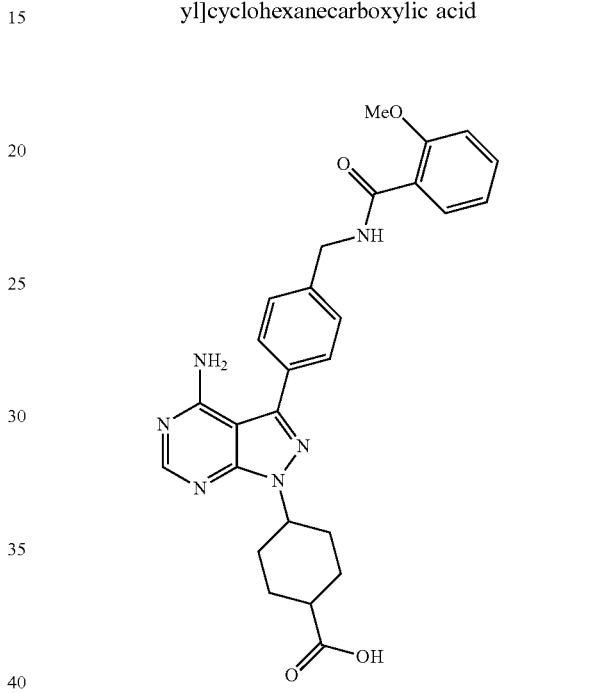

4-[4-Amino-3-[4-[[(2-methoxybenzoyl)amino] methyl]phenyl]pyrazolo[3,4-d]pyrimidin-1-yl]cyclohexanecarboxylic acid To a solution of ethyl 4-[4-amino-3-[4-[[(2-methoxybenzoyl)amino]methyl]phenyl]pyrazolo[3,4-d]pyrimidin-1-yl]cyclohexanecarboxylate (300 mg, 0.57 mmol) in THF (2 mL) and water (2 mL) was added sodium hydroxide (136 mg, 3.41 mmol) and the resulting mixture was stirred overnight. Additional sodium hydroxide (136 mg, 3.41 mmol) was added and the reaction mixture was allowed to stir at 70° C. for 72 h, cooled to room temperature, and then acidified to pH 3 with 1 M HCl. The mixture was partitioned between DCM (10 mL) and H$_2$O (10 mL). The aqueous layer was then extracted with DCM (3×20 mL). The combined organic extracts were then passed through a phase separator and concentrated under reduced pressure. The crude product was further purified by flash column chromatography on silica gel (DCM/MeOH 100:0 to 95:5) to afford 4-[4-amino-3-[4-[[(2-methoxybenzoyl)amino]methyl]phenyl]pyrazolo[3,4-d]pyrimidin-1-yl]cyclohexanecarboxylic acid (229 mg, 0.46 mmol, 81% yield) as an off-white solid.
LC-MS (ES$^+$, Method 1): 2.90 min, m/z 501.2 [M+H]$^+$
UPLC-MS (ES$^+$, Long acidic): 2.94 min, m/z 501.2 [M+H]$^+$ ¹H NMR (400 MHz, DMSO-d$_6$, δ) (1:1 mixture of conformers): 12.7 (br s, 1H), 8.77 (t, J=5.9 Hz, 1H), 8.27-8.21 (m, 1H), 7.78 (d, J=7.6 Hz, 1H), 7.67-7.59 (m, 2H), 7.55-7.45 (m, 3H), 7.17 (d, J=8.4 Hz, 1H), 7.05 (t, J=7.6 Hz, 1H), 4.80-4.60 (m, 1H), 4.59 (d, J=5.9 Hz, 2H), 3.92 (s, 3H), 2.72-2.61 (m, 0.5H), 2.40-2.28 (m, 0.5H), 2.25-2.14 (m, 1H), 2.14-1.92 (m, 4H), 1.89-1.78 (m, 1H), 1.78-1.65 (m, 1H), 1.65-1.49 (m, 1H)

Example 31: N-[[4-[4-amino-1-(3-oxocyclohexyl)pyrazolo[3,4-d]pyrimidin-3-yl]phenyl]methyl]-2-methoxy-benzamide

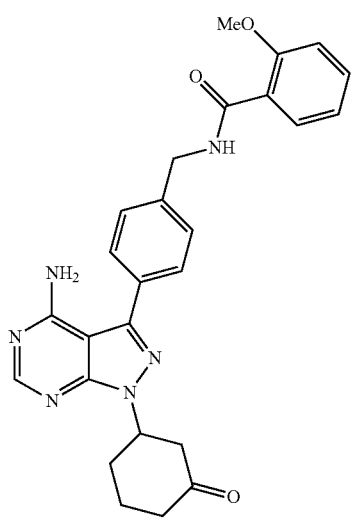 [SMILES: COc1ccccc1C(=O)NCc1ccc(-c2nn(C3CCCC(=O)C3)c3ncnc(N)c23)cc1]

A solution of 1,8-diazabicyclo[5.4.0]undec-7-ene (36 μL, 0.24 mmol) in MeCN (0.5 mL) was added to a solution of N-[[4-(4-amino-1H-pyrazolo[3,4-d]pyrimidin-3-yl)phenyl]methyl]-2-methoxy-benzamide (75 mg, 0.20 mmol) in MeCN (1.5 mL). The reaction mixture was stirred for 30 min and then cyclohex-2-enone (18 μL, 0.19 mmol) was added. The mixture was then stirred for 72 h, quenched with water and diluted with EtOAc. The aqueous layer extracted with EtOAc. The combined organic layer was dried over sodium sulfate and evaporated to dryness. Further purification by flash column chromatography on silica gel afforded N-[[4-[4-amino-1-(3-oxocyclohexyl)pyrazolo[3,4-d]pyrimidin-3-yl]phenyl]methyl]-2-methoxy-benzamide (30 mg, 0.06 mmol, 32% yield) as a white solid.

UPLC-MS (ES⁺, Short acidic): 1.34 min, m/z 471.2 [M+H]⁺

UPLC-MS (ES⁺, Long acidic): 3.04 min, m/z 471.0 [M+H]⁺

¹H NMR (400 MHz, DMSO-d$_6$, δ): 8.78 (t, J=6.2 Hz, 1H), 8.26 (s, 1H), 7.78 (dd, J=7.6, 1.8 Hz, 1H, 7.65-7.63 (m, 2H), 7.52-7.49 (m, 3H), 7.17 (d, J=7.8 Hz, 1H), 7.04 (td, J=11.2, 1.0 Hz, 1H), 5.24-5.17 (m, 1H), 4.59 (d, J=6.2 Hz, 2H), 3.92 (s, 3H), 3.08-2.99 (m, 1H), 2.71-2.66 (m, 1H), 2.53-2.44 (m, 1H), 2.36-2.29 (m, 1H), 2.26-2.20 (m, 1H), 2.15-2.11 (m, 1H), 2.03-1.95 (m, 1H), 1.83-1.72 (m, 1H).

Example 32: ethyl 4-[4-amino-3-[4-[[(2-methoxybenzoyl)amino]methyl]phenyl]pyrazolo[3,4-d]pyrimidin-1-yl]cyclohexanecarboxylate

Ethyl 4-methyl sulfonyloxycyclohexanecarboxylate

Following general procedure L, ethyl 4-hydroxycyclohexanecarboxylate (1.0 mL, 6.20 mmol) afforded crude ethyl 4-methylsulfonyloxycyclohexanecarboxylate (1.55 g, 6.20 mmol, assumed quantitative) as a colourless oil.

¹H NMR (400 MHz, CDCl$_3$, δ) (1:1 mixture of conformers): 4.97-4.90 (m, 0.5H), 4.71-4.61 (m, 0.5H), 4.17 (q, J=7.2 Hz, 1H), 4.15 (q, J=7.2 Hz, 1H), 3.04 (s, 1.5H), 3.03 (s, 1.5H), 2.45-2.28 (m, 1H), 2.26-2.17 (m, 1H), 2.13-2.02 (m, 2H), 2.02-1.89 (m, 1H), 1.87-1.54 (m, 4H), 1.28 (t, J=7.1 Hz, 1.5H), 1.27 (q, J=7.1 Hz, 1.5H)

Ethyl 4-(4-amino-3-iodo-pyrazolo[3,4-d]pyrimidin-1-yl)cyclohexanecarboxylate

Following general procedure M, 3-iodo-1H-pyrazolo[3,4-d]pyrimidin-4-amine (1.40 g, 5.36 mmol) and ethyl 4-methylsulfonyloxycyclohexanecarboxylate (1.61 g, 6.44 mmol) gave ethyl 4-(4-amino-3-iodo-pyrazolo[3,4-d]pyrimidin-1-yl)cyclohexanecarboxylate (0.77 g, 1.49 mmol, 28% yield) as a yellow solid.

LC-MS (ES⁺, Method 1): 2.71 min, m/z 415.9 [M+H]⁺

Ethyl 4-[4-amino-3-[4-[[(2-methoxybenzoyl)amino]methyl]phenyl]pyrazolo[3,4-d]pyrimidin-1-yl]cyclohexanecarboxylate Following general procedure C, ethyl 4-(4-amino-3-iodo-pyrazolo[3,4-d]pyrimidin-1-yl)cyclohexanecarboxylate (544 mg, 1.91 mmol) and [4-[[(2-methoxybenzoyl)amino]methyl]phenyl]boronic acid (660 mg, 1.59 mmol) gave ethyl 4-[4-amino-3-[4-[[(2-methoxybenzoyl)amino]methyl]phenyl]pyrazolo[3,4-d]pyrimidin-1-yl]cyclohexanecarboxylate (762 mg, 1.37 mmol, 86% yield) as an off-white solid.

LC-MS (ES⁺, Method 1): 3.41 min, m/z 529.2 [M+H]⁺

UPLC-MS (ES+, Long acidic): 3.63 min, m/z 529.3 [M+H]+

¹H NMR (400 MHz, DMSO-d₆, δ) (1:1 mixture of conformers): 8.77 (t, J=6.1 Hz, 1H), 8.28-8.22 (m, 1H), 7.83-7.74 (m, 1H), 7.67-7.59 (m, 2H), 7.55-7.44 (m, 3H), 7.17 (d, J=8.3 Hz, 1H), 7.05 (t, J=7.4 Hz, 1H), 4.82-4.62 (m, 1H), 4.59 (d, J=6.0 Hz, 2H), 4.14 (q, J=7.1 Hz, 1H), 4.09 (q, J=7.1 Hz, 1H), 3.92 (s, 3H), 2.76-2.68 (m, 0.5H), 2.47-2.37 (m, 0.5H), 2.25-2.15 (m, 1H), 2.15-1.93 (m, 4H), 1.90-1.80 (m, 1H), 1.80-1.68 (m, 1H), 1.67-1.53 (m, 1H), 1.22 (t, J=7.1 Hz, 1.5H), 1.21 (t, J=7.1 Hz, 1.5H)

Example 33: N-[[4-[4-amino-1-[4-(dimethylcarbamoyl)cyclohexyl]pyrazolo[3,4-d]pyrimidin-3-yl]phenyl]methyl]-2-methoxy-benzamide

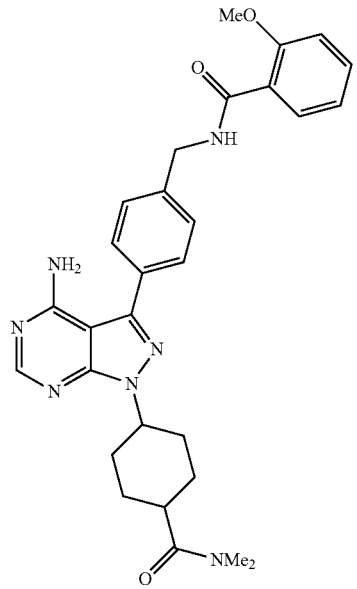 [SMILES: COc1ccccc1C(=O)NCc1ccc(-c2nn(C3CCC(C(=O)N(C)C)CC3)c3ncnc(N)c23)cc1]

N-[[4-[4-Amino-1-[4-(dimethylcarbamoyl)cyclohexyl]pyrazolo[3,4-d]pyrimidin-3-yl]phenyl]methyl]-2-methoxy-benzamide Following general procedure F, 2 M dimethylamine in THF (0.14 mL, 0.28 mmol) and 4-[4-amino-3-[4-[[(2-methoxybenzoyl)amino]methyl]phenyl]pyrazolo[3,4-d]pyrimidin-1-yl]cyclohexanecarboxylic acid (50 mg, 0.10 mmol) gave after purification by flash column chromatography on silica gel (DCM/MeOH 100:0 to 90:10) afforded N-[[4-[4-amino-1-[4-(dimethylcarbamoyl)cyclohexyl]pyrazolo[3,4-d]pyrimidin-3-yl]phenyl]methyl]-2-methoxy-benzamide (17 mg, 0.03 mmol, 32% yield, isomer 1) as a white solid and N-[[4-[4-amino-1-[4-(dimethylcarbamoyl)cyclohexyl]pyrazolo[3,4-d]pyrimidin-3-yl]phenyl]methyl]-2-methoxy-benzamide (20 mg, 0.04 mmol, 37% yield, isomer 2) as a white solid.

UPLC-MS (ES+, Long acidic, isomer 1): 3.09 min, m/z 528.4 [M+H]+

¹H NMR (400 MHz, DMSO-d₆, δ, isomer 1): 8.77 (t, J=6.0 Hz, 1H), 8.24 (s, 1H), 7.78 (dd, J=7.6, 1.8 Hz, 1H), 7.65 (d, J=8.2 Hz, 2H), 7.55-7.46 (m, 3H), 7.17 (d, J=8.2 Hz, 1H), 7.08-7.02 (m, 1H), 4.86-4.76 (m, 1H), 4.60 (d, J=6.0 Hz, 2H), 3.92 (s, 3H), 3.03 (s, 3H), 2.90 (quint, J=5.2 Hz, 1H), 2.82 (s, 3H), 2.43-2.31 (m, 2H), 2.06-1.93 (m, 2H), 1.88-1.77 (m, 2H), 1.72-1.61 (m, 2H)

UPLC-MS (ES+, Long acidic, isomer 2): 3.04 min, m/z 528.4 [M+H]+

¹H NMR (400 MHz, DMSO-d₆, δ, isomer 2): 8.77 (t, J=6.1 Hz, 1H), 8.25 (s, 1H), 7.78 (dd, J=7.6, 1.8 Hz, 1H), 7.65 (d, J=8.2 Hz, 2H), 7.56-7.46 (m, 3H), 7.17 (d, J=8.3 Hz, 1H), 7.10-7.03 (m, 1H), 4.75-4.63 (m, 1H), 4.60 (d, J=6.1 Hz, 2H), 3.92 (s, 3H), 3.06 (s, 3H), 2.83 (s, 3H), 2.80-2.69 (m, 1H), 2.20-2.05 (m, 2H), 2.03-1.92 (m, 2H), 1.91-1.80 (m, 2H), 1.68-1.52 (m, 2H).

Example 34: N-[[4-(4-amino-1-tetrahydropyran-3-yl-pyrazolo[3,4-d]pyrimidin-3-yl)phenyl]methyl]-2-methoxy-benzamide

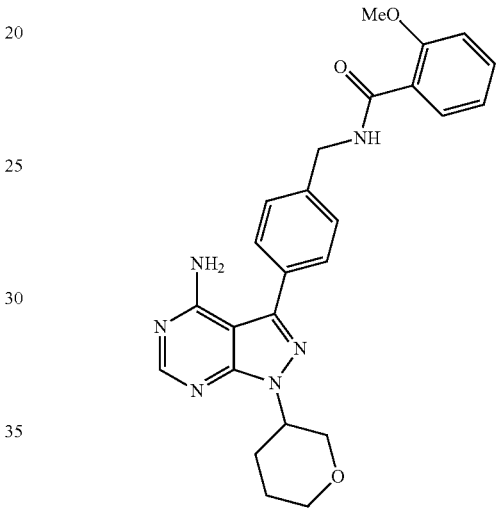

Tetrahydropyran-3-yl methanesulfonate

To a solution of 3-hydroxytetrahydropyran (550 mg, 5.39 mmol) in DCM (30 mL), cooled at 0° C. under nitrogen atmosphere, were added successively triethylamine (0.83 mL, 5.92 mmol) and methanesulfonyl chloride (0.46 mL, 5.92 mmol). The reaction mixture was stirred at 0° C. for 1 h, then quenched with water (15 mL) and extracted with DCM (3×15 mL). The organic phase was separated, filtered over hydrophobic frit and concentrated under reduced pressure to afford tetrahydropyran-3-yl methanesulfonate (967 mg, 4.29 mmol, 80% yield) as a clear pale yellow oil.

¹H NMR (400 MHz, CDCl₃, δ): 4.73 (m, 1H), 3.88-3.84 (m, 1H), 3.72-3.62 (m, 3H), 3.07 (s, 3H), 2.12-2.04 (m, 1H), 2.00-1.88 (m, 2H), 1.69-1.60 (m, 1H).

3-Iodo-1-tetrahydropyran-3-yl-pyrazolo[3,4-d]pyrimidin-4-amine

To a stirred solution of 3-iodo-1H-pyrazolo[3,4-d]pyrimidin-4-amine (700 mg, 2.68 mmol) and tetrahydropyran-3-yl methanesulfonate (967 mg, 5.36 mmol) in DMF (65 mL) was added cesium carbonate (2.9 g, 6.70 mmol). The reaction mixture was stirred for 16 h at 80° C. Once the reaction has proceeded, the reaction mixture was concentrated under reduced pressure. EtOAc (200 mL) was added to the red-orange residue. The mixture was sonicated for 15 minutes, filtered over Buchner. The solid was washed with EtOAc (3×50 mL). The filtrate was then washed with water (2×100 mL), brine (2×100 mL), dried over $Na_2SO_4$, filtered and concentrated under reduced pressure to give an orange solid. Further purification by flash column chromatography on silica gel (DCM/EtOAc 100:0 to 0:100) afforded, 3-iodo-1-tetrahydropyran-3-yl-pyrazolo[3,4-d]pyrimidin-4-amine (536 mg, 0.93 mmol, 35% yield) as a yellow solid.

UPLC-MS (ES$^+$, Short acidic): 1.18 min, m/z 345.9 [M+H]$^+$

N-[[4-(4-Amino-1-tetrahydropyran-3-yl-pyrazolo[3,4-d]pyrimidin-3-yl)phenyl]methyl]-2-methoxy-benzamide Following general procedure D, 3-iodo-1-tetrahydropyran-3-yl-pyrazolo[3,4-d]pyrimidin-4-amine (150 mg, 0.43 mmol) and [4-[[(2-methoxybenzoyl)amino]methyl]phenyl] boronic acid (149 mg, 0.52 mmol) afforded, after further purification by flash column chromatography (DCM/MeOH 100:0 to 95:5), N-[[4-(4-amino-1-tetrahydropyran-3-yl-pyrazolo[3,4-d]pyrimidin-3-yl)phenyl]methyl]-2-methoxy-benzamide (30 mg, 0.06 mmol, 13% yield) as a red-orange solid.

UPLC-MS (ES$^+$, Short acidic): 1.38 min, m/z 459.3 [M+H]$^+$

UPLC-MS (ES$^+$, Long acidic): 3.14 min, m/z 459.2 [M+H]$^+$ $^1$H NMR (400 MHz, DMSO-d$_6$, δ): 8.77 (t, J=6.1 Hz, 1H), 8.26 (s, 1H), 7.77 (dd, J=7.7, 1.8 Hz, 1H), 7.64 (d, J=8.2 Hz, 2H), 7.52-7.47 (m, 3H), 7.17 (d, J=7.7 Hz, 1H), 7.05 (td, J=7.7, 1.0 Hz, 1H), 4.77 (m, 1H), 4.59 (d, J=6.1 Hz, 2H), 3.98-3.88 (m, 5H), 3.72 (t, J=10.6 Hz, 1H), 3.42 (td, J=6.6, 2.8 Hz, 1H), 2.34-2.22 (m, 1H), 2.13-2.11 (m, 1H), 1.85-1.71 (m, 2H).

Example 35: [(1R,4R)-4-[4-amino-3-[4-[[(2-methoxybenzoyl)amino]methyl]phenyl]pyrazolo[3,4-d]pyrimidin-1-yl]cyclopent-2-en-1-yl] acetate

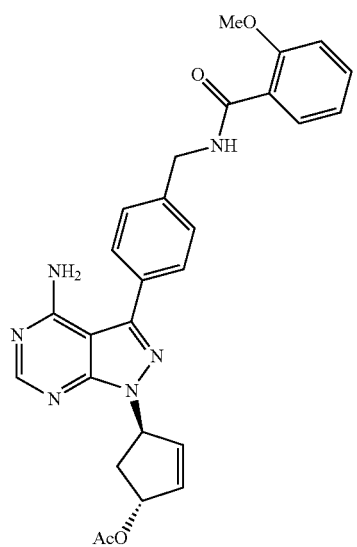 [SMILES: COc1ccccc1C(=O)NCc1ccc(-c2nn([C@H]3C=C[C@H](OC(C)=O)C3)c3ncnc(N)c23)cc1]

[(1R,4R)-4-[4-Amino-3-[4-[[(2-methoxybenzoyl)amino]methyl]phenyl]pyrazolo[3,4-d]pyrimidin-1-yl]cyclopent-2-en-1-yl] acetate Following general procedure G, N-[[4-(4-amino-1H-pyrazolo[3,4-d]pyrimidin-3-yl)phenyl]methyl]-2-methoxy-benzamide (150 mg, 0.40 mmol) and (1S,4R)-cis-4-acetoxy-2-cyclopenten-1-ol (97 mg, 0.68 mmol) afforded [(1R,4R)-4-[4-amino-3-[4-[[(2-methoxybenzoyl)amino]methyl]phenyl]pyrazolo[3,4-d]pyrimidin-1-yl]cyclopent-2-en-1-yl] acetate (98 mg, 0.20 mmol, 49% yield) as a white solid.

UPLC-MS (ES$^+$, Short acidic): 1.44 min, m/z 499.2 [M+H]$^+$

UPLC-MS (ES$^+$, Long acidic): 3.23 min, m/z 499.3 [M+H]$^+$ $^1$H NMR (400 MHz, DMSO-d$_6$, δ): 8.77 (t, J=6.1 Hz, 1H), 8.30 (s, 1H), 7.77 (dd, J=7.7 Hz, 1.8, 1H), 7.65-7.60 (m, 2H), 7.55-7.46 (m, 3H), 7.17 (d, J=7.7 Hz, 1H), 7.05 (dt, J=7.7, 1.0 Hz, 1H), 6.25-6.17 (m, 2H), 6.14-6.08 (m, 1H), 5.95-5.89 (m, 1H), 4.59 (d, J=6.1 Hz, 2H), 3.92 (s, 3H), 2.63-2.55 (m, 1H), 2.43-2.31 (m, 1H), 2.05 (s, 3H).

Example 36: N-[[4-[4-amino-1-[(1R,4R)-4-hydroxy-cyclopent-2-en-1-yl]pyrazolo[3,4-d]pyrimidin-3-yl]phenyl]methyl]-2-methoxy-benzamide

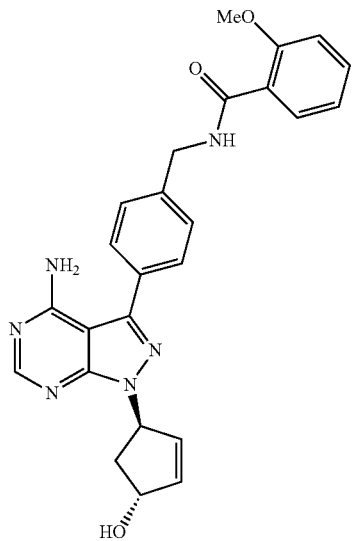 [SMILES: COc1ccccc1C(=O)NCc1ccc(-c2nn([C@H]3C=C[C@H](O)C3)c3ncnc(N)c23)cc1]

N-[[4-[4-Amino-1-[(1R,4R)-4-hydroxycyclopent-2-en-1-yl]pyrazolo[3,4-d]pyrimidin-3-yl]phenyl]methyl]-2-methoxy-benzamide Following general procedure H, [(1R,4R)-4-[4-amino-3-[4-[[(2-methoxybenzoyl)amino]methyl]phenyl]pyrazolo[3,4-d]pyrimidin-1-yl]cyclopent-2-en-1-yl] acetate (211 mg, 0.25 mmol) afforded N-[[4-[4-amino-1-[(1R,4R)-4-hydroxycyclopent-2-en-1-yl]pyrazolo[3,4-d]pyrimidin-3-yl]phenyl]methyl]-2-methoxy-benzamide (47 mg, 0.10 mmol, 41% yield) as a white solid after purification by mass-directed semi-preparative HPLC.

UPLC-MS (ES$^+$, Short acidic): 1.22 min, m/z 457.2 [M+H]$^+$

UPLC-MS (ES$^+$, Long acidic): 2.70 min, m/z 457.2 [M+H]$^+$ $^1$H NMR (400 MHz, DMSO-d$_6$, δ): 8.77 (t, J=6.1 Hz, 1H), 8.21 (m, 1H), 7.77 (dd, J=7.7, 1.8 Hz, 1H), 7.61 (d, J=8.2 Hz, 2H), 7.49 (m, 3H), 7.17 (d, J=7.7 Hz, 1H), 7.05 (dt, J=7.7, 0.9 Hz, 1H), 6.11 (m, 1H), 6.07 (m, 1H), 5.95 (dd, J=7.4, 1.7 Hz, 1H), 5.01 (m, 2H), 4.58 (d, J=6.1 Hz, 2H), 3.91 (s, 3H), 2.43 (m, 1H), 2.16 (m, 1H).

Example 37: N-[[4-[4-amino-1-(3-hydroxycyclohexyl)pyrazolo[3,4-d]pyrimidin-3-yl]phenyl]methyl]-2-methoxy-benzamide

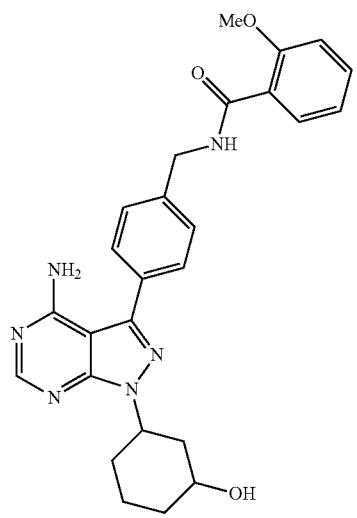 [SMILES: COc1ccccc1C(=O)NCc1ccc(-c2nn(C3CCCC(O)C3)c3ncnc(N)c23)cc1]

N-[[4-[4-Amino-1-(3-hydroxycyclohexyl)pyrazolo[3,4-d]pyrimidin-3-yl]phenyl]methyl]-2-methoxy-benzamide Sodium borohydride (142 mg, 3.76 mmol) was added to a solution of N-[[4-[4-amino-1-(3-oxocyclohexyl)pyrazolo[3,4-d]pyrimidin-3-yl]phenyl]methyl]-2-methoxy-benzamide (177 mg, 0.38 mmol) in methanol (4 mL). The reaction mixture stirred at room temperature for 2 h, and then quenched with a saturated ammonium chloride solution and extracted with DCM. The combined organic layers were dried over sodium sulfate and evaporated to dryness. The crude product was purified by flash column chromatography on silica gel (DCM/MeOH 100:0 to 90:10) to afford N-[[4-[4-amino-1-(3-hydroxycyclohexyl)pyrazolo[3,4-d]pyrimidin-3-yl]phenyl]methyl]-2-methoxy-benzamide (125 mg, 0.27 mmol, 71% yield) as a white solid.

LC-MS (ES$^+$, Short acidic): 2.87 min, m/z 473.3 [M+H]$^+$

UPLC-MS (ES$^+$, Long acidic): 2.87 min, m/z 473.3 [M+H]$^+$ $^1$H NMR (400 MHz, DMSO-d$_6$, δ) (mixture of diastereoisomers): 8.78 (t, J=6.2 Hz, 1H), 8.24 (s, 1H), 7.78 (dd, J=7.7, 1.8, 1H), 7.66-7.63 (m, 2H), 7.52-7.49 (m, 3H), 7.17 (d, J=8.0 Hz, 1H), 7.05 (td, J=11.1, 1.0 Hz, 1H), 4.77 (d, J=4.8 Hz, 1H), 4.75-4.68 (m, 1H), 4.60 (d, J=6.2 Hz, 2H), 3.92 (s, 3H), 3.65-3.57 (m, 1H), 2.13-2.11 (m, 1H), 1.95-1.77 (m, 5H), 1.48-1.38 (m, 1H), 1.25-1.14 (m, 1H).

Example 38: N-[[4-(7-amino-3-cyclopentyl-pyrazolo[4,3-d]pyrimidin-1-yl)phenyl]methyl]-2-methoxy-benzamide

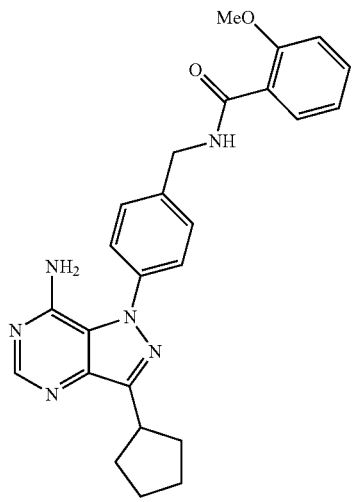 [SMILES: COc1ccccc1C(=O)NCc1ccc(-n2nc(C3CCCC3)c3ncnc(N)c32)cc1]

Methyl 2-cyano-2-cyclopentylidene-acetate

A solution of methyl cyanoacetate (10.5 mL, 118.88 mmol), cyclopentanone (10.5 mL, 118.88 mmol) and ammonium acetate (6.0 g, 77.27 mmol) and acetic acid (2.4 mL) in toluene (12 mL) was heated to reflux under Dean-Stark conditions for 16 h. The reaction mixture was cooled to room temperature and the solvent removed in vacuo to afford the crude methyl 2-cyano-2-cyclopentylidene-acetate (19.6 g, 118.65 mmol, assumed quantitative) as a dark brown thick oil.

$^1$H NMR (400 MHz, CDCl$_3$, δ): 3.81 (s, 3H), 2.98 (t, J=6.7 Hz, 2H), 2.80 (t, J=6.7 Hz, 3H), 1.89-1.77 (m, 4H).

Methyl 2-cyano-2-cyclopentyl-acetate

Methyl 2-cyano-2-cyclopentylidene-acetate (19.6 g, 118.65 mmol) was dissolved in MeOH (50 mL). The flask was evacuated and refilled with nitrogen before palladium (10 wt % on carbon powder, dry) (2.53 g, 2.37 mmol) was added and the flask evacuated and purged with hydrogen. The reaction mixture was stirred at room temperature under an atmosphere of hydrogen for 72 h. The reaction mixture was filtered over celite and the filtrate concentrated in vacuo. The crude product was purified by column chromatography eluting with 0-50% EtOAc in heptane to afford methyl 2-cyano-2-cyclopentyl-acetate (7.00 g, 41.86 mmol, 35% yield) as a yellow oil.

$^1$H NMR (400 MHz, CDCl$_3$, δ): 3.80 (s, 3H), 3.51 (d, J=6.7 Hz, 1H), 2.53-2.43 (m, 1H), 2.93-1.82 (m, 2H), 1.78-1.67 (m, 2H), 1.65-1.55 (m, 2H), 1.51-1.37 (m, 2H).

Methyl 2-[(E)-(4-bromophenyl)azo]-2-cyano-2-cyclopentyl-acetate

4-Bromoaniline (10.3 g, 60.0 mmol) was dissolved in hydrochloric acid (1 M, 150 mL, 150.0 mmol) and dropwise added to an aqueous solution of sodium nitrite (1 M, 60 mL, 60.0 mmol). The reaction mixture was then stirred at room temperature for 1 h and then added dropwise to a solution of methyl 2-cyano-2-cyclopentyl-acetate (5.0 g, 30.0 mmol) in EtOH (42 mL) and water (556 mL) while maintaining a pH value of 7 by addition of sodium acetate. The mixture was stirred in the thawing ice bath for 16 h. The reaction was quenched with saturated ammonium chloride and diluted with EtOAc. The phases were separated and the aqueous layer extracted with EtOAc. The organic layer was washed with brine and dried over sodium sulfate. The solvent was removed under reduced pressure to afford the crude methyl 2-[(E)-(4-bromophenyl)azo]-2-cyano-2-cyclopentyl-acetate (10.8 g, 30.8 mmol, assumed quantitative yield) as a yellow oil.

UPLC-MS (ES+, Short acidic): 2.12 min, m/z 351.9 [M+H]+

(Z)—N-(4-Bromoanilino)cyclopentanecarboximidoyl cyanide

To a solution of methyl 2-[(E)-(4-bromophenyl)azo]-2-cyano-2-cyclopentyl-acetate (10.8 g, 30.8 mmol in THF (308 mL), cooled to 0° C., was added a 0.1 M solution of sodium hydroxide (80.2 mL, 801.8 mmol). The reaction mixture was warmed to room temperature and stirred for another 16 h. Ammonium chloride was added and the mixture was diluted with EtOAc. The phases were separated and the organic phase washed with citric acid, saturated sodium bicarbonate solution and brine. The organic layer was dried over sodium sulfate and concentrated in vacuo. Purification by flash column chromatography on silica gel eluting with 0-20% EtOAc in heptane afforded (Z)—N-(4-bromoanilino)cyclopentanecarboximidoyl cyanide (3.6 g, 12.4 mmol, 40% yield) as an orange oil.

LC-MS (ES+, Method 1): 5.18 min, m/z 293.0 [M+H]+

4-Amino-2-(4-bromophenyl)-5-cyclopentyl-pyrazole-3-carbonitrile

Bromoacetonitrile (1.63 g, 13.63 mmol) and sodium tert-butoxide (1.19 g, 12.39 mmol) were added to a solution of (Z)—N-(4-bromoanilino)cyclopentanecarboximidoyl cyanide (3.62 g, 12.39 mmol) in tert-butanol (62 mL). The reaction was stirred at 25° C. for 1 h, quenched by adding saturated ammonium chloride and diluted with EtOAc. The phases were separated and the aqueous layer was extracted with EtOAc. The combined organic layers were washed with brine and dried over sodium sulfate. The solvent was removed under reduced pressure. Purification by flash column chromatography on silica gel eluting with 0-25% EtOAc in heptane afforded 4-amino-2-(4-bromophenyl)-5-cyclopentyl-pyrazole-3-carbonitrile (2.7 g, 8.15 mmol, 66% yield) as a yellow oil.

UPLC-MS (ES+, Short acidic): 2.12 min, m/z 332.8 [M+H]+

1-(4-Bromophenyl)-3-cyclopentyl-pyrazolo[4,3-d]pyrimidin-7-amine

Formamidine acetate (6.29 g, 60.39 mmol) was added to a solution of 4-amino-2-(4-bromophenyl)-5-cyclopentyl-pyrazole-3-carbonitrile (2.5 g, 7.55 mmol) was dissolved in EtOH (75.5 mL). The reaction mixture was heated to 80° C. for 3 h and concentrated under reduced pressure. The crude product was purified by flash column chromatography on silica gel eluting with 0-100% EtOAc in heptane to afford 1-(4-bromophenyl)-3-cyclopentyl-pyrazolo[4,3-d]pyrimidin-7-amine (1.49 g, 4.16 mmol, 55% yield) as a beige solid.

UPLC-MS (ES+, Short acidic): 1.66 min, m/z 359.8 [M+H]+

2-(Chloromethyl)-4,4,5,5-tetramethyl-1,3,2-dioxaborolane

To a stirred solution of 2-isopropoxy-4,4,5,5-tetramethyl-1,3,2-dioxaborolane (11.0 mL, 53.75 mmol) and chloroiodomethane (4.3 mL, 59.12 mmol) in anhydrous THF (100 mL), cooled to −78° C., was added cold n-butyllithium solution (23.94 mL, 59.12 mmol) dropwise. After stirring for 30 min at this temperature, chlorotrimethylsilane (8.2 mL, 64.50 mmol) was added dropwise. After stirring for 10 min, the reaction mixture was allowed to return to room temperature and stirred for 24 h. Water (80 mL) was added and the mixture extracted with $Et_2O$ (2×80 mL). The organic extracts were combined, washed with water (2×80 mL), dried over $MgSO_4$ and concentrated in vacuo. The crude product was purified by flash column chromatography on silica gel (Heptane/EtOAc 99:1 to 95:5) to yield 2-(chloromethyl)-4,4,5,5-tetramethyl-1,3,2-dioxaborolane (4.35 g, 24.65 mmol, 46% yield) as a colourless oil.

$^1$H NMR (400 MHz, DMSO-$d_6$, δ): 2.99 (s, 2H), 1.32 (s, 12H).

Potassium trifluoro-[[(2-methoxybenzoyl)amino]methyl]boranuide

A solution of freshly prepared potassium bis(trimethylsilyl)amide (4.92 g, 24.65 mmol) in dry THF (50 mL) was added dropwise to a solution of 2-(chloromethyl)-4,4,5,5-tetramethyl-1,3,2-dioxaborolane (4.35 g, 24.65 mmol) in dry THF (50 mL) cooled to −78° C. After stirring for 15 min at −78° C., the cooling bath was removed and the mixture was stirred for an additional 2 h at room temperature. Anhydrous MeOH (2 mL, 49.29 mmol) was then added at 0° C. After stirring for an additional 1 h at 0° C., 2-methoxybenzoyl chloride (7.3 mL, 49.29 mmol) was added. The reaction was warmed to room temperature and stirred for 24 h. The reaction mixture was concentrated under vacuum to remove THF then the resulting residue was diluted in anhydrous MeOH (50 mL) and cooled to 0° C. before the addition of a saturated solution of potassium hydrogen fluoride (7.70 g, 98.59 mmol). The reaction mixture was warmed to room temperature and stirred for 30 min and then concentrated under vacuum. The residue was triturated with hot acetone (2×500 mL) and filtered. The filtrate was concentrated under vacuum until the appearance of the first crystals. $Et_2O$ (1500 mL) was then added. The precipitate was collected by filtration to give potassium trifluoro-[[(2-methoxybenzoyl)amino]methyl]boranuide (1.48 g, 5.45 mmol, 22% yield) as a yellow solid.

$^1$H NMR (400 MHz, DMSO-$d_6$, δ): 10.34 (s, 1H), 7.95 (dd, J=8.0, 1.8 Hz, 1H), 7.74 (m, 1H), 7.31 (d, J=8.0 Hz, 1H), 7.17 (m, 1H), 3.98 (s, 3H), 2.46 (t, J=9.9 Hz, 2H).

N-[[4-(7-Amino-3-cyclopentyl-pyrazolo[4,3-d]pyrimidin-1-yl)phenyl]methyl]-2-methoxy-benzamide Following general procedure K, potassium trifluoro-[[(2-methoxybenzoyl)amino]methyl]boranuide (75.7 mg, 0.28 mmol) and 1-(4-bromophenyl)-3-cyclopentyl-pyrazolo[4,3-d]pyrimidin-7-amine (100.0 mg, 0.28 mmol) afforded N-[[4-(7-amino-3-cyclopentyl-pyrazolo[4,3-d]pyrimidin-1-yl)phenyl]methyl]-2-methoxy-benzamide (72 mg, 0.16 mmol, 58% yield) after purification by flash column chromatography on silica gel (EtOAc/MeOH 100:0 to 80:20).

UPLC-MS (ES+, Short acidic): 1.49 min, m/z 443.4 [M+H]+

UPLC-MS (ES+, Long acidic): 3.44 min, m/z 443.5 [M+H]+

$^{1}$H NMR (400 MHz, DMSO-$d_6$, δ): 8.79 (t, J=6.2 Hz, 1H), 8.29 (s, 1H), 7.77 (dd, J=7.7, 1.8 Hz, 1H), 7.52 (m, 5H), 7.17 (d, J=7.7 Hz, 1H), 7.05 (dt, J=7.7, 1.0 Hz, 1H), 6.46 (s, 2H), 4.60 (d, J=6.2 Hz, 2H), 3.92 (s, 3H), 3.46 (quint, J=8.3 Hz, 1H), 2.03 (m, 4H), 1.80 (m, 2H), 1.69 (m, 2H).

Example 39: N-[[4-[4-amino-1-(4-methoxycyclohexyl)pyrazolo[3,4-d]pyrimidin-3-yl]phenyl]methyl]-2-methoxy-benzamide

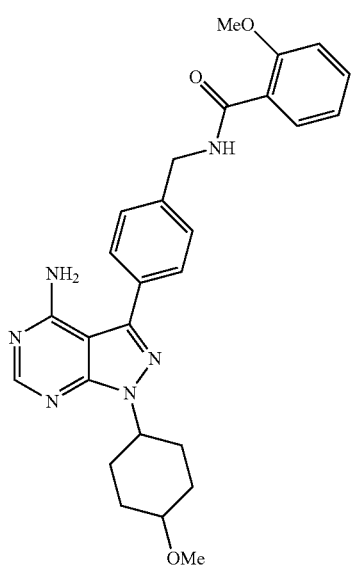 [SMILES: COc1ccccc1C(=O)NCc1ccc(-c2nn(C3CCC(OC)CC3)c3ncnc(N)c23)cc1]

4-[tert-Butyl(dimethyl)silyl]oxycyclohexanol

Sodium borohydride (83 mg, 2.19 mmol) was added to a solution of 4-(tert-butyldimethylsilyloxy)cyclohexanone (0.5 mL, 1.99 mmol) in methanol (4 mL), cooled to 0° C. The reaction mixture was stirred at room temperature for 30 min, and then carefully quenched with a saturated solution of aqueous NH$_4$Cl (10 mL). The aqueous layer was extracted with DCM (3×10 mL) and the combined organic extracts were filtered over a phase separator, concentrated under reduced pressure to give crude 4-[tert-butyl(dimethyl)silyl]oxycyclohexanol (assumed quantitative) which was used directly in the next step.

$^{1}$H NMR (400 MHz, CDCl$_3$, δ) (2:1 mixture of conformers): 3.82-3.72 (m, 0.6H), 3.69-3.53 (m, 1.4H), 1.96-1.18 (m, 9H), 0.90-0.78 (m, 9H), 0.04-0.03 (m, 6H)

tert-Butyl-(4-methoxycyclohexoxy)-dimethyl-silane

To a solution of 4-[tert-butyl(dimethyl)silyl]oxycyclohexanol (0.14 mL, 1.99 mmol) in THF (2.0 mL), cooled at 0° C. under nitrogen atmosphere, was added sodium hydride (60% dispersed in mineral oil) (111 mg, 2.78 mmol). After allowing the reaction mixture to stir at 0° C. for 30 min, iodomethane (0.17 mL, 2.78 mmol) was added. The reaction mixture was stirred at room temperature overnight, then carefully quenched with a saturated solution of ammonium chloride (10 mL). The aqueous layer was extracted with DCM (3×10 mL). The organic layers were combined, filtered over a hydrophobic frit and concentrated under reduced pressure to afford crude tert-butyl-(4-methoxycyclohexoxy)-dimethyl-silane (assumed quantitative) as a yellow oil.

$^{1}$H NMR (400 MHz, CDCl$_3$, δ): 3.80-3.55 (m, 1H), 3.29 (s, 3H), 3.20-3.01 (m, 1H), 2.00-1.86 (m, 1H), 1.86-1.37 (m, 7H), 0.90-0.78 (m, 9H), 0.04-0.02 (m, 6H)

3-Iodo-1-(4-methoxycyclohexyl)pyrazolo[3,4-d]pyrimidin-4-amine

To a solution of tert-butyl-(4-methoxycyclohexoxy)-dimethyl-silane (486 mg, 1.99 mmol) in THF (2.0 mL), cooled at 0° C. under nitrogen atmosphere, was added 1.0 M tetrabutylammonium fluoride in THF (4.0 mL, 4.00 mmol). The reaction mixture was allowed to stir at room temperature overnight, then quenched with water (20 mL). The aqueous layer was extracted with DCM (3×10 mL). The organic extracts were combined, filtered over a hydrophobic frit and concentrated under reduced pressure to provide 4-methoxycyclohexanol (229 mg, 1.76 mmol, 89% yield) as a yellow oil. The residue was dissolved in DCM (2.0 mL), cooled to 0° C. under nitrogen atmosphere, and then methanesulfonyl chloride (0.18 mL, 2.39 mmol) and triethylamine (0.42 mL, 2.98 mmol) were added successively. The reaction mixture was stirred at 0° C. for 1 h, and then quenched with water (20 mL). The aqueous layer was extracted with DCM (3×10 mL). The organic extracts were combined, filtered over a hydrophobic fit and concentrated under reduced pressure to provide (4-methoxycyclohexyl)methanesulfonate (320 mg, 1.55 mmol, 78% yield) as a yellow oil. Then pyrazolo[3,4-d]pyrimidin-4-amine (400 mg, 1.53 mmol) was added and suspended in DMF (3 mL) under a nitrogen atmosphere. Afterwards, cesium carbonate (750 mg, 2.30 mmol) was added and the reaction mixture was allowed to stir at 80° C. for 16 h. Afterwards, the reaction mixture was concentrated under reduced pressure. The residue was then partitioned between a layer of ethyl acetate (15 mL) and water (15 mL). The aqueous layer was extracted with ethyl acetate (3×20 mL). The combined organic layers were washed with a saturated solution of brine, dried over Na$_2$SO$_4$, filtered and concentrated under reduced pressure. Further purification by flash column chromatography on silica gel eluting 0-3% MeOH in DCM afforded 3-iodo-1-(4-methoxycyclohexyl)pyrazolo[3,4-d]pyrimidin-4-amine (174 mg, 0.47 mmol, 30% yield as a mixture of diastereoisomers) as a yellow solid.

UPLC-MS (ES+, Short acidic, isomer 1): 1.25 min, m/z 374.1 [M+H]+

UPLC-MS (ES+, Short acidic, isomer 2): 1.29 min, m/z 374.1 [M+H]+

N-[[4-[4-Amino-1-(4-methoxycyclohexyl)pyrazolo[3,4-d]pyrimidin-3-yl]phenyl]methyl]-2-methoxy-benzamide Following general procedure C, 3-iodo-1-(4-methoxycyclohexyl)pyrazolo[3,4-d]pyrimidin-4-amine (150 mg, 0.40 mmol) and [4-[[(2-methoxybenzoyl)amino]methyl]phenyl]boronic acid (138 mg, 0.48 mmol) gave N-[[4-[4-amino-1-(4-methoxycyclohexyl)pyrazolo[3,4-d]pyrimidin-3-yl]phenyl]methyl]-2-methoxy-benzamide (762 mg, 1.37 mmol, 86% yield as a mixture of diastereoisomers) as a white solid.

UPLC-MS (ES+, Short acidic): 1.42 min, m/z 487.3 [M+H]+ (Isomer 1), 1.45 min, m/z 487.3 [M+H]+ (Isomer 2)

UPLC-MS (ES+, Long acidic): 3.26 min, m/z 487.3 [M+H]+ (Isomer 1), 3.34 min, m/z 487.3 [M+H]+ (Isomer 2)

$^1$H NMR (400 MHz, DMSO-d$_6$, δ) (2:1 mixture of diastereoisomers): 8.77 (t, J=6.0 Hz, 1H), 8.24 (s, 1H), 7.80-7.75 (m, 1H), 7.68-7.60 (m, 2H), 7.55-7.45 (m, 3H), 7.17 (d, J=8.3 Hz, 1H), 7.09-7.02 (m, 1H), 4.80-4.63 (m, 1H), 4.59 (d, J=6.0 Hz, 2H), 3.92 (s, 3H), 3.51-3.44 (m, 0.3H), 3.31-3.21 (m, 3.7H), 2.30-1.89 (m, 5H), 1.74-1.55 (m, 1.3H), 1.45-1.30 (m, 1.7H)

Example 40: N-[[4-(4-amino-1-cyclopent-3-en-1-yl-pyrazolo[3,4-d]pyrimidin-3-yl)phenyl]methyl]-2-methoxy-benzamide

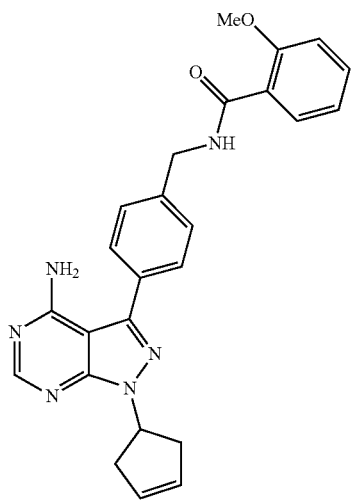 [SMILES: COc1ccccc1C(=O)NCc1ccc(-c2nn(C3CC=CC3)c3ncnc(N)c23)cc1]

1-Cyclopent-3-en-1-yl-3-iodo-pyrazolo[3,4-d]pyrimidin-4-amine

Following general procedure G, a suspension of 3-iodo-1H-pyrazolo[3,4-d]pyrimidin-4-amine (100 mg, 0.38 mmol) and 3-cyclopentene-1-ol (55 mg, 0.65 mmol) gave, after further purification by flash column chromatography on silica gel, 1-cyclopent-3-en-1-yl-3-iodo-pyrazolo[3,4-d]pyrimidin-4-amine (70 mg, 0.11 mmol, 28% yield) as a yellow solid.

UPLC-MS (ES+, Short acidic): 1.30 min, m/z 328.1 [M+H]+

N-[[4-(4-Amino-1-cyclopent-3-en-1-yl-pyrazolo[3,4-d]pyrimidin-3-yl)phenyl]methyl]-2-methoxy-benzamide Following general procedure D, 1-cyclopent-3-en-1-yl-3-iodo-pyrazolo[3,4-d]pyrimidin-4-amine (70 mg, 0.21 mmol) and [4-[[(2-methoxybenzoyl)amino]methyl]phenyl]boronic acid (91 mg, 0.32 mmol) afforded, after further purification by flash column chromatography on silica gel, N-[[4-(4-amino-1-cyclopent-3-en-1-yl-pyrazolo[3,4-d]pyrimidin-3-yl)phenyl]methyl]-2-methoxy-benzamide (25 mg, 0.05 mmol, 24% yield).

UPLC-MS (ES+, Short acidic): 1.47 min, m/z 441.2 [M+H]+

UPLC-MS (ES+, Long acidic): 3.38 min, m/z 441.3 [M+H]+

$^1$H NMR (400 MHz, DMSO-d$_6$, δ): 8.76 (t, J=6.1 Hz, 1H), 8.25 (s, 1H), 7.76 (dd, J=7.6, 1.7 Hz, 1H), 7.66-7.61 (m, 2H), 7.53-7.45 (m, 3H), 7.18-7.14 (m, 1H), 7.07-7.01 (m, 1H), 5.81 (s, 2H), 5.63-5.54 (m, 1H), 4.58 (d, J=6.1 Hz, 2H), 3.91 (s, 3H), 2.94-2.74 (m, 4H).

Example 41: ethyl 3-[4-amino-3-[4-[[(2-methoxy-benzoyl)amino]methyl]phenyl]pyrazolo[3,4-d]pyrimidin-1-yl]cyclohexanecarboxylate

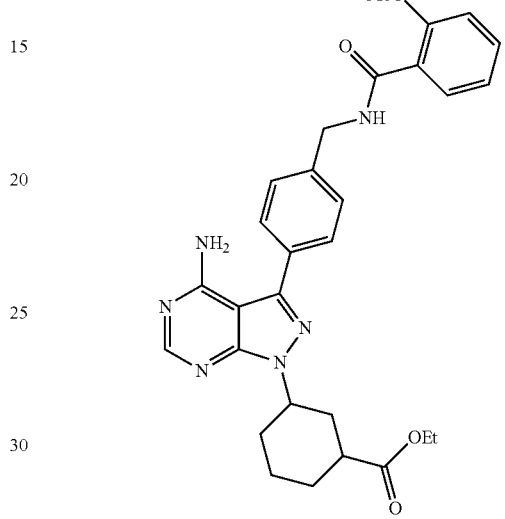

Ethyl 3-(4-amino-3-iodo-pyrazolo[3,4-d]pyrimidin-1-yl)cyclohexanecarboxylate

Following general procedure G, 3-iodo-1H-pyrazolo[3,4-d]pyrimidin-4-amine (500 mg, 1.92 mmol) and ethyl 3-hydroxycyclohexanecarboxylate (0.5 mL, 3.26 mmol) afforded, after further purification by flash column chromatography (DCM/EtOAc 100:0 to 0:100), ethyl 3-(4-amino-3-iodo-pyrazolo[3,4-d]pyrimidin-1-yl)cyclohexanecarboxylate (302 mg, 0.37 mmol, 19% yield) as a yellow solid.

UPLC-MS (ES+, Short acidic): 1.50 min and 1.55 min, m/z 416.1 [M+H]+

Ethyl 3-[4-amino-3-[4-[[(2-methoxybenzoyl)amino]methyl]phenyl]pyrazolo[3,4-d]pyrimidin-1-yl]cyclohexanecarboxylate Following general procedure D, ethyl 3-(4-amino-3-iodo-pyrazolo[3,4-d]pyrimidin-1-yl)cyclohexanecarboxylate (100 mg, 0.29 mmol) and [4-[[(2-methoxybenzoyl)amino]methyl]phenyl]boronic acid (125 mg, 0.44 mmol) gave, after further purification by flash column chromatography (DCM/MeOH 100:0 to 95:5), ethyl 3-[4-amino-3-[4-[[(2-methoxybenzoyl)amino]methyl]phenyl]pyrazolo[3,4-d]pyrimidin-1-yl]cyclohexanecarboxylate (21 mg, 0.03 mmol, 5% yield) as a pale yellow solid.

UPLC-MS (ES+, Short acidic): 1.61 min and 1.63 min, m/z 529.3 [M+H]+

$^1$H NMR (400 MHz, DMSO-d$_6$, δ) (2:1 mixture of diastereoisomers): 8.77 (t, J=6.1 Hz, 1H), 8.25 (s, 1H), 7.77 (dd, J=7.7, 1.8 Hz, 1H), 7.65 (d, J=8.2 Hz, 2H), 7.52-7.47 (m, 3H), 7.17 (d, J=7.7 Hz, 1H), 7.05 (td, J=7.7, 1.0 Hz, 1H), 5.00 (m, 0.3H), 4.79 (m, 0.7H), 4.59 (d, J=6.1 Hz, 2H), 4.14 (q, J=7.3 Hz, 0.7H), 4.06 (q, J=7.1 Hz, 1.3H), 3.92 (s, 3H), 2.28-1.31 (m, 8H), 1.23 (t, J=7.3 Hz, 1H), 1.17 (t, J=7.1 Hz, 2H).

Example 42: N-[[4-[4-amino-1-[3-(dimethylcarbamoyl)cyclohexyl]pyrazolo[3,4-d]pyrimidin-3-yl]phenyl]methyl]-2-methoxy-benzamide

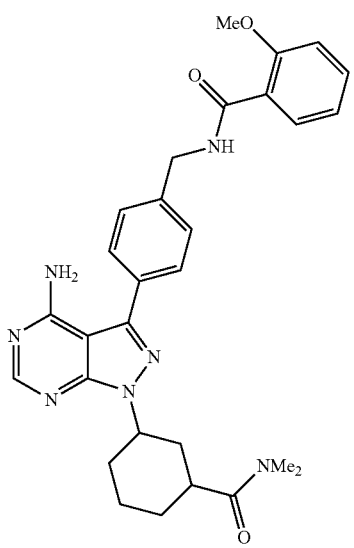 [SMILES: COc1ccccc1C(=O)NCc1ccc(-c2nn(C3CCCC(C(=O)N(C)C)C3)c3ncnc(N)c23)cc1]

Ethyl 3-(4-amino-3-iodo-pyrazolo[3,4-d]pyrimidin-1-yl)cyclohexanecarboxylate

Following general procedure G, 3-iodo-1H-pyrazolo[3,4-d]pyrimidin-4-amine (500 mg, 1.92 mmol) and ethyl 3-hydroxycyclohexanecarboxylate (0.5 mL, 3.26 mmol) afforded, after further purification by flash column chromatography on silica gel (DCM/EtOAc 100:0 to 0:100), ethyl 3-(4-amino-3-iodo-pyrazolo[3,4-d]pyrimidin-1-yl)cyclohexanecarboxylate (302 mg, 0.37 mmol, 19% yield) as a yellow solid.

UPLC-MS (ES+, Short acidic): 1.50 min and 1.55 min, m/z 416.1 [M+H]+

Ethyl 3-[4-amino-3-[4-[[(2-methoxybenzoyl)amino]methyl]phenyl]pyrazolo[3,4-d]pyrimidin-1-yl]cyclohexanecarboxylate Following general procedure D, ethyl 3-(4-amino-3-iodo-pyrazolo[3,4-d]pyrimidin-1-yl)cyclohexanecarboxylate (100 mg, 0.29 mmol) and [4-[[(2-methoxybenzoyl)amino]methyl]phenyl]boronic acid (125 mg, 0.44 mmol) afforded, after further purification by flash column chromatography on silica gel (DCM/MeOH 100:0 to 95:5), ethyl 3-[4-amino-3-[4-[[(2-methoxybenzoyl)amino]methyl]phenyl]pyrazolo[3,4-d]pyrimidin-1-yl]cyclohexanecarboxylate (156 mg, 0.27 mmol, 37% yield) as a pale yellow solid.

UPLC-MS (ES+, Short acidic): 1.61 min and 1.63 min, m/z 529.3 [M+H]+

3-[4-Amino-3-[4-[[(2-methoxybenzoyl)amino]methyl]phenyl]pyrazolo[3,4-d]pyrimidin-1-yl]cyclohexanecarboxylic acid Ethyl 3-[4-amino-3-[4-[[(2-methoxybenzoyl)amino]methyl]phenyl]pyrazolo[3,4-d]pyrimidin-1-yl]cyclohexanecarboxylate (156 mg, 0.30 mmol) was dissolved in a mixture of THF/EtOH (2 mL, 1:1) followed by the addition of sodium hydroxide (70.8 mg, 1.77 mmol) in water (0.9 mL). The resulting mixture was then left to stir at room temperature overnight. Once the reaction has reached completion, 1 M HCl was then added to neutralise the pH of the reaction mixture to pH 3. The solvents were then removed under reduced pressure to afford a yellow gum. The residue was then washed with water and extracted with EtOAc (3×20 mL), washed with brine (10 mL) and dried over anhydrous sodium sulfate. The solvent was removed under reduced pressure to afford 3-[4-amino-3-[4-[[(2-methoxybenzoyl)amino]methyl]phenyl]pyrazolo[3,4-d]pyrimidin-1-yl]cyclohexanecarboxylic acid (130 mg, 0.26 mmol, 88% yield, mixture of diastereoisomers) as a yellow-brown solid.

UPLC-MS (ES+, Short acidic): 1.35 min and 1.38 min, m/z 501.2 [M+H]+

N-[[4-[4-Amino-1-[3-(dimethylcarbamoyl)cyclohexyl]pyrazolo[3,4-d]pyrimidin-3-yl]phenyl]methyl]-2-methoxy-benzamide Following general procedure F, 3-[4-amino-3-[4-[[(2-methoxybenzoyl)amino]methyl]phenyl]pyrazolo[3,4-d]pyrimidin-1-yl]cyclohexanecarboxylic acid (100 mg, 0.20 mmol) and dimethylamine (0.01 mL, 0.26 mmol) afforded, after further purification by flash column chromatography on silica gel (DCM/MeOH 100:0 to 90:10), N-[[4-[4-amino-1-[3-(dimethylcarbamoyl)cyclohexyl]pyrazolo[3,4-d]pyrimidin-3-yl]phenyl]methyl]-2-methoxy-benzamide (17 mg, 0.03 mmol, 14% yield, mixture of diastereoisomers) as a cream solid.

UPLC-MS (ES+, Short acidic): 1.34 and 1.39 min, m/z 528.3 [M+H]+

UPLC-MS (ES+, Long acidic): 3.08 and 3.24 min, m/z 528.4 [M+H]+

$^1$H NMR (400 MHz, DMSO-$d_6$, δ) (2:1 mixture of diastereoisomers): 8.77 (t, J=6.0 Hz, 1H), 8.24 (s, 1H), 7.76 (dd, J=7.7, 1.7 Hz, 1H), 7.65 (d, J=8.2 Hz, 2H), 7.52-7.47 (m, 3H), 7.17 (d, J=8.4 Hz, 1H), 7.07-7.03 (m, 1H), 5.32 (m, 0.3H), 4.84 (m, 0.7H), 4.59 (d, J=6.1 Hz, 2H), 3.92 (s, 3H), 3.05 (s, 2.1H), 3.00 (s, 0.9H), 2.82 (s, 0.9H), 2.80 (s, 2.1H), 2.22-1.24 (m, 8H).

Example 43: N-[[4-(4-amino-1-tert-butyl-pyrazolo[3,4-d]pyrimidin-3-yl)phenyl]methyl]-5-fluoro-2-methoxy-benzamide

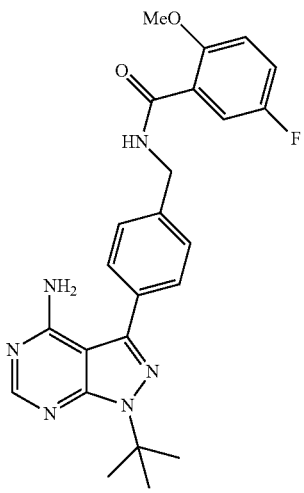 [SMILES: COc1ccc(F)cc1C(=O)NCc1ccc(-c2nn(C(C)(C)C)c3ncnc(N)c23)cc1]

5-Fluoro-2-methoxy-benzoyl chloride

A solution of 5-fluoro-2-methoxybenzoic acid (10.0 g, 58.8 mmol) in DCM (200 mL) was cooled to 0° C. and oxalyl chloride (5.5 mL, 64.7 mmol) was added dropwise. The reaction mixture was allowed to warm to room temperature, stirred overnight and concentrated under reduced pressure. Further purification product by flash column chromatography on silica gel (heptane/EtOAc 70:30 to 0:100) gave the title compound (3.4 g, 18.1 mmol, 31%) as white solid.

LC-MS (ES+, Method 1): 3.81 min, m/z 189.1 [M+H]+

[4-[[(5-Fluoro-2-methoxy-benzoyl)amino]methyl]phenyl]boronic acid

Following general procedure B, 5-fluoro-2-methoxy-benzoyl chloride (2.85 g, 15.1 mmol) and [4-(aminomethyl)phenyl]boronic acid hydrochloride (2.83 g, 15.1 mmol), after further recrystallization in DCM, afforded the title compound (2.60 g, 7.90 mmol, 52%) as an white solid.

UPLC-MS (ES+, Short acidic): 1.46 min, m/z 304.1 [M+H]+

N-[[4-(4-Amino-1-tert-butyl-pyrazolo[3,4-d]pyrimidin-3-yl)phenyl]methyl]-5-fluoro-2-methoxy-benzamide Following general procedure C, 3-bromo-1-tert-butyl-pyrazolo[3,4-d]pyrimidin-4-amine (1.00 g, 3.70 mmol) and [4-[[(5-fluoro-2-methoxy-benzoyl)amino]methyl]phenyl]boronic acid (1.46 g, 4.44 mmol), after further recrystallization in DCM, afforded N-[[4-(4-amino-1-tert-butyl-pyrazolo[3,4-d]pyrimidin-3-yl)phenyl]methyl]-5-fluoro-2-methoxy-benzamide (226 mg, 0.49 mmol, 13%) as a white solid.

UPLC-MS (ES+, Short acidic): 1.77 min, m/z 449.4 [M+H]+

UPLC-MS (ES+, Long acidic): 3.81 min, m/z 449.3 [M+H]+

1H NMR (400 MHz, DMSO-d6, δ): 8.87 (t, J=6.1 Hz, 1H), 8.24 (s, 1H), 7.63 (d, J=8.3 Hz, 2H), 7.56-7.48 (m, 3H), 7.38-7.32 (m, 1H), 7.20 (dd, J=9.2, 4.3 Hz, 1H), 4.60 (d, J=5.9 Hz, 2H), 3.91 (s, 3H), 1.76 (s, 9H).

Example 44: N-[[4-[4-amino-1-[(1S,4R)-4-hydroxycyclopent-2-en-1-yl]pyrazolo[3,4-d]pyrimidin-3-yl]phenyl]methyl]-2-methoxy-benzamide

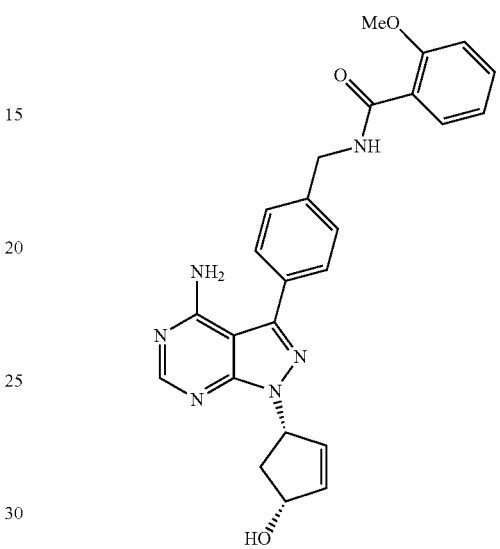

[(1R,4R)-4-Acetoxycyclopent-2-en-1-yl] 2,2-dimethylpropanoate

Following general procedure G, (1S,4R)-cis-4-acetoxy-2-cyclopenten-1-ol (500 mg, 3.52 mmol) and trimethylacetic acid (548 mg, 5.36 mmol) afforded [(1R,4R)-4-acetoxycyclopent-2-en-1-yl] 2,2-dimethylpropanoate (663 mg, 2.93 mmol, 83% yield) after purification by flash column chromatography on silica gel (heptane/EtOAc 100:0 to 75:15).

1H NMR (400 MHz, DMSO-d6, δ): 6.13 (m, 2H), 5.82 (m, 2H), 2.23 (m, 2H), 2.07 (s, 3H), 1.20 (s, 9H).

[(1R,4R)-4-Hydroxycyclopent-2-en-1-yl] 2,2-dimethylpropanoate

A mixture of [(1R,4R)-4-acetoxycyclopent-2-en-1-yl] 2,2-dimethylpropanoate (125 mg, 0.36 mmol) and potassium carbonate (50 mg, 0.36 mmol) in MeOH (3.6 mL) was stirred at room temperature for 90 minutes. The reaction mixture was then diluted with chloroform and washed with an aqueous solution of NH4Cl then brine. The organic layer was dried over Na2SO4 and concentrated under vacuum to give [(1R,4R)-4-hydroxycyclopent-2-en-1-yl] 2,2-dimethylpropanoate (101 mg, 0.36 mmol, 99% yield).

1H NMR (400 MHz, DMSO-d6, δ): 6.14 (m, 1H), 6.04 (m, 1H), 5.82 (m, 1H), 5.09 (m, 1H), 2.22 (m, 2H), 1.33 (m, 1H), 1.19 (s, 9H).

[(1R,4S)-4-[4-Amino-3-[4-[[(2-methoxybenzoyl)amino]methyl]phenyl]pyrazolo[3,4-d]pyrimidin-1-yl]cyclopent-2-en-1-yl] 2,2-dimethylpropanoate Following general procedure G, N-[[4-(4-amino-1H-pyrazolo[3,4-d]pyrimidin-3-yl)phenyl]methyl]-2-methoxybenzamide (217 mg, 0.58 mmol) and [(1R,4R)-4-hydroxy-cyclopent-2-en-1-yl] 2,2-dimethylpropanoate (101 mg, 0.36 mmol) afforded [(1R,4S)-4-[4-amino-3-[4-[[(2-methoxybenzoyl)amino]methyl]phenyl]pyrazolo[3,4-d]pyrimidin-1-yl]cyclopent-2-en-1-yl] 2,2-dimethylpropanoate (42 mg, 0.07 mmol, 19% yield)

UPLC-MS (ES+, Short acidic): 1.65 min, m/z 541.3 [M+H]+

N-[[4-[4-Amino-1-[(1S,4R)-4-hydroxycyclopent-2-en-1-yl]pyrazolo[3,4-d]pyrimidin-3-yl]phenyl]methyl]-2-methoxy-benzamide Following general procedure I, [(1R,4S)-4-[4-amino-3-[4-[[(2-methoxybenzoyl)amino]methyl]phenyl]pyrazolo[3,4-d]pyrimidin-1-yl]cyclopent-2-en-1-yl] 2,2-dimethylpropanoate (42 mg, 0.07 mmol) afforded N-[[4-[4-amino-1-[(1S,4R)-4-hydroxycyclopent-2-en-1-yl]pyrazolo[3,4-d]pyrimidin-3-yl]phenyl]methyl]-2-methoxy-benzamide (5 mg, 0.01 mmol, 15% yield) after purification by mass-directed semi-preparative HPLC.

UPLC-MS (ES+, Short acidic): 1.25 min, m/z 457.2 [M+H]+
UPLC-MS (ES+, Long acidic): 2.83 min, m/z 457.2 [M+H]+

$^1$H NMR (400 MHz, DMSO-$d_6$, δ): 8.77 (t, J=6.1 Hz, 1H), 8.26 (m, 2H), 7.77 (dd, J=7.7, 1.8 Hz, 1H), 7.63 (d, J=8.2 Hz, 2H), 7.48 (m, 3H), 7.17 (d, J=7.7 Hz, 1H), 7.05 (dt, J=7.7, 0.9 Hz, 1H), 6.08 (dt, J=5.6, 2.0 Hz, 1H), 5.92 (dt, J=5.6, 3.3 Hz, 1H), 5.75 (m, 1H), 4.74 (m, 1H), 4.59 (d, J 6.1 Hz, 2H), 3.92 (s, 3H), 2.83 (m, 1H), 1.99 (m, 1H).

Example 45: N-[[4-[4-amino-1-[(2R,4R)-4-hydroxy-2-bicyclo[3.1.0]hexanyl]pyrazolo[3,4-d]pyrimidin-3-yl]phenyl]methyl]-2-methoxy-benzamide

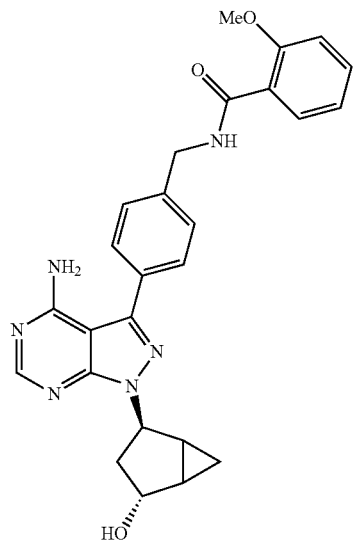 [SMILES: COc1ccccc1C(=O)NCc1ccc(-c2nn([C@@H]3C[C@@H](O)C4CC43)c3ncnc(N)c23)cc1]

[(2S,4R)-2-Hydroxy-4-bicyclo[3.1.0]hexanyl] acetate

Over a cooling bath at 0° C., (1S,4R)-cis-4-acetoxy-2-cyclopenten-1-ol (488 mg, 3.43 mmol) was dissolved in dichloromethane (15 mL) and treated with 1 M diethylzinc solution in hexanes (3.78 mL, 3.78 mmol). After the mixture was stirred at 0° C. for 15 min, diiodomethane (0.61 mL, 7.55 mmol) and 1 M diethylzinc solution in hexanes (3.78 mL, 3.78 mmol) were added. Fifteen minutes later, an additional amount of diiodomethane (0.61 mL, 7.55 mmol) was added. The reaction mixture was allowed to reach room temperature, and after being stirred for 6 h, the content was poured onto a cold aqueous solution of NH$_4$Cl (60 mL). The mixture was extracted with CHCl$_3$ (5×20 mL). The combined organic extracts were dried (MgSO$_4$), filtered, and evaporated in vacuo. The residue was purified by flash column chromatography on silica gel (heptane/EtOAc 100:0 to 50:50) to give [(2S,4R)-2-hydroxy-4-bicyclo[3.1.0]hexanyl] acetate (353 mg, 2.26 mmol, 66% yield) as a colourless oil.

$^1$H NMR (400 MHz, CDCl$_3$, δ): 5.19-5.12 (m, 1H), 4.51-4.41 (m, 1H), 2.32 (dt, J=13.4, 7.8 Hz, 1H), 2.04 (s, 3H), 1.76-1.69 (m, 1H), 1.69-1.60 (m, 2H), 1.16 (dt, J=13.4, 8.9 Hz, 1H), 0.96-0.90 (m, 1H), 0.59-0.51 (m, 1H).

[(2R,4R)-2-[4-Amino-3-[4-[[(2-methoxybenzoyl)amino]methyl]phenyl]pyrazolo[3,4-d]pyrimidin-1-yl]-4-bicyclo[3.1.0]hexanyl] acetate Following general procedure G, N-[[4-(4-amino-1H-pyrazolo[3,4-d]pyrimidin-3-yl)phenyl]methyl]-2-methoxy-benzamide (200 mg, 0.42 mmol) and [(2S,4R)-2-hydroxy-4-bicyclo[3.1.0]hexanyl] acetate (98 mg, 0.63 mmol) afforded [(2R,4R)-2-[4-amino-3-[4-[[(2-methoxybenzoyl)amino]methyl]phenyl]pyrazolo[3,4-d]pyrimidin-1-yl]-4-bicyclo[3.1.0]hexanyl] acetate (26 mg, 0.04 mmol, 10% yield).

UPLC-MS (ES+, Short acidic): 1.47 min, m/z 513.3 [M+H]+

N-[[4-[4-Amino-1-[(2R,4R)-4-hydroxy-2-bicyclo[3.1.0]hexanyl]pyrazolo[3,4-d]pyrimidin-3-yl]phenyl]methyl]-2-methoxy-benzamide Following general procedure H, [(2R,4R)-2-[4-amino-3-[4-[[(2-methoxybenzoyl)amino]methyl]phenyl]pyrazolo[3,4-d]pyrimidin-1-yl]-4-bicyclo[3.1.0]hexanyl] acetate (26 mg, 0.05 mmol) afforded N-[[4-[4-amino-1-[(2R,4R)-4-hydroxy-2-bicyclo[3.1.0]hexanyl]pyrazolo[3,4-d]pyrimidin-3-yl]phenyl]methyl]-2-methoxy-benzamide (10 mg, 0.02 mmol, 39% yield) after purification by flash column chromatography (EtOAc/MeOH 100:0 to 80:20).

UPLC-MS (ES+, Short acidic): 1.22 min, m/z 471.2 [M+H]+
UPLC-MS (ES+, Long acidic): 2.76 min, m/z 471.3 [M+H]+

$^1$H NMR (400 MHz, DMSO-$d_6$, δ): 8.78 (t, J=6.2 Hz, 1H), 8.24 (s, 1H), 7.78 (dd, J=7.6, 1.8 Hz, 1H), 7.65 (d, J=8.3 Hz, 2H), 7.55-7.45 (m, 3H), 7.17 (d, J=8.3 Hz, 1H), 7.05 (dt, J=7.6, 0.9 Hz, 1H), 5.25 (d, J=7.3 Hz, 1H), 5.04-4.94 (m, 1H), 4.64-4.55 (m, 3H), 3.92 (s, 3H), 2.09-1.98 (m, 1H), 1.69-1.58 (m, 2H), 1.46-1.38 (m, 1H), 0.75-0.69 (m, 1H), 0.57-0.49 (m, 1H).

Example 46: [4-[4-amino-3-[4-[[(2-methoxybenzoyl)amino]methyl]phenyl]pyrazolo[3,4-d]pyrimidin-1-yl]cyclohexyl] 4-methylbenzoate

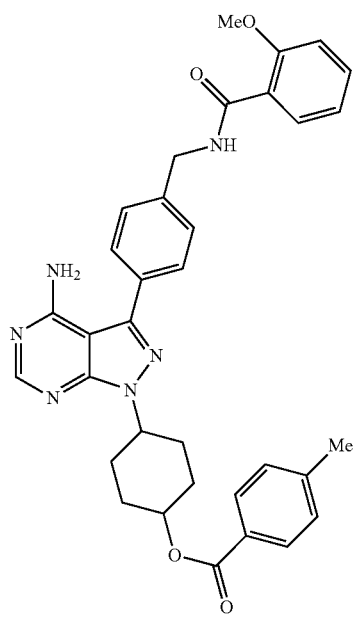 [SMILES: COc1ccccc1C(=O)NCc1ccc(-c2nn(C3CCC(OC(=O)c4ccc(C)cc4)CC3)c3ncnc(N)c23)cc1]

(4-Hydroxycyclohexyl) 4-methylbenzoate

To a solution of 1,4-cyclohexanediol (1.00 g, 8.61 mmol) in THF (40 mL), cooled at 0° C. under nitrogen atmosphere, was added triethylamine (1.2 mL, 8.61 mmol) and p-toluoyl chloride (1.1 mL, 8.61 mmol). The reaction mixture was heated to 70° C. and stirred overnight. Once cooled, the mixture was quenched with a saturated solution of NaHCO$_3$ (15 mL) and extracted with DCM (3×20 mL). The combined organic extracts were filtered over hydrophobic fit and concentrated under reduced pressure. Further purification by flash column chromatography on silica gel eluting 0-40% ethyl acetate in heptane afforded (4-hydroxycyclohexyl) 4-methylbenzoate (0.49 g, 2.09 mmol, 24% yield as a mixture of diastereoisomers) as a white solid.
$^1$H NMR (400 MHz, CDCl$_3$, δ) (3:2 as a mixture of diastereoisomers): 8.00-7.90 (m, 2H), 7.31-7.22 (m, 2H), 5.20-5.11 (m, 0.4H), 5.07-4.98 (m, 0.6H), 3.90-3.77 (m, 1H), 2.46-2.41 (m, 3H), 2.20-1.43 (m, 9H)

(4-Methylsulfonyloxycyclohexyl) 4-methylbenzoate

Following general procedure L, (4-hydroxycyclohexyl) 4-methylbenzoate (490 mg, 2.09 mmol) afforded crude (4-methylsulfonyloxycyclohexyl) 4-methylbenzoate (653 mg, 2.09 mmol, assumed quantitative) as a colourless oil.
$^1$H NMR (400 MHz, CDCl$_3$, δ) (3:2 as a mixture of diastereoisomers): 8.00-7.89 (m, 2H), 7.31-7.22 (m, 2H), 5.18-5.09 (m, 1H), 4.96-4.78 (m, 1H), 3.07 (s, 1H), 3.07 (s, 2H), 2.46-2.42 (m, 3H), 2.23-1.72 (m, 8H)

[4-(4-Amino-3-iodo-pyrazolo[3,4-d]pyrimidin-1-yl)cyclohexyl] 4-methylbenzoate

Following general procedure M, 3-iodo-1H-pyrazolo[3,4-d]pyrimidin-4-amine (550 mg, 2.11 mmol) and (4-methylsulfonyloxycyclohexyl) 4-methylbenzoate (658 mg, 2.11 mmol) gave [4-(4-amino-3-iodo-pyrazolo[3,4-d]pyrimidin-1-yl)cyclohexyl] 4-methylbenzoate (549 mg, 1.15 mmol, 55% yield as a mixture of diasteroisomers) as a yellow solid.
UPLC-MS (ES$^+$, Short acidic, Isomer 1): 1.75 min, m/z 478.1 [M+H]$^+$
UPLC-MS (ES$^+$, Short acidic, Isomer 2): 1.82 min, m/z 478.1 [M+H]$^+$

[4-[4-Amino-3-[4-[[(2-methoxybenzoyl)amino]methyl]phenyl]pyrazolo[3,4-d]pyrimidin-1-yl]cyclohexyl] 4-methylbenzoate Following general procedure C, [4-(4-amino-3-iodo-pyrazolo[3,4-d]pyrimidin-1-yl)cyclohexyl] 4-methylbenzoate (500 mg, 1.05 mmol) and 4-[[(2-methoxybenzoyl)amino]methyl]phenyl]boronic acid (358 mg, 1.26 mmol) gave [4-[4-amino-3-[4-[[(2-methoxybenzoyl)amino]methyl]phenyl]pyrazolo[3,4-d]pyrimidin-1-yl]cyclohexyl] 4-methylbenzoate (350 mg, 0.59 mmol, 57% yield as a mixture of diasteroisomers) as an off-white solid.
UPLC-MS (ES$^+$, Short acidic): 1.77 min and 1.83 min, m/z 591.3 [M+H]$^+$
UPLC-MS (ES$^+$, Long acidic): 4.17 min and 4.34 min, m/z 591.3 [M+H]$^+$
$^1$H NMR (400 MHz, DMSO-d$_6$, δ) (3:2 mixture of diastereoisomers): 8.78 (t, J=6.1 Hz, 1H), 8.27 (s, 0.6H), 8.27 (s, 0.4H), 7.96 (d, J=8.2 Hz, 1.3H), 7.90-7.86 (m, 0.7H), 7.78 (dt, J=7.6, 2.0 Hz, 1H), 7.66 (d, J=8.2 Hz, 2H), 7.55-7.46 (m, 3H), 7.40-7.32 (m, 2H), 7.17 (d, J=8.0 Hz, 1H), 7.09-7.02 (m, 1H), 5.25-5.19 (m, 0.6H), 5.05-4.93 (m, 0.4H), 4.91-4.76 (m, 1H), 4.60 (d, J=6.1 Hz, 2H), 3.93-3.91 (m, 3H), 2.48-2.35 (m, 4H), 2.27-1.69 (m, 7H).

Example 47: N-[[4-[4-amino-1-[(1R,4S)-4-hydroxycyclopent-2-en-1-yl]pyrazolo[3,4-d]pyrimidin-3-yl]phenyl]methyl]-2-methoxy-benzamide

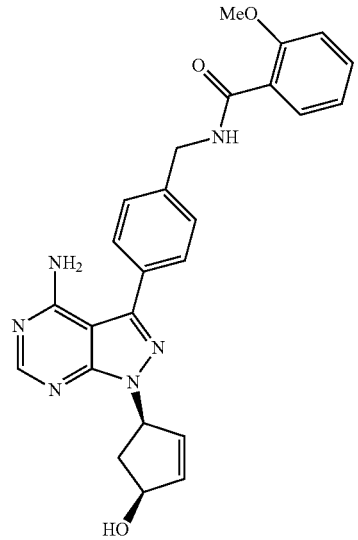 [SMILES: COc1ccccc1C(=O)NCc1ccc(-c2nn([C@H]3C=C[C@@H](O)C3)c3ncnc(N)c23)cc1]

N-[[4-[4-Amino-1-[(1R,4S)-4-hydroxycyclopent-2-en-1-yl]pyrazolo[3,4-d]pyrimidin-3-yl]phenyl]methyl]-2-methoxy-benzamide Following general procedure I, [(1S,4R)-4-[4-amino-3-[4-[[(2-methoxybenzoyl)amino]methyl]phenyl]pyrazolo[3, 4-d]pyrimidin-1-yl]cyclopent-2-en-1-yl] 2,2-dimethylpropanoate (169 mg, 0.31 mmol) afforded N-[[4-[4-amino-1-[(1R,4S)-4-hydroxycyclopent-2-en-1-yl]pyrazolo[3,4-d]pyrimidin-3-yl]phenyl]methyl]-2-methoxy-benzamide (13 mg, 0.03 mmol, 9% yield) as a white solid.

UPLC-MS (ES+, Short acidic): 1.27 min, m/z 457.2 [M+H]+

UPLC-MS (ES+, Long acidic): 2.83 min, m/z 457.3 [M+H]+

¹H NMR (400 MHz, DMSO-d₆, δ): 8.78 (t, J=6.1 Hz, 1H), 8.25 (s, 1H), 7.77 (dd, J=7.7, 1.8 Hz, 1H), 7.63 (m, 2H), 7.49 (m, 3H), 7.16 (dd, J=8.5, 0.5 Hz, 1H), 7.05 (dt, J=7.5, 0.9 Hz, 1H), 6.08 (dt, J=5.5, 2.0 Hz, 1H), 5.91 (dt, J=5.5, 3.3 Hz, 1H), 5.74 (m, 1H), 5.32 (m, 1H), 4.74 (m, 1H), 4.59 (d, J=6.1 Hz, 2H), 3.91 (s, 3H), 2.83 (m, 1H), 1.98 (m, 1H).

Example 48: [(1S,4R)-4-[4-amino-3-[4-[[(2-methoxybenzoyl)amino]methyl]phenyl]pyrazolo[3,4-d]pyrimidin-1-yl]cyclopent-2-en-1-yl] 2,2-dimethylpropanoate

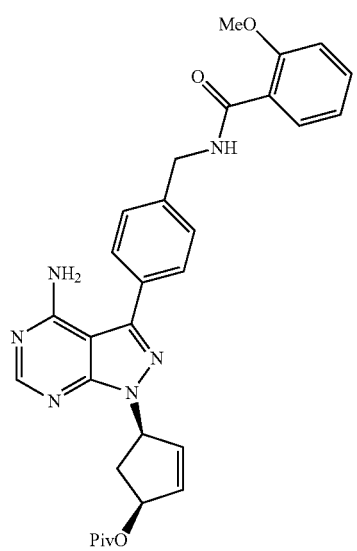

[(1S,4R)-4-[4-Amino-3-[4-[[(2-methoxybenzoyl)amino]methyl]phenyl]pyrazolo[3,4-d]pyrimidin-1-yl]cyclopent-2-en-1-yl] 2,2-dimethylpropanoate Following general procedure G, N-[[4-[4-amino-1-[(1R,4R)-4-hydroxycyclopent-2-en-1-yl]pyrazolo[3,4-d]pyrimidin-3-yl]phenyl]methyl]-2-methoxy-benzamide (250 mg, 0.46 mmol) and trimethylacetic acid (72 mg, 0.70 mmol) afforded [(1S,4R)-4-[4-amino-3-[4-[[(2-methoxybenzoyl)amino]methyl]phenyl]pyrazolo[3,4-d]pyrimidin-1-yl]cyclopent-2-en-1-yl] 2,2-dimethylpropanoate (169 mg, 0.30 mmol, 66% yield).

UPLC-MS (ES+, Short acidic): 1.66 min, m/z 541.3 [M+H]+

UPLC-MS (ES+, Long acidic): 3.93 min, m/z 541.5 [M+H]+

¹H NMR (400 MHz, DMSO-d₆, δ): 8.77 (t, J=6.1 Hz, 1H), 8.27 (s, 1H), 7.77 (dd, J=7.6, 1.8 Hz, 1H), 7.63 (d, J=8.1 Hz, 2H), 7.51-7.47 (m, 3H), 7.17 (d, J=8.1 Hz, 1H), 7.05 (dt, J=7.6, 0.9 Hz, 1H), 6.19-6.17 (m, 1H), 6.12-6.11 (m, 1H), 5.91-5.87 (m, 1H), 5.66-5.63 (m, 1H), 4.58 (d, J=6.1 Hz, 2H), 3.91 (s, 3H), 3.00-2.96 (m, 1H), 2.08-2.03 (m, 1H), 1.14 (s, 9H).

Example 49: N-[[4-(4-amino-1-cyclohex-2-en-1-yl-pyrazolo[3,4-d]pyrimidin-3-yl)phenyl]methyl]-2-methoxy-benzamide

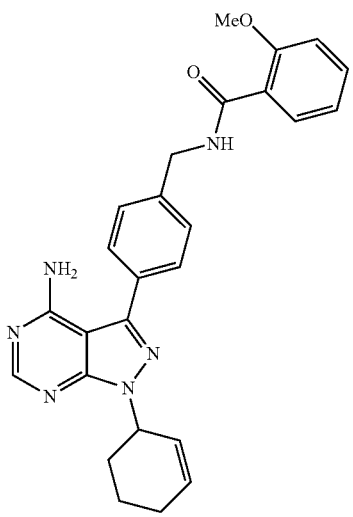 [SMILES: COc1ccccc1C(=O)NCc1ccc(-c2nn(C3C=CCCC3)c3ncnc(N)c23)cc1]

1-Cyclohex-2-en-1-yl-3-iodo-pyrazolo[3,4-d]pyrimidin-4-amine

Following general procedure G, a suspension of 3-iodo-1H-pyrazolo[3,4-d]pyrimidin-4-amine (1.00 g, 3.83 mmol) and 2-cyclohexenol (639 mg, 6.51 mmol) afforded 1-cyclohex-2-en-1-yl-3-iodo-pyrazolo[3,4-d]pyrimidin-4-amine (768 mg, 1.58 mmol, 41% yield) as a yellow solid.

UPLC-MS (ES+, Short acidic): 1.44 min, m/z 342.1 [M+H]+

N-[[4-(4-Amino-1-cyclohex-2-en-1-yl-pyrazolo[3,4-d]pyrimidin-3-yl)phenyl]methyl]-2-methoxy-benzamide Following general procedure D, 1-cyclohex-2-en-1-yl-3-iodo-pyrazolo[3,4-d]pyrimidin-4-amine (100 mg, 0.29 mmol) and [4-[[(2-methoxybenzoyl)amino]methyl]phenyl] boronic acid (125 mg, 0.44 mmol) afforded, after further purification by flash column chromatography on silica gel, N-[[4-(4-amino-1-cyclohex-2-en-1-yl-pyrazolo[3,4-d]pyrimidin-3-yl)phenyl]methyl]-2-methoxy-benzamide (39 mg, 0.08 mmol, 27% yield) as a pale cream solid.

UPLC-MS (ES+, Short acidic): 1.54 min, m/z 455.3 [M+H]+

UPLC-MS (ES+, Long acidic): 3.58 min, m/z 455.5 [M+H]+

¹H NMR (400 MHz, DMSO-d₆, δ): 8.76 (t, J=6.1 Hz, 1H), 8.24 (s, 1H), 7.77 (dd, J=7.6, 1.8 Hz, 1H), 7.65-7.60 (m, 2H), 7.53-7.45 (m, 3H), 7.18-7.14 (m, 1H), 7.04 (td, J=7.6, 0.7 Hz, 1H), 6.00-5.91 (m, 1H), 5.73-5.65 (m, 1H), 5.49-5.40 (m, 1H), 4.58 (d, J=6.1 Hz, 2H), 3.91 (s, 3H), 2.21-1.99 (m, 4H), 1.97-1.88 (m, 1H), 1.80-1.60 (m, 1H).

Example 50: N-[[4-[4-amino-1-[(1S,4S)-4-hydroxy-cyclopent-2-en-1-yl]pyrazolo[3,4-d]pyrimidin-3-yl]phenyl]methyl]-2-methoxy-benzamide

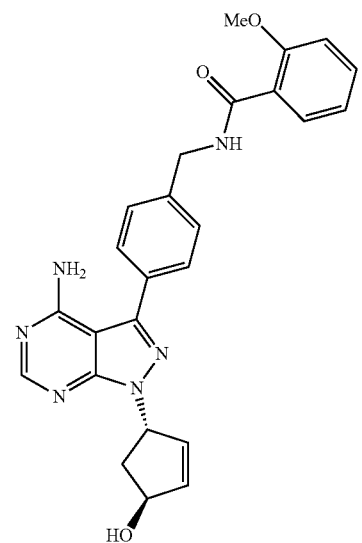 [SMILES: COc1ccccc1C(=O)NCc1ccc(-c2nn([C@@H]3C=C[C@@H](O)C3)c3ncnc(N)c23)cc1]

[(1S,4S)-4-[4-Amino-3-[4-[[(2-methoxybenzoyl)amino]methyl]phenyl]pyrazolo[3,4-d]pyrimidin-1-yl]cyclopent-2-en-1-yl] 2,2-dimethylpropanoate Following general procedure G, N-[[4-[4-amino-1-[(1S,4R)-4-hydroxycyclopent-2-en-1-yl]pyrazolo[3,4-d]pyrimidin-3-yl]phenyl]methyl]-2-methoxy-benzamide (75 mg, 0.16 mmol) and trimethylacetic acid (26 mg, 0.25 mmol) afforded [(1S,4S)-4-[4-amino-3-[4-[[(2-methoxybenzoyl)amino]methyl]phenyl]pyrazolo[3,4-d]pyrimidin-1-yl]cyclopent-2-en-1-yl] 2,2-dimethylpropanoate (61 mg, 0.11 mmol, 69% yield) as a colourless oily solid.

UPLC-MS (ES+, Short acidic): 1.72 min, m/z 541.4 [M+H]+

N-[[4-[4-Amino-1-[(1S,4S)-4-hydroxycyclopent-2-en-1-yl]pyrazolo[3,4-d]pyrimidin-3-yl]phenyl]methyl]-2-methoxy-benzamide Following general procedure I, [(1S,4S)-4-[4-amino-3-[4-[[(2-methoxybenzoyl)amino]methyl]phenyl]pyrazolo[3,4-d]pyrimidin-1-yl]cyclopent-2-en-1-yl] 2,2-dimethylpropanoate (61 mg, 0.11 mmol) afforded N-[[4-[4-amino-1-[(1S,4S)-4-hydroxycyclopent-2-en-1-yl]pyrazolo[3,4-d]pyrimidin-3-yl]phenyl]methyl]-2-methoxy-benzamide (9 mg, 0.02 mmol, 16% yield) as a white solid.

UPLC-MS (ES+, Short acidic): 1.21 min, m/z 457.2 [M+H]+

UPLC-MS (ES+, Long acidic): 2.70 min, m/z 457.2 [M+H]+

1H NMR (400 MHz, DMSO-d6, δ): 8.77 (t, J=6.1 Hz, 1H), 8.26 (s, 1H), 7.77 (dd, J=7.7, 1.8 Hz, 1H), 7.61 (d, J=8.2 Hz, 2H), 7.47 (m, 3H), 7.16 (d, J=7.7 Hz, 1H), 7.05 (dt, J=7.5, 1.0 Hz, 1H), 6.11 (m, 1H), 6.08 (m, 1H), 5.95 (dd, J=7.5, 2.0 Hz, 1H), 5.01 (m, 2H), 4.58 (d, J=6.1 Hz, 2H), 3.91 (s, 3H), 2.45 (m, 1H), 2.14 (m, 1H).

Example 51: N-[[4-(4-amino-1-tert-butyl-pyrazolo[3,4-d]pyrimidin-3-yl)phenyl]methyl]-2-methoxy-benzamide

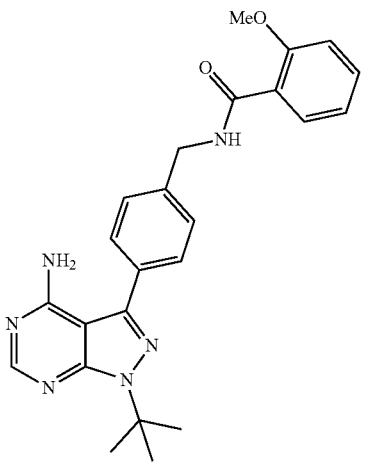 [SMILES: COc1ccccc1C(=O)NCc1ccc(-c2nn(C(C)(C)C)c3ncnc(N)c23)cc1]

N-[[4-(4-Amino-1-tert-butyl-pyrazolo[3,4-d]pyrimidin-3-yl)phenyl]methyl]-2-methoxy-benzamide Following general procedure C, 3-bromo-1-tert-butyl-pyrazolo[3,4-d]pyrimidin-4-amine (3.03 g, 11.22 mmol) and [4-[[(2-methoxybenzoyl)amino]methyl]phenyl]boronic acid (3.20 g, 11.22 mmol) afforded N-[[4-(4-amino-1-tert-butyl-pyrazolo[3,4-d]pyrimidin-3-yl)phenyl]methyl]-2-methoxy-benzamide (2.50 g, 5.86 mmol, 52% yield).

UPLC-MS (ES+, Short acidic): 1.63 min, m/z 431.5 [M+H]+

UPLC-MS (ES+, Long acidic): 3.52 min, m/z 431.4 [M+H]+

1H NMR (400 MHz, DMSO-d6, δ): 8.77 (t, J=6.1 Hz, 1H), 8.24 (s, 1H), 7.78 (dd, J=6.0, 1.7 Hz, 1H), 7.63 (d, J=8.2 Hz, 2H), 7.56-7.44 (m, 3H), 7.17 (d, J=8.2 Hz, 1H), 7.09-7.01 (m, 1H), 6.98-6.16 (br s, 2H), 4.59 (d, J=6.1 Hz, 2H), 3.92 (s, 3H), 1.75 (s, 9H).

Example 52: N-[[4-[4-amino-1-(3-bicyclo[3.1.0]hexanyl)pyrazolo[3,4-d]pyrimidin-3-yl]phenyl]methyl]-2-methoxy-benzamide

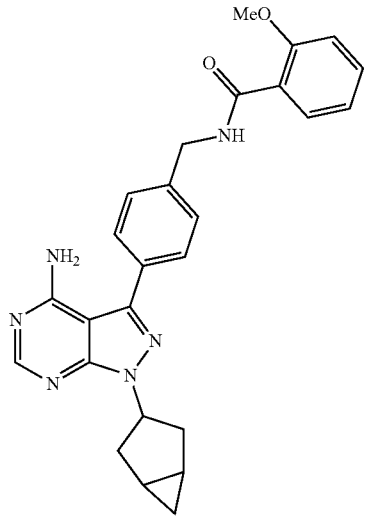 [SMILES: COc1ccccc1C(=O)NCc1ccc(-c2nn(C3CC4CC4C3)c3ncnc(N)c23)cc1]

1-(3-Bicyclo[3.1.0]hexanyl)-3-iodo-pyrazolo[3,4-d]pyrimidin-4-amine

Following general procedure G, a solution of 3-iodo-1H-pyrazolo[3,4-d]pyrimidin-4-amine (300 mg, 0.90 mmol) and cis-bicyclo[3.1.0]hexan-3-ol (132 mg, 1.34 mmol) gave, after purification by flash column chromatography on silica gel, 1-(3-bicyclo[3.1.0]hexanyl)-3-iodo-pyrazolo[3,4-d]pyrimidin-4-amine (120 mg, 0.25 mmol, 27% yield) as a yellow solid.

UPLC-MS (ES+, Short acidic): 1.58 min, m/z 342.1 [M+H]+

N-[[4-[4-Amino-1-(3-bicyclo[3.1.0]hexanyl)pyrazolo[3,4-d]pyrimidin-3-yl]phenyl]methyl]-2-methoxy-benzamide Following general procedure D, 1-(3-bicyclo[3.1.0]hexanyl)-3-iodo-pyrazolo[3,4-d]pyrimidin-4-amine (120 mg, 0.35 mmol) and [4-[[(2-methoxybenzoyl)amino]methyl]phenyl]boronic acid (150 mg, 0.53 mmol) afforded, after further purification by flash column chromatography on silica gel, N-[[4-[4-amino-1-(3-bicyclo[3.1.0]hexanyl)pyrazolo[3,4-d]pyrimidin-3-yl]phenyl]methyl]-2-methoxy-benzamide (63 mg, 0.12 mmol, 35% yield) as a cream solid.

UPLC-MS (ES+, Short acidic): 1.59 min, m/z 455.2 [M+H]+

UPLC-MS (ES+, Long acidic): 3.64 min, m/z 455.2 [M+H]+

$^1$H NMR (400 MHz, DMSO-$d_6$, δ): 8.77 (t, J=6.0 Hz, 1H), 8.22 (s, 1H), 7.77 (dd, J=7.7, 1.8 Hz, 1H), 7.66-7.61 (m, 2H), 7.53-7.45 (m, 3H), 7.18-7.14 (m, 1H), 7.04 (td, J=7.7, 1.0 Hz, 1H), 4.99-4.88 (m, 1H), 4.58 (d, J=6.0 Hz, 2H), 3.91 (s, 3H), 2.44-2.35 (m, 2H), 2.21-2.11 (m, 2H), 1.50-1.37 (m, 2H), 0.53-0.36 (m, 2H).

Example 53: N-[[4-[4-Amino-1-[(1R,4R)-4-hydroxycyclopent-2-en-1-yl]pyrazolo[3,4-d]pyrimidin-3-yl]phenyl]methyl]-5-fluoro-2-methoxy-benzamide

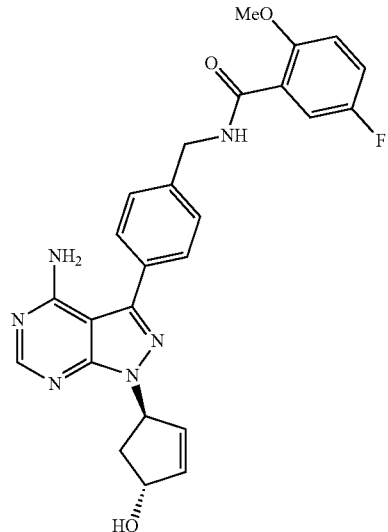 [SMILES: COc1ccc(F)cc1C(=O)NCc1ccc(-c2nn([C@H]3C=C[C@H](O)C3)c3ncnc(N)c23)cc1]

N-[[4-(4-Amino-1H-pyrazolo[3,4-d]pyrimidin-3-yl)phenyl]methyl]-5-fluoro-2-methoxy-benzamide Following general procedure E, N-[[4-(4-amino-1-tert-butyl-pyrazolo[3,4-d]pyrimidin-3-yl)phenyl]methyl]-5-fluoro-2-methoxy-benzamide (2.69 g, 4.19 mmol) gave N-[[4-(4-amino-1H-pyrazolo[3,4-d]pyrimidin-3-yl)phenyl]methyl]-5-fluoro-2-methoxy-benzamide (381 mg, 0.97 mmol, 23% yield).

UPLC-MS (ES+, Short acidic): 1.37 min, m/z 394.1 [M+2]+

[(1R,4R)-4-[4-Amino-3-[4-[[(5-fluoro-2-methoxy-benzoyl)amino]methyl]phenyl]pyrazolo[3,4-d]pyrimidin-1-yl]cyclopent-2-en-1-yl] acetate Following general procedure G, N-[[4-(4-amino-1H-pyrazolo[3,4-d]pyrimidin-3-yl)phenyl]methyl]-5-fluoro-2-methoxy-benzamide (349 mg) afforded [(1R,4R)-4-[4-Amino-3-[4-[[(5-fluoro-2-methoxy-benzoyl)amino]methyl]phenyl]pyrazolo[3,4-d]pyrimidin-1-yl]cyclopent-2-en-1-yl] acetate (81 mg, 0.16 mmol, 18% yield) after purification by reverse phase column chromatography.

UPLC-MS (ES+, Short acidic): 1.61 min, m/z 518.2 [M+2]+

N-[[4-[4-Amino-1-[(1R,4R)-4-hydroxycyclopent-2-en-1-yl]pyrazolo[3,4-d]pyrimidin-3-yl]phenyl]methyl]-5-fluoro-2-methoxy-benzamide Following general procedure H, [(1R,4R)-4-[4-amino-3-[4-[[(5-fluoro-2-methoxy-benzoyl)amino]methyl]phenyl]pyrazolo[3,4-d]pyrimidin-1-yl]cyclopent-2-en-1-yl] acetate (81 mg, 0.16 mmol) afforded N-[[4-[4-amino-1-[(1R,4R)-4-hydroxycyclopent-2-en-1-yl]pyrazolo[3,4-d]pyrimidin-3-yl]phenyl]methyl]-5-fluoro-2-methoxy-benzamide (26 mg, 0.05 mmol, 32% yield) as a white solid.

UPLC-MS (ES+, Short acidic): 1.41 min, m/z 474.2 [M]+

UPLC-MS (ES+, Long acidic): 3.14 min, m/z 476.2 [M+2]+

¹H NMR (400 MHz, DMSO-d₆, δ): 8.81 (t, J=6.0 Hz, 1H), 8.27-8.21 (m, 2H), 8.10 (s, 1H), 7.51 (dd, J=9.2, 3.3 Hz, 1H), 7.41-7.37 (m, 2H), 7.36-7.30 (m, 1H), 7.18 (dd, J=9.2, 4.2 Hz, 1H), 6.14 (dt, J=5.6, 2.1 Hz, 1H), 6.05-5.99 (m, 1H), 5.95 (ddd, J=5.6, 2.1, 1.0 Hz, 1H), 5.09-5.01 (m, 2H), 4.53 (d, J=6.0 Hz, 2H), 3.90 (s, 3H), 2.47-2.39 (m, 1H), 2.15 (ddd, J=13.7, 8.2, 3.1 Hz, 1H).

Example 54: N-[(4-{4-amino-1-[(1R,4R)-4-fluoro-cyclopent-2-en-1-yl]-1H-pyrazolo[3,4-d]pyrimidin-3-yl}phenyl)methyl]-2-methoxybenzamide

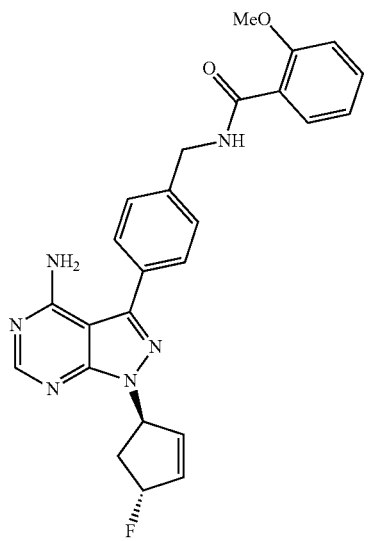 [SMILES: COc1ccccc1C(=O)NCc1ccc(-c2nn([C@H]3C=C[C@H](F)C3)c3ncnc(N)c23)cc1]

N-[(4-{4-Amino-1-[(1R,4R)-4-fluorocyclopent-2-en-1-yl]-1H-pyrazolo[3,4-d]pyrimidin-3-yl}phenyl)methyl]-2-methoxybenzamide To a solution of N-[[4-[4-amino-1-[(1R,4S)-4-hydroxy-cyclopent-2-en-1-yl]pyrazolo[3,4-d]pyrimidin-3-yl]phenyl]methyl]-2-methoxy-benzamide (47 mg, 0.10 mmol) in anhydrous DCM (2 mL) at −78° C. under a nitrogen atmosphere, was added neat diethylaminosulfurtrifluoride (41 µL, 0.31 mmol) over 10 minutes and the mixture was stirred at −78° C. for 105 minutes. After this time reaction was quenched with the careful addition of a saturated aqueous Na₂CO₃ solution (5 mL). The organic layer was washed with brine (10 mL), dried over Na₂SO₄ and concentrated under vacuum. The crude material was purified by flash column chromatography on silica gel (Heptane/EtOAc 100:0 to 0:100) to give N-[(4-{4-amino-1-[(1R,4R)-4-fluorocyclopent-2-en-1-yl]-1H-pyrazolo[3,4-d]pyrimidin-3-yl}phenyl)methyl]-2-methoxybenzamide (24 mg, 0.05 mmol, 48% yield) as a white solid.

UPLC-MS (ES+, Short acidic): 1.48 min, m/z 459.2 [M+H]+

UPLC-MS (ES+, Long acidic): 3.31 min, m/z 459.3 [M+H]+

¹H NMR (400 MHz, DMSO-d₆, δ): 8.77 (t, J=6.0 Hz, 1H), 8.27 (s, 1H), 7.77 (dd, J=7.8, 1.8 Hz, 1H), 7.62 (d, J=8.2 Hz, 2H), 7.49 (m, 3H), 7.17 (d, J=7.8 Hz, 1H), 7.05 (dt, J=7.5, 0.9 Hz, 1H), 6.36 (m, 11H), 6.32 (m, 1H), 6.16 (m, 11H), 6.05 (m, 1H) 4.58 (d, J=6.0 Hz, 2H), 3.92 (s, 3H), 2.52 (m, 2H).

Example 55: N-[(4-{4-amino-1-[(1R,4R)-4-ethoxy-cyclopent-2-en-1-yl]-1H-pyrazolo[3,4-d]pyrimidin-3-yl}phenyl)methyl]-2-methoxybenzamide

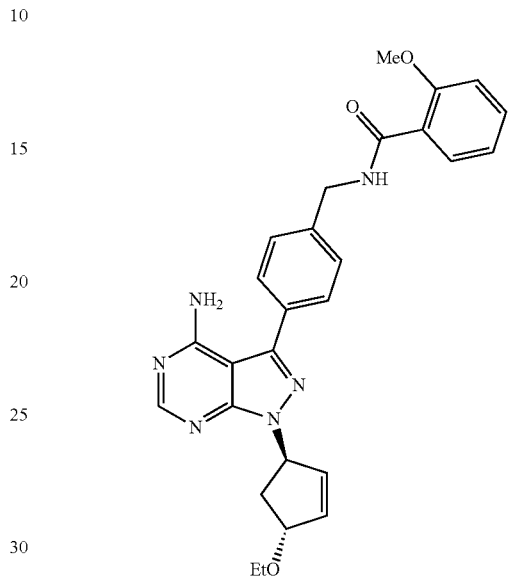

N-[(4-{4-Amino-1-[(1R,4R)-4-ethoxycyclopent-2-en-1-yl]-1H-pyrazolo[3,4-d]pyrimidin-3-yl}phenyl)methyl]-2-methoxybenzamide To a solution of N-[[4-[4-amino-1-[(1R,4R)-4-hydroxy-cyclopent-2-en-1-yl]pyrazolo[3,4-d]pyrimidin-3-yl]phenyl]methyl]-2-methoxy-benzamide (50 mg, 0.11 mmol) in toluene (2.7 mL) was added sodium hydride (60% dispersed in mineral oil) (5 mg, 0.12 mmol) at 0° C. and the mixture stirred at 0° C. for 1 h. After this time iodoethane (10 µL, 0.12 mmol) was added and the reaction mixture was stirred at 0° C. for another hour and then heated to reflux for 24 h. The mixture was cooled to room temperature, quenched with water and partitioned. The aqueous layer was extracted with DCM, dried over Na₂SO₄ and concentrated under vacuum. The crude material was purified by mass-directed semi-preparative HPLC to give N-[(4-{4-amino-1-[(1R, 4R)-4-ethoxycyclopent-2-en-1-yl]-1H-pyrazolo[3,4-d]pyrimidin-3-yl}phenyl)methyl]-2-methoxybenzamide (5 mg, 0.01 mmol, 8% yield).

UPLC-MS (ES+, Short acidic): 1.47 min, m/z 485.2 [M+H]+

UPLC-MS (ES+, Long acidic): 3.18 min, m/z 485.3 [M+H]+

¹H NMR (400 MHz, DMSO-d₆, δ): 8.77 (t, J=6.1 Hz, 1H), 8.33 (s, 1H), 7.77 (dd, J=7.6, 1.8, 1H), 7.61 (d, J=8.1 Hz, 2H), 7.50 (m, 3H), 7.17 (d, J=8.1 Hz, 1H), 7.05 (dt, J=7.6, 0.9 Hz, 1H), 6.33 (t, J=5.6 Hz, 1H), 6.11 (m, 1H), 6.06 (m, 1H), 5.95 (dd, J=5.6, 2.1 Hz, 11H), 5.01 (br, 2H), 4.59 (d, J, =6.1 Hz, 2H), 3.92 (s, 3H), 3.52 (m, 2H), 2.43 (m, 1H), 2.17 (m, 1H), 1.13 (t, J=7.1 Hz, 3H).

Example 56: N-[(4-{4-amino-1-[(1R)-2,3-dihydro-1H-inden-1-yl]-1H-pyrazolo[3,4-d]pyrimidin-3-yl}phenyl)methyl]-2-methoxybenzamide

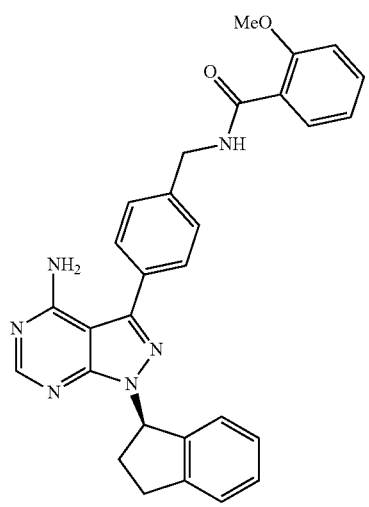 [SMILES: COc1ccccc1C(=O)NCc1ccc(-c2nn([C@@H]3CCc4ccccc43)c3ncnc(N)c23)cc1]

N-[(4-{4-amino-1-[(1R)-2,3-dihydro-1H-inden-1-yl]-1H-pyrazolo[3,4-d]pyrimidin-3-yl}phenyl)methyl]-2-methoxybenzamide Following general procedure G, N-[[4-(4-amino-1H-pyrazolo[3,4-d]pyrimidin-3-yl)phenyl]methyl]-2-methoxy-benzamide (75 mg, 0.20 mmol) and (1S)-indan-1-ol (46 mg, 0.34 mmol) afforded N-[(4-{4-amino-1-[(1R)-2,3-dihydro-1H-inden-1-yl]-1H-pyrazolo[3,4-d]pyrimidin-3-yl}phenyl)methyl]-2-methoxybenzamide (20 mg, 0.04 mmol, 20% yield) as a white solid.

UPLC-MS (ES+, Short acidic): 1.71 min, m/z 491.2 [M+H]+

UPLC-MS (ES+, Long acidic): 3.84 min, m/z 491.3 [M+H]+

$^1$H NMR (400 MHz, DMSO-$d_6$, δ): 8.74 (t, J=6.0 Hz, 1H), 8.31 (s, 1H), 7.76 (dd, J=7.7, 1.7 Hz, 1H), 7.58 (d, J=8.1 Hz, 2H), 7.48 (m, 3H), 7.35 (d, J=7.5 Hz, 1H), 7.25 (t, J=7.5 Hz, 1H), 7.12 (m, 2H), 7.04 (t, J=7.3 Hz, 1H), 6.94 (d, J=7.3 Hz, 1H), 6.45 (t, J=7.5 Hz, 1H), 4.56 (d, J 6.0 Hz, 2H), 3.90 (s, 3H), 3.22 (m, 1H), 3.03 (m, 1H), 2.64 (m, 2H).

Example 57: N-[[4-[4-amino-1-[(1R,4R)-4-(2-methoxyethoxy)cyclopent-2-en-1-yl]pyrazolo[3,4-d]pyrimidin-3-yl]phenyl]methyl]-2-methoxy-benzamide

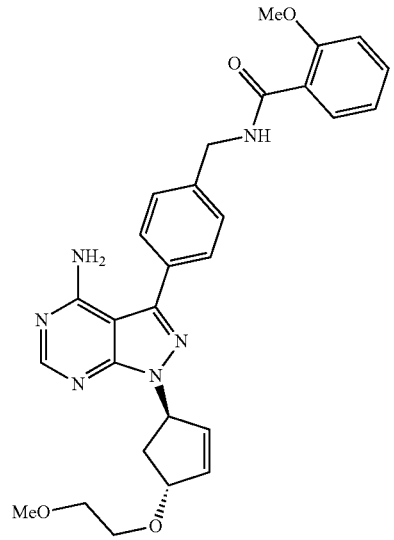 [SMILES: COCCO[C@H]1C=C[C@H](n2nc(-c3ccc(CNC(=O)c4ccccc4OC)cc3)c3c(N)ncnc32)C1]

Example 58: N-[[4-[1-[(1R,4R)-4-hydroxycyclopent-2-en-1-yl]-4-(2-methoxyethylamino)pyrazolo[3,4-d]pyrimidin-3-yl]phenyl]methyl]-2-methoxy-benzamide

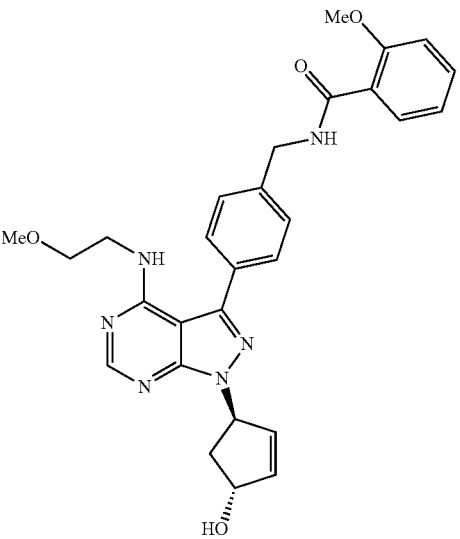 [SMILES: COCCNc1ncnc2c1c(-c1ccc(CNC(=O)c3ccccc3OC)cc1)nn2[C@H]1C=C[C@H](O)C1]

N-[[4-[1-[(1R,4R)-4-hydroxycyclopent-2-en-1-yl]-4-(2-methoxyethylamino)pyrazolo[3,4-d]pyrimidin-3-yl]phenyl]methyl]-2-methoxy-benzamide (Example 58) and N-[[4-[4-amino-1-[(1R,4R)-4-(2-methoxyethoxy)cyclopent-2-en-1-yl]pyrazolo[3,4-d]pyrimidin-3-yl]phenyl]methyl]-2-methoxy-benzamide (Example 57)

Example 57 and Example 58 were prepared from the same synthetic procedure and separated.

To a solution of N-[[4-[4-amino-1-[(1R,4R)-4-hydroxy-cyclopent-2-en-1-yl]pyrazolo[3,4-d]pyrimidin-3-yl]phenyl]

methyl]-2-methoxy-benzamide (95 mg, 0.21 mmol) in DMF (5 mL) was added sodium hydride (60% dispersed in mineral oil) (9 mg, 0.23 mmol) at 0° C. and the mixture stirred at 0° C. for 1 h. After this time 1-bromo-2-methoxy-ethane (22 μL, 0.23 mmol) was added and the reaction warmed to room temperature and stirred for 72 h. A further sodium hydride (60% dispersed in mineral oil) (9 mg, 0.23 mmol) and 1-bromo-2-methoxy-ethane (22 μL, 0.23 mmol) were added. The reaction stirred at room temperature for 1 h then heated to 40° C. and stirred for 48 h. The mixture was cooled to room temperature, quenched with water and partitioned. The aqueous layer was extracted with DCM, dried over $Na_2SO_4$ and concentrated under vacuum. The crude material was purified after purification by mass-directed semi-preparative HPLC, followed by salt removal SCX SPE cartridge filtration to give N-[[4-[1-[(1R,4R)-4-hydroxycyclopent-2-en-1-yl]-4-(2-methoxyethylamino)pyrazolo[3,4-d]pyrimidin-3-yl]phenyl]methyl]-2-methoxy-benzamide (2 mg, 0.01 mmol, 2% yield) and N-[[4-[4-amino-1-[(1R,4R)-4-(2-methoxyethoxy)cyclopent-2-en-1-yl]pyrazolo[3,4-d]pyrimidin-3-yl]phenyl]methyl]-2-methoxy-benzamide (6 mg, 0.01 mmol, 5% yield).

N-[[4-[1-[(1R,4R)-4-hydroxycyclopent-2-en-1-yl]-4-(2-methoxyethylamino)pyrazolo[3,4-d]pyrimidin-3-yl]phenyl]methyl]-2-methoxy-benzamide UPLC-MS (ES$^+$, Short acidic): 1.29 min, m/z 515.3 [M+H]$^+$ UPLC-MS (ES$^+$, Long acidic): 3.18 min, m/z 515.3 [M+H]$^+$ $^1$H NMR (400 MHz, DMSO-d$_6$, δ): 8.77 (t, J=6.1 Hz, 1H), 8.26 (s, 1H), 7.77 (dd, J=7.7, 1.8 Hz, 1H), 7.61 (d, J=8.3 Hz, 2H), 7.50 (m, 3H), 7.17 (d, J=7.7 Hz, 1H), 7.05 (dt, J=7.7, 1.0 Hz, 1H), 6.30-6.24 (m, 1H), 6.11-6.00 (m, 2H), 4.92-4.86 (m, 1H), 4.58 (d, J=6.1 Hz, 2H), 3.91 (s, 3H), 3.62-3.56 (m, 21H), 3.49-3.44 (m, 2H), 3.26 (s, 3H), 2.57.2.52 (m, 21H), 2.46-2.38 (m, 1H 2.35-2.24 (m, 1H).

N-[[4-[4-amino-1-[(1R,4R)-4-(2-methoxyethoxy)cyclopent-2-en-1-yl]pyrazolo[3,4-d]pyrimidin-3-yl]phenyl]methyl]-2-methoxy-benzamide UPLC-MS (ES$^+$, Short acidic): 1.43 min, m/z 515.3 [M+H]$^+$ UPLC-MS (ES$^+$, Long acidic): 3.23 min, m/z 515.3 [M+H]$^+$ $^1$H NMR (400 MHz, DMSO-d$_6$, δ): 8.79 (t, J=6.2 Hz, 1H), 8.34 (s, 11H), 7.77 (dd, J=7.7, 1.8 Hz, 1H), 7.61 (d, J=8.2 Hz, 2H), 7.50 (m, 3H), 7.17 (d, J==7.7 Hz, 1H), 7.05 (dt, J=7.7, 1.0 Hz, 1H), 6.22 (t, J=5.4 Hz, 1H), 6.11 (m, 1H), 6.08 (m, 1H), 5.96 (m, 1H), 5.01 (br s, 2H), 4.60 (d, J=6.2 Hz, 2H), 3.92 (s, 3H), 3.65 (quint, J=5.5 Hz, 2H), 3.49 (t, J=5.5 Hz, 2H), 3.23 (s, 3H), 2.44 (m, 1H), 2.15 (m, 1H).

Example 59: N-[(4-{4-amino-1-[(1R,4R)-4-amino-cyclopent-2-en-1-yl]-1H-pyrazolo[3,4-d]pyrimidin-3-yl}phenyl)methyl]-2-methoxybenzamide

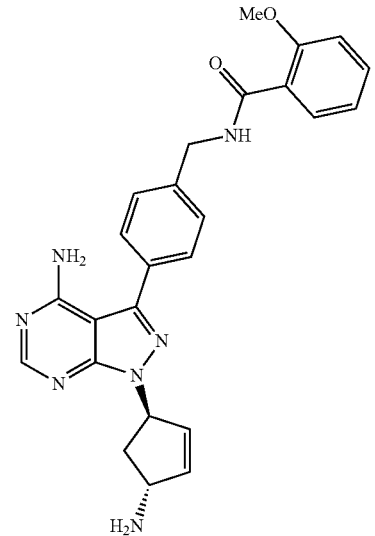 [SMILES: COc1ccccc1C(=O)NCc1ccc(-c2nn([C@H]3C=C[C@H](N)C3)c3ncnc(N)c23)cc1]

N-[[4-[4-Amino-1-[(1R,4R)-4-azidocyclopent-2-en-1-yl]pyrazolo[3,4-d]pyrimidin-3-yl]phenyl]methyl]-2-methoxy-benzamide To a solution of N-[[4-[4-amino-1-[(1R,4S)-4-hydroxycyclopent-2-en-1-yl]pyrazolo[3,4-d]pyrimidin-3-yl]phenyl]methyl]-2-methoxy-benzamide (562 mg, 1.23 mmol) in toluene (12 mL), cooled to 0° C., were added diphenyl phosphoryl azide (318 μL, 1.48 mmol) and 1,8-diazabicyclo[5.4.0]undec-7-ene (258 μL, 1.72 mmol). The reaction mixture was stirred at room temperature overnight, cooled to 0° C. and a further diphenyl phosphoryl azide (318 μL, 1.48 mmol) and 1,8-diazabicyclo[5.4.0]undec-7-ene (258 μL, 1.72 mmol) were added. The reaction mixture was stirred at room temperature for another 2 h, partitioned between EtOAc and water. The organic layer was washed sequentially with water, 1 M HCl and brine, dried over $Na_2SO_4$ and concentrated under vacuum to give N-[[4-[4-amino-1-[(1R,4R)-4-azidocyclopent-2-en-1-yl]pyrazolo[3,4-d]pyrimidin-3-yl]phenyl]methyl]-2-methoxy-benzamide (709 mg, 0.96 mmol, 78% yield) as a white solid.

UPLC-MS (ES$^+$, Short acidic): 1.57 min, m/z 482.2 [M+H]$^+$

N-[[4-[4-Amino-1-[(1R,4R)-4-aminocyclopent-2-en-1-yl]pyrazolo[3,4-d]pyrimidin-3-yl]phenyl]methyl]-2-methoxy-benzamide A solution of N-[[4-[4-amino-1-[(1R,4R)-4-azidocyclopent-2-en-1-yl]pyrazolo[3,4-d]pyrimidin-3-yl]phenyl]methyl]-2-methoxy-benzamide (150 mg, 0.31 mmol) was dissolved in MeOH (5 mL) and treated with tin(II) chloride dihydrate (127 mg, 0.56 mmol). The reaction mixture was stirred at room temperature overnight before being treated with 1 M aq. NaOH and partitioned. The aqueous layer was extracted with EtOAc (×2). The combined organic extracts were washed with 1 M aq. HCl then water. The pH of the combined aqueous layers was adjusted to 11 with a 5 M aq.

NaOH solution and then extracted with EtOAc (×2). The combined organic extracts were dried over Na$_2$SO$_4$ and concentrated under vacuum. The crude material was purified by flash column chromatography on silica gel (DCM/MeOH 100:0 to 70:30) to give N-[[4-[4-amino-1-[(1R,4R)-4-aminocyclopent-2-en-1-yl]pyrazolo[3,4-d]pyrimidin-3-yl]phenyl]methyl]-2-methoxy-benzamide (17 mg, 0.04 mmol, 11% yield).

UPLC-MS (ES$^+$, Short acidic): 1.15 min, m/z 456.2 [M+H]$^+$

UPLC-MS (ES$^+$, Long acidic): 2.46 min, m/z 456.3 [M+H]$^+$ $^1$H NMR (400 MHz, DMSO-d$_6$, δ): 8.77 (t, J=6.1 Hz, 1H), 8.26 (s, 1H), 7.77 (dd, J=7.7, 1.8 Hz, 1H), 7.61 (d, J=8.2 Hz, 2H), 7.51 (m, 3H), 7.17 (d, J=7.7 Hz, 1H), 7.05 (dt, J=7.7, 0.9 Hz, 1H), 6.13 (m, 1H), 6.09 (m, 1H), 6.04 (m, 1H), 4.59 (d, J=6.1 Hz, 2H), 4.38 (m, 1H), 3.92 (s, 3H), 2.47 (m, 1H), 2.20 (m, 1H), 1.91 (s, 2H).

Example 60: N-[[4-[1-[(1R,4R)-4-acetamidocyclopent-2-en-1-yl]-4-amino-pyrazolo[3,4-d]pyrimidin-3-yl]phenyl]methyl]-2-methoxy-benzamide

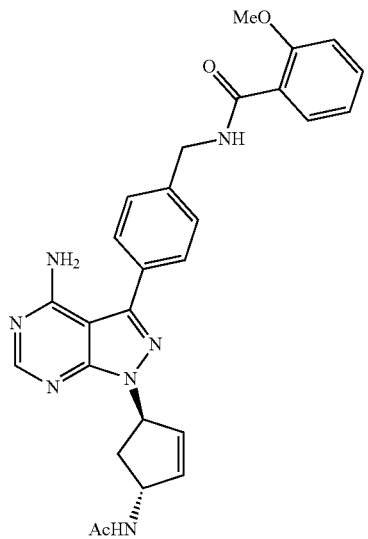 [SMILES: COc1ccccc1C(=O)NCc1ccc(-c2nn([C@H]3C=C[C@H](NC(C)=O)C3)c3ncnc(N)c23)cc1]

N-[[4-[1-[(1R,4R)-4-acetamidocyclopent-2-en-1-yl]-4-amino-pyrazolo[3,4-d]pyrimidin-3-yl]phenyl]methyl]-2-methoxy-benzamide A solution of N-[[4-[4-amino-1-[(1R,4R)-4-aminocyclopent-2-en-1-yl]pyrazolo[3,4-d]pyrimidin-3-yl]phenyl]methyl]-2-methoxy-benzamide (60 mg, 0.09 mmol) and N,N-diisopropylethylamine (18 μL, 0.10 mmol) in DCM (2 mL) was cooled to −78° C. Acetyl chloride (7 μL, 0.10 mmol) was added dropwise and the reaction mixture was stirred at −78° C. for 2 h, quenched with a saturated aqueous solution of NH$_4$Cl and partitioned. The aqueous layer was extracted with DCM, dried over Na$_2$SO$_4$ and concentrated under vacuum. The crude material was purified by flash column chromatography on silica gel (EtOAc/7N NH$_3$ in MeOH 90:10 to 80:20) to give N-[[4-[1-[(1R,4R)-4-acetamidocyclopent-2-en-1-yl]-4-amino-pyrazolo[3,4-d]pyrimidin-3-yl]phenyl]methyl]-2-methoxy-benzamide (12 mg, 0.02 mmol, 24% yield)

UPLC-MS (ES$^+$, Short acidic): 1.29 min, m/z 498.4 [M+H]$^+$

UPLC-MS (ES$^+$, Long acidic): 2.80 min, m/z 498.2 [M+H]$^+$ $^1$H NMR (400 MHz, DMSO-d$_6$, δ): 8.77 (t, J=6.1 Hz, 1H), 8.26 (s, 1H), 8.12 (d, 1=7.7 Hz, 1H), 7.77 (dd, J=7.7, 1.8 Hz, 1H), 7.62 (d, J=8.3 Hz, 2H), 7.49 (m, 3H), 7.17 (d, J=8.3 Hz, 1H), 7.05 (dt, J=7.7, 1.0, 1H), 6.09 (m, 1H), 6.04 (m, 1H), 6.00 (m, 1H), 5.14 (m, 1H), 4.59 (d, J=6.1 Hz, 2H), 3.92 (s, 3H), 2.46 (m, 1H), 2.15 (m, 1H), 1.83 (s, 3H).

Example 61: N-[[4-[4-amino-1-[(1R,4R)-4-(triazol-1-yl)cyclopent-2-en-1-yl]pyrazolo[3,4-d]pyrimidin-3-yl]phenyl]methyl]-2-methoxy-benzamide

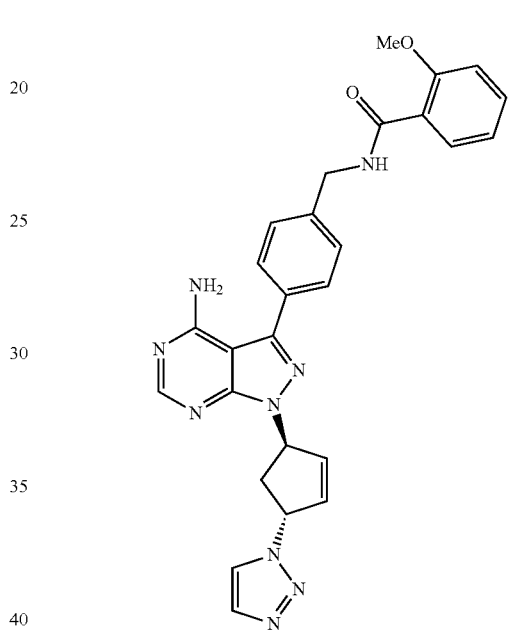

N-[[4-[4-amino-1-[(1R,4R)-4-(triazol-1-yl)cyclopent-2-en-1-yl]pyrazolo[3,4-d]pyrimidin-3-yl]phenyl]methyl]-2-methoxy-benzamide 2,5-Norbornadiene (0.1 mL, 0.97 mmol) was added to a mixture of N-[[4-[4-amino-1-[(1R,4R)-4-azidocyclopent-2-en-1-yl]pyrazolo[3,4-d]pyrimidin-3-yl]phenyl]methyl]-2-methoxy-benzamide (47 mg, 0.10 mmol) in 1,4-dioxane (5 mL). The reaction mixture was heated for 18 h at 110° C. The reaction mixture was cooled to room temperature and concentrated under vacuum. Further purification by mass-directed semi-preparative HPLC gave N-[[4-[4-amino-1-[(1R,4R)-4-(1H-1,2,3-triazol-1-yl)cyclopent-2-en-1-yl]-1H-pyrazolo[3,4-d]pyrimidin-3-yl]phenyl]methyl]-2-methoxybenzamide (5 mg, 0.01 mmol, 9% yield).

UPLC-MS (ES$^+$, Short acidic): 1.38 min, m/z 508.3 [M+H]$^+$

UPLC-MS (ES$^+$, Long acidic): 2.96 min, m/z 508.2 [M+H]$^+$ $^1$H NMR (400 MHz, DMSO-d$_6$, δ): 8.78 (t, J=6.1 Hz, 1H), 8.40 (br, 2H), 8.29 (s, 1H), 8.24 (d, J=1.0 Hz, 1H), 7.78 (m, 2H), 7.66 (d, J=8.3 Hz, 2H), 7.50 (m, 3H), 7.17 (d, J=7.8 Hz, 1H), 7.05 (dt, J=7.8, 1.0 Hz, 1H), 6.32 (m, 3H), 6.16 (m, 1H), 4.60 (d, J=6.1 Hz, 2H), 3.92 (s, 3H), 3.00 (m, 2H).

Example 62: N-[[4-[4-amino-1-(3-methylcyclopentyl)pyrazolo[3,4-d]pyrimidin-3-yl]phenyl]methyl]-2-methoxy-benzamide

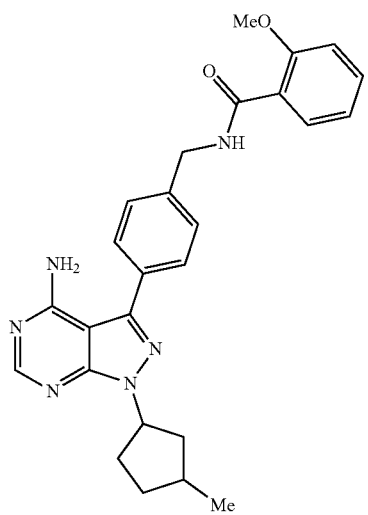 [SMILES: COc1ccccc1C(=O)NCc1ccc(-c2nn(C3CCC(C)C3)c3ncnc(N)c23)cc1]

N-[[4-[4-Amino-1-(3-methylcyclopentyl)pyrazolo[3,4-d]pyrimidin-3-yl]phenyl]methyl]-2-methoxy-benzamide Following general procedure G, N-[[4-(4-amino-1H-pyrazolo[3,4-d]pyrimidin-3-yl)phenyl]methyl]-2-methoxy-benzamide (150 mg, 0.40 mmol) and 3-methylcyclopentanol (79 mg, 0.40 mmol) afforded N-[[4-[4-amino-1-(3-methylcyclopentyl)pyrazolo[3,4-d]pyrimidin-3-yl]phenyl]methyl]-2-methoxy-benzamide (7 mg, 0.02 mmol, 4% yield) as a white solid.

UPLC-MS (ES+, Short acidic): 1.71 min, m/z 457.2 [M+H]+

UPLC-MS (ES+, Long acidic): 3.91 min, m/z 457.3 [M+H]+

$^1$H NMR (400 MHz, DMSO-$d_6$, δ) (mixture of diastereoisomers): 8.78 (t, J=6.1 Hz, 1H), 8.24 (s, 1H), 7.78 (dd, J=7.6, 1.8 Hz, 1H), 7.68-7.61 (m, 2H), 7.54-7.46 (m, 3H), 7.17 (d, J=7.8 Hz, 1H), 7.05 (dt, J=7.5, 0.9 Hz, 1H), 5.40-5.20 (m, 1H), 4.59 (d, J=6.1 Hz, 2H), 3.92 (s, 3H), 2.50-1.20 (m, 7H), 1.14-0.99 (m, 3H).

Example 63: N-[[4-(4-Amino-1-cyclopentyl-pyrazolo[3,4-d]pyrimidin-3-yl)-2-fluoro-phenyl]methyl]-5-fluoro-2-methoxy-benzamide

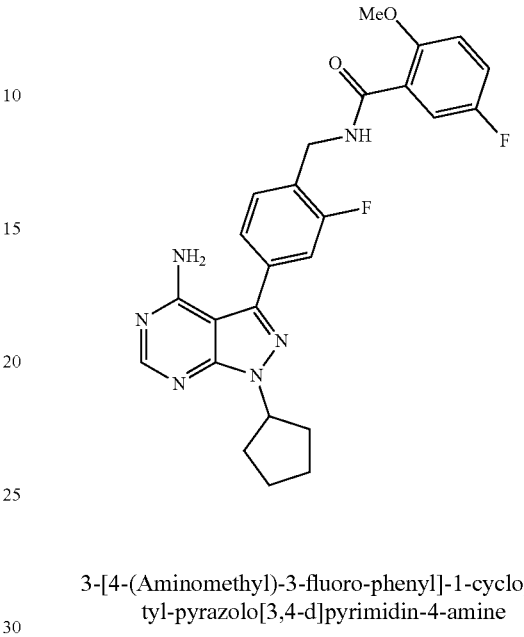

3-[4-(Aminomethyl)-3-fluoro-phenyl]-1-cyclopentyl-pyrazolo[3,4-d]pyrimidin-4-amine Following general procedure D, a mixture of 3-bromo-1-cyclopentyl-pyrazolo[3,4-d]pyrimidin-4-amine (329 mg, 1.17 mmol) and [4-(aminomethyl)-3-fluoro-phenyl]boronic acid (369 mg, 1.75 mmol) gave, after further purification by flash column chromatography (DCM/7 N NH$_3$ in MeOH 90:10 to 80:20) 3-[4-(aminomethyl)-3-fluoro-phenyl]-1-cyclopentyl-pyrazolo[3,4-d]pyrimidin-4-amine (251 mg, 0.77 mmol, 66% yield) as a beige solid.

UPLC-MS (ES+, Short acidic): 1.10 min, m/z 327.3 [M+H]+

N-[[4-(4-Amino-1-cyclopentyl-pyrazolo[3,4-d]pyrimidin-3-yl)-2-fluoro-phenyl]methyl]-5-fluoro-2-methoxy-benzamide Following general procedure F, 3-[4-(aminomethyl)-3-fluoro-phenyl]-1-cyclopentyl-pyrazolo[3,4-d]pyrimidin-4-amine (75 mg, 0.23 mmol) and 5-fluoro-2-methoxybenzoic acid (37 mg, 0.22 mmol) gave, after further purification by flash column chromatography (DCM/MeOH 100:0 to 90:10) and filtration over Si—CO$_3$ SPE cartridge, N-[[4-(4-amino-1-cyclopentyl-pyrazolo[3,4-d]pyrimidin-3-yl)-2-fluoro-phenyl]methyl]-5-fluoro-2-methoxy-benzamide (36 mg, 0.07 mmol, 32% yield) as an off-white solid.

UPLC-MS (ES+, Short acidic): 1.80 min, m/z 479.3 [M+H]+

UPLC-MS (ES+, Long acidic): 4.04 min, m/z 479.3 [M+H]+

$^1$H NMR (400 MHz, DMSO-$d_6$, δ): 8.85 (t, J=6.1 Hz, 1H), 8.24 (s, 1H), 7.57-7.50 (m, 2H), 7.48 (dd, J=7.8, 1.6 Hz, 1H), 7.44 (dd, J=10.9, 1.6 Hz, 1H), 7.17 (ddd, J=9.2, 7.8, 3.3 Hz, 1H), 7.20 (dd, J=9.2, 7.8 Hz, 1H), 5.27-5-19 (m, 1H), 4.61 (d, J=6.1 Hz, 2H), 3.91 (s, 3H), 2.15-1.98 (m, 4H), 1.95-1.82 (m, 2H), 1.75-1.62 (m, 2H).

Example 64: N-[1-[4-(4-amino-1-cyclopentyl-pyrazolo[3,4-d]pyrimidin-3-yl)phenyl]ethyl]-2-methoxy-benzamide

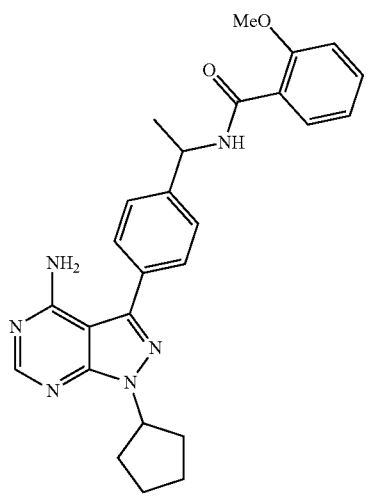 [SMILES: COc1ccccc1C(=O)NC(C)c1ccc(-c2nn(C3CCCC3)c3ncnc(N)c23)cc1]

N-[1-(4-Bromophenyl)ethyl]-2-methoxy-benzamide

To a solution of 4-bromo-α-methylbenzylamine (1.31 g, 6.57 mmol) and DIPEA (1.72 mL, 9.85 mmol) in anhydrous THF (30 mL) was added 2-methoxybenzoyl chloride (1.08 mL, 7.22 mmol) at 0° C. The reaction mixture was then allowed to return to room temperature and stirred overnight. The mixture was quenched with a saturated solution of ammonimum chloride (40 mL), extracted with EtOAc (3×20 mL). The combined organic extracts were washed with water (2×30 mL), brine (30 mL), dried over sodium sulfate, filtered and concentrated under reduced pressure. Further purification by flash column chromatography (heptane/EtOAc 90:10 to 60:40) gave N-[1-(4-bromophenyl)ethyl]-2-methoxy-benzamide (2.07 g, 6.19 mmol, 94% yield) as a white solid.

UPLC-MS (ES+, Short acidic): 1.96 min, m/z 336.1[M+2]+

2-Methoxy-N-[1-[4-(4,4,5,5-tetramethyl-1,3,2-dioxaborolan-2-yl)phenyl]ethyl]benzamide Following general procedure N, N-[1-(4-bromophenyl)ethyl]-2-methoxy-benzamide (261 mg, 0.78 mmol) afforded crude 2-methoxy-N-[1-[4-(4,4,5,5-tetramethyl-1,3,2-dioxaborolan-2-yl)phenyl]ethyl]benzamide (288 mg, 0.75 mmol, 97% yield).

UPLC-MS (ES+, Short acidic): 2.12 min, m/z 382.2 [M+H]+

N-[1-[4-(4-Amino-1-cyclopentyl-pyrazolo[3,4-d]pyrimidin-3-yl)phenyl]ethyl]-2-methoxy-benzamide Following general procedure D, 2-methoxy-N-[1-[4-(4,4,5,5-tetramethyl-1,3,2-dioxaborolan-2-yl)phenyl]ethyl]benzamide (139 mg, 0.36 mmol) and 1-cyclopentyl-3-iodo-pyrazolo[3,4-d]pyrimidin-4-amine (100 mg, 0.30 mmol) afforded, after further purification by flash column chromatography (DCM/MeOH 100:0 to 95:5) and SCX, N-[1-[4-(4-amino-1-cyclopentyl-pyrazolo[3,4-d]pyrimidin-3-yl)phenyl]ethyl]-2-methoxy-benzamide (38.3 mg, 0.08 mmol, 25% yield).

UPLC-MS (ES+, Short acidic): 1.74 min, m/z 457.4 [M+H]+

UPLC-MS (ES+, Long acidic): 3.80 min, m/z 457.3 [M+H]+

$^1$H NMR (400 MHz, DMSO-$d_6$, δ): 8.56 (d, J=7.9 Hz, 1H), 8.24 (s, 1H), 7.69-7.62 (m, 3H), 7.60-7.54 (m, 2H), 7.50-7.44 (m, 1H), 7.18-7.13 (m, 1H), 7.06-7.00 (m, 1H), 5.29-5.15 (m, 2H), 3.91 (s, 3H), 2.15-1.97 (m, 4H), 1.95-1.82 (m, 2H), 1.75-1.61 (m, 2H), 1.51 (d, J=7.0 Hz, 3H).

Example 65: N-[[4-(4-amino-1-cyclopentyl-pyrazolo[3,4-d]pyrimidin-3-yl)-2-fluoro-phenyl]methyl]-2-methoxy-5-methyl-benzamide

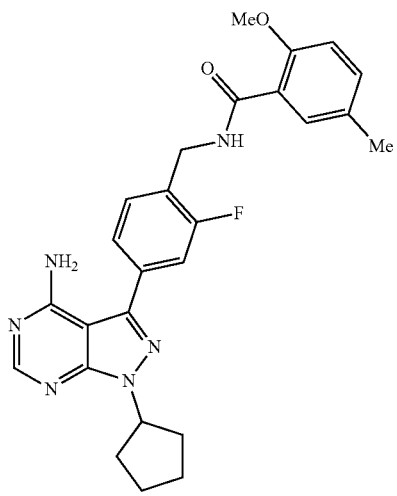 [SMILES: COc1ccc(C)cc1C(=O)NCc1ccc(-c2nn(C3CCCC3)c3ncnc(N)c23)cc1F]

N-[[4-(4-Amino-1-cyclopentyl-pyrazolo[3,4-d]pyrimidin-3-yl)-2-fluoro-phenyl]methyl]-2-methoxy-5-methyl-benzamide Following general procedure F, 3-[4-(aminomethyl)-3-fluoro-phenyl]-1-cyclopentyl-pyrazolo[3,4-d]pyrimidin-4-amine (68 mg, 0.21 mmol) and 2-methoxy-5-methylbenzoic acid (35 mg, 0.21 mmol) gave, after further purification by flash column chromatography (DCM/MeOH 100:0 to 90:10) and filtration over Si—CO$_3$ SPE cartridge, N-[[4-(4-amino-1-cyclopentyl-pyrazolo[3,4-d]pyrimidin-3-yl)-2-fluoro-phenyl]methyl]-2-methoxy-5-methyl-benzamide (36 mg, 0.08 mmol, 36% yield).

UPLC-MS (ES+, Short acidic): 1.83 min, m/z 475.4 [M+H]+

UPLC-MS (ES+, Long acidic): 4.10 min, m/z 475.4 [M+H]+

$^1$H NMR (400 MHz, DMSO-$d_6$, δ): 8.73 (t, J=5.8 Hz, 1H), 8.24 (s, 1H), 7.61-7.40 (m, 4H), 7.29 (dd, J=8.3, 2.3 Hz, 1H), 7.44 (d, J=8.3 Hz, 1H), 5.28-5-18 (m, 1H), 4.60 (d, J=5.8 Hz, 2H), 3.89 (s, 3H), 2.27 (s, 3H), 2.14-1.97 (m, 4H), 1.95-1.83 (m, 2H), 1.74-1.62 (m, 2H).

Example 66: N-[[4-(4-amino-1-cyclopentyl-pyrazolo[3,4-d]pyrimidin-3-yl)-2-fluoro-phenyl]methyl]-2-methoxy-benzamide

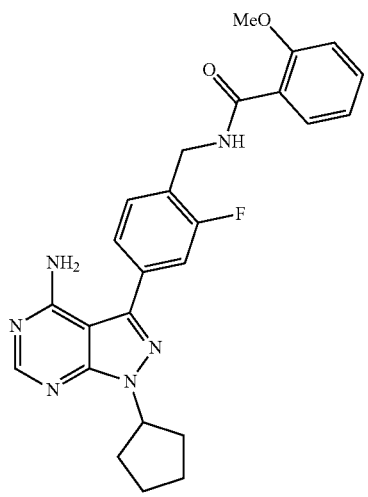 [SMILES: COc1ccccc1C(=O)NCc1ccc(-c2nn(C3CCCC3)c3ncnc(N)c23)cc1F]

N-[[4-(4-Amino-1-cyclopentyl-pyrazolo[3,4-d]pyrimidin-3-yl)-2-fluoro-phenyl]methyl]-2-methoxy-benzamide Following general procedure F, 3-[4-(aminomethyl)-3-fluoro-phenyl]-1-cyclopentyl-pyrazolo[3,4-d]pyrimidin-4-amine (73 mg, 0.22 mmol) and 2-methoxybenzoic acid (33 mg, 0.21 mmol) gave, after further purification by flash column chromatography (DCM/MeOH 100:0 to 90:10) and filtration over Si—CO$_3$ SPE cartridge, N-[[4-(4-amino-1-cyclopentyl-pyrazolo[3,4-d]pyrimidin-3-yl)-2-fluoro-phenyl]methyl]-2-methoxy-benzamide (15 mg, 0.03 mmol, 15% yield) as a beige solid.

UPLC-MS (ES$^+$, Short acidic): 1.73 min, m/z 461.4 [M+H]$^+$

UPLC-MS (ES$^+$, Long acidic): 3.83 min, m/z 461.4 [M+H]$^+$ $^1$H NMR (400 MHz, DMSO-d$_6$, δ): 8.76 (t, J=6.0 Hz, 1H), 8.24 (s, 1H), 7.77 (dd, J=7.7, 1.8 Hz, 1H), 7.57-7.41 (m, 4H), 7.19-7.15 (m, 1H), 7.07-7.02 (m, 1H), 5.28-5-18 (m, 1H), 4.61 (d, J=6.0 Hz, 2H), 3.92 (s, 3H), 2.15-1.97 (m, 4H), 1.95-1.83 (m, 2H), 1.74-1.63 (m, 2H).

Example 67: N-[1-[4-(4-amino-1-cyclopentyl-pyrazolo[3,4-d]pyrimidin-3-yl)phenyl]cyclopropyl]-2-methoxy-benzamide

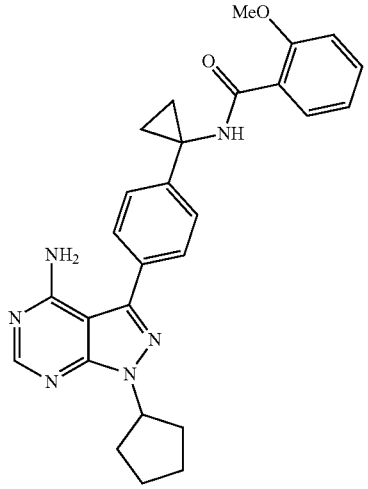 [SMILES: COc1ccccc1C(=O)NC1(c2ccc(-c3nn(C4CCCC4)c4ncnc(N)c34)cc2)CC1]

N-[1-(4-Bromophenyl)cyclopropyl]-2-methoxy-benzamide

To a solution of 1-(4-bromophenyl)cyclopropanamine (534 mg, 2.52 mmol) and DIPEA (0.66 mL, 3.77 mmol) in anhydrous THF (10 mL) was added 2-methoxybenzoyl chloride (0.41 mL, 2.77 mmol) at 0° C. The reaction mixture was then allowed to return to room temperature and stirred overnight. The mixture was quenched with a saturated solution of ammonimum chloride (20 mL), extracted with EtOAc (3×10 mL). The combined organic extracts were washed with water (2×10 mL), brine (10 mL), dried over sodium sulfate, filtered and concentrated under reduced pressure. Further purification by flash column chromatography (heptane/EtOAc 90:10 to 60:40) gave N-[1-(4-bromophenyl)cyclopropyl]-2-methoxy-benzamide (362 mg, 1.05 mmol, 42% yield) as a white fluffy solid.

UPLC-MS (ES$^+$, Short acidic): 1.98 min, m/z 346.1 [M]$^+$

2-Methoxy-N-[1-[4-(4,4,5,5-tetramethyl-1,3,2-dioxaborolan-2-yl)phenyl]cyclopropyl]benzamide Following general procedure N, N-[1-(4-bromophenyl)cyclopropyl]-2-methoxy-benzamide (261 mg, 0.75 mmol) afforded crude 2-methoxy-N-[1-[4-(4,4,5,5-tetramethyl-1,3,2-dioxaborolan-2-yl)phenyl]cyclopropyl]benzamide (280 mg, 0.71 mmol, 95% yield)

UPLC-MS (ES$^+$, Short acidic): 2.10 min, m/z 394.2 [M+H]$^+$

N-[1-[4-(4-Amino-1-cyclopentyl-pyrazolo[3,4-d]pyrimidin-3-yl)phenyl]cyclopropyl]-2-methoxy-benzamide Following general procedure D, 2-methoxy-N-[1-[4-(4,4,5,5-tetramethyl-1,3,2-dioxaborolan-2-yl)phenyl]cyclopropyl]benzamide (143 mg, 0.36 mmol) and 1-cyclopentyl-3-iodo-pyrazolo[3,4-d]pyrimidin-4-amine (100 mg, 0.30 mmol) afforded, after further purification by flash column chromatography (DCM: MeOH 100:0 to 95:5) and SCX, N-[1-[4-(4-amino-1-cyclopentyl-pyrazolo[3,4-d]pyrimidin-3-yl)phenyl]cyclopropyl]-2-methoxy-benzamide (83 mg, 0.16 mmol, 53% yield).

UPLC-MS (ES+, Short acidic): 1.67 min, m/z 469.3 [M+H]+

UPLC-MS (ES+, Long acidic): 3.77 min, m/z 469.3 [M+H]+

$^1$H NMR (400 MHz, DMSO-d$_6$, δ): 8.82 (s, 1H), 8.24 (s, 1H), 7.65-7.60 (m, 3H), 7.49-7.45 (m, 1H), 7.42-7.40 (m, 2H), 7.18-7.13 (m, 1H), 7.06-7.00 (m, 1H), 5.29-5.15 (m, 1H), 3.91 (s, 3H), 2.15-1.97 (m, 4H), 1.95-1.82 (m, 2H), 1.75-1.61 (m, 2H), 1.35 (s, 4H).

Example 68—: N-[[4-(4-amino-1-cyclopentyl-pyrazolo[3,4-d]pyrimidin-3-yl)phenyl]methyl]-2-methoxy-naphthalene-1-carboxamide

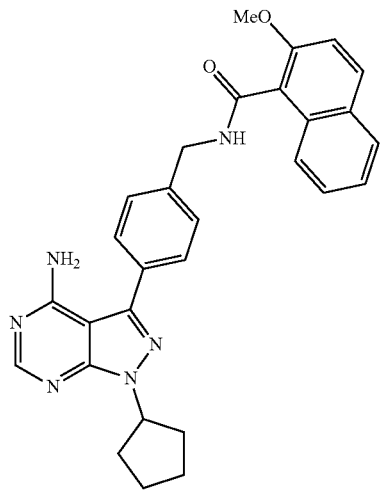 [SMILES: COc1ccc2ccccc2c1C(=O)NCc1ccc(-c2nn(C3CCCC3)c3ncnc(N)c23)cc1]

[4-[[(2-Methoxynaphthalene-1-carbonyl)amino]methyl]phenyl]boronic acid

DMF (1 drop) was added to a cooled solution of 2-methoxynaphthalene-1-carboxylic acid (0.17 mL, 0.84 mmol) and oxalyl chloride (0.07 mL, 0.84 mmol) in DCM (10 mL) and stirred at room temperature for 1 h until a clear solution was obtained. To this was added carefully 4-aminomethylphenylboronic acid hydrochloride (150 mg, 0.80 mmol) and N,N-diisopropylethylamine (0.41 mL, 2.40 mmol). The resultant yellow suspension was stirred at room temperature overnight, diluted with further DCM (10 mL), quenched with sat NH$_4$Cl aq. (10 mL) and the layers separated. The aqueous layer was extracted with DCM (2×10 mL). The combined organic layers were washed with brine, dried over MgSO$_4$, and concentrated in vacuo to give a cream solid. Further purification by flash column chromatography on silica gel eluting with 0-10% MeOH in DCM gave [4-[[(2-methoxynaphthalene-1-carbonyl)amino]methyl]phenyl]boronic acid (148 mg, 0.42 mmol, 52% yield) as a white solid.

LC-MS (ES+, method 3): 3.67 min, m/z 336.0 [M+H]+

N-[[4-(4-Amino-1-cyclopentyl-pyrazolo[3,4-d]pyrimidin-3-yl)phenyl]methyl]-2-methoxy-naphthalene-1-carboxamide Following general procedure C, 1-cyclopentyl-3-iodopyrazolo[3,4-d]pyrimidin-4-amine (64 mg, 0.19 mmol) and [4-[[(2-methoxynaphthalene-1-carbonyl)amino]methyl]phenyl]boronic acid (65 mg, 0.19 mmol) gave, after further purification by flash column chromatography on silica gel eluting with 0-8% MeOH/DCM, N-[[4-(4-amino-1-cyclopentyl-pyrazolo[3,4-d]pyrimidin-3-yl)phenyl]methyl]-2-methoxy-naphthalene-1-carboxamide (50 mg, 0.10 mmol, 52% yield).

LC-MS (ES+, method 4): 7.20 min, m/z 493.3 [M+H]+

$^1$H NMR (500 MHz, MeOH-d$_4$, δ): 8.24 (s, 1H), 7.97 (d, J=9.1 Hz, 1H), 7.86-7.83 (m, 1H), 7.79-7.76 (m, 1H), 7.74-7.67 (m, 4H), 7.51-7.45 (m, 2H), 7.37 (ddd, J=8.2, 6.9, 1.3 Hz, 1H), 5.29 (quint, J=7.5 Hz, 1H), 4.77 (s, 2H), 4.01 (s, 3H), 2.20-2.13 (m, 4H), 2.05-1.95 (m, 2H), 1.82-1.72 (m, 2H).

Example 69: N-[[4-(4-amino-1-cyclopentyl-pyrazolo[3,4-d]pyrimidin-3-yl)phenyl]methyl]isoquinoline-1-carboxamide

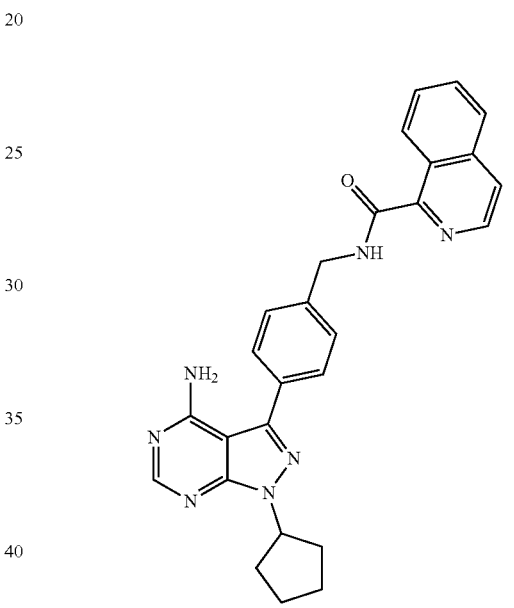

[4-[(Isoquinoline-1-carbonylamino)methyl]phenyl]boronic acid

Following general procedure A, suspension of 4-aminomethylphenylboronic acid hydrochloride (88 mg, 0.47 mmol) and isoquinoline-1-carboxylic acid (100 mg, 0.57 mmol) afforded crude [4-[(isoquinoline-1-carbonylamino)methyl]phenyl]boronic acid (114 mg, 0.26 mmol, 56% yield) as light brown crystals.

LC-MS (ES+, method 3): 3.16 min, m/z 307.0 [M+H]+

N-[[4-(4-Amino-1-cyclopentyl-pyrazolo[3,4-d]pyrimidin-3-yl)phenyl]methyl]isoquinoline-1-carboxamide Following general procedure C, 1-cyclopentyl-3-iodopyrazolo[3,4-d]pyrimidin-4-amine (56 mg, 0.17 mmol) and [4-[(isoquinoline-1-carbonylamino)methyl]phenyl]boronic acid (47 mg, 0.15 mmol) yielded N-[[4-(4-amino-1-cyclopentyl-pyrazolo[3,4-d]pyrimidin-3-yl)phenyl]methyl]isoquinoline-1-carboxamide (25 mg, 0.05 mmol, 33% yield).

LC-MS (ES+, method 3): 4.26 min, m/z 463.9 [M+H]+

LC-MS (ES+, method 4): 8.45 min, m/z 464.2 [M+H]+

¹H NMR (500 MHz, DMSO-d₆, δ): 9.50 (t, J=6.3 Hz, 1H), 8.98 (dd, J=8.5, 0.6 Hz, 1H), 8.58 (d, J=5.7 Hz, 1H), 8.23 (s, 1H), 8.09-8.03 (m, 2H), 7.84 (ddd, J=8.2, 6.8, 1.3 Hz, 1H), 7.74 (ddd, J=8.2, 6.6, 1.3 Hz, 1H), 7.68-7.63 (m, 2H), 7.60-7.55 (m, 2H), 5.27-5.19 (m, 1H), 4.65 (d, J=6.3 Hz, 2H), 2.13-1.98 (m, 4H), 1.93-1.84 (m, 2H), 1.73-1.63 (m, 2H).

Example 70: —N-[[4-(4-amino-1-cyclopentyl-pyrazolo[3,4-d]pyrimidin-3-yl)phenyl]methyl]quinoline-8-carboxamide

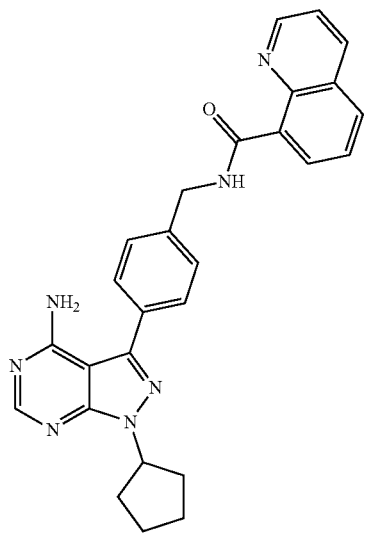 [SMILES: Nc1ncnc2c1c(-c1ccc(CNC(=O)c3cccc4cccnc34)cc1)nn2C1CCCC1]

[4-[(Quinoline-8-carbonylamino)methyl]phenyl]boronic acid

Following general procedure O, quinoline-8-carboxylic acid (81 mg, 0.47 mmol) and 4-aminomethylphenylboronic acid hydrochloride (80 mg, 0.43 mmol) gave [4-[(quinoline-8-carbonylamino)methyl]phenyl]boronic acid (56 mg, 0.18 mmol, 43% yield).

LC-MS (ES⁺, method 3): 3.48 min, m/z 306.9 [M+H]⁺

N-[[4-(4-Amino-1-cyclopentyl-pyrazolo[3,4-d]pyrimidin-3-yl)phenyl]methyl]quinoline-8-carboxamide Following general procedure C, 1-cyclopentyl-3-iodo-pyrazolo[3,4-d]pyrimidin-4-amine (67 mg, 0.20 mmol) and [4-[(quinoline-8-carbonylamino)methyl]phenyl]boronic acid (56 mg, 0.18 mmol) gave, after purification by flash column chromatography on silica gel eluting with 5-10% MeOH in DCM, N-[[4-(4-amino-1-cyclopentyl-pyrazolo[3,4-d]pyrimidin-3-yl)phenyl]methyl]quinoline-8-carboxamide (13 mg, 0.03 mmol, 15% yield).

LC-MS (ES⁺, method 4): 8.03 min, m/z 464.0 [M+H]⁺
¹H NMR (500 MHz, CDCl₃, δ): 11.87-11.80 (m, 1H), 8.95-8.91 (m, 2H), 8.36 (s, 1H), 8.31 (dd, J=8.2, 1.6 Hz, 1H), 8.00 (dd, J=8.2, 1.6 Hz, 1H), 7.74-7.70 (m, 1H), 7.69-7.66 (m, 2H), 7.64-7.60 (m, 2H), 7.51 (dd, J=8.2, 4.4 Hz, 1H), 5.50-5.41 (br s, 2H), 5.35-5.26 (m, 1H), 4.92 (d, J=6.0 Hz, 2H), 2.21-2.12 (m, 4H), 2.03-1.92 (m, 2H), 1.76-1.69 (m, 2H).

Example 71: N-[[4-(4-amino-1-cyclopentyl-pyrazolo[3,4-d]pyrimidin-3-yl)phenyl]methyl]-3-methoxy-naphthalene-2-carboxamide

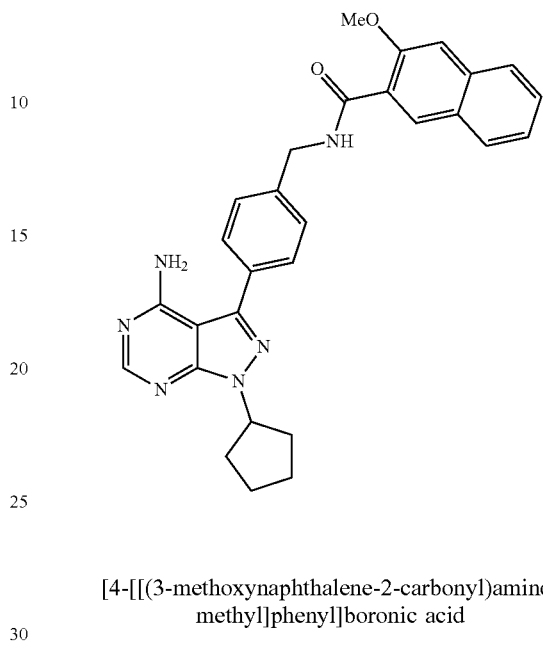

[4-[[(3-methoxynaphthalene-2-carbonyl)amino]methyl]phenyl]boronic acid

Following general procedure A, 4-aminomethylphenylboronic acid hydrochloride (228 mg, 1.21 mmol) and 3-methoxynaphthalene-2-carboxylic acid (300 mg, 1.48 mmol) gave after work-up [4-[[(3-methoxynaphthalene-2-carbonyl)amino]methyl]phenyl]boronic acid (327 mg, 0.98 mmol, 66% yield) as a white solid.

LC-MS (ES⁺, method 2): 3.42 min, m/z 336.0 [M+H]⁺

N-[[4-(4-Amino-1-cyclopentyl-pyrazolo[3,4-d]pyrimidin-3-yl)phenyl]methyl]-3-methoxy-naphthalene-2-carboxamide Following general procedure D, [4-[[(3-methoxynaphthalene-2-carbonyl)amino]methyl]phenyl]boronic acid (50 mg, 0.15 mmol) and 1-cyclopentyl-3-iodo-pyrazolo[3,4-d]pyrimidin-4-amine (49 mg, 0.15 mmol) afforded, after purification by flash column chromatography on silica gel eluting with 0-6% MeOH in DCM, N-[[4-(4-amino-1-cyclopentyl-pyrazolo[3,4-d]pyrimidin-3-yl)phenyl]methyl]-3-methoxy-naphthalene-2-carboxamide (20 mg, 0.03 mmol, 23% yield).

LC-MS (ES⁺, method 4): 8.80 min, m/z 493.2 [M+H]⁺
¹H NMR (500 MHz, CDCl₃, δ): 8.82 (s, 1H), 8.43 (t, J=5.6 Hz, 1H), 8.37 (s, 1H), 7.94-7.90 (m, 1H), 7.78-7.74 (m, 1H), 7.71-7.67 (m, 2H), 7.59-7.50 (m, 3H), 7.41 (ddd, J=8.2, 6.9, 1.1 Hz, 1H), 7.28-7.21 (m, 1H), 5.57-5.44 (br s, 2H), 5.35-5.25 (m, 1H), 4.82 (d, J=5.6 Hz, 2H), 4.07 (s, 3H), 2.21-2.14 (m, 4H), 2.03-1.92 (m, 2H), 1.77-1.69 (m, 2H).

Example 72—N-[[4-(4-amino-1-cyclopentyl-pyrazolo[3,4-d]pyrimidin-3-yl)phenyl]methyl]naphthalene-2-carboxamide

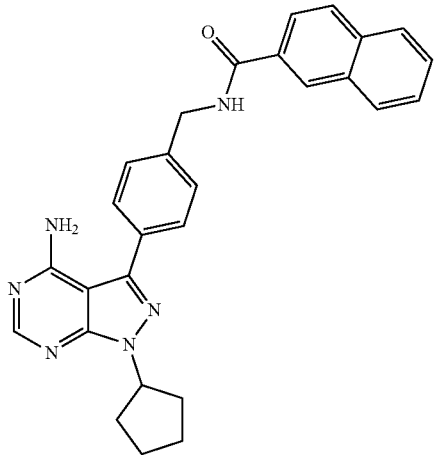 [SMILES: Nc1ncnc2c1c(-c1ccc(CNC(=O)c3ccc4ccccc4c3)cc1)nn2C1CCCC1]

[4-[(Naphthalene-2-carbonylamino)methyl]phenyl] boronic acid

Following general procedure O, 2-naphthoic acid (303 mg, 1.76 mmol) and 4-aminomethyl phenyl boronic acid hydrochloride (300 mg, 1.60 mmol) afforded [4-[(naphthalene-2-carbonylamino)methyl]phenyl]boronic acid (327 mg, 1.07 mmol, 67% yield) as a white solid.

LC-MS (ES$^+$, method 3): 3.86 min, m/z 306.0 [M+H]$^+$

N-[[4-(4-Amino-1-cyclopentyl-pyrazolo[3,4-d]pyrimidin-3-yl)phenyl]methyl]naphthalene-2-carboxamide Following general procedure C, 1-cyclopentyl-3-iodo-pyrazolo[3,4-d]pyrimidin-4-amine (90 mg, 0.27 mmol) and [4-[(naphthalene-2-carbonylamino)methyl]phenyl]boronic acid (100 mg, 0.33 mmol) gave, after purification by flash column chromatography on silica gel eluting with 0-10% MeOH/DCM, N-[[4-(4-amino-1-cyclopentyl-pyrazolo[3,4-d]pyrimidin-3-yl)phenyl]methyl]naphthalene-2-carboxamide (115 mg, 0.25 mmol, 76% yield) as a brown solid.

LC-MS (ES$^+$, method 4): 8.27 min, m/z 463.1 [M+H]$^+$ $^1$H NMR (500 MHz, DMSO-d$_6$, δ): 9.29 (t, J=6.1 Hz, 1H), 8.54 (s, 1H), 8.23 (s, 1H), 8.07-7.95 (m, 4H), 7.68-7.57 (m, 4H), 7.56-7.52 (m, 2H), 5.26-5-19 (m, 1H), 4.62 (d, J=6.1 Hz, 2H), 2.13-1.97 (m, 4H), 1.93-1.83 (m, 2H), 1.73-1.62 (m, 2H).

Example 73: N-[[4-(4-amino-1-cyclopentyl-pyrazolo[3,4-d]pyrimidin-3-yl)-2,6-difluoro-phenyl]methyl]-2-methoxy-benzamide

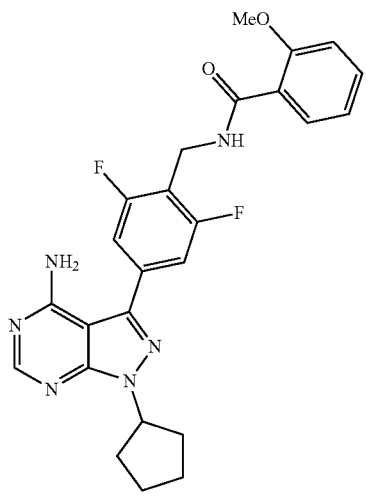 [SMILES: COc1ccccc1C(=O)NCc1c(F)cc(-c2nn(C3CCCC3)c3ncnc(N)c23)cc1F]

(4-Bromo-2,6-difluoro-phenyl)methanamine

Following general procedure P, 4-bromo-2,6-difluorobenzonitrile (350 mg, 1.61 mmol) yielded (4-bromo-2,6-difluoro-phenyl)methanamine (260 mg, 1.17 mmol, 73% yield) as a yellow liquid.

LC-MS (ES$^+$, method 2): 1.33 min, m/z 221.9 [M]$^+$

N-[(4-Bromo-2,6-difluoro-phenyl)methyl]-2-methoxy-benzamide

Following general procedure O, 2-methoxybenzoic acid (196 mg, 1.29 mmol) and (4-bromo-2,6-difluoro-phenyl) methanamine (260 mg, 1.17 mmol) gave, after trituration with diethyl ether (5 mL), N-[(4-bromo-2,6-difluoro-phenyl)methyl]-2-methoxy-benzamide (250 mg, 0.70 mmol, 60% yield) as a white solid.

LC-MS (ES$^+$, method 3): 4.82 min, m/z 358.0 [M+H]$^+$

N-[[2,6-Difluoro-4-(4,4,5,5-tetramethyl-1,3,2-dioxaborolan-2-yl)phenyl]methyl]-2-methoxy-benzamide Following general procedure R, N-[(4-bromo-2,6-difluoro-phenyl)methyl]-2-methoxy-benzamide (250 mg, 0.70 mmol) yielded crude N-[[2,6-difluoro-4-(4,4,5,5-tetramethyl-1,3,2-dioxaborolan-2-yl)phenyl]methyl]-2-methoxy-benzamide (280 mg, 0.99 mmol, assumed quantitative) as a brown gum.

LC-MS (ES$^+$, method 3): 3.78 min, m/z 322.07 [M+H]$^+$

N-[[4-(4-Amino-1-cyclopentyl-pyrazolo[3,4-d]pyrimidin-3-yl)-2,6-difluoro-phenyl]methyl]-2-methoxy-benzamide Following general procedure C, a mixture of N-[[2,6-difluoro-4-(4,4,5,5-tetramethyl-1,3,2-dioxaborolan-2-yl) phenyl]methyl]-2-methoxy-benzamide (121 mg, 0.30 mmol) and 1-cyclopentyl-3-iodo-pyrazolo[3,4-d]pyrimidin-4-amine (82 mg, 0.25 mmol) afforded, after purification by flash column chromatography on silica gel eluting with 50-100% ethyl acetate in heptane, N-[[4-(4-amino-1-cyclopentyl-pyrazolo[3,4-d]pyrimidin-3-yl)-2,6-difluoro-phenyl]methyl]-2-methoxy-benzamide (60 mg, 0.12 mmol, 48% yield) as a solid.

LC-MS (ES+, method 3): 4.45 min, m/z 479.1 [M+H]+
LC-MS (ES+, method 4): 8.48 min, m/z 479.1 [M+H]+
$^1$H NMR (500 MHz, DMSO-d$_6$, δ): 8.65 (t, J=5.7 Hz, 1H), 8.50 (s, 1H), 7.76 (dd, J=7.9, 1.8 Hz, 1H), 7.48 (ddd, J=8.5, 7.3, 1.9 Hz, 1H), 7.40-7.32 (m, 2H), 7.16 (d, J=8.2 Hz, 1H), 7.06-7.01 (m, 1H), 5.32-5.24 (m, 1H), 4.64 (d, J=5.7 Hz, 2H), 3.90 (s, 3H), 2.18-2.08 (m, 2H), 2.07-1.97 (m, 2H), 1.94-1.84 (m, 2H), 1.75-1.64 (m, 2H).

Example 74: N-[[4-[4-amino-1-(2-hydroxypropyl)pyrazolo[3,4-d]pyrimidin-3-yl]phenyl]methyl]-2-methoxy-benzamide

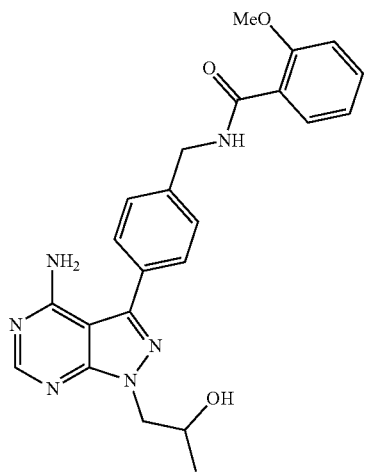 [SMILES: COc1ccccc1C(=O)NCc1ccc(-c2nn(CC(C)O)c3ncnc(N)c23)cc1]

1-(4-Amino-3-iodo-pyrazolo[3,4-d]pyrimidin-1-yl)propan-2-ol

Following general procedure M, 3-iodo-1H-pyrazolo[3,4-d]pyrimidin-4-amine (200 mg, 0.77 mmol) and 1-bromopropan-2-ol (282 mg, 2.03 mmol) afforded, after purification by flash column chromatography on silica gel eluting with 0-10% MeOH in DCM, 1-(4-amino-3-iodo-pyrazolo[3,4-d]pyrimidin-1-yl)propan-2-ol (55 mg, 0.16 mmol, 21% yield) as a white solid.

LC-MS (ES+, method 2): 2.34 min, m/z 320.0 [M+H]+

N-[[4-[4-Amino-1-(2-hydroxypropyl)pyrazolo[3,4-d]pyrimidin-3-yl]phenyl]methyl]-2-methoxy-benzamide Following general procedure C, [4-[[(2-methoxybenzoyl)amino]methyl]phenyl]boronic acid (59 mg, 0.21 mmol) and 1-(4-amino-3-iodo-pyrazolo[3,4-d]pyrimidin-1-yl)propan-2-ol (55 mg, 0.16 mmol) gave, after further purification by flash column chromatography on silica gel eluting with 0-10% MeOH in EtOAc, N-[[4-[4-amino-1-(2-hydroxypropyl)pyrazolo[3,4-d]pyrimidin-3-yl]phenyl]methyl]-2-methoxy-benzamide (39 mg, 0.09 mmol, 53% yield) as an off-white solid.

LC-MS (ES+, method 2): 1.72 min, m/z 433.2 [M+H]+
LC-MS (ES+, method 4): 5.42 min, m/z 433.1 [M+H]+

$^1$H NMR (500 MHz, DMSO-d$_6$, δ): 8.78 (t, J=6.1 Hz, 1H), 8.24 (s, 1H), 7.77 (dd, J=7.6, 1.6 Hz, 1H), 7.67-7.62 (m, 2H), 7.54-7.46 (m, 3H), 7.18-7.14 (m, 1H), 7.07-7.02 (m, 1H), 4.92 (d, J=5.0 Hz, 1H), 4.59 (d, J=6.1 Hz, 2H), 4.34-4.4.26 (m, 1H), 4.19-4.10 (m, 2H), 3.91 (s, 3H), 1.08 (d, J=6.0 Hz, 3H).

Example 75: N-[[4-(4-amino-1-cyclopentyl-pyrazolo[3,4-d]pyrimidin-3-yl)-2-methoxy-phenyl]methyl]-2-m ethoxy-benzamide

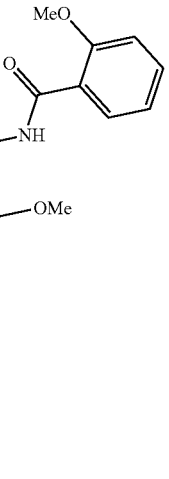

(4-Bromo-2-methoxy-phenyl)methanamine

Following general procedure Q, 4-bromo-2-methoxybenzonitrile (108 mg, 0.51 mmol) gave (4-bromo-2-methoxy-phenyl)methanamine (67.2 mg, 0.31 mmol, 61% yield).
$^1$H NMR (500 MHz, CDCl$_3$, δ): 7.12-7.02 (m, 2H), 7.00-6.96 (m, 1H), 3.84 (s, 3H), 3.77 (s, 2H).

N-[(4-Bromo-2-methoxy-phenyl)methyl]-2-methoxy-benzamide

Following general procedure O, 2-methoxybenzoic acid (57 mg, 0.37 mmol) and (4-bromo-2-methoxy-phenyl)methanamine (67 mg, 0.31 mmol) gave crude N-[(4-bromo-2-methoxy-phenyl)methyl]-2-methoxy-benzamide (55 mg, 0.16 mmol, 51% yield).

LC-MS (ES+, method 3): 4.79 min, m/z 352.0 [M+H]+

2-Methoxy-N-[[2-methoxy-4-(4,4,5,5-tetramethyl-1,3,2-dioxaborolan-2-yl)phenyl]methyl]benzamide Following general procedure R, N-[(4-bromo-2-methoxy-phenyl)methyl]-2-methoxy-benzamide (54 mg, 0.16 mmol) gave crude 2-methoxy-N-[[2-methoxy-4-(4,4,5,5-tetramethyl-1,3,2-dioxaborolan-2-yl)phenyl]methyl]benzamide (84 mg, 0.14 mmol, 92% yield) as a brown gum.

LC-MS (ES+, method 3): 5.05 min, m/z 398.1 [M+H]+

N-[[4-(4-Amino-1-cyclopentyl-pyrazolo[3,4-d]pyrimidin-3-yl)-2-methoxy-phenyl]methyl]-2-methoxy-benzamide Following general procedure C, 2-methoxy-N-[[2-methoxy-4-(4,4,5,5-tetramethyl-1,3,2-dioxaborolan-2-yl)

phenyl]methyl]benzamide (57 mg, 0.14 mmol) and 1-cyclopentyl-3-iodo-pyrazolo[3,4-d]pyrimidin-4-amine (52 mg, 0.16 mmol) afforded, after purification by flash column chromatography on silica gel eluting with 30-100% EtOAc in petrol ether, N-[[4-(4-amino-1-cyclopentyl-pyrazolo[3,4-d]pyrimidin-3-yl)-2-methoxy-phenyl]methyl]-2-methoxy-benzamide (23 mg, 0.05 mmol, 34% yield).

LC-MS (ES$^+$, method 2): 2.67 min, m/z 473.2 [M+H]$^+$ $^1$H NMR (500 MHz, CDCl$_3$, δ): 8.44 (t, J=6.0 Hz, 1H), 8.41-8.31 (m, 1H), 8.24 (dd, J=7.8, 1.6 Hz, 1H), 7.52-7.49 (m, 1H), 7.39 (ddd, J=8.3, 7.3, 1.6 Hz, 1H), 7.23-7.19 (m, 2H), 7.11-7.06 (m, 1H), 7.00-6.99 (m, 1H), 5.84-5.61 (m, 2H), 5.34-5.25 (m, 1H), 4.72 (d, J=6.0 Hz, 2H), 3.99 (s, 3H), 3.98 (s, 3H), 2.22-2.13 (m, 4H), 2.11-1.94 (m, 2H), 1.78-1.68 (m, 2H).

Example 76—N-[[4-(4-amino-1-isobutyl-pyrazolo[3,4-d]pyrimidin-3-yl)phenyl]methyl]-2-methoxy-benzamide

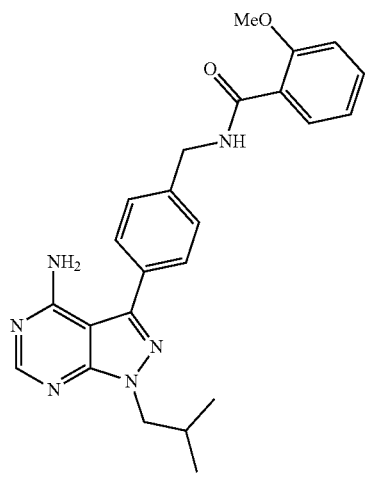 [SMILES: COc1ccccc1C(=O)NCc1ccc(-c2nn(CC(C)C)c3ncnc(N)c23)cc1]

3-Iodo-1-isobutyl-pyrazolo[3,4-d]pyrimidin-4-amine

Following general procedure M, 4-amino-3-iodo-1H-pyrazolo[3,4-d]pyrimidine (400 mg, 1.53 mmol) and 1-bromo-2-methylpropane (0.15 mL, 1.69 mmol) gave crude 3-iodo-1-isobutyl-pyrazolo[3,4-d]pyrimidin-4-amine (126 mg, 0.38 mmol, 25% yield).

LC-MS (ES$^+$, method 3): 3.45 min, m/z 318.0 [M+H]$^+$

N-[[4-(4-Amino-1-isobutyl-pyrazolo[3,4-d]pyrimidin-3-yl)phenyl]methyl]-2-methoxy-benzamide Following general procedure D, 3-iodo-1-isobutyl-pyrazolo[3,4-d]pyrimidin-4-amine (120 mg, 0.38 mmol) and [4-[[(2-methoxybenzoyl)amino]methyl]phenyl]boronic acid (98 mg, 0.34 mmol) gave, after purification by flash column chromatography on silica gel eluting with 1% methanol in ethyl acetate, N-[[4-(4-amino-1-isobutyl-pyrazolo[3,4-d]pyrimidin-3-yl)phenyl]methyl]-2-methoxy-benzamide (42 mg, 0.09 mmol, 24% yield).

LC-MS (ES$^+$, method 4): 6.49 min, m/z 431.2 [M+H]$^+$ $^1$H NMR (500 MHz, CDCl$_3$, δ): 8.39 (s, 1H), 8.34-8.29 (m, 1H), 8.27 (dd, J=7.9, 1.9 Hz, 1H), 7.70-7.66 (m, 2H), 7.56-7.51 (m, 2H), 7.51-7.45 (m, 1H), 7.14-7.09 (m, 1H), 7.02-6.98 (m, 1H), 5.53-5.43 (m, 2H), 4.77 (d, J=6.0 Hz, 2H), 4.25 (d, J=7.6 Hz, 2H), 3.96 (s, 3H), 2.46-2.36 (m, 1H), 0.96 (d, J=6.6 Hz, 6H).

Example 77—N-[[4-(4-amino-1-cyclopentyl-pyrazolo[3,4-d]pyrimidin-3-yl)-3-methoxy-phenyl]methyl]-2-methoxy-benzamide

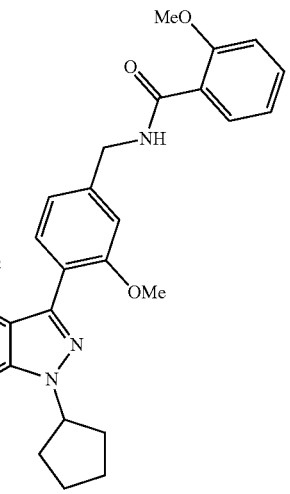

(4-Bromo-3-methoxy-phenyl)methanamine

Following general procedure Q, 4-bromo-3-methoxy-benzonitrile (212 mg, 1.0 mmol) afforded (4-bromo-3-methoxy-phenyl)methanamine (135 mg, 0.62 mmol, 62% yield).

$^1$H NMR (500 MHz, CDCl$_3$, δ): 7.47 (d, J=8.2 Hz, 1H), 6.92-6.89 (m, 1H), 6.79 (dd, J=8.2, 1.9 Hz, 1H), 3.91 (s, 3H), 3.84 (s, 2H).

N-[(4-Bromo-3-methoxy-phenyl)methyl]-2-methoxy-benzamide

Following general procedure O, 2-methoxybenzoic acid (110 mg, 0.72 mmol) and (4-bromo-3-methoxy-phenyl)methanamine (130 mg, 0.60 mmol) gave, after further purification by flash column chromatography on silica gel eluting 30-60% with EtOAc in petrol ether, N-[(4-bromo-3-methoxy-phenyl)methyl]-2-methoxy-benzamide (172 mg, 0.49 mmol, 82% yield).

LC-MS (ES$^+$, method 3): 4.55 min, m/z 351.9 [M+H]$^+$

2-Methoxy-N-[[3-methoxy-4-(4,4,5,5-tetramethyl-1,3,2-dioxaborolan-2-yl)phenyl]methyl]benzamide Following general procedure R, N-[(4-bromo-3-methoxy-phenyl)methyl]-2-methoxy-benzamide (167 mg, 0.48 mmol) gave, after purification by flash column chromatography on silica gel eluting with 1-7% MeOH in DCM), an inseparable 2:1 mixture of 2-methoxy-N-[(3-methoxyphenyl)methyl]benzamide (50 mg, 0.18 mmol, 39% yield) and 2-methoxy-N-[[3-methoxy-4-(4,4,5,5-tetramethyl-1,3,2-dioxaborolan-2-yl)phenyl]methyl]benzamide (100 mg, 0.25 mmol, 53% yield).

LC-MS (ES$^+$, method 2): 2.60 min, m/z 272.2 [M+H]$^+$ and 2.96 min, m/z 398.2 [M+H]$^+$

N-[[4-(4-Amino-1-cyclopentyl-pyrazolo[3,4-d]pyrimidin-3-yl)-3-methoxy-phenyl]methyl]-2-methoxy-benzamide Following general procedure D, 1-cyclopentyl-3-iodo-pyrazolo[3,4-d]pyrimidin-4-amine (46 mg, 0.14 mmol) and 2-methoxy-N-[[3-methoxy-4-(4,4,5,5-tetramethyl-1,3,2-dioxaborolan-2-yl)phenyl]methyl]benzamide (50 mg, 0.13 mmol) afforded, after purification by preparative HPLC (30-80% MeCN in H$_2$O), N-[[4-(4-amino-1-cyclopentyl-pyrazolo[3,4-d]pyrimidin-3-yl)-3-methoxy-phenyl]methyl]-2-methoxy-benzamide (28 mg, 0.06 mmol, 47% yield) as an off-white solid.

LC-MS (ES$^+$, method 4): 6.59 min, m/z 473.2 [M+H]$^+$ $^1$H NMR (500 MHz, MeOD-d$_4$, δ): 8.19 (s, 1H), 7.91 (dd, J=7.6, 1.9 Hz, 1H), 7.52 (ddd, J=8.2, 7.3, 1.9 Hz, 1H), 7.42 (d, J=7.6 Hz, 1H), 7.23-7.21 (m, 1H), 7.19-7.11 (m, 2H), 7.08 (td, J=7.5, 0.9 Hz, 1H), 5.25 (quint, J=7.6 Hz, 1H), 4.71 (s, 2H), 3.99 (s, 3H), 3.86 (s, 3H), 2.21-2.08 (m, 4H), 2.02-1.92 (m, 2H), 1.80-1.70 (m, 2H).

Example 78—N-[[4-(4-amino-1-isopropyl-pyrazolo[3,4-d]pyrimidin-3-yl)phenyl]methyl]-2-methoxy-benzamide

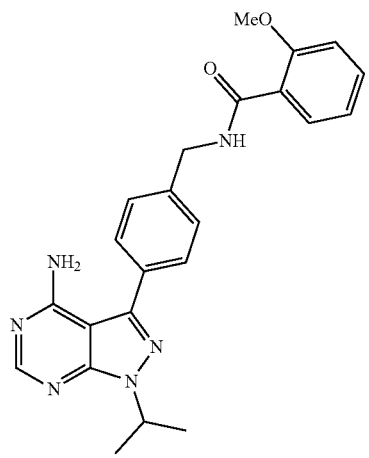 [SMILES: COc1ccccc1C(=O)NCc1ccc(-c2nn(C(C)C)c3ncnc(N)c23)cc1]

3-Iodo-1-isopropyl-pyrazolo[3,4-d]pyrimidin-4-amine

Following general procedure M, 3-iodo-1H-pyrazolo[3,4-d]pyrimidin-4-amine (535 mg, 2.03 mmol) and 2-bromopropane (0.21 mL, 2.24 mmol) gave, after further purification by flash column chromatography on silica gel eluting with 1-10% MeOH in DCM, 3-iodo-1-isopropyl-pyrazolo[3,4-d]pyrimidin-4-amine (242 mg, 0.80 mmol, 39% yield) as a pale yellow solid.

LC-MS (ES$^+$, method 2): 3.04 min, m/z 304.0 [M+H]$^+$

N-[[4-(4-Amino-1-isopropyl-pyrazolo[3,4-d]pyrimidin-3-yl)phenyl]methyl]-2-methoxy-benzamide Following general procedure C, [4-[[(2-methoxybenzoyl)amino]methyl]phenyl]boronic acid (97 mg, 0.34 mmol) and 3-iodo-1-isopropyl-pyrazolo[3,4-d]pyrimidin-4-amine (86 mg, 0.28 mmol) gave, after purification by preparative HPLC (5-95% MeCN in H$_2$O with 0.1% ammonia), N-[[4-(4-amino-1-isopropyl-pyrazolo[3,4-d]pyrimidin-3-yl)phenyl]methyl]-2-methoxy-benzamide (42 mg, 0.10 mmol, 36% yield) as an off-white solid.

LC-MS (ES$^+$, method 4): 6.59 min, m/z 417.3 [M+H]$^+$ $^1$H NMR (500 MHz, DMSO-d$_6$, δ): 8.77 (t, J=6.2 Hz, 1H), 8.24 (s, 1H), 7.77 (dd, J=7.6, 1.9 Hz, 1H), 7.66-7.62 (m, 2H), 7.53-7.46 (m, 3H), 7.18-7.14 (m, 1H), 7.05 (td, J=7.6, 0.9 Hz, 1H), 5.06 (quint, J=6.9 Hz, 1H), 4.59 (d, J=6.2 Hz, 2H), 3.91 (s, 3H), 1.49 (d, J=6.9 Hz, 6H).

Example 79—N-[[4-(4-amino-1-cyclopentyl-pyrazolo[3,4-d]pyrimidin-3-yl)-3-methyl-phenyl]methyl]-2-methoxy-benzamide

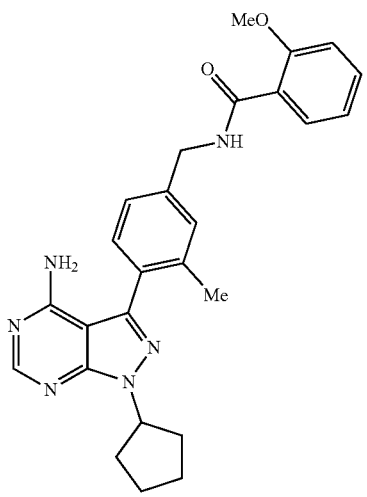 [SMILES: COc1ccccc1C(=O)NCc1ccc(-c2nn(C3CCCC3)c3ncnc(N)c23)c(C)c1]

(4-Bromo-3-methyl-phenyl)methanamine

Following general procedure Q, 4-bromo-3-methylbenzonitrile (200 mg, 1.02 mmol) gave (4-bromo-3-methyl-phenyl)methanamine (126 mg, 0.63 mmol, 62% yield) as a white solid.

$^1$H NMR (500 MHz, CDCl$_3$, δ): 7.47 (d, J=8.2 Hz, 1H), 7.21-7.18 (m, 1H), 6.99 (dd, J=8.2, 1.9 Hz, 1H), 3.80 (s, 2H), 2.39 (s, 3H).

N-[(4-Bromo-3-methyl-phenyl)methyl]-2-methoxy-benzamide

Following general procedure O, 2-methoxybenzoic acid (105 mg, 0.69 mmol) and (4-bromo-3-methyl-phenyl)methanamine (126 mg, 0.63 mmol) gave N-[(4-bromo-3-methyl-phenyl)methyl]-2-methoxy-benzamide (146 mg, 0.27 mmol, 43% yield).

LC-MS (ES$^+$, method 3): 4.88 min, m/z 336.0 [M+H]$^+$

2-Methoxy-N-[[3-methyl-4-(4,4,5,5-tetramethyl-1,3,2-dioxaborolan-2-yl)phenyl]methyl]benzamide Following general procedure R, N-[(4-bromo-3-methyl-phenyl)methyl]-2-methoxy-benzamide (146 mg, 0.44 mmol) gave crude 2-methoxy-N-[[3-methyl-4-(4,4,5,5-tetramethyl-1,3,2-dioxaborolan-2-yl)phenyl]methyl]benzamide (162 mg, 0.30 mmol, 68% yield) as an brown gum.

LC-MS (ES$^+$, method 2): 3.50 min, m/z 382.2 [M+H]$^+$

N-[[4-(4-Amino-1-cyclopentyl-pyrazolo[3,4-d]pyrimidin-3-yl)-3-methyl-phenyl]methyl]-2-methoxy-benzamide Following general procedure C, 1-cyclopentyl-3-iodo-pyrazolo[3,4-d]pyrimidin-4-amine (117 mg, 0.36 mmol) and 2-methoxy-N-[[3-methyl-4-(4,4,5,5-tetramethyl-1,3,2-dioxaborolan-2-yl)phenyl]methyl]benzamide (163 mg, 0.43 mmol) gave, after purification by preparative HPLC (5-95% MeCN in H$_2$O and 0.1% ammonia), N-[[4-(4-amino-1-cyclopentyl-pyrazolo[3,4-d]pyrimidin-3-yl)-3-methyl-phenyl]methyl]-2-methoxy-benzamide (18 mg, 0.04 mmol, 11% yield) as a brown solid.

LC-MS (ES$^+$, method 4): 7.39 min, m/z 457.4 [M+H]$^+$ $^1$H NMR (500 MHz, DMSO-d$_6$, δ): 8.72 (t, J=6.0 Hz, 1H), 8.23 (s, 1H), 7.76 (dd, J=7.8, 1.8 Hz, 1H), 7.48 (ddd, J=8.2, 7.6, 1.9 Hz, 1H), 7.37-7.29 (m, 3H), 7.18-7.14 (m, 1H), 7.05 (td, J=7.5, 0.6 Hz, 1H), 5.27-5.19 (m, 1H), 4.55 (d, J=6.0 Hz, 2H), 3.91 (s, 3H), 2.25 (s, 3H), 2.14-2.05 (m, 2H), 2.04-1.95 (m, 2H), 1.91-1.80 (m, 2H), 1.73-1.62 (m, 2H).

Example 80: N-[[4-(4-amino-1-cyclopentyl-pyrazolo[3,4-d]pyrimidin-3-yl)phenyl]methyl]-2-isopropyl-benzamide

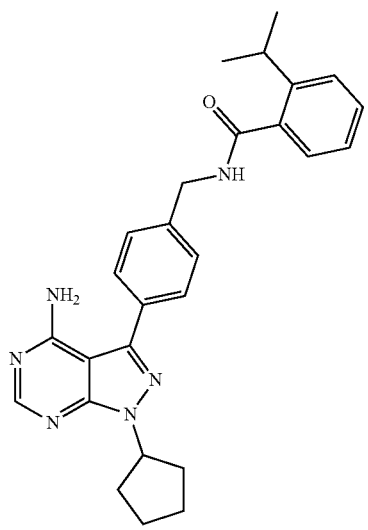 [SMILES: CC(C)c1ccccc1C(=O)NCc1ccc(-c2nn(C3CCCC3)c3ncnc(N)c23)cc1]

[4-[[(2-Isopropylbenzoyl)amino]methyl]phenyl]boronic acid

Following general procedure A, a suspension of 4-aminomethylphenylboronic acid hydrochloride (1.41 g, 7.50 mmol) and 2-isopropylbenzoic acid (1.51 g, 9.00 mmol) gave after work-up, crude [4-[[(2-isopropylbenzoyl)amino]methyl]phenyl]boronic acid (82 mg, 0.27 mmol, 4% yield) as a white solid.

UPLC-MS (ES$^+$, Short acidic): 1.53 min, m/z 298.2 [M+H]$^+$

N-[[4-(4-Amino-1-cyclopentyl-pyrazolo[3,4-d]pyrimidin-3-yl)phenyl]methyl]-2-isopropyl-benzamide Following general procedure D, a mixture of 1-cyclopentyl-3-iodo-pyrazolo[3,4-d]pyrimidin-4-amine (75 mg, 0.23 mmol) and [4-[[(2-isopropylbenzoyl)amino]methyl]phenyl]boronic acid (81 mg, 0.27 mmol) gave, after further purification by flash column chromatography (DCM/MeOH 100:0 to 90:10), N-[[4-(4-amino-1-cyclopentyl-pyrazolo[3,4-d]pyrimidin-3-yl)phenyl]methyl]-2-isopropyl-benzamide (82 mg, 0.18 mmol, 79% yield) as a light beige foam.

UPLC-MS (ES$^+$, Short acidic): 1.75 min, m/z 455.3 [M+H]$^+$

UPLC-MS (ES$^+$, Long acidic): 3.93 min, m/z 455.3 [M+H]$^+$ $^1$H NMR (400 MHz, DMSO-d$_6$, δ): 8.91 (t, J=6.0 Hz, 1H), 8.26 (s, 1H), 7.69-7.62 (m, 2H), 7.56-7.48 (m, 2H), 7.43-7.36 (m, 2H), 7.34-7.28 (m, 1H), 7.27-7.19 (m, 1H), 5.29-5.19 (m, 1H), 4.52 (d, J=6.0 Hz, 2H), 3.32-3.18 (m, 1H), 2.15-1.97 (m, 4H), 1.95-1.82 (m, 2H), 1.76-1.62 (m, 2H), 1.21 (s, 6H).

Example 81: N-[[4-(4-amino-1-tert-butyl-pyrazolo[3,4-d]pyrimidin-3-yl)phenyl]methyl]benzofuran-2-carboxamide

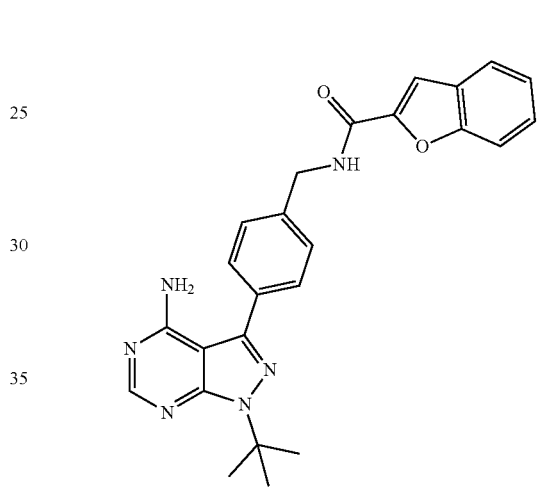

[4-[(Benzofuran-2-carbonylamino)methyl]phenyl]boronic acid

Following general procedure O, benzofuran-2-carboxylic acid (291 mg, 1.76 mmol) and 4-aminomethylphenylboronic acid hydrochloride (300 mg, 1.60 mmol) yielded [4-[(benzofuran-2-carbonylamino)methyl]phenyl]boronic acid (340 mg, 1.15 mmol, 72% yield) as a white solid LC-MS (ES$^+$, method 3): 3.11 min, m/z 296.0 [M+H]$^+$

N-[[4-(4-Amino-1-tert-butyl-pyrazolo[3,4-d]pyrimidin-3-yl)phenyl]methyl]benzofuran-2-carboxamide Following general procedure C, a mixture of 3-bromo-1-tert-butyl-pyrazolo[3,4-d]pyrimidin-4-amine (85 mg, 0.31 mmol) and [4-[(benzofuran-2-carbonylamino)methyl]phenyl]boronic acid (111 mg, 0.38 mmol) gave, after further purification by flash column chromatography on silica gel eluting 0-5% MeOH in DCM, N-[[4-(4-amino-1-tert-butyl-pyrazolo[3,4-d]pyrimidin-3-yl)phenyl]methyl]benzofuran-2-carboxamide (110 mg, 0.24 mmol, 75% yield) as a white solid.

LC-MS (ES$^+$, method 2): 2.91 min, m/z 441.5 [M+H]$^+$

LC-MS (ES$^+$, method 4): 7.93 min, m/z 441.5 [M+H]$^+$ $^1$H NMR (500 MHz, CDCl$_3$, δ): 8.36 (s, 1H), 7.73-7.66 (m, 3H), 7.56-7.52 (m, 3H), 7.49-7.46 (m, 1H), 7.44-7.39

(m, 1H), 7.32-7.28 (m, 1H), 7.10-7.03 (m, 1H), 5.57-5-44 (br s, 2H), 4.75 (d, J=6.3 Hz, 2H), 1.83 (s, 9H).

Example 82: N-[[4-(4-amino-1-cyclopentyl-pyrazolo[3,4-d]pyrimidin-3-yl)phenyl]methyl]-1,3-benzothiazole-2-carboxamide

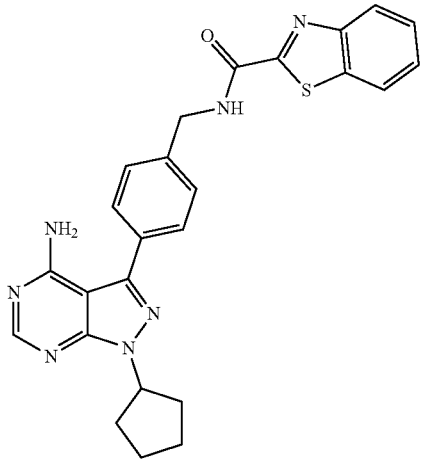 [SMILES: Nc1ncnc2c1c(-c1ccc(CNC(=O)c3nc4ccccc4s3)cc1)nn2C1CCCC1]

[4-[(1,3-Benzothiazole-2-carbonylamino)methyl]phenyl]boronic acid

DMF (1 drop) was added to a cooled solution of benzothiazole-2-carboxylicacid (0.17 mL, 0.84 mmol) and oxalyl chloride (0.07 mL, 0.84 mmol) in DCM (10 mL), then stirred at rt for 1.5 h until a clear solution was observed. 4-Aminomethylphenylboronic acid hydrochloride (150 mg, 0.80 mmol) and N,N-diisopropylethylamine (0.41 mL, 2.40 mmol) was carefully added. The resultant yellow suspension stirred at rt overnight, diluted with further DCM (10 mL) and quenched with sat NH$_4$Cl aq (10 mL) and the layers separated. The aqueous was extracted with DCM (2×10 mL). The combined organic layers were washed with brine, dried over MgSO$_4$, and concentrated in vacuo to give a cream solid. Further purification by flash column chromatography on silica gel eluting 0-10% MeOH in DCM gave [4-[(1,3-benzothiazole-2-carbonylamino)methyl]phenyl]boronic acid (110 mg, 0.35 mmol, 44% yield).

LC-MS (ES$^+$, method 3): 3.95 min, m/z 313.0 [M+H]$^+$

N-[[4-(4-Amino-1-cyclopentyl-pyrazolo[3,4-d]pyrimidin-3-yl)phenyl]methyl]-1,3-benzothiazole-2-carboxamide Following general procedure C, 1-cyclopentyl-3-iodopyrazolo[3,4-d]pyrimidin-4-amine (53 mg, 0.16 mmol) and [4-[(1,3-benzothiazole-2-carbonylamino)methyl]phenyl]boronic acid (50 mg, 0.16 mmol) gave, after purification by flash column chromatography on silica gel eluting 0-8% MeOH/DCM, N-[[4-(4-amino-1-cyclopentyl-pyrazolo[3,4-d]pyrimidin-3-yl)phenyl]methyl]-1,3-benzothiazole-2-carboxamide (50 mg, 0.11 mmol, 66% yield) as an off-white solid.

LC-MS (ES$^+$, method 3): 8.58 min, m/z 470.0 [M+H]$^+$ $^1$H NMR (500 MHz, DMSO-d$_6$, δ): 9.84 (t, J=6.3 Hz, 1H), 8.28-8.22 (m, 2H), 8.18-8.13 (m, 1H), 7.68-7.57 (m, 4H), 7.56-7.51 (m, 2H), 5.26-5.19 (m, 1H), 4.59 (d, J=6.3 Hz, 2H), 2.13-1.96 (m, 4H), 1.93-1.81 (m, 2H), 1.72-1.61 (m, 2H).

Example 83: N-[[4-(4-amino-1-cyclopentyl-pyrazolo[3,4-d]pyrimidin-3-yl)phenyl]methyl]benzofuran-2-carboxamide

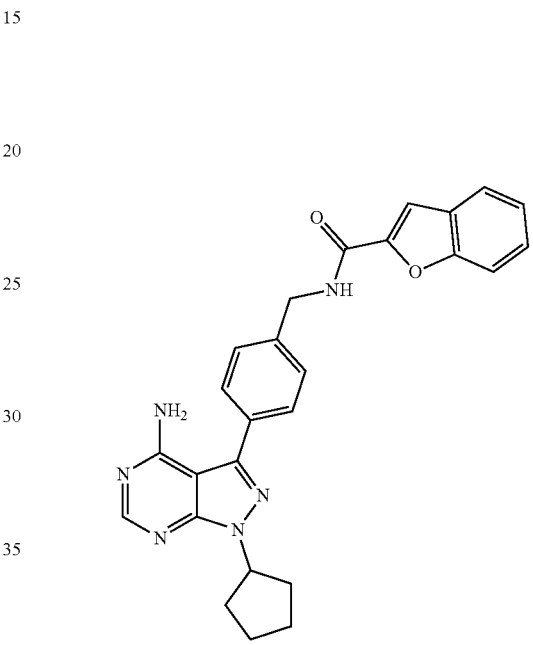

Following general procedure C, 1-cyclopentyl-3-iodopyrazolo[3,4-d]pyrimidin-4-amine (70 mg, 0.21 mmol) and [4-[(benzofuran-2-carbonylamino)methyl]phenyl]boronic acid (69 mg, 0.23 mmol) gave, after purification by flash column chromatography on silica gel (50-100% ethyl acetate in 40/60 petroleum ether), N-[[4-(4-amino-1-cyclopentyl-pyrazolo[3,4-d]pyrimidin-3-yl)phenyl]methyl]benzofuran-2-carboxamide (50 mg, 0.11 mmol, 49% yield) as a white solid.

LC-MS (ES$^+$, method 3): 4.13 min, m/z 453.1 [M+H]$^+$

LC-MS (ES$^+$, method 4): 7.50 min, m/z 453.5 [M+H]$^+$ $^1$H NMR (500 MHz, DMSO-d$_6$, δ): 9.39 (t, J=6.2 Hz, 1H), 8.24 (s, 1H), 7.82-7.78 (m, 1H), 7.70-7.67 (m, 1H), 7.66-7.63 (m, 2H), 7.62-7.60 (m, 1H), 7.54-7.51 (m, 2H), 7.51-7.46 (m, 1H), 7.38-7.33 (m, 1H), 5.23 (quint, J=7.4 Hz, 1H), 4.58 (d, J=6.2 Hz, 2H), 2.14-2.00 (m, 4H), 1.94-1.83 (m, 2H), 1.74-1.63 (m, 2H).

Example 84: N-[[4-(4-amino-1-cyclopentyl-pyrazolo[3,4-d]pyrimidin-3-yl)phenyl]methyl]benzothiophene-2-carboxamide

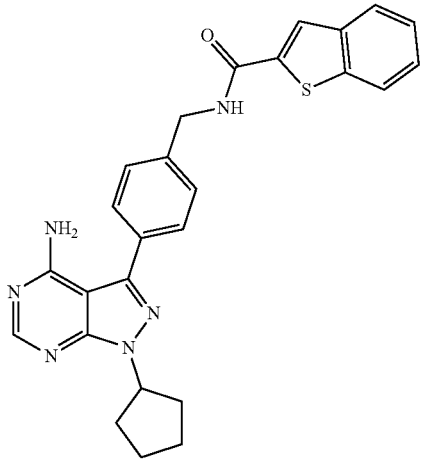 [SMILES: Nc1ncnc2c1c(-c1ccc(CNC(=O)c3cc4ccccc4s3)cc1)nn2C1CCCC1]

[4-[(Benzothiophene-2-carbonylamino)methyl]phenyl]boronic acid

Following general procedure O, benzothiophene-2-carboxylic acid (103 mg, 0.58 mmol) and 4-aminomethylphenylboronic acid hydrochloride (98 mg, 0.52 mmol) yielded [4-[(benzothiophene-2-carbonylamino)methyl]phenyl]boronic acid (106 mg, 0.34 mmol, 65% yield).

LC-MS (ES$^+$, method 3): 3.89 min, m/z 312.0 [M+H]$^+$

N-[[4-(4-amino-1-cyclopentyl-pyrazolo[3,4-d]pyrimidin-3-yl)phenyl]methyl]benzothiophene-2-carboxamide Following general procedure C, a mixture of 1-cyclopentyl-3-iodo-pyrazolo[3,4-d]pyrimidin-4-amine (65 mg, 0.20 mmol) and [4-[(benzothiophene-2-carbonylamino)methyl]phenyl]boronic acid (68 mg, 0.22 mmol) gave, after further purification by flash column chromatography on silica gel eluting 50-100% EtOAc in 40:60 petroleum ether, N-[[4-(4-amino-1-cyclopentyl-pyrazolo[3,4-d]pyrimidin-3-yl)phenyl]methyl]benzothiophene-2-carboxamide (28 mg, 0.06 mmol, 30% yield).

LC-MS (ES$^+$, method 3): 4.30 min, m/z 469.0 [M+H]$^+$

LC-MS (ES$^+$, method 4): 7.60 min, m/z 469.0 [M+H]$^+$ $^1$H NMR (500 MHz, DMSO-d$_6$, δ): 9.40 (t, J=6.0 Hz, 1H), 8.23 (s, 1H), 8.17 (s, 1H), 8.05-8.01 (m, 1H), 7.98-7.94 (m, 1H), 7.68-7.62 (m, 2H), 7.55-7.50 (m, 2H), 7.49-7.41 (m, 2H), 5.26-5.19 (m, 1H), 4.58 (d, J=6.0 Hz, 2H), 2.14-1.99 (m, 4H), 1.94-1.83 (m, 2H), 1.73-1.62 (m, 2H).

Example 85: N-[[4-(4-amino-1-cyclopentyl-pyrazolo[3,4-d]pyrimidin-3-yl)phenyl]methyl]quinoline-2-carboxamide

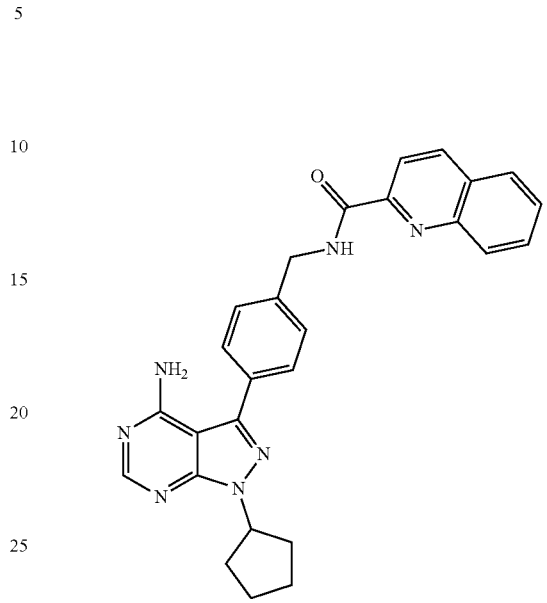

[4-[(Quinoline-2-carbonylamino)methyl]phenyl]boronic acid

Following general procedure O, quinoline-2-carboxylic acid (63 mg, 0.36 mmol) and 4-aminomethylphenylboronic acid hydrochloride (62 mg, 0.33 mmol) gave crude [4-[(quinoline-2-carbonylamino)methyl]phenyl]boronic acid (63 mg, 0.21 mmol, 63% yield).

LC-MS (ES$^+$, method 3): 3.88 min, m/z 307.0 [M+H]$^+$

N-[[4-(4-Amino-1-cyclopentyl-pyrazolo[3,4-d]pyrimidin-3-yl)phenyl]methyl]quinoline-2-carboxamide Following general procedure C, 1-cyclopentyl-3-iodo-pyrazolo[3,4-d]pyrimidin-4-amine (75 mg, 0.23 mmol) and [4-[(quinoline-2-carbonylamino)methyl]phenyl]boronic acid (63 mg, 0.21 mmol) gave after purification by flash column chromatography on silica gel, N-[[4-(4-amino-1-cyclopentyl-pyrazolo[3,4-d]pyrimidin-3-yl)phenyl]methyl]quinoline-2-carboxamide (16 mg, 0.03 mmol, 17% yield).

LC-MS (ES$^+$, method 4): 8.55 min, m/z 462.0 [M−H]$^-$ $^1$H NMR (500 MHz, CDCl$_3$, δ): 8.72 (t, J=5.9 Hz, 1H), 8.36-8.29 (m, 3H), 8.08-8.04 (m, 1H), 7.91-7.84 (m, 1H), 7.77-7.71 (m, 1H), 7.69-7.64 (m, 2H), 7.62-7.54 (m, 1H), 7.56-7.51 (m, 2H), 5.89-5.82 (br s, 2H), 5.32-5.21 (m, 1H), 4.78 (d, J=5.9 Hz, 2H), 2.20-2.09 (m, 4H), 1.99-1.88 (m, 2H), 1.74-1.63 (m, 2H).

Example 86: N-[[4-(4-Amino-1-cyclopentyl-pyrazolo[3,4-d]pyrimidin-3-yl)phenyl]methyl]-3,4-dihydro-2H-1,4-benzoxazine-2-carboxamide

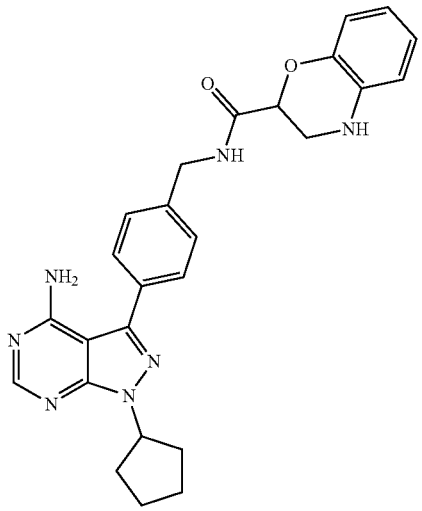 [SMILES: Nc1ncnc2c1c(-c1ccc(CNC(=O)C3CNc4ccccc4O3)cc1)nn2C1CCCC1]

N-[(4-Bromophenyl)methyl]-3,4-dihydro-2H-1,4-benzoxazine-2-carboxamide

HATU (485 mg, 1.28 mmol) was added in one portion to a mixture of 3,4-dihydro-2H-benzo[1,4]oxazine-2-carboxylic acid hydrochloride (250 mg, 1.16 mmol), 4-bromobenzylamine hydrochloride (774 mg, 3.48 mmol) and triethylamine (0.81 mL, 5.80 mmol) in anhydrous DMF (5 mL), cooled at 0° C. The reaction mixture was stirred at 0° C. for 1 h and then partitioned between brine and ethyl acetate. The organic layer was washed with brine (×2), dried over sodium sulfate, filtered and concentrated under reduced pressure. Further purification by flash column chromatography on silica gel eluting 0-50% ethyl acetate in 40/60 petroleum ether yielded N-[(4-bromophenyl)methyl]-3,4-dihydro-2H-1,4-benzoxazine-2-carboxamide (220 mg, 0.63 mmol, 55% yield).

LC-MS (ES+, method 2): 2.87 min, m/z 349.4 [M+H]$^+$

N-[[4-(4,4,5,5-tetramethyl-1,3,2-dioxaborolan-2-yl)phenyl]methyl]-3,4-dihydro-2H-1,4-benzoxazine-2-carboxamide Following general procedure R, N-[(4-bromophenyl)methyl]-3,4-dihydro-2H-1,4-benzoxazine-2-carboxamide (205 mg, 0.59 mmol) afforded crude N-[[4-(4,4,5,5-tetramethyl-1,3,2-dioxaborolan-2-yl)phenyl]methyl]-3,4-dihydro-2H-1,4-benzoxazine-2-carboxamide (205 mg, 0.52 mmol, 88% yield) as a black solid.

LC-MS (ES$^+$, method 2): 3.10 min, m/z 395.6 [M+H]$^+$

N-[[4-(4-Amino-1-cyclopentyl-pyrazolo[3,4-d]pyrimidin-3-yl)phenyl]methyl]-3,4-dihydro-2H-1,4-benzoxazine-2-carboxamide Following general procedure C, N-[[4-(4,4,5,5-tetramethyl-1,3,2-dioxaborolan-2-yl)phenyl]methyl]-3,4-dihydro-2H-1,4-benzoxazine-2-carboxamide (101 mg, 0.26 mmol) and 1-cyclopentyl-3-iodo-pyrazolo[3,4-d]pyrimidin-4-amine (70 mg, 0.21 mmol) afforded, after further purification by flash column chromatography on silica gel eluting 0-2% MeOH in EtOAc, N-[[4-(4-amino-1-cyclopentyl-pyrazolo[3,4-d]pyrimidin-3-yl)phenyl]methyl]-3,4-dihydro-2H-1,4-benzoxazine-2-carboxamide (25 mg, 0.05 mmol, 25% yield) as a white solid.

LC-MS (ES$^+$, method 3): 3.11 min, m/z 470.2 [M+H]$^+$
LC-MS (ES$^+$, method 4): 6.72 min, m/z 470.2 [M+H]$^+$
$^1$H NMR (500 MHz, DMSO-d$_6$, δ): 8.56 (t, J=6.2 Hz, 1H), 8.24 (s, 1H), 7.60-7.56 (m, 2H), 7.39-7.34 (m, 2H), 6.82 (dd, J=8.0, 1.4 Hz, 1H), 6.73 (td, J=7.6, 1.4 Hz, 1H), 6.61 (dd, J=7.9, 1.6 Hz, 1H), 6.56-6.51 (m, 1H), 5.90-5.85 (m, 1H), 5.23 (quint, J=7.4 Hz, 1H), 4.62 (dd, J=6.8, 2.8 Hz, 1H), 4.45 (dd, J=15.3, 6.3 Hz, 1H), 4.37 (dd, J=15.3, 6.3 Hz, 1H), 3.47 (dt, J=12.0, 3.0 Hz, 1H), 3.31-3.27 (m, 1H), 2.13-2.00 (m, 4H), 1.95-1.83 (m, 2H), 1.74-1.63 (m, 2H).

Example 87: N-[[4-(4-amino-1-cyclopentyl-pyrazolo[3,4-d]pyrimidin-3-yl)phenyl]methyl]-1,3-benzoxazole-7-carboxamide

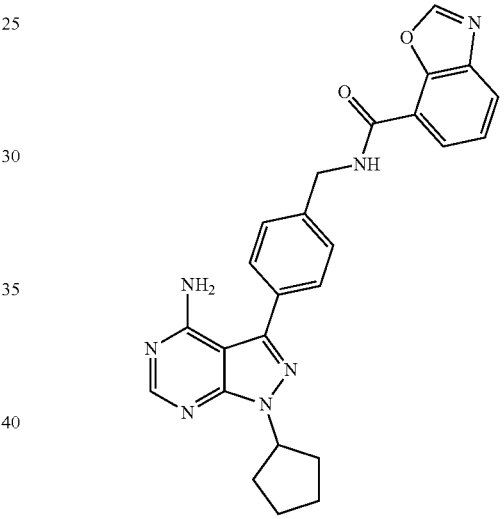

[4-[(1,3-Benzoxazole-7-carbonylamino)methyl]phenyl]boronic acid

Following general procedure O, 4-aminomethylphenylboronic acid hydrochloride (281 mg, 1.50 mmol) and 1,3-benzoxazole-7-carboxylic acid (204 mg, 1.25 mmol) gave crude [4-[(1,3-benzoxazole-7-carbonylamino)methyl]phenyl]boronic acid (227 mg, 0.66 mmol, 53% yield) a pale yellow/orange solid.

LC-MS (ES$^+$, method 3): 3.02 min, m/z 297.1 [M+H]$^+$

N-[[4-(4-amino-1-cyclopentyl-pyrazolo[3,4-d]pyrimidin-3-yl)phenyl]methyl]-1,3-benzoxazole-7-carboxamide Following general procedure C, 1-cyclopentyl-3-iodopyrazolo[3,4-d]pyrimidin-4-amine (79 mg, 0.24 mmol) and [4-[(1,3-benzoxazole-7-carbonylamino)methyl]phenyl]boronic acid (71 mg, 0.24 mmol) afforded, after purification by flash column chromatography on silica gel eluting 0-15% MeOH in DCM, N-[[4-(4-amino-1-cyclopentyl-pyrazolo[3, 4-d]pyrimidin-3-yl)phenyl]methyl]-1,3-benzoxazole-7-carboxamide (11 mg, 0.02 mmol, 10% yield).

LC-MS (ES+, method 2): 2.18 min, m/z 454.0 [M+H]+

$^1$H NMR (500 MHz, DMSO-$d_6$, δ): 8.90 (s, 1H), 8.24 (s, 1H), 8.01-7.96 (m, 1H), 7.87-7.83 (m, 1H), 7.67-7.63 (m, 2H), 7.58-7.50 (m, 3H), 5.26-5.19 (m, 1H), 4.66-4.62 (m, 2H), 2.13-1.97 (m, 4H), 1.94-1.83 (m, 2H), 1.74-1.63 (m, 2H).

Example 88: N-[[4-(4-amino-1-cyclopentyl-pyrazolo[3,4-d]pyrimidin-3-yl)phenyl]methyl]-1H-indole-2-carboxamide

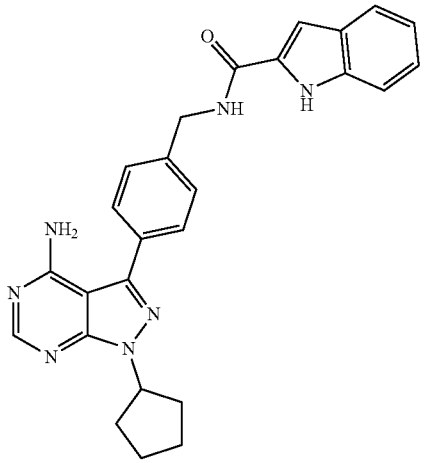 [SMILES: Nc1ncnc2c1c(-c1ccc(CNC(=O)c3cc4ccccc4[nH]3)cc1)nn2C1CCCC1]

[4-[(1H-Indole-2-carbonylamino)methyl]phenyl]boronic acid

Following general procedure O, 1H-indole-2-carboxylic acid (250 mg, 1.55 mmol) and 4-aminomethylphenylboronic acid hydrochloride (291 mg, 1.55 mmol) gave, after further purification by flash column chromatography on silica gel eluting 0-20% MeOH in EtOAc, [4-[(1H-indole-2-carbonylamino)methyl]phenyl]boronic acid (124 mg, 0.42 mmol, 27%).

LC-MS (ES+, method 3): 3.76 min, m/z 295.0 [M+H]+

N-[[4-(4-Amino-1-cyclopentyl-pyrazolo[3,4-d]pyrimidin-3-yl)phenyl]methyl]-1H-indole-2-carboxamide Following general procedure C, 1-cyclopentyl-3-iodopyrazolo[3,4-d]pyrimidin-4-amine (100 mg, 0.30 mmol) and [4-[(1H-indole-2-carbonylamino)methyl]phenyl]boronic acid (107 mg, 0.36 mmol) afforded, after purification by flash column chromatography on silica gel eluting 0-10% MeOH/EtOAc, N-[[4-(4-amino-1-cyclopentyl-pyrazolo[3,4-d]pyrimidin-3-yl)phenyl]methyl]-1H-indole-2-carboxamide (56 mg, 0.12 mmol, 41% yield) as a pale brown powder.

LC-MS (ES+, method 4): 7.67 min, m/z 452.2 [M+H]+

$^1$H NMR (500 MHz, DMSO-$d_6$, δ): 11.63 (s, 1H), 9.11 (t, J=6.2 Hz, 1H), 8.23 (s, 1H), 7.67-7.60 (m, 3H), 7.54-7.50 (m, 2H), 7.45-7.42 (m, 1H), 7.22-7.16 (m, 2H), 7.06-7.01 (m, 1H), 5.26-5.19 (m, 1H), 4.60 (d, J=6.2 Hz, 2H), 2.13-1.98 (m, 4H), 1.93-1.84 (m, 2H), 1.73-1.63 (m, 2H).

Example 89: N-[[4-(4-Amino-1-cyclopentyl-pyrazolo[3,4-d]pyrimidin-3-yl)-2-methyl-phenyl]methyl]-2-methoxy-benzamide

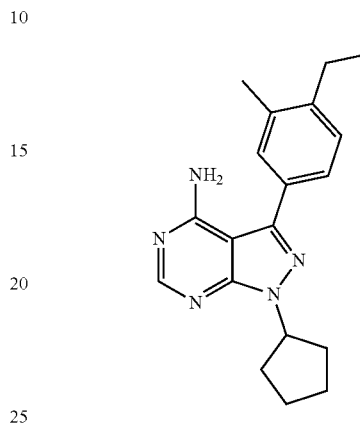

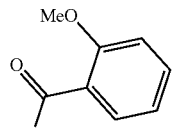

(4-Bromo-2-methyl-phenyl)methanamine

Following general procedure P, 4-bromo-2-methyl-benzonitrile (1.0 g, 5.10 mmol) gave crude (4-bromo-2-methyl-phenyl)methanamine (1.4 g, 6.87 mmol, assumed quantitative yield), which was used without further purification.

UPLC-MS (ES+, Short acidic): 1.04 min, m/z 201.8 [M+2]+

N-[(4-Bromo-2-methyl-phenyl)methyl]-2-methoxy-benzamide

To a suspension of (4-bromo-2-methyl-phenyl)methanamine (1.02 g, 5.10 mmol) and DIPEA (2.66 mL, 15.29 mmol) in anhydrous THF (20 mL), cooled at 0° C. under a nitrogen atmosphere, was added 2-methoxybenzoyl chloride (0.83 mL, 5.61 mmol). The reaction mixture was stirred overnight at room temperature, quenched with a saturated aqueous solution of ammonium chloride and then extracted with EtOAc (×3). The combined organics were washed with brine, dried over Na$_2$SO$_4$ and filtered then concentrated under reduced pressure. Further purification by flash column chromatography on silica gel eluting with 0-30% EtOAc in heptane gave N-[(4-bromo-2-methyl-phenyl)methyl]-2-methoxy-benzamide (0.83 g, 2.49 mmol, 49% yield) as a white solid.

UPLC-MS (ES+, Short acidic): 1.85 min, m/z 336.1 [M+2]+

2-Methoxy-N-[[2-methyl-4-(4,4,5,5-tetramethyl-1,3,2-dioxaborolan-2-yl)phenyl]methyl]benzamide Following general procedure R, N-[(4-bromo-2-methyl-phenyl)methyl]-2-methoxy-benzamide (0.83 g, 2.49 mmol) gave crude 2-methoxy-N-[[2-methyl-4-(4,4,5,5-tetramethyl-1,3,2-dioxaborolan-2-yl)phenyl]methyl]benzamide (1.20 g, 3.22 mmol, assumed quantitative yield) as a black oil, which was used without further purification.

UPLC-MS (ES+, Short acidic): 1.95 min, m/z 382.2 [M+H]+

N-[[4-(4-Amino-1-cyclopentyl-pyrazolo[3,4-d]pyrimidin-3-yl)-2-methyl-phenyl]methyl]-2-methoxy-benzamide Following general procedure D, 1-cyclopentyl-3-iodo-pyrazolo[3,4-d]pyrimidin-4-amine (50 mg, 0.15 mmol) and 2-methoxy-N-[[2-methyl-4-(4,4,5,5-tetramethyl-1,3,2-dioxaborolan-2-yl)phenyl]methyl]benzamide (139 mg, 0.36 mmol) gave, after purification by flash column chromatography on silica gel eluting with 50-100% EtOAc in heptane, N-[[4-(4-amino-1-cyclopentyl-pyrazolo[3,4-d]pyrimidin-3-yl)-2-methyl-phenyl]methyl]-2-methoxy-benzamide (18 mg, 0.04 mmol, 25% yield) as a white solid.

UPLC-MS (ES+, Short acidic): 1.61 min, m/z 457.3 [M+H]+

UPLC-MS (ES+, Long acidic): 4.07 min, m/z 457.2 [M+H]+

$^1$H NMR (400 MHz, DMSO-$d_6$, δ): 8.64 (t, J=5.9 Hz, 1H), 8.22 (s, 1H), 7.75 (dd, J=7.7, 1.8 Hz, 1H), 7.51-7.46 (m, 4H), 7.18-7.15 (m, 1H), 7.05 (td, J=7.5, 0.9 Hz, 1H), 5.22 (quint, J=7.4 Hz, 1H), 4.54 (d, J=5.9 Hz, 2H), 3.91 (s, 3H), 2.42 (s, 3H), 2.10-2.00 (m, 4H), 1.93-1.86 (m, 2H), 1.74-1.65 (m, 2H).

Example 90: N-[[4-[4-Amino-1-(2,2,2-trifluoroethyl)pyrazolo[3,4-d]pyrimidin-3-yl]phenyl]methyl]-2-methoxy-benzamide

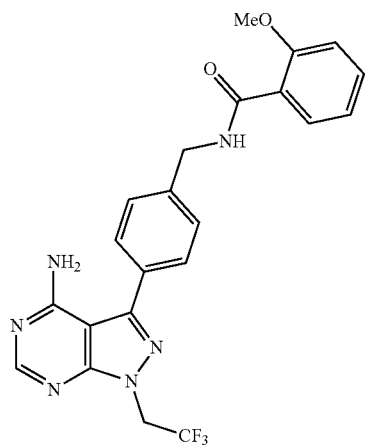 [SMILES: COc1ccccc1C(=O)NCc1ccc(-c2nn(CC(F)(F)F)c3ncnc(N)c23)cc1]

N-[[4-[4-Amino-1-(2,2,2-trifluoroethyl)pyrazolo[3,4-d]pyrimidin-3-yl]phenyl]methyl]-2-methoxy-benzamide To a solution of N-[[4-(4-amino-1H-pyrazolo[3,4-d]pyrimidin-3-yl)phenyl]methyl]-2-methoxy-benzamide (120 mg, 0.32 mmol) in DMF (3 mL) were added 1,1,1-trifluoro-2-iodoethane (87.5 mg, 0.42 mmol) and cesium carbonate (261 mg, 3.34 mmol). The reaction mixture was heated to 85° C. and stirred for 16 h. The reaction mixture was poured into brine and extracted with DCM. The combined organic extracts were filtered over a hydrophobic frit and concentrated under reduced pressure. Further purification by reverse phase column chromatography (water/MeCN 95:5 to 40:60) followed by flash column chromatography on silica gel eluting with 0-5% MeOH in DCM and recrystallization from MeOH gave the title compound (23 mg, 0.05 mmol, 16% yield) as a white solid.

UPLC-MS (ES+, Short acidic): 1.48 min, m/z 457.1 [M+H]+

UPLC-MS (ES+, Long acidic): 3.39 min, m/z 457.1 [M+H]+

$^1$H NMR (400 MHz, DMSO-$d_6$, δ): 8.79 (t, J=6.0 Hz, 1H), 8.33 (s, 1H), 7.78 (dd, J=7.6, 1.7 Hz, 1H), 7.67 (d, J=8.1 Hz, 2H), 7.55-7.48 (m, 3H), 7.17 (d, J=8.3 Hz, 1H), 7.06 (t, J=7.5 Hz, 1H), 5.28 (q, J=9.0 Hz, 2H), 4.61 (d, J=5.8 Hz, 2H), 3.92 (s, 3H).

Example 91: N-[[4-[4-amino-1-(4-hydroxy-4-methyl-cyclohexyl)pyrazolo[3,4-d]pyrimidin-3-yl]phenyl]methyl]-2-methoxy-benzamide (Isomer 1)

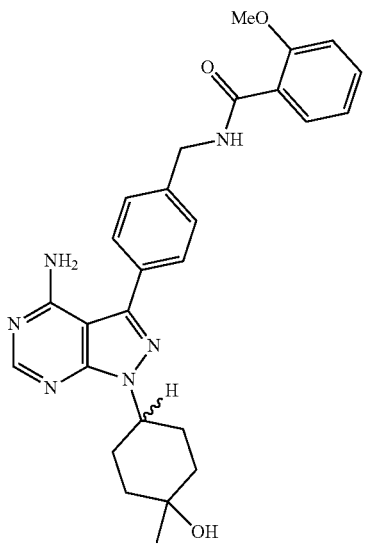 [SMILES: COc1ccccc1C(=O)NCc1ccc(-c2nn(C3CCC(C)(O)CC3)c3ncnc(N)c23)cc1]

8-Methyl-1,4-dioxaspiro[4.5]decan-8-ol

To a solution of 1,4-cyclohexanedione monoethylene acetal (6.00 g, 38.4 mmol) in THF (48 mL) at 0° C. was added bromo(methyl)magnesium in diethyl ether (3 M, 19.2 mL, 42.26 mmol) under a nitrogen atmosphere. The reaction mixture was allowed to stir at room temperature for 2 h and then quenched with a saturated NH$_4$Cl solution. Water was added and the mixture was extracted with DCM. The combined organic extracts were dried over Na$_2$SO$_4$, filtered and concentrated under reduced pressure to give 8-methyl-1,4-dioxaspiro[4.5]decan-8-ol (5.82 g, 27.7 mmol, 72% yield), which was used without further purification.

$^1$H NMR (400 MHz, CDCl$_3$, δ): 4.01-3.93 (m, 4H), 1.93-1.86 (m, 4H), 1.73-1.68 (m 4H), 1.29 (s, 3H), 1.15 (s, 1H).

4-Hydroxy-4-methyl-cyclohexanone

To a solution of 8-methyl-1,4-dioxaspiro[4.5]decan-8-ol (11.78 g, 68.4 mmol) in THF (50 mL) was added aqueous HCl (1 M, 205 mL, 205.2 mmol). The reaction mixture was allowed to stir overnight at room temperature. Then, a saturated solution of Na$_2$CO$_3$ was added and the mixture extracted with DCM. The combined organic extracts were dried over Na$_2$SO$_4$, filtered and concentrated under reduced pressure to afford crude 4-hydroxy-4-methyl-cyclohexanone (6.18 g, 48.2 mmol, 71% yield).

¹H NMR (400 MHz, CDCl₃, δ): 2.70-2.61 (m, 2H), 2.21-2.14 (m, 2H), 1.94-1.87 (m, 2H), 1.83-1.75 (m, 2H), 1.31 (s, 3H), 1.23 (s, 1H).

tert-Butyl N-[(4-hydroxy-4-methyl-cyclohexylidene)amino]carbamate

To a solution of 4-hydroxy-4-methyl-cyclohexanone (6.14 g, 47.88 mmol) in MeOH (60 mL) was added tert-butyl carbazate (6.64 g, 50.28 mmol). The reaction mixture was stirred at room temperature for 2 days. Then, the solvent was removed under reduced pressure and the obtained residue dissolved in DCM, washed with water, dried over Na₂SO₄ and concentrated under reduced pressure. Further purification by flash column chromatography on silica gel eluting with 0-100% EtOAc in heptane followed by column chromatography on silica gel eluting with 0-10% MeOH in DCM and recrystallization from ether and column chromatography on silica gel eluting with 0-100% EtOAc in DCM gave tert-butyl N-[(4-hydroxy-4-methyl-cyclohexylidene)amino]carbamate (1.39 g, 2.76 mmol, 6% yield) as a solid.

UPLC-MS (ES⁺, Short acidic): 3.50 min, m/z 243.2 [M+H]⁺

5-Amino-3-(4-bromophenyl)-1-(4-hydroxy-4-methyl-cyclohexyl)pyrazole-4-carbonitrile (Isomers 1 and 2)

To a solution of tert-butyl N-[(4-hydroxy-4-methyl-cyclohexylidene)amino]carbamate (400 mg, 1.65 mmol) in THF (8 mL) was added borane-tetrahydrofuran (1:1) (1 M in THF, 3.30 mL, 3.30 mmol) at 0° C. The reaction mixture was allowed to return to room temperature and stirred for 16 hours. The reaction was quenched with MeOH (3 mL) and all volatiles were removed under reduced pressure. Hydrogen chloride in dioxane (4 M, 4.13 mL, 16.51 mmol) was added and the reaction mixture allowed to stir for 1 hour at room temperature. All volatiles were removed under reduce pressure. The residue was dissolved in EtOH and triethylamine (0.79 mL, 5.70 mmol) and 2-[(4-bromophenyl)methoxy-methylene]propanedinitrile (300 mg, 1.14 mmol) were added. The reaction mixture was allowed to stir at room temperature overnight. Water was added and the mixture extracted with DCM. The combined extracts were filtered over a hydrophobic frit and concentrated under reduced pressure. Further purification by flash column chromatography on silica gel eluting with 55% EtOAc in heptane gave 5-amino-3-(4-bromophenyl)-1-(4-hydroxy-4-methyl-cyclohexyl)pyrazole-4-carbonitrile (isomer 1: 246 mg, 0.65 mmol, 57% yield over three steps) and further elution with 0-8% MeOH in DCM afforded 5-amino-3-(4-bromophenyl)-1-(4-hydroxy-4-methyl-cyclohexyl)pyrazole-4-carbonitrile (isomer 2, 132 mg, 0.35 mmol, 31% yield over 3 steps).

UPLC-MS (ES⁺, Short acidic, isomer 1): 1.63 min, m/z 376.9 [M+2]⁺

UPLC-MS (ES⁺, Short acidic, isomer 2): 1.70 min, m/z 374.9 [M]⁺

4-[4-Amino-3-(4-bromophenyl)pyrazolo[3,4-d]pyrimidin-1-yl]-1-methyl-cyclohexanol (Isomer 1)

Following general procedure S, 5-amino-3-(4-bromophenyl)-1-(4-hydroxy-4-methyl-cyclohexyl)pyrazole-4-carbonitrile (isomer 1, 100 mg, 0.27 mmol) afforded, after purification by flash column chromatography on silica gel eluting with 2-6% MeOH in DCM, 4-[4-amino-3-(4-bromophenyl)pyrazolo[3,4-d]pyrimidin-1-yl]-1-methyl-cyclohexanol (40 mg, 0.10 mmol, 37% yield) as an off-white solid.

UPLC-MS (ES⁺, Short acidic): 1.37 min, m/z 403.9 [M+2]⁺

N-[[4-[4-Amino-1-(4-hydroxy-4-methyl-cyclohexyl)pyrazolo[3,4-d]pyrimidin-3-yl]phenyl]methyl]-2-methoxy-benzamide (Isomer 1)

Following general procedure K, 4-[4-amino-3-(4-bromophenyl)pyrazolo[3,4-d]pyrimidin-1-yl]-1-methyl-cyclohexanol (isomer 1, 40 mg, 0.10 mmol) and potassium trifluoro-[[(2-methoxybenzoyl)amino]methyl]boranuide (40 mg, 0.15 mmol) gave, after purification by flash column chromatography on silica gel eluting with 4-6% MeOH in DCM, followed by reverse phase chromatography (water/MeCN 70:30 to 65:35), N-[[4-[4-amino-1-(4-hydroxy-4-methyl-cyclohexyl)pyrazolo[3,4-d]pyrimidin-3-yl]phenyl]methyl]-2-methoxy-benzamide (isomer 1, 6 mg, 0.01 mmol, 12% yield) as a white solid.

UPLC-MS (ES⁺, Short acidic): 1.33 min, m/z 487.2 [M+H]⁺

UPLC-MS (ES⁺, Long acidic): 2.95 min, m/z 487.2 [M+H]⁺

¹H NMR (400 MHz, DMSO-d₆, δ): 8.78 (t, J=6.1 Hz, 1H), 8.23 (s, 1H), 7.78 (dd, J=7.6, 1.7 Hz, 1H), 7.65 (d, J=8.1 Hz, 2H), 7.54-7.46 (m, 3H), 7.17 (d, J=8.3 Hz, 1H), 7.09-7.02 (m, 1H), 4.70-4.60 (m, 1H), 4.59 (d, J=6.1 Hz, 2H), 4.20 (s, 1H), 3.92 (s, 3H), 2.44-2.32 (m, 2H), 1.74-1.60 (m, 4H), 1.60-1.47 (m, 2H), 1.18 (s, 3H).

Example 92: N-[[4-[4-Amino-1-(4-hydroxy-4-methyl-cyclohexyl)pyrazolo[3,4-d]pyrimidin-3-yl]phenyl]methyl]-2-methoxy-benzamide (Isomer 2)

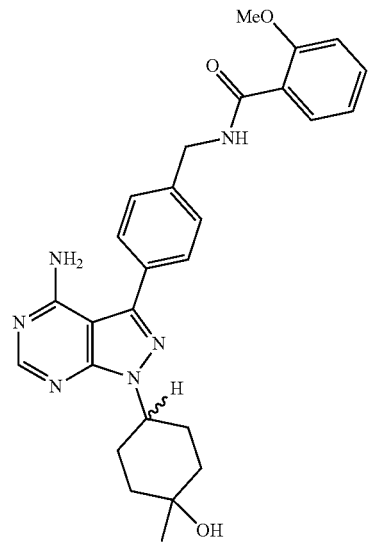 [SMILES: COc1ccccc1C(=O)NCc1ccc(-c2nn(C3CCC(C)(O)CC3)c3ncnc(N)c23)cc1]

4-[4-Amino-3-(4-bromophenyl)pyrazolo[3,4-d]pyrimidin-1-yl]-1-methyl-cyclohexanol (Isomer 2)

Following general procedure S, 5-amino-3-(4-bromophenyl)-1-(4-hydroxy-4-methyl-cyclohexyl)pyrazole-4-carbonitrile (isomer 2, 100 mg, 0.27 mmol) gave, after purification by flash column chromatography on silica gel eluting with 4-9% MeOH in DCM, 4-[4-amino-3-(4-bromophenyl)pyrazolo[3,4-d]pyrimidin-1-yl]-1-methyl-cyclohexanol (isomer 2, 41 mg, 0.10 mmol, 38% yield) as an off-white solid.

UPLC-MS (ES$^+$, Short acidic): 1.39 min, m/z 402.0 [M]$^+$

N-[[4-[4-Amino-1-(4-hydroxy-4-methyl-cyclohexyl)pyrazolo[3,4-d]pyrimidin-3-yl]phenyl]methyl]-2-methoxy-benzamide (Isomer 2)

Following general procedure K, 4-[4-amino-3-(4-bromophenyl)pyrazolo[3,4-d]pyrimidin-1-yl]-1-methyl-cyclohexanol (isomer 2, 40 mg, 0.10 mmol) and potassium trifluoro-[[(2-methoxybenzoyl)amino]methyl]boranuide (54 mg, 0.20 mmol) gave, after purification by flash column chromatography on silica gel eluting with 5-8% MeOH in DCM followed by further purification with reverse phase chromatography (water/MeCN 70:30 to 65:35), N-[[4-[4-amino-1-(4-hydroxy-4-methyl-cyclohexyl)pyrazolo[3,4-d]pyrimidin-3-yl]phenyl]methyl]-2-methoxy-benzamide (isomer 2, 7 mg, 0.02 mmol, 15% yield) as a white solid.

UPLC-MS (ES$^+$, Short acidic): 1.30 min, m/z 487.2 [M+H]$^+$

UPLC-MS (ES$^+$, Long acidic): 2.89 min, m/z 487.2 [M+H]$^+$ $^1$H NMR (400 MHz, DMSO-d$_6$, δ): 8.88 (t, J=6.1 Hz, 1H), 8.27 (s, 1H), 7.78 (dd, J=7.7, 1.7 Hz, 1H), 7.64 (d, J=8.1 Hz, 2H), 7.54-7.46 (m, 3H), 7.17 (d, J=8.2 Hz, 1H), 7.08-7.02 (m, 1H), 4.75-4.64 (m, 1H), 4.59 (d, J=6.1 Hz, 2H), 3.92 (s, 3H), 2.15-1.95 (m, 2H), 1.95-1.82 (m, 2H), 1.78-1.68 (m, 2H), 1.68-1.54 (m, 2H), 1.24 (s, 3H).

Example 93: N-[[4-[4-Amino-1-(2,2,2-trifluoroethyl)pyrazolo[3,4-d]pyrimidin-3-yl]phenyl]methyl]-5-fluoro-2-methoxy-benzamide

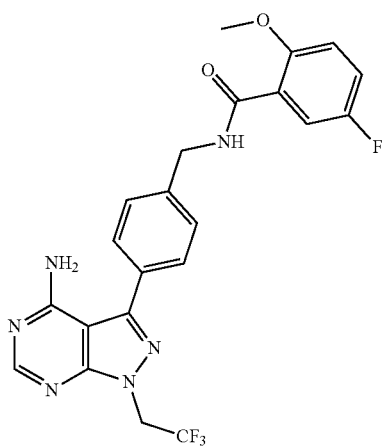 [SMILES: COc1ccc(F)cc1C(=O)NCc1ccc(-c2nn(CC(F)(F)F)c3ncnc(N)c23)cc1]

5-Amino-3-(4-bromophenyl)-1-(2,2,2-trifluoroethyl)pyrazole-4-carbonitrile

To a solution of 2,2,2-trifluoroethyl hydrazine (465 mg, 2.85 mmol) in EtOH (10 mL) was added triethylamine (1.1 mL, 7.60 mmol). The reaction mixture was stirred at room temperature for 10 min before 2-[(4-bromophenyl)-methoxy-methylene]propanedinitrile (500 mg, 1.90 mmol) was added. The reaction mixture was heated to 95° C. and allowed to stir for 16 hours. The reaction mixture was diluted with DCM and the mixture washed with saturated NH$_4$Cl solution, water and brine. The combined organic extracts were filtered through a hydrophobic frit and concentrated under reduced pressure. Further purification by flash column chromatography on silica gel eluting with 0-100% EtOAc in heptane gave 5-amino-3-(4-bromophenyl)-1-(2,2,2-trifluoroethyl)pyrazole-4-carbonitrile (568 mg, 1.65 mmol, 87% yield) as a pale yellow solid.

UPLC-MS (ES$^+$, Short acidic): 1.78 min, m/z 436.8 [M+H]$^+$ 3-(4-Bromophenyl)-1-(2,2,2-trifluoroethyl)pyrazolo[3,4-d]pyrimidin-4-amine A solution of 5-amino-3-(4-bromophenyl)-1-(2,2,2-trifluoroethyl)pyrazole-4-carbonitrile (150 mg, 0.43 mmol) in formamide (0.75 mL, 22.17 mmol) was stirred overnight at 185° C. The reaction mixture was cooled to room temperature, diluted with water and extracted with EtOAc. The combined organics were washed with sat. NaHCO$_3$ solution, dried over Na$_2$SO$_4$, filtered and concentrated under reduced pressure to give 3-(4-bromophenyl)-1-(2,2,2-trifluoroethyl)pyrazolo[3,4-d]pyrimidin-4-amine (161 mg, 0.43 mmol, quantitative yield), which was used without further purification.

$^1$H NMR (400 MHz, DMSO-d$_6$, δ): 8.33 (s, 1H), 7.76 (d, J=8.6 Hz, 2H), 7.63 (d, J=8.6 Hz, 2H), 5.28 (q, J=9.1 Hz, 2H).

N-[[4-[4-Amino-1-(2,2,2-trifluoroethyl)pyrazolo[3,4-d]pyrimidin-3-yl]phenyl]methyl]-5-fluoro-2-methoxy-benzamide Following general procedure K, 3-(4-bromophenyl)-1-(2,2,2-trifluoroethyl)pyrazolo[3,4-d]pyrimidin-4-amine (105 mg, 0.28 mmol) and potassium trifluoro-[[(5-fluoro-2-methoxy-benzoyl)amino]methyl]boranuide (162 mg, 0.56 mmol) gave, after purification by flash column chromatography on silica gel eluting with 0-5% MeOH in DCM, N-[[4-[4-amino-1-(2,2,2-trifluoroethyl)pyrazolo[3,4-d]pyrimidin-3-yl]phenyl]methyl]-5-fluoro-2-methoxy-benzamide (15 mg, 0.03 mmol, 11% yield) as a yellow solid.

UPLC-MS (ES$^+$, Short acidic): 1.59 min, m/z 475.1 [M+H]$^+$

UPLC-MS (ES$^+$, Long acidic): 3.63 min, m/z 475.1 [M+H]$^+$ $^1$H NMR (400 MHz, DMSO-d$_6$, δ): 8.88 (t, J=6.0 Hz, 1H), 8.32 (s, 1H), 7.67 (d, J=8.2 Hz, 2H), 7.55-7.52 (m, 3H), 7.38-7.32 (m, 1H), 7.20 (dd, J=9.1, 4.3 Hz, 1H), 5.27 (q, J=9.0 Hz, 2H), 4.60 (d, J=6.0 Hz, 2H), 3.91 (s, 3H).

Example 94: N-[[4-[4-Amino-1-(4-hydroxy-4-methyl-cyclohexyl)pyrazolo[3,4-d]pyrimidin-3-yl]phenyl]methyl]-5-fluoro-2-methoxy-benzamide (Isomer 1)

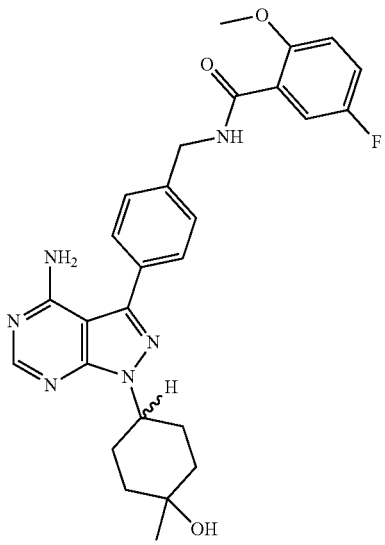 [SMILES: COc1ccc(F)cc1C(=O)NCc1ccc(-c2nn(C3CCC(C)(O)CC3)c3ncnc(N)c23)cc1]

Following general procedure K, 4-[4-amino-3-(4-bromophenyl)pyrazolo[3,4-d]pyrimidin-1-yl]-1-methyl-cyclohexanol (isomer 1, 30 mg, 0.07 mmol) and potassium trifluoro-[[(5-fluoro-2-methoxy-benzoyl)amino]methyl]boranuide (32 mg, 0.11 mmol) gave, after purification by flash column chromatography on silica gel eluting with 0-6% MeOH in DCM and further purification by reverse phase (water/MeCN, 100:0 to 65:35), N-[[4-[4-amino-1-(4-hydroxy-4-methyl-cyclohexyl)pyrazolo[3,4-d]pyrimidin-3-yl]phenyl]methyl]-5-fluoro-2-methoxy-benzamide (isomer 1, 3 mg, 0.01 mmol, 9% yield) as a white solid.

UPLC-MS (ES$^+$, Short acidic): 1.38 min, m/z 505.2 [M+H]$^+$

UPLC-MS (ES$^+$, Long acidic): 3.07 min, m/z 505.2 [M+H]$^+$ $^1$H NMR (400 MHz, DMSO-d$_6$, δ): 8.87 (t, J=5.8 Hz, 1H), 8.22 (s, 1H), 7.65 (d, J=8.1 Hz, 2H), 7.55-7.47 (m, 3H), 7.35 (ddd, J=9.0, 8.0, 3.3 Hz, 1H), 7.19 (dd, J=9.1, 4.3 Hz, 1H), 4.70-4.59 (m, 1H), 4.59 (d, J=6.1 Hz, 2H), 4.19 (s, 1H), 3.91 (s, 3H), 2.46-2.30 (m, 2H), 1.73-1.59 (m, 4H), 1.59-1.41 (m, 2H), 1.17 (s, 3H).

Example 95: N-[[4-[4-Amino-1-(4-hydroxy-4-methyl-cyclohexyl)pyrazolo[3,4-d]pyrimidin-3-yl]phenyl]methyl]-5-fluoro-2-methoxy-benzamide—(Isomer 2)

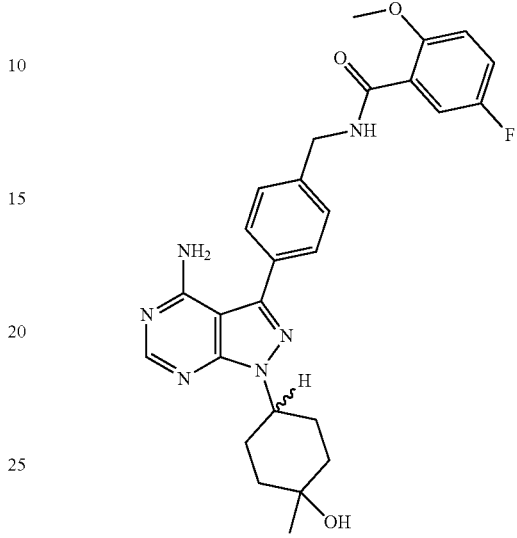

Following general procedure K, 4-[4-amino-3-(4-bromophenyl)pyrazolo[3,4-d]pyrimidin-1-yl]-1-methyl-cyclohexanol (isomer 2, 3 mg, 0.07 mmol) and potassium trifluoro-[[(5-fluoro-2-methoxy-benzoyl)amino]methyl]boranuide (32 mg, 0.11 mmol) gave, after purification by flash column chromatography on silica gel eluting with 0-10% MeOH in DCM, followed by reverse phase chromatography (water/MeCN 100:0 to 67:33), N-[[4-[4-amino-1-(4-hydroxy-4-methyl-cyclohexyl)pyrazolo[3,4-d]pyrimidin-3-yl]phenyl]methyl]-5-fluoro-2-methoxy-benzamide (isomer 2, 4 mg, 0.01 mmol, 12% yield) as an off-white solid.

UPLC-MS (ES$^+$, Short acidic): 1.34 min, m/z 505.2 [M+H]$^+$

UPLC-MS (ES$^+$, Long acidic): 3.01 min, m/z 505.2 [M+H]$^+$ $^1$H NMR (400 MHz, DMSO-d$_6$, δ): 8.87 (t, J=6.0 Hz, 1H), 8.24 (s, 1H), 7.64 (d, J=8.1 Hz, 2H), 7.56-7.47 (m, 3H), 7.39-7.31 (m, 1H), 7.20 (dd, J=9.1, 4.3 Hz, 1H), 4.75-4.62 (m, 1H), 4.58 (d, J=6.0 Hz, 2H), 4.46 (s, 1H), 3.91 (s, 3H), 2.16-1.94 (m, 2H), 1.94-1.83 (m, 2H), 1.78-1.68 (m, 2H), 1.68-1.55 (m, 2H), 1.24 (s, 3H)

Example 96: BTK$^{WT}$ Binding Affinity

BTK$^{WT}$ binding affinity of each compound tested was determined using a time-resolved fluorescence resonance energy transfer (TR-FRET) methodology. 2.5 nM Recombinant BTK$^{WT}$ kinase, varying concentrations of inhibitor, 2 nM LanthaScreen™ Eu anti-His Antibody and 15 nM Kinase Tracer 236 was incubated in 1× LanthaScreen™ Kinase Buffer A for 5 h. Recombinant BTK kinase and all LanthaScreen™ components were purchased from Invitrogen. Measurements were performed in a reaction volume of 30 μL using half-area 96-well assay plates. The TR-FRET signal was read on a plate reader with an excitation wavelength of 340 nm and detection wavelengths of 615 and 665 nm. Binding affinity was determined for each compound by measuring TR-FRET signal at various concentrations of compound and plotting the relative fluorescence units against the inhibitor concentration to estimate the $IC_{50}$ from log [Inhibitor] vs response using the Variable Slope model in Graphpad prism from Graphpad software (SanDiego, Calif.).

Results of the $BTK^{WT}$ Binding Affinity are shown below in Table 5

Table 5 shows the $BTK^{WT}$ Binding affinity, as determined by the assay described above, for compounds of formula (I), categorised based on the BTK $IC_{50}$ value of the compound as "A", "B", "C", "D" and "E".

$IC_{50}$: A≤10 nM; 10 nM<B≤100 nM; 100 nM<C≤1 μM; 1 μM<D≤10 μM; E>10 μM

Example 97: $BTK^{C481S}$ Binding Affinity $BTK^{C481S}$ binding affinity of each compound tested was determined using a time-resolved fluorescence resonance energy transfer (TR-FRET) methodology. 5 nM Recombinant $BTK^{WT}$ kinase, varying concentrations of inhibitor, 2 nM LanthaScreen™ Eu anti-His Antibody and 30 nM Kinase Tracer 236 was incubated in 1× LanthaScreen™ Kinase Buffer A for 5 h. Recombinant $BTK^{C481S}$ kinase was purchased from SignalChem and all LanthaScreen™ components were purchased from Invitrogen. Measurements were performed in a reaction volume of 30 μL using half-area 96-well assay plates. The TR-FRET signal was read on a plate reader with an excitation wavelength of 340 nm and detection wavelengths of 615 and 665 nm. Binding affinity was determined for each compound by measuring TR-FRET signal at various concentrations of compound and plotting the relative fluorescence units against the inhibitor concentration to estimate the $IC_{50}$ from log [Inhibitor] vs response using the Variable Slope model in Graphpad prism from Graphpad software (SanDiego, Calif.).

Table 5 shows the $BTK^{C481S}$ Binding affinity, as determined by the assay described above, for compounds of formula (I), categorised based on the BTK $IC_{50}$ value of the compound as "A", "B", "C", "D" and "E".

$IC_{50}$: A≤10 nM; 10 nM<B≤100 nM; 100 nM<C≤1 μM; 1 μM<D≤10 μM; E>10 μM

Example 98: EGFR Binding Affinity

EGFR binding affinity was determined using a time-resolved fluorescence resonance energy transfer (TR-FRET) methodology. 2.5 nM Recombinant EGFR, varying concentrations of inhibitor, 2 nM LanthaScreen™ Eu anti-GST Antibody and 3 nM Kinase Tracer 199 was incubated in 1× LanthaScreen™ Kinase Buffer A for 5 h. Recombinant EGFR and all LanthaScreen™ components were purchased from Invitrogen. Measurements were performed in a reaction volume of 30 μL using half-area 96-well assay plates. The TR-FRET signal was read on a plate reader with an excitation wavelength of 340 nm and detection wavelengths of 615 and 665 nm. Binding affinity was determined for each compound by measuring TR-FRET signal at various concentrations of compound and plotting the relative fluorescence units against the inhibitor concentration to estimate the $IC_{50}$ from log [Inhibitor] vs response using the Variable Slope model in Graphpad prism from Graphpad software (SanDiego, Calif.).

Results of the EGFR binding affinity are shown in Table 5 below.

Table 5 shows the EGFR Binding Affinity, as determined by the assay described above, for compounds of formula (I), categorised based on the EGFR $IC_{50}$ value of the compound as "A", "B", "C", "D" and "E".

$IC_{50}$: A≤10 nM; 10 nM<B≤100 nM; 100 nM<C≤1 μM; 1 μM<D≤10 μM; E>10 μM

Example 99: OCI-Ly10 Anti-proliferative activity

Compounds were assayed for effects on the growth of OCI-Ly10 human DLBCL cells that are dependent on NFκB signalling. OCI-Ly10 cells were grown in suspension in T225 flasks, centrifuged and re-suspended in 2.5% FBS containing media. Cells were then plated at 7.5×10³ cells per well in 96-well plates in varying concentrations of compound and incubated for 72 h at 37° C. An additional plate of cells to be used as the Day 0 read was seeded without compound addition, Resazurin was added to each well, incubated for 5 h and the fluorescence measured at 590 nm. After 72 h of compound treatment, Resazurin was added to each well of the compound treated plates, incubated for 5 h and the fluorescence measured at 590 nm. The $IC_{50}$ was then calculated by subtracting the average Day 0 value from each well value from the treated plates, each treatment was then calculated as a percentage of the DMSO control and the percentages plotted against the inhibitor concentration to estimate the $IC_{50}$ from log [Inhibitor] vs response using the Variable Slope model in Graphpad prism from Graphpad software (SanDiego, Calif.).

Table 5 shows the OCI-Ly10 anti-proliferative activity, as determined by the assay described above, for compounds of formula (I), categorised based on the OCI-Ly10 $IC_{50}$ value of the compound as "A", "B", "C", "D" and "E".

$IC_{50}$: A≤10 nM; 10 nM<B≤100 nM; 100 nM<C≤1 μM; 1 μM<D≤10 μM; E>10 μM

"ND" in Table 5 means "Not Determined" and refers to compounds that have not been tested in the indicated assay.

TABLE 5

| Example | $BTK^{WT}$ $IC_{50}$ | $BTK^{C481S}$ $IC_{50}$ | EGFR $IC_{50}$ | Proliferation OCI-Ly10-$IC_{50}$ |
|---|---|---|---|---|
| 1 | A | A | C | B |
| 2 | C | ND | B | D |
| 3 | C | ND | ND | ND |
| 4 | A | A | C | B |
| 5 | B | B | D | C |
| 6 | C | ND | C | ND |
| 7 | A | A | D | C |
| 8 | B | A | D | D |
| 9 | C | ND | E | C |
| 10 | C | ND | E | C |
| 11 | A | A | D | B |
| 12 | A | A | D | B |
| 13 | C | ND | E | C |
| 14 | C | ND | D | C |
| 15 | C | ND | D | B |
| 16 | C | ND | D | D |
| 17 | C | ND | D | ND |
| 18 | B | B | D | C |
| 19 | A | A | C | C |
| 20 | C | ND | D | ND |
| 21 | A | A | D | C |
| 22 | C | ND | D | ND |
| 23-isomer1 | A | A | C | C |
| 23-isomer2 | A | A | C | B |
| 24 | A | A | C | B |
| 25 | A | A | C | B |
| 26 | B | A | C | C |
| 27 | B | B | C | C |
| 28 | B | B | C | C |

TABLE 5-continued

| Example | BTK$^{WT}$ IC$_{50}$ | BTK$^{C481S}$ IC$_{50}$ | EGFR IC$_{50}$ | Proliferation OCI-Ly10-IC$_{50}$ |
|---|---|---|---|---|
| 29 | A | A | C | C |
| 30 | A | A | C | ND |
| 31 | A | A | C | B |
| 32 | A | A | C | B |
| 33-isomer 1 | A | A | C | B |
| 33-isomer 2 | A | A | D | B |
| 33-isomer 2 | A | A | C | C |
| 34 | A | A | D | B |
| 35 | A | A | B | B |
| 36 | A | A | C | C |
| 37 | A | A | C | C |
| 38 | A | A | B | B |
| 39 | A | A | C | B |
| 40 | A | A | C | B |
| 41 | A | A | C | C |
| 42 | A | A | D | C |
| 43 | A | A | C | B |
| 44 | A | A | D | C |
| 45 | A | A | C | C |
| 46 | B | B | C | C |
| 47 | A | A | C | C |
| 48 | B | A | D | C |
| 49 | A | A | B | B |
| 50 | A | A | C | C |
| 51 | A | A | B | B |
| 52 | A | A | B | B |
| 53 | B | A | D | D |
| 54 | A | A | D | C |
| 55 | B | B | D | C |
| 56 | A | A | C | C |
| 57 | C | D | D | C |
| 58 | A | A | D | C |
| 59 | B | B | D | C |
| 60 | A | A | D | C |
| 61 | A | A | D | C |
| 62 | A | A | C | B |
| 63 | A | A | D | B |
| 64 | C | C | D | D |
| 65 | A | A | D | C |
| 66 | A | A | C | B |
| 67 | D | D | D | ND |
| 68 | C | C | D | D |
| 69 | C | C | D | D |
| 70 | A | A | C | C |
| 71 | C | C | ND | ND |
| 72 | C | ND | ND | ND |
| 73 | C | B | D | ND |
| 74 | B | B | D | C |
| 75 | A | A | D | B |
| 76 | A | A | C | C |
| 77 | A | A | E | B |
| 78 | A | A | D | ND |
| 79 | A | A | D | ND |
| 80 | D | C | D | D |
| 81 | D | ND | ND | D |
| 82 | E | C | E | ND |
| 83 | E | ND | ND | ND |
| 84 | D | ND | ND | ND |
| 85 | D | ND | ND | ND |
| 86 | E | E | ND | ND |
| 87 | D | ND | ND | ND |
| 88 | D | C | D | ND |
| 89 | A | A | C | C |
| 90 | B | B | E | D |
| 91 | A | A | C | C |
| 92 | A | A | C | B |
| 93 | A | A | E | C |
| 94 | A | A | C | B |
| 95 | A | A | C | B |

The following table, Table 6, provides values of the BTK binding efficacy of a selection of compounds of the invention.

TABLE 6

| ID. No. | Name | BTK Binding IC50 (nM) |
|---|---|---|
| 4 | N-[[4-(4-amino-1-cyclopentyl-pyrazolo[3,4-d]pyrimidin-3-yl)phenyl]methyl]-5-fluoro-2-methoxy-benzamide | 0.8 |
| 23-isomer 2 | N-[[4-[4-amino-1-(4-hydroxycyclohexyl)pyrazolo[3,4-d]pyrimidin-3-yl]phenyl]methyl]-2-methoxy-benzamide | 0.4 |
| 24 | N-[[4-[4-amino-1-[(1R*,3S*)-3-hydroxycyclopentyl]pyrazolo[3,4-d]pyrimidin-3-yl]phenyl]methyl]-2-methoxy-benzamide | 2.2 |
| 30 | N-[[4-[4-amino-1-[(1R,4R)-4-hydroxycyclopent-2-en-1-yl]pyrazolo[3,4-d]pyrimidin-3-yl]phenyl]methyl]-2-methoxy-benzamide | 1.4 |
| 37 | N-[[4-[4-amino-1-(3-hydroxycyclohexyl)pyrazolo[3,4-d]pyrimidin-3-yl]phenyl]methyl]-2-methoxy-benzamide | 1.7 |
| 39 | N-[[4-[4-amino-1-(4-methoxycyclohexyl)pyrazolo[3,4-d]pyrimidin-3-yl]phenyl]methyl]-2-methoxy-benzamide | 1.4 |
| 41 | Ethyl 3-[4-amino-3-[4-[[(2-methoxybenzoyl)amino]methyl]phenyl]pyrazolo[3,4-d]pyrimidin-1-yl]cyclohexanecarboxylate | 1.2 |
| 49 | N-[[4-(4-amino-1-cyclohex-2-en-1-yl-pyrazolo[3,4-d]pyrimidin-3-yl)phenyl]methyl]-2-methoxy-benzamide | 0.4 |
| 51 | N-[[4-(4-amino-1-tert-butyl-pyrazolo[3,4-d]pyrimidin-3-yl)phenyl]methyl]-2-methoxy-benzamide | 0.6 |
| 54 | N-[[4-[4-amino-1-[(1R,4R)-4-fluorocyclopent-2-en-1-yl]pyrazolo[3,4-d]pyrimidin-3-yl]phenyl]methyl]-2-methoxy-benzamide | 0.7 |
| 56 | N-[[4-[4-amino-1-[(1R)-indan-1-yl]pyrazolo[3,4-d]pyrimidin-3-yl]phenyl]methyl]-2-methoxy-benzamide | 1.2 |
| 66 | N-[[4-(4-amino-1-cyclopentyl-pyrazolo[3,4-d]pyrimidin-3-yl)-2-fluoro-phenyl]methyl]-2-methoxy-benzamide | 4.0 |

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A compound selected from the group consisting of:
N-[[4-(4-amino-1-cyclopentyl-pyrazolo[3,4-d]pyrimidin-3-yl)phenyl]methyl]-5-chloro-2-methoxy-benzamide;
N-[[4-(4-amino-1-cyclopentyl-pyrazolo[3,4-d]pyrimidin-3-yl)phenyl]methyl]-2-methoxy-5-methyl-benzamide;
ethyl 4-[4-amino-3-[4-[[(2-methoxybenzoyl)amino]methyl]phenyl]pyrazol[3,4-d]pyrimidin-1-yl]cyclohexanecarboxylate;
N-[[4-(4-amino-1-tetrahydropyran-3-yl-pyrazolo[3,4-d]pyrimidin-3-yl)phenyl]methyl]-2-methoxy-benzamide;
N-[[4-(7-amino-3-cyclopentyl-pyrazolo[4,3-d]pyrimidin-1-yl)phenyl]methyl]-2-methoxy-benzamide;
N-[[4-(4-amino-1-cyclopent-3-en-1-yl-pyrazolo[3,4-d]pyrimidin-3-yl)phenyl]methyl]-2-methoxy-benzamide;
N-[[4-(4-amino-1-cyclopentyl-pyrazolo[3,4-d]pyrimidin-3-yl)-2-fluorophenyl]methyl]-5-fluoro-2-methoxy-benzamide;
N-[[4-(4-amino-1-cyclopentyl-pyrazolo[3,4-d]pyrimidin-3-yl)-2-methoxyphenyl]methyl]-2-methoxy-benzamide; and
N-[[4-(4-amino-1-cyclopentyl-pyrazolo[3,4-d]pyrimidin-3-yl)-3-methoxyphenyl]methyl]-2-methoxy-benzamide;
or a pharmaceutically acceptable salt thereof.

2. The compound of claim 1, wherein the compound is N-[[4-(4-amino-1-cyclopentyl-pyrazolo[3,4-d]pyrimidin-3-yl)phenyl]methyl]-5-chloro-2-methoxy-benzamide, or a pharmaceutically acceptable salt thereof.

3. The compound of claim 1, wherein the compound is N-[[4-(4-amino-1-cyclopentyl-pyrazolo[3,4-d]pyrimidin-3-yl)phenyl]methyl]-2-methoxy-5-methyl-benzamide, or a pharmaceutically acceptable salt thereof.

4. The compound of claim 1, wherein the compound is ethyl 4-[4-amino-3-[4-[[(2-methoxybenzoyl)amino]methyl]phenyl]pyrazolo[3,4-d]pyrimidin-1-yl]cyclohexanecarboxylate, or a pharmaceutically acceptable salt thereof.

5. The compound of claim 1, wherein the compound is N-[[4-(4-amino-1-tetrahydropyran-3-yl-pyrazolo[3,4-d]pyrimidin-3-yl)phenyl]methyl]-2-methoxy-benzamide, or a pharmaceutically acceptable salt thereof.

6. The compound of claim 1, wherein the compound is N-[[4-(7-amino-3-cyclopentyl-pyrazolo[4,3-d]pyrimidin-1-yl)phenyl]methyl]-2-methoxy-benzamide, or a pharmaceutically acceptable salt thereof.

7. The compound of claim 1, wherein the compound is N-[[4-(4-amino-1-cyclopent-3-en-1-yl-pyrazolo[3,4-d]pyrimidin-3-yl)phenyl]methyl]-2-methoxy-benzamide, or a pharmaceutically acceptable salt thereof.

8. The compound of claim 1, wherein the compound is N-[[4-(4-amino-1-cyclopentyl-pyrazolo[3,4-d]pyrimidin-3-yl)-2-fluorophenyl]methyl]-5-fluoro-2-methoxy-benzamide, or a pharmaceutically acceptable salt thereof.

9. The compound of claim 1, wherein the compound is N-[[4-(4-amino-1-cyclopentyl-pyrazolo[3,4-d]pyrimidin-3-yl)-2-methoxyphenyl]methyl]-2-methoxy-benzamide, or a pharmaceutically acceptable salt thereof.

10. The compound of claim 1, wherein the compound is N-[[4-(4-amino-1-cyclopentyl-pyrazolo[3,4-d]pyrimidin-3-yl)-3-methoxyphenyl]methyl]-2-methoxy-benzamide, or a pharmaceutically acceptable salt thereof.

11. The compound of claim 1, wherein the compound is selected from the group consisting of:
N-[[4-(4-amino-1-cyclopentyl-pyrazolo[3,4-d]pyrimidin-3-yl)phenyl]methyl]-5-chloro-2-methoxy-benzamide;
N-[[4-(4-amino-1-cyclopentyl-pyrazolo[3,4-d]pyrimidin-3-yl)phenyl]methyl]-2-methoxy-5-methyl-benzamide;
ethyl 4-[4-amino-3-[4-[[(2-methoxybenzoyl)amino]methyl]phenyl]pyrazolo[3,4-d]pyrimidin-1-yl]cyclohexanecarboxylate;
N-[[4-(4-amino-1-tetrahydropyran-3-yl-pyrazolo[3,4-d]pyrimidin-3-yl)phenyl]methyl]-2-methoxy-benzamide;
N-[[4-(7-amino-3-cyclopentyl-pyrazolo[4,3-d]pyrimidin-1-yl)phenyl]methyl]-2-methoxy-benzamide;
N-[[4-(4-amino-1-cyclopent-3-en-1-yl-pyrazolo[3,4-d]pyrimidin-3-yl)phenyl]methyl]-2-methoxy-benzamide;
N-[[4-(4-amino-1-cyclopentyl-pyrazolo[3,4-d]pyrimidin-3-yl)-2-fluorophenyl]methyl]-5-fluoro-2-methoxy-benzamide;
N-[[4-(4-amino-1-cyclopentyl-pyrazolo[3,4-d]pyrimidin-3-yl)-2-methoxyphenyl]methyl]-2-methoxy-benzamide; and
N-[[4-(4-amino-1-cyclopentyl-pyrazolo[3,4-d]pyrimidin-3-yl)-3-methoxyphenyl]methyl]-2-methoxy-benzamide.

12. The compound of claim 1, wherein the compound is in the form of a pharmaceutically acceptable salt.

13. A pharmaceutical composition comprising a compound selected from the group consisting of:
N-[[4-(4-amino-1-cyclopentyl-pyrazolo[3,4-d]pyrimidin-3-yl)phenyl]methyl]-5-chloro-2-methoxy-benzamide;
N-[[4-(4-amino-1-cyclopentyl-pyrazolo[3,4-d]pyrimidin-3-yl)phenyl]methyl]-2-methoxy-5-methyl-benzamide;
ethyl 4-[4-amino-3-[4-[[(2-methoxybenzoyl)amino]methyl]phenyl]pyrazolo[3,4-d]pyrimidin-1-yl]cyclohexanecarboxylate;
N-[[4-(4-amino-1-tetrahydropyran-3-yl-pyrazolo[3,4-d]pyrimidin-3-yl)phenyl]methyl]-2-methoxy-benzamide;

N-[[4-(7-amino-3-cyclopentyl-pyrazolo[4,3-d]pyrimidin-1-yl)phenyl]methyl]-2-methoxy-benzamide;
N-[[4-(4-amino-1-cyclopent-3-en-1-yl-pyrazolo[3,4-d]pyrimidin-3-yl)phenyl]methyl]-2-methoxy-benzamide;
N-[[4-(4-amino-1-cyclopentyl-pyrazolo[3,4-d]pyrimidin-3-yl)-2-fluorophenyl]methyl]-5-fluoro 2-methoxy-benzamide;
N-[[4-(4-amino-1-cyclopentyl-pyrazolo[3,4-d]pyrimidin-3-yl)-2-methoxyphenyl]methyl]-2-methoxy-benzamide; and
N-[[4-(4-amino-1-cyclopentyl-pyrazolo[3,4-d]pyrimidin-3-yl)-3-methoxyphenyl]methyl]-2-methoxy-benzamide;
or a pharmaceutically acceptable salt thereof; and a pharmaceutically acceptable excipient.

14. The pharmaceutical composition of claim 13, wherein the compound is
N-[[4-(4-amino-1-cyclopentyl-pyrazolo[3,4-d]pyrimidin-3-yl)phenyl]methyl]-5-chloro-2-methoxy-benzamide, or a pharmaceutically acceptable salt thereof.

15. The pharmaceutical composition of claim 13, wherein the compound is
N-[[4-(4-amino-1-cyclopentyl-pyrazolo[3,4-d]pyrimidin-3-yl)phenyl]methyl]-2-methoxy-5-methyl-benzamide, or a pharmaceutically acceptable salt thereof.

16. The pharmaceutical composition of claim 13, wherein the compound is
ethyl 4-[4-amino-3-[4-[[(2-methoxybenzoyl)amino]methyl]phenyl]pyrazolo[3,4-d]pyrimidin-1-yl]cyclohexanecarboxylate, or a pharmaceutically acceptable salt thereof.

17. The pharmaceutical composition of claim 13, wherein the compound is
N-[[4-(4-amino-1-tetrahydropyran-3-yl-pyrazolo[3,4-d]pyrimidin-3-yl)phenyl]methyl]-2-methoxy-benzamide, or a pharmaceutically acceptable salt thereof.

18. The pharmaceutical composition of claim 13, wherein the compound is
N-[[4-(7-amino-3-cyclopentyl-pyrazolo[4,3-d]pyrimidin-1-yl)phenyl]methyl]-2-methoxy-benzamide, or a pharmaceutically acceptable salt thereof.

19. The pharmaceutical composition of claim 13, wherein the compound is
N-[[4-(4-amino-1-cyclopent-3-en-1-yl-pyrazolo[3,4-d]pyrimidin-3-yl)phenyl]methyl]-2-methoxy-benzamide, or a pharmaceutically acceptable salt thereof.

20. The pharmaceutical composition of claim 13, wherein the compound is
N-[[4-(4-amino-1-cyclopentyl-pyrazolo[3,4-d]pyrimidin-3-yl)-2-fluorophenyl]methyl]-5-fluoro-2-methoxy-benzamide, or a pharmaceutically acceptable salt thereof.

21. The pharmaceutical composition of claim 13, wherein the compound is
N-[[4-(4-amino-1-cyclopentyl-pyrazolo[3,4-d]pyrimidin-3-yl)-2-methoxyphenyl]methyl]-2-methoxy-benzamide, or a pharmaceutically acceptable salt thereof.

22. The pharmaceutical composition of claim 13, wherein the compound is
N-[[4-(4-amino-1-cyclopentyl-pyrazolo[3,4-d]pyrimidin-3-yl)-3-methoxyphenyl]methyl]-2-methoxy-benzamide, or a pharmaceutically acceptable salt thereof.

23. The pharmaceutical composition of claim 13, wherein the compound is selected from the group consisting of:
N-[[4-(4-amino-1-cyclopentyl-pyrazolo[3,4-d]pyrimidin-3-yl)phenyl]methyl]-5-chloro-2-methoxy-benzamide;
N-[[4-(4-amino-1-cyclopentyl-pyrazolo[3,4-d]pyrimidin-3-yl)phenyl]methyl]-2-methoxy-5-methyl-benzamide;
ethyl 4-[4-amino-3-[4-[[(2-methoxybenzoyl)amino]methyl]phenyl]pyrazolo[3,4-d]pyrimidin-1-yl]cyclohexanecarboxylate;
N-[[4-(4-amino-1-tetrahydropyran-3-yl-pyrazolo[3,4-d]pyrimidin-3-yl)phenyl]methyl]-2-methoxy-benzamide;
N-[[4-(7-amino-3-cyclopentyl-pyrazolo[4,3-d]pyrimidin-1-yl)phenyl]methyl]-2-methoxy-benzamide;
N-[[4-(4-amino-1-cyclopent-3-en-1-yl-pyrazolo[3,4-d]pyrimidin-3-yl)phenyl]methyl]-2-methoxy-benzamide;
N-[[4-(4-amino-1-cyclopentyl-pyrazolo[3,4-d]pyrimidin-3-yl)-2-fluorophenyl]methyl]-5-fluoro-2-methoxy-benzamide;
N-[[4-(4-amino-1-cyclopentyl-pyrazolo[3,4-d]pyrimidin-3-yl)-2-methoxyphenyl]methyl]-2-methoxy-benzamide; and
N-[[4-(4-amino-1-cyclopentyl-pyrazolo[3,4-d]pyrimidin-3-yl)-3-methoxyphenyl]methyl]-2-methoxy-benzamide.

24. The composition of claim 13, wherein the compound is in the form of a pharmaceutically acceptable salt.

* * * * *

UNITED STATES PATENT AND TRADEMARK OFFICE
CERTIFICATE OF CORRECTION

PATENT NO. : 10,399,989 B2
APPLICATION NO. : 16/109223
DATED : September 3, 2019
INVENTOR(S) : Nicolas Guisot Page 1 of 1

It is certified that error appears in the above-identified patent and that said Letters Patent is hereby corrected as shown below:

On the Title Page

Column 1 (Related US Application Data), Line 4, below "2016." insert:
-- Foreign Application Priority Data
Sep. 16, 2015 (GB)................1516445.2
Dec. 16, 2015 (GB)................1522246.6
Aug. 15, 2016 (GB)..............1613947.9 --, as a new field entry.

Signed and Sealed this
Twenty-sixth Day of November, 2019

Andrei Iancu
*Director of the United States Patent and Trademark Office*